United States Patent
Ciaramella et al.

(10) Patent No.: US 11,911,453 B2
(45) Date of Patent: Feb. 27, 2024

(54) RSV RNA VACCINES

(71) Applicant: ModernaTX, Inc., Cambridge, MA (US)

(72) Inventors: Giuseppe Ciaramella, Sudbury, MA (US); Kapil Bahl, Medford, MA (US); Amy Espeseth, Chalfont, PA (US); Andrew J. Bett, Lansdale, PA (US); Pedro Cejas, Oreland, PA (US); Lan Zhang, Chalfont, PA (US); Christine Shaw, Reading, MA (US)

(73) Assignee: ModernaTX, Inc., Cambridge, MA (US)

( * ) Notice: Subject to any disclaimer, the term of this patent is extended or adjusted under 35 U.S.C. 154(b) by 617 days.

(21) Appl. No.: 16/965,589

(22) PCT Filed: Jan. 28, 2019

(86) PCT No.: PCT/US2019/015412
§ 371 (c)(1),
(2) Date: Jul. 28, 2020

(87) PCT Pub. No.: WO2019/148101
PCT Pub. Date: Aug. 1, 2019

(65) Prior Publication Data
US 2021/0046173 A1    Feb. 18, 2021

Related U.S. Application Data

(60) Provisional application No. 62/623,240, filed on Jan. 29, 2018.

(51) Int. Cl.
A61K 39/12    (2006.01)
A61K 9/00    (2006.01)
A61K 39/00    (2006.01)

(52) U.S. Cl.
CPC ............ *A61K 39/12* (2013.01); *A61K 9/0019* (2013.01); *A61K 2039/53* (2013.01); *A61K 2039/55555* (2013.01)

(58) Field of Classification Search
None
See application file for complete search history.

(56) References Cited

U.S. PATENT DOCUMENTS 6,040,427 A     3/2000  Locht et al.
6,500,419 B1   12/2002  Hone et al.
(Continued)

FOREIGN PATENT DOCUMENTS

AU         652831 B2    9/1994
AU      2015210364 A1   3/2017
(Continued)

OTHER PUBLICATIONS

Geneseq database accession No. BGP67180, Sep. 2019 sequence alignment with instant Seq Id No. 5.*
(Continued)

*Primary Examiner* — Shanon A. Foley
(74) *Attorney, Agent, or Firm* — Wolf, Greenfield & Sacks, P.C.

(57) ABSTRACT

The disclosure relates to respiratory syncytial virus (RSV) ribonucleic acid (RNA) vaccines as well as methods of using the vaccines and compositions comprising the vaccines. The vaccine can be formulated in a lipid nanoparticle.

13 Claims, 9 Drawing Sheets

Specification includes a Sequence Listing.

(56) References Cited

U.S. PATENT DOCUMENTS

| | | |
|---|---|---|
| 6,514,948 B1 | 2/2003 | Raz et al. |
| 6,610,044 B2 | 8/2003 | Mathiesen |
| 7,001,890 B1 | 2/2006 | Wagner et al. |
| 8,569,256 B2 | 10/2013 | Heyes et al. |
| 8,609,142 B2 | 12/2013 | Troiano et al. |
| 8,613,954 B2 | 12/2013 | Zale et al. |
| 8,617,608 B2 | 12/2013 | Zale et al. |
| 8,691,966 B2 | 4/2014 | Kariko et al. |
| 8,710,200 B2 | 4/2014 | Schrum et al. |
| 8,734,832 B2 | 5/2014 | O'Hagan et al. |
| 8,734,853 B2 | 5/2014 | Sood et al. |
| 8,754,062 B2 | 6/2014 | De Fougerolles et al. |
| 8,822,663 B2 | 9/2014 | Schrum et al. |
| 8,980,864 B2 | 3/2015 | Hoge et al. |
| 8,999,380 B2 | 4/2015 | Bancel et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,572,896 B2 | 2/2017 | Bancel et al. |
| 9,597,380 B2 | 3/2017 | Chakraborty et al. |
| 9,803,199 B2 | 10/2017 | Koizumi et al. |
| 9,868,691 B2 | 1/2018 | Benenato et al. |
| 9,872,900 B2 | 1/2018 | Ciaramella et al. |
| 10,023,626 B2 | 7/2018 | Bolen et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,266,735 B2 | 3/2022 | Kallen et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,564,893 B2 | 1/2023 | Smith |
| 2001/0001066 A1 | 5/2001 | Cezayirli et al. |
| 2003/0032615 A1 | 2/2003 | Felgner et al. |
| 2005/0032730 A1 | 2/2005 | Von Der Mulbe et al. |
| 2005/0059624 A1 | 3/2005 | Hoerr et al. |
| 2005/0250723 A1 | 11/2005 | Hoerr et al. |
| 2005/0287540 A1 | 12/2005 | Murphy et al. |
| 2006/0172003 A1 | 8/2006 | Meers et al. |
| 2006/0172966 A1 | 8/2006 | Lipford et al. |
| 2007/0280929 A1 | 12/2007 | Hoerr et al. |
| 2010/0068226 A1 | 3/2010 | Taylor et al. |
| 2010/0130588 A1 | 5/2010 | Yaworski et al. |
| 2010/0189729 A1 | 7/2010 | Hoerr et al. |
| 2010/0203076 A1 | 8/2010 | Fotin-Mleczek et al. |
| 2010/0239608 A1 | 9/2010 | Von Der Mulbe et al. |
| 2010/0303851 A1 | 12/2010 | Hoerr et al. |
| 2011/0250225 A1 | 10/2011 | Fotin-Mleczek et al. |
| 2011/0269950 A1 | 11/2011 | Von Der Mulbe et al. |
| 2011/0311472 A1 | 12/2011 | Hoerr et al. |
| 2012/0101148 A1 | 4/2012 | Aking et al. |
| 2012/0189700 A1 | 7/2012 | Aguilar et al. |
| 2012/0258046 A1 | 10/2012 | Mutske |
| 2012/0263648 A1 | 10/2012 | Shapiro et al. |
| 2013/0102034 A1 | 4/2013 | Schrum et al. |
| 2013/0121988 A1 | 5/2013 | Hoerr et al. |
| 2013/0142818 A1 | 6/2013 | Baumhof et al. |
| 2013/0171241 A1 | 7/2013 | Geall |
| 2013/0183355 A1 | 7/2013 | Jain et al. |
| 2013/0189351 A1 | 7/2013 | Geall |
| 2013/0195867 A1 | 8/2013 | Hoerr et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236533 A1 | 9/2013 | Von Andrian et al. |
| 2013/0236974 A1 | 9/2013 | De Fougerolles |
| 2013/0245103 A1 | 9/2013 | de Fougerolles et al. |
| 2013/0245107 A1 | 9/2013 | De Fougerolles et al. |
| 2013/0259923 A1 | 10/2013 | Bancel et al. |
| 2013/0266640 A1 | 10/2013 | De Fougerolles et al. |
| 2013/0295043 A1 | 11/2013 | Kallen et al. |
| 2013/0336998 A1 | 12/2013 | Kallen et al. |
| 2014/0065228 A1 | 3/2014 | Yarowoski et al. |
| 2014/0134201 A1 | 5/2014 | Tureci et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0248314 A1 | 9/2014 | Swanson et al. |
| 2014/0271699 A1 | 9/2014 | Kwong et al. |
| 2014/0271829 A1 | 9/2014 | Lilja et al. |
| 2014/0308304 A1 | 10/2014 | Manoharan et al. |
| 2014/0378538 A1 | 12/2014 | Bancel |
| 2015/0030622 A1 | 1/2015 | Marshall et al. |
| 2015/0051268 A1 | 2/2015 | Bancel et al. |
| 2015/0056253 A1 | 2/2015 | Bancel et al. |
| 2015/0079121 A1 | 3/2015 | Weiner et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0376115 A1 | 12/2015 | Ansell et al. |
| 2016/0022580 A1 | 1/2016 | Ramsay et al. |
| 2016/0024140 A1 | 1/2016 | Issa et al. |
| 2016/0024141 A1 | 1/2016 | Issa et al. |
| 2016/0151284 A1 | 1/2016 | Heyes et al. |
| 2016/0032273 A1 | 2/2016 | Shahrokh et al. |
| 2016/0038612 A1 | 2/2016 | Hoge et al. |
| 2016/0046675 A1* | 2/2016 | Kwong ............... A61P 31/14 530/400 |
| 2016/0243221 A1 | 8/2016 | Hoge et al. |
| 2016/0317647 A1* | 11/2016 | Ciaramella ............... C12N 7/00 |
| 2016/0376224 A1 | 12/2016 | Du et al. |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0239371 A1 | 8/2017 | Guild et al. |
| 2017/0130255 A1 | 10/2017 | Wang et al. |
| 2017/0340724 A1 | 11/2017 | Ciaramella et al. |
| 2018/0000953 A1 | 1/2018 | Almarsson et al. |
| 2018/0002393 A1 | 1/2018 | Bancel et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0296663 A1 | 10/2018 | Hipp et al. |
| 2018/0303925 A1 | 10/2018 | Weissman et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0326039 A1 | 11/2018 | Haruta |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |

(56) References Cited

U.S. PATENT DOCUMENTS

| | | |
|---|---|---|
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0297634 A1 | 9/2020 | Karmali et al. |
| 2020/0306191 A1 | 10/2020 | Schariter et al. |
| 2020/0368162 A1 | 11/2020 | Martini |
| 2021/0046173 A1* | 2/2021 | Ciaramella ........ A61K 31/7115 |
| 2021/0060175 A1 | 3/2021 | Baumhof et al. |
| 2021/0087135 A1 | 3/2021 | Benenato et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |

FOREIGN PATENT DOCUMENTS

| | | |
|---|---|---|
| CA | 2473135 A1 | 6/2003 |
| CN | 110974954 A | 4/2020 |
| EP | 1083232 B1 | 2/2005 |
| EP | 1301614 B1 | 11/2006 |
| EP | 1383556 B1 | 10/2007 |
| EP | 1905844 A2 | 2/2008 |
| EP | 1026253 B2 | 12/2012 |
| EP | 2188379 B1 | 1/2013 |
| WO | WO 1990/011092 A1 | 10/1990 |
| WO | WO 1996/040945 A2 | 12/1996 |
| WO | WO 1999/052503 A2 | 10/1999 |
| WO | WO 2001/021810 A1 | 3/2001 |
| WO | WO 2004/058166 A2 | 7/2004 |
| WO | WO 2005/007689 A1 | 1/2005 |
| WO | WO 2005/120152 | 12/2005 |
| WO | WO 2006/050280 A2 | 5/2006 |
| WO | WO 2008/014979 A3 | 2/2008 |
| WO | WO 2008/052770 A2 | 5/2008 |
| WO | WO 2008/083949 A3 | 7/2008 |
| WO | WO 2008/103276 A2 | 8/2008 |
| WO | WO 2010/037408 A1 | 4/2010 |
| WO | WO 2010/042877 A1 | 4/2010 |
| WO | WO 2010/054401 A1 | 5/2010 |
| WO | WO 2010/054406 A1 | 5/2010 |
| WO | WO 2010/077717 A1 | 7/2010 |
| WO | WO 2010/088927 A1 | 8/2010 |
| WO | WO 2010/115046 A2 | 10/2010 |
| WO | WO 2011/005799 A2 | 1/2011 |
| WO | WO 2011/069529 A1 | 6/2011 |
| WO | WO 2011/069586 A1 | 6/2011 |
| WO | WO 2011/140627 A1 | 11/2011 |
| WO | WO 2011/144358 A1 | 11/2011 |
| WO | WO 2012/006369 A2 | 1/2012 |
| WO | WO 2012/006376 A2 | 1/2012 |
| WO | WO 2012/006378 A1 | 1/2012 |
| WO | WO 2012/006380 A2 | 1/2012 |
| WO | WO 2012/019630 A1 | 2/2012 |
| WO | WO 2012/019780 A2 | 2/2012 |
| WO | WO 2012/030901 A1 | 3/2012 |
| WO | WO 2012/075040 A2 | 6/2012 |
| WO | WO 2012/089225 A1 | 7/2012 |
| WO | WO 2012/113513 A1 | 8/2012 |
| WO | WO 2012/116714 A1 | 9/2012 |
| WO | WO 2012/116715 A1 | 9/2012 |
| WO | WO 2012/116810 A1 | 9/2012 |
| WO | WO 2012/116811 A1 | 9/2012 |
| WO | WO 2013/006825 A1 | 1/2013 |
| WO | WO 2013/006837 A1 | 1/2013 |
| WO | WO 2013/006838 A1 | 1/2013 |
| WO | WO 2013/006842 A2 | 1/2013 |
| WO | WO 2013/030778 A2 | 3/2013 |
| WO | WO 2013/052167 A2 | 4/2013 |
| WO | WO 2013/056132 A2 | 4/2013 |
| WO | WO 2013/059496 A1 | 4/2013 |
| WO | WO 2013/113502 A1 | 8/2013 |
| WO | WO 2013/174409 A1 | 11/2013 |
| WO | WO 2013/185069 A1 | 12/2013 |
| WO | WO 2014/071963 A1 | 5/2014 |
| WO | WO 2014/072061 A1 | 5/2014 |
| WO | WO 2017/075531 A1 | 5/2014 |
| WO | WO 2014/089239 A1 | 6/2014 |
| WO | WO 2014/089486 A1 | 6/2014 |
| WO | WO 2014/127917 A1 | 8/2014 |
| WO | WO 2014/136086 A1 | 9/2014 |
| WO | WO 2014/144196 A1 | 9/2014 |
| WO | WO 2014/152027 A1 | 9/2014 |
| WO | WO 2014/152774 A1 | 9/2014 |
| WO | WO 2014/159813 A1 | 10/2014 |
| WO | WO 2014/160243 A1 | 10/2014 |
| WO | WO 2014/160463 A1 | 10/2014 |
| WO | WO 2014/174018 A1 | 10/2014 |
| WO | WO 2014/202570 A1 | 12/2014 |
| WO | WO 2015/005253 A1 | 1/2015 |
| WO | WO 2015/013551 A1 | 1/2015 |
| WO | WO 2015/024667 A1 | 2/2015 |
| WO | WO 2015/024668 A2 | 2/2015 |
| WO | WO 2015/024669 A1 | 2/2015 |
| WO | WO 2015/095340 A1 | 6/2015 |
| WO | WO 2015/095346 A1 | 6/2015 |
| WO | WO 2015/130584 A2 | 9/2015 |
| WO | WO 2015/189425 A1 | 12/2015 |
| WO | WO 2015/199952 A1 | 12/2015 |
| WO | WO 2016/037053 A1 | 3/2016 |
| WO | WO 2016/164762 A1 | 10/2016 |
| WO | WO 2016/176330 A1 | 11/2016 |
| WO | WO 2016/201377 A1 | 12/2016 |
| WO | WO 2016/203025 A1 | 12/2016 |
| WO | WO 2017/011773 A2 | 1/2017 |
| WO | WO 2017/015457 A1 | 1/2017 |
| WO | WO 2017/015463 A1 | 1/2017 |
| WO | WO 2017/019935 A1 | 2/2017 |
| WO | WO 2017/020026 A1 | 2/2017 |
| WO | WO 2017/153936 A1 | 3/2017 |

(56) References Cited

FOREIGN PATENT DOCUMENTS

| | | |
|---|---|---|
| WO | WO 2017/172890 A1 | 3/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070616 A1 | 4/2017 |
| WO | WO 2017/070618 A1 | 4/2017 |
| WO | WO 2017/070620 A1 | 4/2017 |
| WO | WO 2017/070622 A1 | 4/2017 |
| WO | WO 2017/070623 A1 | 4/2017 |
| WO | WO 2017/070626 A2 | 4/2017 |
| WO | WO 2017/075038 A1 | 5/2017 |
| WO | WO 2017/081082 A1 | 5/2017 |
| WO | WO 2017/127750 A1 | 7/2017 |
| WO | WO 2017/174564 A1 | 10/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2017/201349 A1 | 11/2017 |
| WO | WO 2018/053209 A1 | 3/2018 |
| WO | WO 2018/075980 A1 | 4/2018 |
| WO | WO 2018/078053 A1 | 5/2018 |
| WO | WO 2018/081459 A1 | 5/2018 |
| WO | WO 2018/081462 A1 | 5/2018 |
| WO | WO 2018/081638 A1 | 5/2018 |
| WO | WO 2018/089801 A1 | 5/2018 |
| WO | WO 2018/089851 * | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/151816 A1 | 8/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2019/202035 A1 | 10/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/163719 A2 | 8/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/016430 A1 | 1/2021 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/155274 A1 | 8/2021 |
| WO | WO 2021/159040 A2 | 8/2021 |
| WO | WO 2021/159130 A2 | 8/2021 |
| WO | WO 2021/204175 A1 | 10/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |
| WO | WO 2021/237084 A1 | 11/2021 |
| WO | WO 2021/239880 A1 | 12/2021 |
| WO | WO 2021/247817 A1 | 12/2021 |
| WO | WO 2022/067010 A1 | 3/2022 |
| WO | WO 2022/076562 A1 | 4/2022 |
| WO | WO 2022/099003 A1 | 5/2022 |
| WO | WO 2022/101469 A1 | 5/2022 |
| WO | WO 2022/155524 A1 | 7/2022 |
| WO | WO 2022/155530 A1 | 7/2022 |
| WO | WO 2022/187698 A1 | 9/2022 |
| WO | WO 2022/204491 A1 | 9/2022 |
| WO | WO 2022/212191 A1 | 10/2022 |
| WO | WO 2022/212442 A1 | 10/2022 |
| WO | WO 2022/212711 A2 | 10/2022 |
| WO | WO 2022/221335 A1 | 10/2022 |
| WO | WO 2022/221336 A1 | 10/2022 |
| WO | WO 2022/221359 A1 | 10/2022 |
| WO | WO 2022/221440 A1 | 10/2022 |
| WO | WO 2022/232585 A1 | 11/2022 |
| WO | WO 2022/241103 A1 | 11/2022 |
| WO | WO 2022/266010 A1 | 12/2022 |
| WO | WO 2022/266012 A1 | 12/2022 |
| WO | WO 2022/266389 A1 | 12/2022 |
| WO | WO 2023/283642 A2 | 1/2023 |
| WO | WO 2023/283645 A1 | 1/2023 |
| WO | WO 2023/283651 A1 | 1/2023 |

OTHER PUBLICATIONS

Geneseq database accession No. BCI53556 Jan. 2016 sequence alignment with Seq Id No. 5.*
McLellan et al. (Science. 2013; 342: 592-598).*
Aliprantis et al. (Human Vaccines and Immunotherapeutics; 2021; 17 (5): 1248-1261).*
Austin et al. (Molecular Pharmaceutics. 2023; 20: 279-289).*
[No Author Listed], Clinical trial NCT04528719: A Dose Escalation Study to Evaluate Safety, Reactogenicity, and Immunogenicity of mRNA-1345 in Healthy Adults and in Children Who are Respiratory Syncytial Virus Seropositive (ModernaTX, Inc.) First Posted Aug. 27, 2020. Retrieved online on Mar. 15, 2021 at https://www.clinicaltrials.gov/ct2/show/NCT04528719?term=NCT04528719&draw=2&rank=1. 9 pages.
Buschmann et al., Nanomaterial Delivery Systems for mRNA Vaccines. Vaccines (Basel). Jan. 19, 2021;9(1):65. doi: 10.3390/vaccines9010065.
Chaudhary et al., mRNA vaccines for infectious diseases: principles, delivery and clinical translation. Nature Reviews Drug Discovery vol. 20, pp. 817-838 (2021).
Cross, Without these lipid shells, there would be no mRNA vaccines for COVID-19. C&EN. Mar. 6, 2021;99(8):1-8.
Geall et al., RNA: the new revolution in nucleic acid vaccines. Semin Immunol. Apr. 2013;25(2):152-9. doi: 10.1016/j.smim.2013.05.001. Epub Jun. 2, 2013.
Hou et al., Lipid nanoparticles for mRNA delivery. Nature Reviews Materials vol. 6, pp. 1078-1094 (2021).
Kramps et al., Messenger RNA-based vaccines: progress, challenges, applications. Wiley Interdiscip Rev RNA. Nov.-Dec. 2013;4(6):737-49. doi: 10.1002/wrna.1189. Epub Jul. 25, 2013.
Li et al., Lipid-based nanoparticles for nucleic acid delivery. Pharm Res. Mar. 2007;24(3):Li438-49. doi: 10.1007/s11095-006-9180-5.
Liang et al., Enhanced Neutralizing Antibody Response Induced by Respiratory Syncytial Virus Prefusion F Protein Expressed by a Vaccine Candidate. J Virol. Sep. 2015;89(18):9499-510. doi: 10.1128/JVI.01373-15. Epub Jul. 8, 2015.
Maruggi et al., mRNA as a Transformative Technology for Vaccine Development to Control Infectious Diseases. Mol Ther. Apr. 10, 2019;27(4):757-772. doi: 10.1016/j.ymthe.2019.01.020. Epub Feb. 7, 2019.
McLellan et al., Structure of respiratory syncytial virus fusion glycoprotein in the postfusion conformation reveals preservation of neutralizing epitopes. J Virol. Aug. 2011;85(15):7788-96. doi: 10.1128/JVI.00555-11. Epub May 25, 2011.
Patel et al., Naturally-occurring cholesterol analogues in lipid nanoparticles induce polymorphic shape and enhance intracellular delivery of mRNA. Nat Commun. Feb. 20, 2020;11(1):983. doi: 10.1038/s41467-020-14527-2.

(56) References Cited

OTHER PUBLICATIONS

Rosa et al., mRNA vaccines manufacturing: Challenges and bottlenecks. Vaccine. Apr. 15, 2021;39(16):2190-2200.
Shin et al., Recent Advances in RNA Therapeutics and RNA Delivery Systems Based on Nanoparticles. Adv. Therap., Nov. 2018;1(7):1800065. Review.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
To et al., An overview of rational design of mRNA-based therapeutics and vaccines. Expert Opin Drug Discov. Nov. 2021;16(11):1307-1317. doi: 10.1080/17460441.2021.1935859. Epub Jul. 19, 2021.
Youn et al., Modified mRNA as an alternative to plasmid DNA (pDNA) for transcript replacement and vaccination therapy. Expert Opin Biol Ther. 2015;15(9):1337-48. doi: 10.1517/14712598.2015.1057563. Epub Jun. 30, 2015.
Zeng et al., Formulation and Delivery Technologies for mRNA Vaccines. Curr Top Microbiol Immunol. Jun. 2, 2020;10.1007/82_2020_217. doi: 10.1007/82_2020_217.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 15/748,773, filed Jan. 30, 2018, Ciaramella et al.
U.S. Appl. No. 17/554,182, filed Dec. 17, 2021, Ciaramella et al.
U.S. Appl. No. 18/161,857, filed Jan. 30, 2023, Smith.
U.S. Appl. No. 15/767,587, filed Apr. 11, 2018, Ciaramella.
U.S. Appl. No. 17/819,414, filed Aug. 12, 2022, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 15/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 17/830,742, filed Jun. 2, 2022, Miracco.
U.S. Appl. No. 16/001,765, filed Jun. 6, 2018, Marquardt et al.
U.S. Appl. No. 17/852,974, filed Jun. 29, 2022, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/483,012, filed Aug. 1, 2019, Mauger et al.
U.S. Appl. No. 18/093,119, filed Jan. 4, 2023, Mauger et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 18/055,193, filed Nov. 14, 2022, Ciaramella et al.
U.S. Appl. No. 16/494,130, filed Sep. 13, 2019, Ciaramella et al.
U.S. Appl. No. 17/823,255, filed Aug. 30, 2022, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/938,823, filed Oct. 7, 2022, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/816,696, filed Aug. 1, 2022, Dousis et al.
U.S. Appl. No. 17/737,581, filed May 5, 2022, Panther et al.
U.S. Appl. No. 16/794,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 17/615,202, filed Nov. 30, 2021, Hopson.
U.S. Appl. No. 17/641,967, filed Mar. 10, 2022, John et al.
U.S. Appl. No. 17/840,478, filed Jun. 14, 2022, Kramarczyk et al.
U.S. Appl. No. 18/008,139, filed Dec. 2, 2022, Smith et al.
U.S. Appl. No. 17/796,4001, filed Jul. 29, 2022, Shaw et al.
U.S. Appl. No. 17/926,353, filed Nov. 18, 2022, Brader et al.
U.S. Appl. No. 17/925,114, filed Nov. 14, 2022, White et al.
U.S. Appl. No. 17/797,784, filed Aug. 5, 2022, Stewart-Jones et al.
U.S. Appl. No. 17/572,465, filed Jan. 10, 2022, Nachbagauer et al.
U.S. Appl. No. 17/726,971, filed Apr. 22, 2022, Hennessy.
U.S. Appl. No. 17/925,125, filed Nov. 14, 2022, White et al.
U.S. Appl. No. 18/085,457, filed Dec. 20, 2022, Joyal et al.
Furuichi et al., Viral and cellular mRNA capping: past and prospects. Adv Virus Res. 2000;55:135-84. doi: 10.1016/s0065-3527(00)55003-9.
Graham et al., Novel antigens for RSV vaccines. Curr Opin Immunol. Aug. 2015;35:30-8. doi: 10.1016/j.coi.2015.04.005. Epub Jun. 10, 2015.
Jorquera et al., Nanoparticle vaccines encompassing the respiratory syncytial virus (RSV) G protein CX3C chemokine motif induce robust immunity protecting from challenge and disease. PLoS One. Sep. 10, 2013;8(9):e74905. doi: 10.1371/journal.pone.0074905. eCollection 2013.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Schlake et al., Developing mRNA-vaccine technologies. RNA Biol. Nov. 2012;9(11):1319-30. doi: 10.4161/rna.22269. Epub Oct. 12, 2012.
Zhao et al., Nanoparticle vaccines. Vaccine. Jan. 9, 2014;32(3):327-37. doi: 10.1016/j.vaccine.2013.11.069. Epub Dec. 2, 2013.
International Search Report and Written Opinion for Application No. PCT/US2019/015412, dated Apr. 16, 2019.
Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.
Ausar et al., High-throughput screening of stabilizers for respiratory syncytial virus: identification of stabilizers and their effects on the conformational thermostability of viral particles. Hum Vaccin. May-Jun. 2007;3(3):94-103. Epub May 15, 2007.
Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Cheng et al., Multifunctional triblock copolymers for intracellular messenger RNA delivery. Biomaterials. Oct. 2012; 33(28): 6868-6876.
Cross et al., Can mRNA disrupt the drug industry? C&EN, 2018: 96(35);35-40.
Cu et al., Enhanced Delivery and Potency of Self-Amplifying mRNA Vaccines by Electroporation in Situ, Vaccines, 2013, 1, 367-383. Abstract Only.
Deering et al., Nucleic acid vaccines: prospects for non-viral delivery of mRNA vaccines. Expert Opin Drug Deliv. Jun. 2014;11(6):885-99. doi: 10.1517/17425247.2014.901308. Epub Mar. 26, 2014.

(56) References Cited

OTHER PUBLICATIONS

Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Espeseth et al., Modified mRNA/lipid nanoparticle-based vaccines expressing respiratory syncytial virus F protein variants are immunogenic and protective in rodent models of RSV infection. NPJ Vaccines. Feb. 14, 2020;5:16. doi: 10.1038/s41541-020-0163-z. eCollection 2020.
Ewert et al., Cationic liposome-nucleic acid complexes for gene delivery and silencing: pathways and mechanisms for plasmid DNA and siRNA. Top Curr Chem. 2010;296:191-226.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.
Holtkamp et al., Modification of antigen-encoding RNA increases stability, translational efficacy, and T-cell stimulatory capacity of dendritic cells. Blood. Dec. 15, 2006;108(13):4009-17.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kowalski et al., Delivering the Messenger: Advances in Technologies for Therapeutic mRNA Delivery. Molecular Therapy vol. 27 No. 4 Apr. 2019.
Kuhn et al., mRNA as a versatile tool for exogenous protein expression. Current Gene Therapy. Oct. 2012; 12 (5): 347-361.
Kulkarni et al., Lipid Nanoparticles Enabling Gene Therapies: From Concepts to Clinical Utility. Nucleic Acid Ther. Jun. 2018;28(3):146-157. doi: 10.1089/nat.2018.0721. Epub Apr. 23, 2018.
Leitner et al., DNA and RNA-based vaccines: principles, progress and prospects. Vaccine. Dec. 10, 1999;18 (9-10):765-77.
Lian et al., Trends and developments in liposome drug delivery systems. J Pharm Sci. Jun. 2001;90(6):667-80.
Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.
Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection.
Lorenzi et al., Intranasal vaccination with messenger RNA as a new approach in gene therapy: Use against tuberculosis. BMC Biotechnol. Oct. 2010; 10(77): 1-11.
MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Martinon et al., Induction of virus-specific cytotoxic T lymphocytes in vivo by liposome-entrapped mRNA. EurJ lmmunol. Jul. 1993;23(7):1719-22.
McKenzie et al., Nucleic acid vaccines: tasks and tactics. lmmunol Res. 2001 ;24(3):225-44.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell et al., RNA transfected dendritic cells as cancer vaccines. Curr Opin Mol Ther. Apr. 2000;2(2):176-81.
Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Petsch et al., Protective efficacy of in vitro synthesized, specific mRNA vaccines against influenza a virus infection. Nat Biotechnol. Dec. 2012;30(12):1210-6. doi: 10.1038/nbt.2436. Epub Nov. 25, 2012.
Pollard et al., Type I IFN counteracts the induction of antigen-specific immune responses by lipid-based delivery of mRNA vaccines. Mol Ther. Jan. 2013; 21 (1): 251-259.
Reichmuth et al., mRNA Vaccine Delivery Using Lipid Nanoparticles. Ther Deliv. 2016;7(5):319-34. doi: 10.4155/tde-2016-0006.
Schirrmacher et al., Intra-pinna anti-tumor vaccination with self-replicating infectious RNA or with DNA encoding a model tumor antigen and a cytokine. Gene Ther. Jul. 2000;7(13):1137-47.
Schott et al., Viral and non-viral approaches for transient delivery of mRNA and proteins. Current Gene Ther. 2011; 11 (5): 382-398.
Schwendener, Liposomes as vaccine delivery systems: a review of the recent advances. Ther Adv Vaccines. Nov. 2014;2(6):159-82. doi: 10.1177/2051013614541440.
Stab et al., Protective efficacy and immunogenicity of a combinatory DNA vaccine against Influenza A Virus and the Respiratory Syncytial Virus. PLoS One. Aug. 14, 2013;8(8):e72217. doi: 10.1371/journal.pone.0072217. eCollection 2013.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Vassilev et al., Microparticle-mediated RNA immunization against bovine viral diarrhea virus. Vaccine. Feb. 28, 2001;19(15-16):2012-9.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Wong et al., An mRNA vaccine for influenza. Nat Biotechnol. Dec. 2012;30(12):1202-4. doi: 10.1038/nbt.2439.
Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Ying et al., Cancer therapy using a self-replicating RNA vaccine. Nat Med. Jul. 1999;5(7):823-7.
U.S. Appl. No. 90/014,395, filed Oct. 24, 2019, Ciaramella et al.
U.S. Appl. No. 15/753,293, filed Feb. 17, 2018, Smith.

(56) References Cited

OTHER PUBLICATIONS

U.S. Appl. No. 15/748,782, filed Jan. 30, 2018, Mousavi et al.
U.S. Appl. No. 16/833,409, filed Mar. 27, 2020, Ciaramella.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/898,268, filed Jun. 10, 2020, Ciaramella et al.
U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/880,829, filed May 21, 2020, Ciaramella et al.
U.S. Appl. No. 16/468,838, filed Jun. 12, 2019, Miracco.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/496,135, filed Sep. 20, 2019, Narayanan et al.
U.S. Appl. No. 16/657,122, filed Oct. 18, 2019, Rabideau et al.
U.S. Appl. No. 16/494,103, filed Sep. 13, 2019, Ciaramella et al.
U.S. Appl. No. 16/494,162, filed Sep. 13, 2019, Ciaramella.
U.S. Appl. No. 16/848,318, filed Apr. 14, 2020, Ciaramella et al.
U.S. Appl. No. 16/608,451, filed Oct. 25, 2019, Ciaramella et al.
U.S. Appl. No. 16/788,182, filed Feb. 11, 2020, Panther et al.
U.S. Appl. No. 17/000,201, filed Aug. 21, 2020, Stewart-Jones et al.
U.S. Appl. No. 17/000,215, filed Aug. 21, 2020, Stewart-Jones et al.
PCT/US2019/015412, Apr. 16, 2019, International Search Report and Written Opinion.

\* cited by examiner

RSV RNA VACCINES

RELATED APPLICATIONS

This application is a national stage filing under 35 U.S.C. § 371 of international application number PCT/US2019/015412, filed Jan. 28, 2019, which was published under PCT Article 21(2) in English and claims the benefit under 35 U.S.C. § 119(e) of U.S. provisional application No. 62/623,240, filed Jan. 29, 2018, each of which is incorporated by reference herein in its entirety.

BACKGROUND

The human respiratory syncytial virus (RSV) is a negative-sense, single-stranded RNA virus of the genus Pneumovirinae and of the family Paramyxoviridae. Symptoms in adults typically resemble a sinus infection or the common cold, although the infection may be asymptomatic. In older adults (e.g., >60 years), RSV infection may progress to bronchiolitis or pneumonia. Symptoms in children are often more severe. It is estimated that in the United States, most children are infected with RSV by the age of three. The RSV virion includes of an internal nucleocapsid comprised of the viral RNA bound to nucleoprotein (N), phosphoprotein (P), and large polymerase protein (L). The nucleocapsid is surrounded by matrix protein (M) and is encapsulated by a lipid bilayer into which the viral fusion (F) and attachment (G) proteins as well as the small hydrophobic protein (SH) are incorporated. The viral genome also encodes two non-structural proteins (NS1 and NS2), which inhibit type I interferon activity as well as the M-2 protein. Currently, there is no vaccine to prevent primary infection or disease.

SUMMARY

Provided herein, in some embodiments, are highly immunogenic respiratory syncytial virus (RSV) ribonucleic acid (RNA) (e.g., mRNA) compositions (e.g, vaccines) that elicit potent neutralizing antibodies responses at a dose that is at least 5-fold lower than a control, wherein the control is, for example, a RNA vaccine encoding a membrane-bound DS-CAV1-stabilized prefusion F protein of RSV (e.g., SEQ ID NO: 90 or SEQ ID NO: 92). The envelope of RSV contains three surface glycoproteins: F, G, and SH. The G and F proteins are protective antigens and targets of neutralizing antibodies. The F protein, however, is more conserved across RSV strains and types (A and B). RSV F is a type I viral fusion protein that structurally rearranges from a metastable prefusion form to a highly stable postfusion form. Although targets for neutralizing monoclonal antibodies exist on the postfusion conformation of F protein, the neutralizing Ab response primarily targets the F protein prefusion conformation in people naturally infected with RSV (Magro M et al., Proc Natl Acad Sci USA; 109(8): 3089-94, 2012; Ngwuta J O et al., Sci Transl Med 2015; 7(309):309ra162). Thus, the present disclosure focuses, in some aspects, on RNA vaccines encoding RSV F protein (e.g., F protein trimer) stabilized in its prefusion conformation. These RNA vaccines encode antigens that elicit an even greater immune response and that are even more stable in the prefusion form, relative to previously described recombinant RSV F trimers, which includes RSV F trimers containing the "DS-CAV1" substitutions (155C, 290C, 190F, and 207L).

In some aspects, the RSV vaccines of the present disclosure include a RNA comprising an open reading frame (ORF) encoding a RSV antigen, wherein intramuscular (IM) administration of a therapeutically effective amount of the vaccine to a subject induces in the subject a neutralizing antibody titer.

Some aspects of the present disclosure provide respiratory syncytial virus (RSV) vaccines comprising a ribonucleic acid (RNA) that comprises an open reading frame (ORF) encoding an RSV antigen, wherein the ORF comprises (or consists of, or consists essentially of) a sequence that is at least 95% (e.g., at least 96%, at least 97%, at least 98%, at least 99%) or 95%-99% identical to a sequence identified by any one of SEQ ID NOS: 3, 7, 10, 13, 16, 19, 22, 24, 26, 28, 30, 32, 34, 37, 40, 43, 46, 49, 52, 54, 56, 58, 60, 63, 66, 69, 75, 96, or 97.

In some aspects, the vaccine is formulated in a lipid nanoparticle. In some embodiments, the ORF comprises a sequence that is at least 98% identical to a sequence identified by any one of SEQ ID NOS: 3, 7, 10, 13, 16, 19, 22, 24, 26, 28, 30, 32, 34, 37, 40, 43, 46, 49, 52, 54, 56, 58, 60, 63, 66, 69, 75, 96, or 97. In some embodiments, the RNA comprises an ORF encoding an RSV antigen, wherein the ORF comprises a sequence identified by (is 100% identical to) any one of SEQ ID NOS: 3, 7, 10, 13, 16, 19, 22, 24, 26, 28, 30, 32, 34, 37, 40, 43, 46, 49, 52, 54, 56, 58, 60, 63, 66, 69, 72, 75, 96 or 97.

In some embodiments, the ORF comprises (or consists of, or consists essentially of) a sequence that is identified by (is 100% identical to) SEQ ID NO: 22. In some embodiments, the ORF comprises a sequence that is identified by (is 100% identical to) SEQ ID NO: 75. In some embodiments, the ORF comprises (or consists of, or consists essentially of) a sequence that is identified by (is 100% identical to) SEQ ID NO: 3. In some embodiments, the ORF comprises (or consists of, or consists essentially of) a sequence that is identified by (is 100% identical to) SEQ ID NO: 52. In some embodiments, the ORF comprises a sequence that is identified by (is 100% identical to) SEQ ID NO: 54. In some embodiments, the ORF comprises a sequence that is identified by (is 100% identical to) SEQ ID NO: 56. In some embodiments, the ORF comprises a sequence that is identified by (is 100% identical to) SEQ ID NO: 58.

Other aspects of the present disclosure provide a RSV vaccine comprising (or consisting of, or consisting essentially of) a RNA that comprises an ORF encoding an RSV antigen, wherein the ORF encodes a sequence identified by any one of SEQ ID NOS: 5, 8, 11, 14, 17, 20, 22, 35, 38, 41, 44, 47, 50, 61, 65, 67, 70, 73, 76. In some aspects, said RSV vaccine is formulated in a lipid nanoparticle.

In some embodiments, the RNA comprises (or consists of, or consists essentially of) an ORF encoding a single chain recombinant RSV F peptide comprising a deletion of wild type RSV F amino acid positions 98-146 and a linker of eight to fourteen amino acids between wildtype RSV F amino acid positions 97 and 147, wherein the recombinant F peptide comprises the following amino acid modifications to stabilize the recombinant RSV F peptide when oligermized to form a trimer in a perfusion conformations: (i) 190F and 207L amino acid substitutions, (ii) 155C and 290C amino acid substitutions, and (iii) one (or more) of (a) 486C and 490C amino acid substitutions; (b) 180C and 186C amino acid substitutions; (c) 486C and 489C amino acid substitutions; (d) 512C and 513C amino acid substitutions; and (e) an 505C amino acid substitution. The amino acid substitutions that introduce additional cysteine amino acid residues may result in either intra-peptide or inter-peptide disulfide bonds, specifically between the recited substitution pairs (e.g., a non-native intra peptide disulfide bond between 155C and 290C or between 180C and 186C; a non-native inter-peptide disulfide bond between 486C and 490C, between 486C and 489C or between 512C and 513C).

In some embodiments, intramuscular (IM) administration of a therapeutically effective amount of the vaccine to a subject induces in the subject a neutralizing antibody titer to (or against) the RSV F.

In some embodiments, the neutralizing antibody titer is at least 5-fold to at least 100-fold (e.g., at least 5-fold, at least 10-fold, at least 15-fold, at least 20-fold, at least 25-fold, or at least 50-fold) higher relative to control. In some embodiments the control is a RNA vaccine encoding a membrane-bound DS-CAV1-stabilized prefusion F protein of RSV. In some embodiments, the control RNA vaccine encoding a membrane-bound DS-CAV1-stabilized prefusion F protein of RSV comprises (or consists of, or consists essentially of) a sequence identified by SEQ ID NO: 90 or SEQ ID NO: 92. In some embodiments, the control is a live attenuated RSV vaccine, an inactivated RSV vaccine, or a protein subunit RSV vaccine.

In some embodiments, the at least 5-fold to at least 100-fold (e.g., at least 5-fold, at least 10-fold, at least 15-fold, at least 20-fold, at least 25-fold, or at least 50-fold) higher neutralizing antibody titer is induced in the subject following administration of a dose of the vaccine that is at least 5-fold (e.g., at least 6-fold, at least 7-fold, at least 8-fold, at least 9-fold, at least 10-fold) lower relative to the control.

In some embodiments, IM administration of a therapeutically effective amount of the vaccine to a subject induces in the subject at least 10-fold, at least 15-fold, at least 20-fold, or at least 25-fold higher prefusion RSV F-specific neutralizing antibody titers relative to the control.

In some embodiments, IM administration of a therapeutically effective amount of the vaccine to a subject confers prophylactic protection at a 5-fold (e.g., at least 6-fold, at least 7-fold, at least 8-fold, at least 9-fold, at least 10-fold) lower dose relative to the control.

In some embodiments, the RSV F neutralizing antibody titer is induced in the subject following fewer than three (e.g., one or two) doses of the vaccine.

In some embodiments, a single dose is of 5 µg-25 µg (e.g., 5 µg, 10 µg, 15 µg, 20 µg, or 25 µg).

In some embodiments, a 5 µg booster dose of the vaccine induces in African green monkeys a $NT_{50}$ neutralizing antibody titer of about $10^3$. In some embodiments, a 5 g booster dose of the vaccine induces in African green monkeys a $NT_{50}$ neutralizing antibody titer of at least $10^3$. In some embodiments, a 5 g booster dose of the vaccine induces in African green monkeys a $NT_{50}$ neutralizing antibody titer of about $10^4$. In some embodiments, a 5 g booster dose of the vaccine induces in African green monkeys a $NT_{50}$ neutralizing antibody titer of at least $10^4$. In some embodiments, the $NT_{50}$ neutralizing antibody titer (e.g., of about $10^3$ or about 104) is induced 2 weeks post vaccine administration. Methods of assessing neutralizing antibody titers are known and described, for example, by Zhang L, et al. Design and characterization of a fusion glycoprotein vaccine for Respiratory Syncytial Virus with improved stability. Vaccine 2018; 36: 8119-8130; and Shambaugh C, et al. Development of a high-throughput respiratory syncytial virus fluorescent focus-based microneutralization assay. Clin Vaccine Immunol 2017; 24: e00225-17, each of which is incorporated by reference herein in its entirety.

In some embodiments, the RSV vaccine comprises (a) a ribonucleic acid (RNA) comprising an open reading frame (ORF) encoding two RSV antigens, or (b) two RNAs, each comprising an ORF encoding an RSV antigen.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, the RSV antigen is fused to a scaffold moiety. In some embodiments, the scaffold moiety is selected from the group consisting of: ferritin, encapsulin, lumazine synthase, hepatitis B surface antigen, and hepatitis B core antigen.

In some embodiments, the RNA comprises messenger RNA (mRNA).

In some embodiments, the RNA further comprises a 5'UTR. In some embodiments, the 5'UTR comprises a sequence identified by SEQ ID NO: 2 or SEQ ID NO: 77. In some embodiments, the RNA further comprises a 3' UTR. In some embodiments, the 3'UTR comprises a sequence identified by SEQ ID NO: 4 or SEQ ID NO: 78.

In some embodiments, the RNA is unmodified. In some embodiments, the RNA comprise at least one modified nucleotide. In some embodiments, at least 80% of the uracil in the ORF comprise a 1-methyl-pseudouridine modification.

Some aspects of the present disclosure provide methods comprising administering to a subject the RSV RNA vaccine as provided herein in a therapeutically effective amount to induce in the subject a neutralizing antibody titer against the RSV antigen delivered to the subject. In some embodiments, provided are methods comprising administering to a subject the RSV RNA vaccine as provided herein in a therapeutically effective amount to induct in the subject a RSV F neutralizing antibody titer.

In some embodiments, the vaccine is administered intramuscularly.

Also provided herein, in some aspects, are methods comprising intramuscularly administering to a subject a respiratory syncytial virus (RSV) vaccine, comprising a ribonucleic acid (RNA) that comprises a sequence that is at least 95% identical to a sequence identified by SEQ ID NO: 21 formulated in a lipid nanoparticle, wherein an at least 5-fold neutralizing antibody titer is induced in the subject following administration of a dose of the vaccine that is at least 5-fold lower relative to a control, wherein the control is a RNA vaccine encoding a membrane-bound DS-CAV1-stabilized prefusion F protein of RSV, optionally wherein the control comprises a sequence identified by SEQ ID NO: 90 or SEQ ID NO: 92. In some embodiments, the RNA of the RSV vaccine comprise a sequence identified by SEQ ID NO: 22.

Provided herein in other aspects are methods comprising intramuscularly administering to a subject a respiratory syncytial virus (RSV) vaccine, comprising a ribonucleic acid (RNA) that comprises a sequence that is at least 95% identical to a sequence identified by SEQ ID NO: 75 formulated in a lipid nanoparticle, wherein an at least 5-fold neutralizing antibody titer is induced in the subject following administration of a dose of the vaccine that is at least 5-fold lower relative to a control, wherein the control is a RNA vaccine encoding a membrane-bound DS-CAV1-stabilized prefusion F protein of RSV. In some embodiments, the RNA of the RSV vaccine comprises a sequence identified by SEQ ID NO: 75. In some embodiments, the control RNA RSV vaccine encodes a membrane-bound DS-CAV1-stabilized prefusion F protein of RSV and the sequence of the control comprises a sequence identified by SEQ ID NO: 90 or SEQ ID NO: 92.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 22. In some embodiments, the ORF shares at least 96% identity with SEQ ID NO: 22. In other embodiments, the ORF shares at least 97% identity with SEQ ID NO: 22. In some embodiments, the ORF shares at least 98% identity with SEQ ID NO: 22. In some embodiments, the ORF shares at least 99% identity SEQ ID NO: 22. In some embodiments, the ORF comprises the sequence of SEQ ID NO: 22.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 3. In some embodiments, the ORF shares at least 96% identity with SEQ ID NO: 3. In other embodiments, the ORF shares at least 97% identity with SEQ ID NO: 3. In some embodiments, the ORF shares at least 98% identity with SEQ ID NO: 3. In some embodiments, the ORF shares at least 99% identity SEQ ID NO: 22. In some embodiments, the ORF comprises the sequence of SEQ ID NO: 3.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 52. In some embodiments, the ORF shares at least 96% identity with SEQ ID NO: 52. In other embodiments, the ORF shares at least 97% identity with SEQ ID NO: 52. In some embodiments, the ORF shares at least 98% identity with SEQ ID NO: 52. In some embodiments, the ORF shares at least 99% identity SEQ ID NO: 52. In some embodiments, the ORF comprises the sequence of SEQ ID NO: 52.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 54. In some embodiments, the ORF shares at least 96% identity with SEQ ID NO: 54. In other embodiments, the ORF shares at least 97% identity with SEQ ID NO: 54. In some embodiments, the ORF shares at least 98% identity with SEQ ID NO: 54. In some embodiments, the ORF shares at least 99% identity SEQ ID NO: 54. In some embodiments, the ORF comprises the sequence of SEQ ID NO: 54.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 56. In some embodiments, the ORF shares at least 96% identity with SEQ ID NO: 56. In other embodiments, the ORF shares at least 97% identity with SEQ ID NO: 56. In some embodiments, the ORF shares at least 98% identity with SEQ ID NO: 56. In some embodiments, the ORF shares at least 99% identity SEQ ID NO: 56. In some embodiments, the ORF comprises the sequence of SEQ ID NO: 56.

In some aspects, the present disclosure provides an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 58. In some embodiments, the ORF shares at least 96% identity with SEQ ID NO: 58. In other embodiments, the ORF shares at least 97% identity with SEQ ID NO: 58. In some embodiments, the ORF shares at least 98% identity with SEQ ID NO: 58. In some embodiments, the ORF shares at least 99% identity SEQ ID NO: 58. In some embodiments, the ORF comprises the sequence of SEQ ID NO: 58.

In some aspects, the present disclosure provides an immunogenic composition (e.g., vaccine) comprising a RNA (e.g., mRNA) that comprises an ORF encoding an RSV antigen, wherein the RSV antigen comprises (or consists of, or consists essentially of) SEQ ID NO: 5 (with or without a signal sequence MELLILKANAITTILTAVTFCFASG (SEQ ID NO: 100)).

In some embodiments, the immunogenic composition is formulated in a lipid nanoparticle. In some embodiments, the lipid nanoparticle comprises a molar ratio of 20-60% ionizable cationic lipid, 5-25% non-cationic lipid, 25-55% sterol, and 0.5-15% PEG-modified lipid. In some embodiments, the lipid nanoparticle comprises (13Z,16Z)—N,N-dimethyl-2-nonylhenicosa-12,15-dien-1-amine, cholesterol, DSPC, and PEG-2000 DMG. In some embodiments, the lipid nanoparticle comprises 55-65 mole % (13Z,16Z)—N,N-dimethyl-2-nonylhenicosa-12,15-dien-1-amine, 25-35 mole % cholesterol, 5-15 mole % DSPC, and 1-5 mole % PEG-2000 DMG. In some embodiments, the lipid nanoparticle comprises 58 mole % (13Z,16Z)—N,N-dimethyl-2-nonylhenicosa-12,15-dien-1-amine, 30 mole % cholesterol, 10 mole % DSPC, and 2 mole % PEG-2000 DMG.

Thus, in some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 22, wherein the RNA is formulated in a lipid nanoparticle that comprises (13Z, 16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 3, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 52, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 54, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 56, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, immunogenic compositions of the present disclosure comprise a RNA (e.g., mRNA) that comprises an ORF that comprises (or consists of, or consists essentially of) a sequence that shares at least 95% identity with a sequence of SEQ ID NO: 58, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some embodiments of the immunogenic compositions of the present disclosure, the RNA further comprises a 5' cap. In some embodiments, the 5' cap comprises 7mG(5')ppp(5')NlmpNp.

In some embodiments of the immunogenic compositions of the present disclosure, the RNA further comprises a 5' UTR and/or 3' UTR. In some embodiments, the RNA further comprises a 5' UTR comprising a sequence of SEQ ID NO: 2. In some embodiments, the RNA further comprises a 3' UTR comprising a sequence of SEQ ID NO: 4. In some embodiments, the RNA further comprises a 5' UTR comprising a sequence of SEQ ID NO: 2 and a 3' UTR comprising a sequence of SEQ ID NO: 4.

In some embodiments, the RNA further comprises a polyA tail. In some embodiments, the polyA tail has a length of 100 nucleotides. In some embodiments, the polyA tail has at least 50 nucleotides. In some embodiments, the polyA tail has at least 60 nucleotides. In some embodiments, the polyA tail has at least 70 nucleotides. In some embodiments, the polyA tail has at least 80 nucleotides. In some embodiments, the polyA tail has at least 90 nucleotides. In some embodiments, the polyA tail has at least 100 nucleotides. In some embodiments, the polyA tail has 100 nucleotides.

In some embodiments of the immunogenic compositions of the present disclosure, the RNA is chemically modified. In some embodiments, at least 80%, at least 90%, 80%-100%, 90%-100%, or 100% of the uracil residues of the RNA comprise a chemical modification. In some embodiments, the chemical modification is 1-methylpseudouridine.

In some aspects, an immunogenic composition comprises a RNA (e.g., mRNA) that comprises an ORF that comprises (or consists of, or consists essentially of) a sequence that shares at least 95% identity with a sequence of SEQ ID NO: 22, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 22, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 3, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 3, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 52, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 52, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 54, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 54, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 56, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 56, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, an immunogenic composition comprises a RNA (e.g., mRNA) that comprises an ORF that comprises (or consists of, or consists essentially of) a sequence that shares at least 95% identity with a sequence of SEQ ID NO: 58, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

Thus, in some aspects, an immunogenic composition comprises a RNA (e.g., mRNA) that comprises an ORF that comprises (or consists of, or consists essentially of) a sequence that shares at least 95% identity with a sequence of SEQ ID NO: 58, wherein the RNA further comprise a 5' 7mG(5')ppp(5')NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 21. In some embodiments, the RNA comprises a sequence that shares at least 96% identity with SEQ ID NO: 21. In some embodiments, the RNA comprises a sequence that shares at least 97% identity with SEQ ID NO: 21. In other embodiments, the RNA comprises a sequence that shares at least 98% identity with SEQ ID NO: 21. In some embodiments, the RNA comprises a sequence that shares at least 99% identity with SEQ ID NO: 21. In some embodiments, the RNA comprises the sequence of SEQ ID NO: 21. In some embodiments, the RNA consists of the sequence of SEQ ID NO: 21. In some embodiments, the RNA consists essentially of the sequence of SEQ ID NO: 21.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 1. In some embodiments, the RNA comprises a sequence that shares at least 96% identity with SEQ ID NO: 1. In some embodiments, the RNA comprises a sequence that shares at least 97% identity with SEQ ID NO: 1. In other embodiments, the RNA comprises a sequence that shares at least 98% identity with SEQ ID NO: 1. In some embodiments, the RNA comprises a sequence that shares at least 99% identity with SEQ ID NO: 1. In some embodiments, the RNA comprises the sequence of SEQ ID NO: 1. In some embodiments, the RNA consists of the sequence of SEQ ID NO: 1. In some embodiments, the RNA consists essentially of the sequence of SEQ ID NO: 1.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 51. In some embodiments, the RNA comprises a sequence that shares at least 96% identity with SEQ ID NO: 51. In some embodiments, the RNA comprises a sequence that shares at least 97% identity with SEQ ID NO: 51. In other embodiments, the RNA comprises a sequence that shares at least 98% identity with SEQ ID NO: 51. In some embodiments, the RNA comprises a sequence that shares at least 99% identity with SEQ ID NO: 51. In some embodiments, the RNA comprises the sequence of SEQ ID NO: 51. In some embodiments, the RNA consists of the sequence of SEQ ID NO: 51. In some embodiments, the RNA consists essentially of the sequence of SEQ ID NO: 51.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 53. In some embodiments, the RNA comprises a sequence that shares at least 96% identity with SEQ ID NO: 53. In some embodiments, the RNA comprises a sequence that shares at least 97% identity with SEQ ID NO: 53. In other embodiments, the RNA comprises a sequence that shares at least 98% identity with SEQ ID NO: 53. In some embodiments, the RNA comprises a sequence that shares at least 99% identity with SEQ ID NO: 53. In some embodiments, the RNA comprises the sequence of SEQ ID NO: 53. In some embodiments, the RNA consists of the sequence of SEQ ID NO: 53. In some embodiments, the RNA consists essentially of the sequence of SEQ ID NO: 53.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 55. In some embodiments, the RNA comprises a sequence that shares at least 96% identity with SEQ ID NO: 55. In some embodiments, the RNA comprises a sequence that shares at least 97% identity with SEQ ID NO: 55. In other embodiments, the RNA comprises a sequence that shares at least 98% identity with SEQ ID NO: 55. In some embodiments, the RNA comprises a sequence that shares at least 99% identity with SEQ ID NO: 55. In some embodiments, the RNA comprises the sequence of SEQ ID NO: 55. In some embodiments, the RNA consists of the sequence of SEQ ID NO: 55. In some embodiments, the RNA consists essentially of the sequence of SEQ ID NO: 55.

In some aspects, the present disclosure provides an immunogenic composition (e.g., vaccine) comprising a RNA (e.g., mRNA) that comprises (or consists of, or consists essentially of) a sequence that shares at least 95% identity with SEQ ID NO: 57. In some embodiments, the RNA comprises a sequence that shares at least 96% identity with SEQ ID NO: 57. In some embodiments, the RNA comprises a sequence that shares at least 97% identity with SEQ ID NO: 57. In other embodiments, the RNA comprises a sequence that shares at least 98% identity with SEQ ID NO: 57. In some embodiments, the RNA comprises a sequence that shares at least 99% identity with SEQ ID NO: 57. In some embodiments, the RNA comprises the sequence of SEQ ID NO: 57. In some embodiments, the RNA consists of the sequence of SEQ ID NO: 57. In some embodiments, the RNA consists essentially of the sequence of SEQ ID NO: 57.

In some aspects, the present disclosure provides an immunogenic composition (e.g., vaccine) comprising a mRNA that comprises (or consists of, or consists essentially of) the sequence of SEQ ID NO: 21 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')N1mpNp cap, and wherein at least 80% of the uracil of the mRNA are 1-methylpseudouridine.

Also provided herein are methods of inducing in a subject an immune response to RSV, the methods comprising administering to the subject any of the immunogenic compositions (e.g., vaccines) described above.

Thus, in some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 22. In some embodiments, the ORF shares at least 96% identity with SEQ ID NO: 22. In other embodiments, the ORF shares at least 97% identity with SEQ ID NO: 22. In some embodiments, the ORF shares at least 98% identity with SEQ ID NO: 22. In some embodiments, the ORF shares at least 99% identity SEQ ID NO: 22. In some embodiments, the ORF comprises the sequence of SEQ ID NO: 22.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 3. In some embodiments, the ORF shares at least 96% identity with SEQ ID NO: 3. In other embodiments, the ORF shares at least 97% identity with SEQ ID NO: 3. In some embodiments, the ORF shares at least 98% identity with SEQ ID NO: 3. In some embodiments, the ORF shares at least 99% identity SEQ ID NO: 3. In some embodiments, the ORF comprises the sequence of SEQ ID NO: 3.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 52. In some embodiments, the ORF shares at least 96% identity with SEQ ID NO: 52. In other embodiments, the ORF shares at least 97% identity with SEQ ID NO: 52. In some embodiments, the ORF shares at least 98% identity with SEQ ID NO: 52. In some embodiments, the ORF shares at least 99% identity SEQ ID NO: 52. In some embodiments, the ORF comprises the sequence of SEQ ID NO: 52.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 54. In some embodiments, the ORF shares at least 96% identity with SEQ ID NO: 54. In other embodiments, the ORF shares at least 97% identity with SEQ ID NO: 54. In some embodiments, the ORF shares at least 98% identity with SEQ ID NO: 54. In some embodiments, the ORF shares at least 99% identity SEQ ID NO: 54. In some embodiments, the ORF comprises the sequence of SEQ ID NO: 54.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 56. In some embodiments, the ORF shares at least 96% identity with SEQ ID NO: 56. In other embodiments, the ORF shares at least 97% identity with SEQ ID NO: 56. In some embodiments, the ORF shares at least 98% identity with SEQ ID NO: 56. In some embodiments, the ORF shares at least 99% identity SEQ ID NO: 56. In some embodiments, the ORF comprises the sequence of SEQ ID NO: 56.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the ORF comprises (or consists of, or consists essentially of) a sequence that shares at least 95% identity with SEQ ID NO: 58. In some embodiments, the ORF shares at least 96% identity with SEQ ID NO: 58. In other embodiments, the ORF shares at least 97% identity with SEQ ID NO: 58. In some embodiments, the ORF shares at least 98% identity with SEQ ID NO: 58. In some embodiments, the ORF shares at least 99% identity SEQ ID NO: 58. In some embodiments, the ORF comprises the sequence of SEQ ID NO: 58.

In some aspects, the present disclosure provides methods that comprise delivering to a subject (e.g., via intramuscular administration) an immunogenic composition (e.g., vaccine) comprising a RNA (e.g., mRNA) that comprises an ORF encoding an RSV antigen, wherein the RSV antigen comprises (or consists of, or consists essentially of) SEQ ID NO: 5 (with or without a signal sequence MELLILKANAIT-TILTAVTFCFASG (SEQ ID NO: 100). In some embodiments, the immunogenic composition used in the methods is formulated in a lipid nanoparticle. In some embodiments, the lipid nanoparticle comprises a molar ratio of 20-60% ionizable cationic lipid, 5-25% non-cationic lipid, 25-55% sterol, and 0.5-15% PEG-modified lipid. In some embodiments, the lipid nanoparticle comprises (13Z,16Z)—N,N-dimethyl-2-nonylhenicosa-12,15-dien-1-amine, cholesterol, DSPC, and PEG-2000 DMG. In some embodiments, the lipid nanoparticle comprises 55-65 mole % (13Z,16Z)—N, N-dimethyl-2-nonylhenicosa-12,15-dien-1-amine, 25-35 mole % cholesterol, 5-15 mole % DSPC, and 1-5 mole % PEG-2000 DMG. In some embodiments, the lipid nanoparticle comprises 58 mole % (13Z,16Z)—N,N-dimethyl-2-nonylhenicosa-12,15-dien-1-amine, 30 mole % cholesterol, 10 mole % DSPC, and 2 mole % PEG-2000 DMG.

Thus, in some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 22, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG. In some embodiments, the RNA further comprises a 5' cap. In some embodiments, the 5' cap comprises 7mG(5')ppp(5')NlmpNp. In some embodiments, the RNA of the immunogenic composition used in the methods provided herein further comprises a 5' UTR and/or 3' UTR. In some embodiments, the RNA further comprises a 5' UTR comprising a sequence of SEQ ID NO: 2. In some embodiments, the RNA further comprises a 3' UTR comprising a sequence of SEQ ID NO: 4. In some embodiments, the RNA further comprises a 5' UTR comprising a sequence of SEQ ID NO: 2 and a 3' UTR comprising a sequence of SEQ ID NO: 4.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 3, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 52, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 54, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 56, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG.

In some aspects, the methods comprise delivering to a subject (e.g., via intramuscular administration) an immunogenic composition that comprises a RNA (e.g., mRNA) that comprises an ORF that comprises (or consists of, or consists essentially of) a sequence that shares at least 95% identity with a sequence of SEQ ID NO: 58, wherein the RNA is formulated in a lipid nanoparticle that comprises (13Z,16Z)—N,N-dimethyl-2-nonylhenicosa-12,15-dien-1-amine, cholesterol, DSPC, and PEG-2000 DMG. In some embodiments, the RNA of the immunogenic composition used in the methods provided herein further comprises a polyA tail. In some embodiments, the polyA tail has a length of 100 nucleotides. In some embodiments, the polyA tail has at least 50 nucleotides. In some embodiments, the polyA tail has at least 60 nucleotides. In some embodiments, the polyA tail has at least 70 nucleotides. In some embodiments, the polyA tail has at least 80 nucleotides. In some embodiments, the polyA tail has at least 90 nucleotides. In some embodiments, the polyA tail has at least 100 nucleotides. In some embodiments, the polyA tail has 100 nucleotides.

In some embodiments, the RNA of the immunogenic composition used in the methods provided herein is chemically modified. In some embodiments, at least 80%, at least 90%, 80%-100%, 90%-100%, or 100% of the uracil residues of the RNA comprise a chemical modification. In some embodiments, the chemical modification is 1-methylpseudouridine.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 22, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 3, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 52, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 54, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12, 15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 56, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12, 15-dien-1-amine, cholesterol, DSPC, and PEG-2000 DMG.

In some aspects, the RNA (e.g., mRNA) of the immunogenic composition used in the methods provided herein comprises an ORF that comprises (or consists of, or consists essentially of) a sequence that shares at least 95% identity with a sequence of SEQ ID NO: 58, wherein the RNA further comprise a 5' cap, a 5' UTR, a 3' UTR and a polyA tail. In some embodiments, RNA is formulated in a lipid nanoparticle. In some embodiments, the lipid nanoparticle comprises (13Z,16Z)—N,N-dimethyl-2-nonylhenicosa-12, 15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 22, wherein the RNA further comprise a 5' 7mG(5')ppp(5') NlmpNp cap, a 5' UTR comprising the sequence of SEQ ID NO: 2, and a 3' UTR comprising the sequence of SEQ ID NO: 4, and a polyA tail.

In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 3, wherein the RNA further comprise a 5' 7mG(5')ppp(5') NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 52, wherein the RNA further comprise a 5' 7mG(5')ppp(5') NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 54, wherein the RNA further comprise a 5' 7mG(5')ppp(5') NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 56, wherein the RNA further comprise a 5' 7mG(5')ppp(5') NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the methods of the present disclosure provide delivering to a subject (e.g., via intramuscular injection) an immunogenic composition comprising a RNA (e.g., mRNA) that comprises an ORF that comprises (or consists of, or consists essentially of) a sequence that shares at least 95% identity with a sequence of SEQ ID NO: 58, wherein the RNA further comprise a 5' 7mG(5')ppp(5') NlmpNp cap, a 5' UTR comprising the sequence of SEQ ID NO: 2, and a 3' UTR comprising the sequence of SEQ ID NO: 4, and a polyA tail. In some embodiments, the polyA tail has a length of at least 100 nucleotides. In some embodiments, the RNA is formulated in a lipid nanoparticle. In some embodiments, the lipid nanoparticle comprises (13Z,16Z)—N,N-dimethyl-2-nonylhenicosa-12,15-dien-1-amine, cholesterol, DSPC, and PEG-2000 DMG.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 21. In some embodiments, the RNA comprises a sequence that shares at least 96% identity with SEQ ID NO: 21. In some embodiments, the RNA comprises a sequence that shares at least 97% identity with SEQ ID NO: 21. In other embodiments, the RNA comprises a sequence that shares at least 98% identity with SEQ ID NO: 21. In some embodiments, the RNA comprises a sequence that shares at least 99% identity with SEQ ID NO: 21. In some embodiments, the RNA comprises the sequence of SEQ ID NO: 21. In some embodiments, the RNA consists of the sequence of SEQ ID NO: 21. In some embodiments, the RNA consists essentially of the sequence of SEQ ID NO: 21.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 1. In some embodiments, the RNA comprises a sequence that shares at least 96% identity with SEQ ID NO: 1. In some embodiments, the RNA comprises a sequence that shares at least 97% identity with SEQ ID NO: 1. In other embodiments, the RNA comprises a sequence that shares at least 98% identity with SEQ ID NO: 1. In some embodiments, the RNA comprises a sequence that shares at least 99% identity with SEQ ID NO:

1. In some embodiments, the RNA comprises the sequence of SEQ ID NO: 1. In some embodiments, the RNA consists of the sequence of SEQ ID NO: 1. In some embodiments, the RNA consists essentially of the sequence of SEQ ID NO: 1.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 51. In some embodiments, the RNA comprises a sequence that shares at least 96% identity with SEQ ID NO: 51. In some embodiments, the RNA comprises a sequence that shares at least 97% identity with SEQ ID NO: 51. In other embodiments, the RNA comprises a sequence that shares at least 98% identity with SEQ ID NO: 51. In some embodiments, the RNA comprises a sequence that shares at least 99% identity with SEQ ID NO: 51. In some embodiments, the RNA comprises the sequence of SEQ ID NO: 51. In some embodiments, the RNA consists of the sequence of SEQ ID NO: 51. In some embodiments, the RNA consists essentially of the sequence of SEQ ID NO: 51.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 53. In some embodiments, the RNA comprises a sequence that shares at least 96% identity with SEQ ID NO: 53. In some embodiments, the RNA comprises a sequence that shares at least 97% identity with SEQ ID NO: 53. In other embodiments, the RNA comprises a sequence that shares at least 98% identity with SEQ ID NO: 53. In some embodiments, the RNA comprises a sequence that shares at least 99% identity with SEQ ID NO: 53. In some embodiments, the RNA comprises the sequence of SEQ ID NO: 53. In some embodiments, the RNA consists of the sequence of SEQ ID NO: 53. In some embodiments, the RNA consists essentially of the sequence of SEQ ID NO: 53.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 55. In some embodiments, the RNA comprises a sequence that shares at least 96% identity with SEQ ID NO: 55. In some embodiments, the RNA comprises a sequence that shares at least 97% identity with SEQ ID NO: 55. In other embodiments, the RNA comprises a sequence that shares at least 98% identity with SEQ ID NO: 55. In some embodiments, the RNA comprises a sequence that shares at least 99% identity with SEQ ID NO: 55. In some embodiments, the RNA comprises the sequence of SEQ ID NO: 55. In some embodiments, the RNA consists of the sequence of SEQ ID NO: 55. In some embodiments, the RNA consists essentially of the sequence of SEQ ID NO: 55.

In some aspects, the present disclosure provides methods comprising delivering to a subject (e.g., via intramuscular injection) an immunogenic composition (e.g., vaccine) comprising a RNA (e.g., mRNA) that comprises (or consists of, or consists essentially of) a sequence that shares at least 95% identity with SEQ ID NO: 57. In some embodiments, the RNA comprises a sequence that shares at least 96% identity with SEQ ID NO: 57. In some embodiments, the RNA comprises a sequence that shares at least 97% identity with SEQ ID NO: 57. In other embodiments, the RNA comprises a sequence that shares at least 98% identity with SEQ ID NO: 57. In some embodiments, the RNA comprises a sequence that shares at least 99% identity with SEQ ID NO: 57. In some embodiments, the RNA comprises the sequence of SEQ ID NO: 57. In some embodiments, the RNA consists of the sequence of SEQ ID NO: 57. In some embodiments, the RNA consists essentially of the sequence of SEQ ID NO: 57.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 21 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 1 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 51 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 53 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 55 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

In some aspects, the present disclosure provides methods that comprise delivering to a subject (e.g., via intramuscular injection) an immunogenic composition (e.g., vaccine) comprising a mRNA that comprises (or consists of, or consists essentially of) the sequence of SEQ ID NO: 57 formulated in a lipid nanoparticle comprising 58 mole % (13Z,16Z)—N,N-dimethyl-2-nonylhenicosa-12,15-dien-1-amine, 30 mole % cholesterol, 10 mole % DSPC, and 2 mole % PEG-2000 DMG, wherein the mRNA further comprises a 5' 7mG(5')ppp(5')NlmpNp cap, and wherein at least 80% of the uracil of the mRNA are 1-methylpseudouridine.

BRIEF DESCRIPTION OF THE DRAWINGS

FIG. 6A: High dose immunization. FIG. 6B: Low dose immunization. FIG. 6C: Area under the curve.

DETAILED DESCRIPTION

Figure 1:
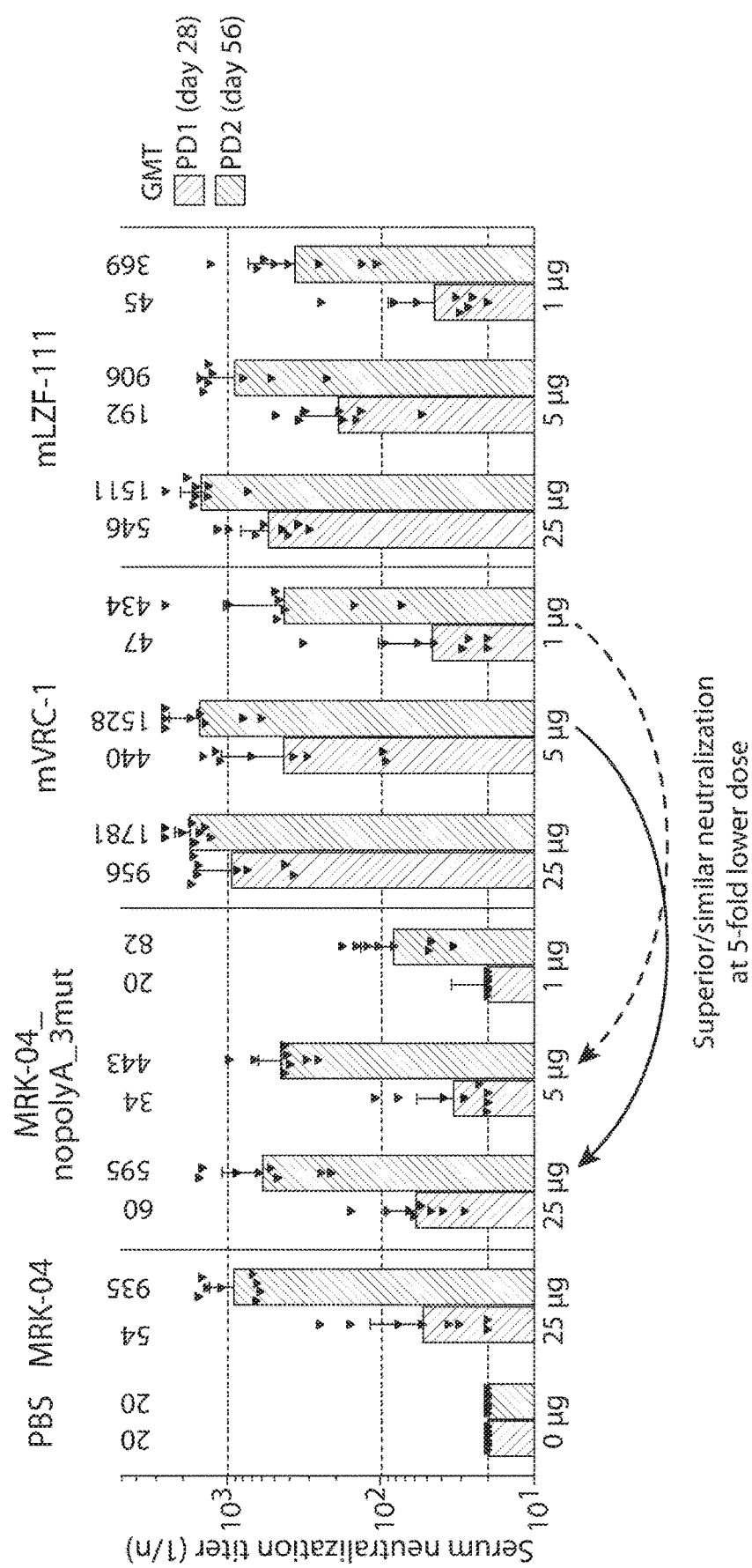
FIG. 1 shows a graph of serum neutralizing antibody titers ($NT_{50}$ individual and GMT with 95% confidence intervals) to RSV A induced in cotton rats by mRNA vaccines and control formulations.

Embodiments of the present disclosure provide highly immunogenic RNA (e.g., mRNA) compositions (e.g., vaccines) that include a (at least one) polynucleotide encoding a respiratory syncytial virus (RSV) antigen and elicit potent neutralizing antibodies. RSV is a negative-sense, single-stranded RNA virus of the genus Pneumovirinae. The virus is present in at least two antigenic subgroups, known as Group A and Group B, primarily resulting from differences in the surface G glycoproteins. Two RSV surface glycoproteins—G and F—mediate attachment with and attachment to cells of the respiratory epithelium. F surface glycoproteins mediate coalescence of neighboring cells. This results in the formation of syncytial cells. RSV is the most common cause of bronchiolitis. Most infected adults develop mild cold-like symptoms such as congestion, low-grade fever, and wheezing. Infants and small children may suffer more severe symptoms such as bronchiolitis and pneumonia. The disease may be transmitted among humans via contact with respiratory secretions.

RSV F protein is a type I fusion glycoprotein that is well conserved between clinical isolates, including between RSV-A and RSV-B antigenic subgroups. The F protein transitions between prefusion and more stable postfusion states, thereby facilitating entry into target cells. RSV F glycoprotein is initially synthesized as an F0 precursor protein. RSV F0 folds into a trimer, which is activated by furin cleavage into the mature prefusion protein comprising F1 and F2 subunits (Bolt, et al., Virus Res., 68:25, 2000). RSV F protein stabilized in the prefusion conformation produce a greater neutralizing immune response in animal models than that observed with RSV F protein stabilized in the post fusion conformation (McLellan et al., Science, 342: 592-598, 2013). As such, stabilized prefusion RSV F proteins are good candidates for inclusion in an RSV vaccine. Soluble RSV ectodomains stablized in the prefusion conformation have previously been generated, including the DS-CAV1 substitutions. "DS-CAV1" and "DS-CAV1 substitutions," each as used herein, refers to genetic modifications to the RSV F protein, which contains the "DS" substitutions 155C and 290C so as to introduce a non-native disulfide bond between cysteines introduced by the substitutions (such as S155C and S290C substitutions) and the "CAV1" substitutions, which include 190F and 207L cavity filling amino acid substitutions (such as S190F and V207L). mVRC-1 (e.g., SEQ ID NO: 21), used in some of the immunogenic compositions of the present disclosure, as compared to DS-CAV1, includes an additional stabilizing disulfide bond (resulting from the introduction of the amino acid substitutions A149C and Y458C) and is engineered so that the $F_2$ and $F_1$ subunits are genetically linked, with the fusion peptide and p27 region deleted. See, WO 2014/160463A1 and WO 2017/172890A1, the contents of each of which are hereby incorporated by reference.

It has been previously shown that the prefusion stabilized RSV F construct, DS-CAV1, undergoes conformational changes and forms intermediate structures upon long-term storage at 4° C. (Flynn J A et al., PLoS ONE 2016; 11(10): e0164789). Long term stability at 4° C. or higher is a desirable attribute for a RSV F subunit vaccine antigen. Described herein are additional structure-based modifications to further improve the stability of the RSV F trimer in the prefusion conformation. Such constructs have increased stability at 4° C. as compared to DS-CAV1 while retaining immunogenicity.

"RSV Fusion Protein" or "RSV F protein", each as used herein, refers to an RSV envelope glycoprotein that facilitates fusion of viral and cellular membranes. In nature, the RSV F protein is synthesized into a single polypeptide precursor designated F0, which includes a signal peptide that directs localization to the endoplasmic reticulum, where the signal peptide is cleaved. The remaining F0 residues oligomerize to form a trimer and are proteolytically processed by a protease at two conserved furin cleavage sequences to generate two disulfide linked fragments, F1 and F2. In nature, three F2-F1 peptides oligomerize into a trimer to form the mature F protein, which adopts a prefusion conformation that is metastable and can undergo a conformation change to a postfusion conformation.

The genome of RSV encodes at least three surface glycoproteins, including F, G, and SH, four nucleocapsid proteins, including L, P, N, and M2, and one matrix protein, M. Glycoprotein F directs viral penetration by fusion between the virion and the host membrane. Glycoprotein G is a type II transmembrane glycoprotein and is the major attachment protein. SH is a short integral membrane protein. Matrix protein M is found in the inner layer of the lipid bilayer and assists virion formation. Nucleocapsid proteins L, P, N, and M2 modulate replication and transcription of the RSV genome. It is thought that glycoprotein G tethers and stabilizes the virus particle at the surface of bronchial epithelial cells, while glycoprotein F interacts with cellular glycosaminoglycans to mediate fusion and delivery of the RSV virion contents into the host cell (Krzyzaniak M A et al. PLoS Pathog 2013; 9(4)).

The present disclosure is not limited by a particular strain of RSV. The strain of RSV used in a vaccine may be any strain of RSV.

The RSV RNA vaccines described herein are superior to current vaccines in several ways. For example, the lipid nanoparticle (LNP) delivery system used herein increases the efficacy of RNA vaccines in comparison to other formulations, including a protamine-based approach described in the literature. The use of this LNP delivery system enables the effective delivery of chemically-modified RNA vaccines or unmodified RNA vaccines, without requiring additional adjuvant to produce a therapeutic result (e.g., production neutralizing antibody titer). In some embodiments, the RSV RNA vaccines disclosed herein are superior to conventional vaccines by a factor of at least 10 fold, 20, fold, 40, fold, 50 fold, 100 fold, 500 fold, or 1,000 fold when administered intramuscularly (IM) or intradermally (ID). These results can be achieved even when significantly lower doses of the RNA (e.g., mRNA) are administered in comparison with RNA doses used in other classes of lipid based formulations.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the present disclosure, a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the present disclosure have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the present disclosure do not require viral replication to produce enough protein to result in a strong immune response. Thus, the mRNA of the present disclosure are not self-replicating RNA and do not include components necessary for viral replication.

It should also be understood that the immunogenic compositions, e.g, vaccines, of the present disclosure are not naturally-occuring. That is, the immunogenic compositions, e.g, vaccines, provided herein do not occur in nature.

Exemplary Respiratory Syncytial Virus (RSV) Antigens

Antigens are proteins capable of inducing an immune response (e.g., causing an immune system to produce antibodies against the antigens). Herein, use of the term antigen encompasses immunogenic proteins and immunogenic fragments (an immunogenic fragment that induces (or is capable of inducing) an immune response to RSV), unless otherwise stated. It should be understood that the term "protein' encompasses peptides and the term "antigen" encompasses antigenic fragments.

A number of different antigens are associated with RSV. RSV vaccines, as provided herein, comprise at least one (one or more) ribonucleic acid (RNA, e.g., mRNA) comprising an open reading frame encoding at least one RSV antigen. Non-limiting examples of RSV antigens are provided below.

Exemplary RSV antigens are provided in the Sequence Listing elsewhere herein. For example, the antigens may be encoded by (thus the RNA may comprise or consist of) any one of sequences set forth in SEQ ID NOS: 3, 7, 10, 13, 16, 19, 22, 24, 26, 28, 30, 32, 34, 37, 40, 43, 46, 49, 52, 54, 56, 58, 60, 63, 66, 69, 72, or 75. In some embodiments, the aforementioned sequences may further comprise a 5' cap (e.g., 7mG(5')ppp(5')NlmpNp), a polyA tail, or a 5' cap and a polyA tail).

It should be understood that the RSV vaccines of the present disclosure may comprise any of the RNA open reading frames (ORFs), or encode any of the protein ORFs, described herein, with or without a signal sequence. It should also be understood that the RSV vaccines of the present disclosure may include any 5' untranslated region (UTR) and/or any 3' UTR. Exemplary UTR sequences are provided in the Sequence Listing (e.g., SEQ ID NOS: 2, 4, 77, and 78); however, other UTR sequences (e.g., of the prior art) may be used or exchanged for any of the UTR sequences described herein. UTRs may also be omitted from the vaccine constructs provided herein.

At least two antigenic subgroups (A and B) of RSV are known to exist. This antigenic dimorphism is due primarily to difference in the surface G glycoproteins. Two surface glycoproteins, G and F, are present in the envelope and mediate attachment and fusion with cells of the respiratory epithelium. The F proteins also mediate coalescence of neighboring cells to form the characteristic syncytial cells for which the virus receives its name. The epidemiologic and biologic significance of the two antigenic variants of RSV is uncertain. Nonetheless, there is some evidence to suggest that Group A infections tend to be more severe.

The RSV genome is ~15,000 nucleotides in length and is composed of a single strand of RNA with negative polarity. It has 10 genes encoding 11 proteins—there are 2 open reading frames of M2. The genome is transcribed sequentially from NS1 to L with reduction in expression levels along its length.

SH protein, G protein and F protein form the viral coat. The G protein is a surface protein that is heavily glycosylated and functions as the attachment protein. The F protein is another important surface protein that mediates fusion, allowing entry of the virus into the cell cytoplasm and also allowing the formation of syncytia. The F protein is homologous in both subtypes of RSV; antibodies directed at the F protein are neutralizing. In contrast, the G protein differs considerably between the two RSV subtypes. In some embodiments, a RSV vaccine comprises a RNA (e.g., mRNA) polynucleotide comprising an ORF encoding RSV F protein and a RNA (e.g., mRNA) polynucleotide comprising an ORF encoding RSV SH protein. In some embodiments, a RSV vaccine comprises a RNA (e.g., mRNA) polynucleotide comprising an ORF encoding RSV F protein and a RNA (e.g., mRNA) polynucleotide comprising an ORF encoding RSV G protein.

NS1 and NS2 inhibit type I interferon activity. In some embodiments, a RSV vaccine comprises a RNA (e.g., mRNA) polynucleotide comprising an ORF encoding RSV F protein and a RNA (e.g., mRNA) polynucleotide comprising an ORF encoding RSV NS1 and/or RSV NS2.

N encodes nucleocapsid protein that associates with the genomic RNA forming the nucleocapsid. In some embodiments, a RSV vaccine comprises a RNA (e.g., mRNA) polynucleotide comprising an ORF encoding RSV F protein and a RNA (e.g., mRNA) polynucleotide comprising an ORF encoding RSV nucleocapsid protein.

M encodes the Matrix protein required for viral assembly. In some embodiments, a RSV vaccine comprises a RNA (e.g., mRNA) polynucleotide comprising an ORF encoding RSV F protein and a RNA (e.g., mRNA) polynucleotide comprising an ORF encoding RSV Matrix protein.

Nucleolin at the cell surface is the receptor for the RSV fusion protein. Interference with the nucleolin-RSV fusion protein interaction has been shown to be therapeutic against RSV infection in cell cultures and animal models. In some embodiments, a RSV vaccine comprises a RNA (e.g., mRNA) polynucleotide comprising an ORF encoding RSV F protein and a RNA (e.g., mRNA) polynucleotide comprising an ORF encoding RSVnucleolin.

M2 is the second matrix protein also required for transcription and encodes M2-1 (elongation factor) and M2-2 (transcription regulation). M2 contains CD8 epitopes. In some embodiments, a RSV vaccine comprises a RNA (e.g., mRNA) polynucleotide comprising an ORF encoding RSV F protein and a RNA (e.g., mRNA) polynucleotide comprising an ORF encoding RSV second matrix protein.

L encodes the RNA polymerase. In some embodiments, a RSV vaccine comprises a RNA (e.g., mRNA) polynucleotide comprising an ORF encoding RSV F protein and a RNA (e.g., mRNA) polynucleotide comprising an ORF encoding RSV RNA polymerase (L).

The phosphoprotein P is a cofactor for the L protein. In some embodiments, a RSV vaccine comprises a RNA (e.g., mRNA) polynucleotide comprising an ORF encoding RSV F protein and a RNA (e.g., mRNA) polynucleotide comprising an ORF encoding RSV phosphoprotein P.

Some embodiments of the present disclosure provide RSV vaccines that include at least one RNA (e.g., mRNA) polynucleotide comprising an open reading frame encoding RSV glycoprotein F.

Some embodiments of the present invention disclose RSV vaccines that include at least one RNA (e.g. mRNA) polynucleotide comprising an open reading frame encoding a polypeptide in the post-fusion form. Some embodiments of the present invention disclose RSV vaccines that include at least one RNA (e.g. mRNA) polynucleotide comprising an open reading frame encoding a polypeptide in the pre-fusion form. In some embodiments, the polypeptides comprise glycoproteins in a prefusion conformation, for example, but not limited to, prefusion glycoprotein F or DS-CAV1. Without wishing to be bound by theory, certain polypeptides, when in a prefusion conformation, may contain more epitopes for neutralizing antibodies relative to the postfusion conformation of the same proteins. For example, prefusion glycoprotein F has a unique antigen site ("antigenic site 0") at its membrane distal apex. Antigenic site 0 may, but not necessarily, comprise residues 62-69 and 196-209 of a RSV F protein sequence. In some instances, such as, but not limited to, prefusion glycoprotein F, prefusion polypeptides may exhibit many fold greater immune responses than those achieved with post-fusion polypeptides. Prefusion RSV glycoproteins and their methods of use are described in WO 2014/160463 and in WO 2017/172890, each of which is incorporated by reference herein in its entirety.

In some embodiments, RSV vaccines include at least one RNA (e.g., mRNA) polynucleotide comprising an open reading frame encoding glycoprotein F obtained from RSV strain A2 (RSV A2). Other RSV strains are encompassed by the present disclosure, including subtype A strains and subtype B strains.

Nucleic Acids

The RSV vaccines of the present disclosure comprise at least one (one or more) ribonucleic acid (RNA) comprising an open reading frame encoding at least one RSV antigen. In some embodiments, the RNA is a messenger RNA (mRNA) comprising an open reading frame encoding at least one RSV antigen. In some embodiments, the RNA (e.g., mRNA) further comprises a (at least one) 5' UTR, 3' UTR, a polyA tail and/or a 5' cap.

Nucleic acids comprise a polymer of nucleotides (nucleotide monomers), also referred to as polynucleotides. Nucleic acids may be or may include, for example, deoxyribonucleic acids (DNAs), ribonucleic acids (RNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Messenger RNA (mRNA) is any ribonucleic acid that encodes a (at least one) protein (a naturally-occurring, non-naturally-occurring, or modified polymer of amino acids) and can be translated to produce the encoded protein in vitro, in vivo, in situ or ex vivo. The skilled artisan will appreciate that, except where otherwise noted, nucleic acid sequences set forth in the instant application may recite "T"s in a representative DNA sequence but where the sequence represents RNA (e.g., mRNA), the "T"s would be substituted for "U". Thus, any of the DNAs disclosed and identified by a particular sequence identification number herein also disclose the corresponding RNA (e.g., mRNA) sequence complementary to the DNA, where each "T" of the DNA sequence is substituted with "U." Likewise, any of the RNAs disclosed and identified by a particular sequence identification number herein also disclose the corresponding DNA sequence complementary to the RNA, where each "U" of the RNA sequence is substituted with "T."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in a vaccine of the present disclosure.

Variants

In some embodiments, an RNA of the present disclosure encodes an RSV antigen variant. Antigen or other polypeptide variants refers to molecules that differ in their amino acid sequence from a wild-type, native or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, or at least 90% identity with a wild-type, native or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, an RSV vaccine comprises an mRNA ORF comprising a nucleotide sequence identified by any one of the sequences provided herein (see e.g., Sequence Listing), or comprising a nucleotide sequence at least 85%, at least 90%, at least 95%, at least 96%, at least 97%, at least 98%, or at least 99% identical to a nucleotide sequence identified by any one of the sequence provided herein.

The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 85%, 86%, 87%, 88%, 89%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs". *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

As recognized by those skilled in the art, protein fragments, functional protein domains, and homologous proteins are also considered to be within the scope of RSV antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the RSV pathogen. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a vaccine includes at least one RNA polynucleotide comprising an open reading frame encoding at least one antigenic polypeptide comprising at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp (5') G [the ARCA cap]; G(5')ppp(5')A; G(5')ppp(5')G; m7G (5')ppp(5')A; m7G(5')ppp(5')G (New England BioLabs, Ipswich, MA). 5'-capping of modified RNA may be completed post-transcriptionally using a Vaccinia Virus Capping Enzyme to generate the "Cap 0" structure: m7G(5')ppp(5')G (New England BioLabs, Ipswich, MA). Cap 1 structure may be generated using both Vaccinia Virus Capping Enzyme and a 2'-O methyl-transferase to generate: m7G(5')ppp(5') G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-0 methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, RSV RNA vaccines may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, RSV RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, RSV RNA vaccines do not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

In some embodiments, RSV RNA vaccines may or may not contain an enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments, RSV RNA vaccines may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Signal Peptides

In some embodiments, an RSV vaccine comprises a RNA comprising an ORF that encodes a signal peptide fused to the RSV antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than RSV antigens in nature) are known in the art and can be tested for desired properties and then incorporated into a nucleic acid of the disclosure. In some embodiments, the signal peptide is a bovine prolactin signal peptide. For example, the bovine prolactin signal peptide may comprise sequence MDSKGSSQKGSR-LLLLLVVSNLLLPQGVVG (SEQ ID NO: 79). Other signal peptide sequences may also be used. For example, the signal peptide may comprise one of the following sequences: MDWTWILFLVAAATRVHS (SEQ ID NO: 80); METPAQLLFLLLLWLPDTTG (SEQ ID NO:81); MLGSNSGQRVVFTILLLLVAPAYS (SEQ ID NO: 82); MKCLLYLAFLFIGVNCA (SEQ ID NO: 83); MWLVSLAIVTACAGA (SEQ ID NO: 84); or MELLILKANAITTILTAVTFCFASG (SEQ ID NO:100).

Fusion Proteins

In some embodiments, an RSV RNA vaccine of the present disclosure includes an RNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the RSV antigen. Antigenic fusion proteins, in some embodiments, retain the functional property from each original protein.

Scaffold Moieties

The RNA (e.g., mRNA) vaccines as provided herein, in some embodiments, encode fusion proteins which comprise RSV antigens linked to scaffold moieties. In some embodiments, such scaffold moieties impart desired properties to an antigen encoded by a nucleic acid of the disclosure. For example scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J. et al. *Computational and Structural Biotechnology Journal* 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments an RSV antigen is fused to HBsAG or HBcAG to facilitate self-assembly of nanoparticles displaying the RSV antigen.

In another embodiment, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. *J Mol Biol.* 2009; 390:83-98). Several high-resolution structures of ferritin have been determined, confirming that *Helicobacter pylori* ferritin is made of 24 identical protomers, whereas in animals, there are ferritin light and heavy chains that can assemble alone or combine with different ratios into particles of 24 subunits (Granier T. et al. *J Biol Inorg Chem.* 2003; 8:105-111; Lawson D. M. et al. *Nature.* 1991; 349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. *Flavins and Flavoproteins*. Methods and Protocols, Series: Methods in Molecular Biology. 2014). The LS monomer is 150 amino acids long, and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. *J Mol Biol.* 2006; 362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. *Nat Struct Mol Biol.* 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. *FEBS J.* 2013, 280: 2097-2104).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) *PLoS ONE* 6:e18556). In some embodiments, the linker is an F2A linker. In some embodiments, the linker is a GGGS linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures;

minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding an RSV antigen). In some embodiments, a codon optimized sequence shares less than 90% sequence identity to a naturally-occurring or wild-type sequence (e.g., a naturally-occurring or wild-type mRNA sequence encoding an RSV antigen). In some embodiments, a codon optimized sequence shares less than 85% sequence identity to a naturally-occurring or wild-type sequence (e.g., a naturally-occurring or wild-type mRNA sequence encoding an RSV antigen). In some embodiments, a codon optimized sequence shares less than 80% sequence identity to a naturally-occurring or wild-type sequence (e.g., a naturally-occurring or wild-type mRNA sequence encoding an RSV antigen). In some embodiments, a codon optimized sequence shares less than 75% sequence identity to a naturally-occurring or wild-type sequence (e.g., a naturally-occurring or wild-type mRNA sequence encoding an RSV antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding an RSV antigen). In some embodiments, a codon optimized sequence shares between 65% and 75% or about 80% sequence identity to a naturally-occurring or wild-type sequence (e.g., a naturally-occurring or wild-type mRNA sequence encoding an RSV antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than an RSV antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, at least one RNA (e.g., mRNA) of an RSV vaccines of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

RSV RNA vaccines of the present disclosure comprise, in some embodiments, at least one nucleic acid (e.g., RNA) comprising an open reading frame encoding at least one RSV antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids comprising at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises 1-methyl-pseudouridine (m1ψ) substitutions at one or more or all uridine positions of the nucleic acid.

In some embodiments, a RNA nucleic acid of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Untranslated Regions (UTRs)

The nucleic acids of the present disclosure may comprise one or more regions or parts which act or function as an untranslated region. Where nucleic acids are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 85), where R is a purine (adenine or guanine) three bases upstream of the start codon (AUG), which is followed by another 'G'0.5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include *Xenopus* or human derived a-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063; 9,012,219). CMV immediate-early 1 (IE1) gene (US20140206753, WO2013/185069), the sequence GGGAUCCUACC (SEQ ID NO: 86) (WO2014144196) may also be used. In another embodiment, 5' UTR of a TOP gene is a 5' UTR of a TOP gene lacking the 5' TOP motif (the oligopyrimidine tract) (e.g., WO/2015101414, WO2015101415, WO/2015/062738, WO2015024667, WO2015024667; 5' UTR element derived from ribosomal protein Large 32 (L32) gene (WO/2015101414, WO2015101415, WO/2015/062738), 5' UTR element derived from the 5'UTR of an hydroxysteroid (17-0) dehydrogenase 4 gene (HSD17B4) (WO2015024667), or a 5' UTR element derived from the 5' UTR of ATP5A1 (WO2015024667) can be used. In some embodiments, an internal ribosome entry site (IRES) is used instead of a 5' UTR.

In some embodiments, a 5' UTR of the present disclosure comprises a sequence selected from SEQ ID NO: 2 and SEQ ID NO: 77.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 87) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

3' UTRs may be heterologous or synthetic. With respect to 3' UTRs, globin UTRs, including *Xenopus* β-globin UTRs and human β-globin UTRs are known in the art (U.S. Pat. Nos. 8,278,063, 9,012,219, US20110086907). A modified β-globin construct with enhanced stability in some cell types by cloning two sequential human β-globin 3'UTRs head to tail has been developed and is well known in the art (US2012/0195936, WO2014/071963). In addition a2-globin, a1-globin, UTRs and mutants thereof are also known in the art (WO2015101415, WO2015024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified)

(WO2013/185069, US20140206753, WO2014/152774), rabbit B globin and hepatitis B virus (HBV), α-globin 3' UTR and Viral VEEV 3' UTR sequences are also known in the art. In some embodiments, the sequence UUUGAAUU (WO2014/144196) is used. In some embodiments, 3' UTRs of human and mouse ribosomal protein are used. Other examples include rps9 3'UTR (WO2015101414), FIG. 4 (WO2015/101415), and human albumin 7 (WO2015/101415).

In some embodiments, a 3' UTR of the present disclosure comprises a sequence selected from SEQ ID NO: 4 and SEQ ID NO: 78.

Those of ordinary skill in the art will understand that 5'UTRs that are heterologous or synthetic may be used with any desired 3' UTR sequence. For example, a heterologous 5'UTR may be used with a synthetic 3'UTR with a heterologous 3" UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 20090226470, herein incorporated by reference in its entirety, and those known in the art.

In Vitro Transcription of RNA cDNA encoding the polynucleotides described herein may be transcribed using an in vitro transcription (IVT) system. In vitro transcription of RNA is known in the art and is described in International Publication WO/2014/152027, which is incorporated by reference herein in its entirety.

In some embodiments, the RNA transcript is generated using a non-amplified, linearized DNA template in an in vitro transcription reaction to generate the RNA transcript.

In some embodiments, the template DNA is isolated DNA. In some embodiments, the template DNA is cDNA. In some embodiments, the cDNA is formed by reverse transcription of a RNA polynucleotide, for example, but not limited to RSV RNA, e.g. RSV mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates.

A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present invention may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Pharmaceutical Formulations

Provided herein are compositions (e.g., pharmaceutical compositions), methods, kits and reagents for prevention or treatment of RSV in humans and other mammals, for example. RSV RNA (e.g., mRNA) vaccines can be used as therapeutic or prophylactic agents. They may be used in medicine to prevent and/or treat infectious disease.

In some embodiments, an RSV vaccine containing RNA polynucleotides as described herein can be administered to a subject (e.g., a mammalian subject, such as a human subject), and the RNA polynucleotides are translated in vivo to produce an antigenic polypeptide (antigen).

An "effective amount" of an RSV vaccine is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of an RSV vaccine provides an induced or boosted immune response as a function of antigen production in the cells of the subject. In some embodiments, an effective amount of the RSV RNA vaccine containing RNA polynucleotides comprising at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of RSV. RSV RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

RSV RNA (e.g., mRNA) vaccines may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, RSV RNA vaccines may be administered intramuscularly, intranasally or intradermally, similarly to the administration of inactivated vaccines known in the art.

The RSV RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including RSV RNA vaccines and RNA vaccine compositions and/or complexes optionally in combination with one or more pharmaceutically acceptable excipients.

RSV RNA (e.g., mRNA) vaccines may be formulated or administered alone or in conjunction with one or more other components. For instance, RSV RNA vaccines (vaccine compositions) may comprise other components including, but not limited to, adjuvants.

In some embodiments, RSV RNA vaccines do not include an adjuvant (they are adjuvant free).

RSV RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, RSV RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, RSV RNA vaccines are formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with RSV RNA vaccines (e.g., for transplantation into a subject), hyaluronidase, nanoparticle mimics and combinations thereof.

Lipid Nanoparticles (LNPs)

In some embodiments, RSV RNA (e.g., mRNA) vaccines of the disclosure are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, an ionizable cationic lipid of the disclosure comprises a compound of Formula (I):

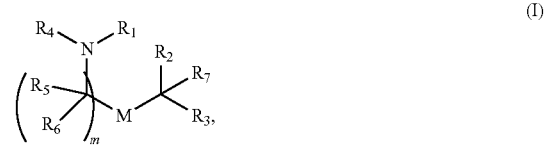

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CO$(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —C(O)N$(R)_2$, —N(R)C(O)R, —N(R)S(O)$_2$R, —N(R)C(O)N$(R)_2$, —N(R)C(S)N$(R)_2$, —N(R)R$_8$, —O(CH$_2$)$_n$OR, —N(R)C(=NR$_9$)N$(R)_2$, —N(R)C(=CHR$_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=NR$_9$)N$(R)_2$, —N(OR)C(=CHR$_9$)N$(R)_2$, —C(=NR$_9$)N$(R)_2$, —C(=NR$_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_nQ$, —$(CH_2)_n$CHQR, —CHQR, or —CO$(R)_2$, then (i) Q is not —N$(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CO$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N$(R)_2$, —C(O)OR, —OC(O)R, —$CX_3$, —$CX_2H$, —$CXH_2$, —CN, —C(O)N$(R)_2$, —N(R)C(O)R, —N(R)S(O)$_2$R, —N(R)C(O)N$(R)_2$, —N(R)C(S)N$(R)_2$, —CRN$(R)_2$C(O)OR, —N(R)R$_8$, —O(CH$_2$)$_n$OR, —N(R)C(=NR$_9$)N$(R)_2$, —N(R)C(=CHR$_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=NR$_9$)N$(R)_2$, —N(OR)C(=CHR$_9$)N$(R)_2$, —C(=NR$_9$)N$(R)_2$, —C(=NR$_9$)R, —C(O)N(R)OR, and a 5- to 14-membered heterocycloalkyl comprising one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CO$(R)_2$, and unsubstituted $C_{1-6}$ alkyl, where Q is selected from a $C_{3-6}$ carbocycle, a 5- to 14-membered heterocycle comprising one or more heteroatoms selected from N, O, and S, —OR, —O(CH$_2$)$_n$N$(R)_2$, —C(O)OR, —OC(O)R, —$CX_3$, —$CX_2H$, —$CXH_2$, —CN, —C(O)N$(R)_2$, —N(R)C(O)R, —N(R)S(O)$_2$R, —N(R)C(O)N$(R)_2$, —N(R)C(S)N$(R)_2$, —CRN$(R)_2$C(O)OR, —N(R)R$_8$, —O(CH$_2$)$_n$OR, —N(R)C(=NR$_9$)N$(R)_2$, —N(R)C(=CHR$_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=NR$_9$)N$(R)_2$, —N(OR)C(=CHR$_9$)N$(R)_2$, —C(=NR$_9$)R, —C(O)N(R)OR, and —C(=NR$_9$)N$(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_n$CHQR in which n is 1, or (iii) $R_4$ is —CHQR, and —$CO(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CO(R)$_2$, and unsubstituted $C_{1-6}$ alkyl, where Q is selected from a $C_{3-6}$ carbocycle, a 5- to 14-membered heteroaryl comprising one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_n$CHQR, where Q is —N(R)$_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

R$_2$ and R$_3$ are independently selected from the group consisting of C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of —(CH$_2$)$_n$Q, —(CH$_2$)$_n$CHQR, —CHQR, and —CO(R)$_2$, where Q is —N(R)$_2$, and n is selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

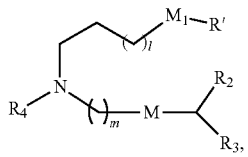

(IA)

or a salt or isomer thereof, wherein 1 is selected from 1, 2, 3, 4, and 5; m is selected from 5, 6, 7, 8, and 9; M$_1$ is a bond or M'; R$_4$ is unsubstituted C$_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-4}$ alkyl, and C$_{2-14}$ alkenyl.

In some embodiments, a subset of compounds of Formula (I) includes those of Formula (II):

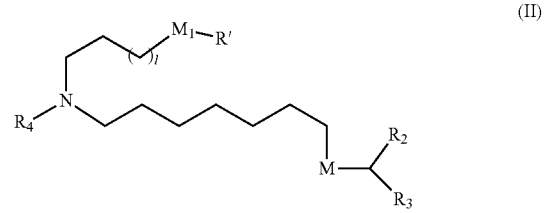

(II)

or a salt or isomer thereof, wherein 1 is selected from 1, 2, 3, 4, and 5; M$_1$ is a bond or M'; R$_4$ is unsubstituted C$_{1-3}$ alkyl, or —(CH$_2$)$_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-4}$ alkyl, and C$_{2-4}$ alkenyl.

In some embodiments, a subset of compounds of Formula (I) includes those of Formula (IIa), (IIb), (IIc), or (IIe):

(IIa)

(IIb)

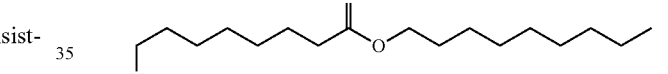
(IIc) , or

(IIe)

or a salt or isomer thereof, wherein R$_4$ is as described herein.

In some embodiments, a subset of compounds of Formula (I) includes those of Formula (IId):

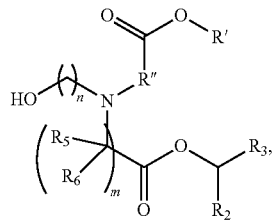
(IId)

or a salt or isomer thereof, wherein n is 2, 3, or 4; and m, R', R'', and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable cationic lipid of the disclosure comprises a compound having structure:

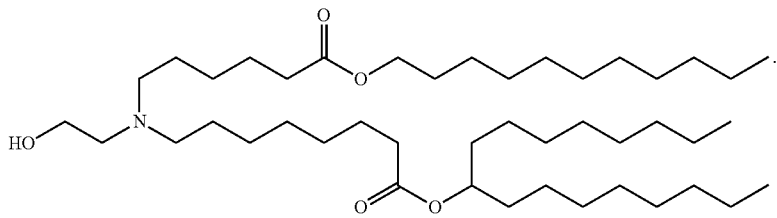
(Compound 1)

In some embodiments, an ionizable cationic lipid of the disclosure comprises a compound having structure:

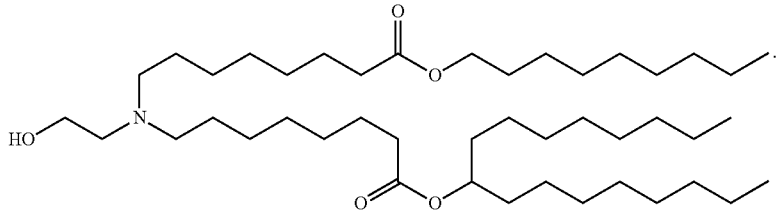
(Compound 2)

In some embodiments, an ionizable cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), (13Z,16Z)—N,N-dimethyl-3-nonyldocosa-13,16-dien-1-amine, (12Z,15Z)—N,N-dimethyl-2-nonylhenicosa-12,15-dien-1-amine, and N,N-dimethyl-1-[(1S,2R)-2-octylcyclopropyl]heptadecan-8-amine. In one embodiment, the lipid is (13Z,16Z)—N,N-dimethyl-3-nonyldocosa-13,16-dien-1-amine or N,N-dimethyl-1-[(1S,2R)-2-octylcyclopropyl]heptadecan-8-amine, each of which are described in PCT/US2011/052328, the entire contents of which are hereby incorporated by reference. In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is PEG-DMG.

In some embodiments, a LNP of the disclosure comprises an ionizable cationic lipid selected from the group consisting of (2S)-1-({6-[(3))-cholest-5-en-3-yloxy]hexyl}oxy)-N,N-dimethyl-3-[(9 Z)-octadec-9-en-1-yloxy]propan-2-amine; (13Z,16Z)—N,N-dimethyl-3-nonyldocosa-13,16-dien-1-amine; and N,N-dimethyl-1-[(1S,2R)-2-octylcyclopropyl]

heptadecan-8-amine; or a pharmaceutically acceptable salt thereof, or a stereoisomer of any of the foregoing.

In some embodiments, the LNP comprises 30-75 mole % ionizable cationic lipid and 0.1-20 mole % PEG-lipid.

In some embodiments, the LNP further comprises one or more non-cationic lipids selected from a phospholipid, a phospholipid derivative, a fatty acid, a sterol, or a combination thereof. In some embodiments, the sterol is cholesterol, stigmasterol or stigmastanol.

In some embodiments, the phospholipid is selected from phosphatidylserine, 1,2-Distearoyl-sn-glycero-3-phosphocholine (DSPC), 1,2-dipalmitoleoyl-sn-glycero-3-phosphocholine, 1,2-dimyristoyl-sn-glycero-3-phosphocholine (DMPC), dilauroylphosphatidylcholine (DLPC), 1,2-dieicosenoyl-sn-glycero-3-phosphocholine, and 1,2-dioleoyl-sn-glycero-3-phosphocholine (DOPC).

In some embodiments, the PEG-lipid is 1,2-Dimyristoyl-sn-glycerol methoxypolyethylene glycol (PEG-DMG), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG-lipid is PEG coupled to dimyristoylglycerol (PEG-DMG), e.g., as described in Abrams et al., 2010, Molecular Therapy 18(1): 171, and U.S. Patent Application Publication Nos. US 2006/0240554 and US 2008/0020058, including for example, 2KPEG/PEG200-DMG.

In some embodiments, the LNP comprises 20-99.8 mole % ionizable cationic lipids, 0.1-65 mole % non-cationic lipids, and 0.1-20 mole % PEG-lipid.

In some embodiments, the non-cationic lipids comprise a mixture of cholesterol and DSPC.

In some embodiments, the LNP comprises 34-59 mole % ionizable cationic lipids selected from the group consisting of (2S)-1-({6-[(3))-cholest-5-en-3-yloxy]hexyl}oxy)-N,N-dimethyl-3-[(9 Z)-octadec-9-en-1-yloxy]propan-2-amine; (13Z,16Z)—N,N-dimethyl-3-nonyldocosa-13,16-dien-1-amine; and N,N-dimethyl-1-[(1S,2R)-2-octylcyclopropyl]heptadecan-8-amine, 30-48 mole % cholesterol, 10-24% DSPC and 1-2 mole % PEG-DMG.

In some embodiments, the LNP comprises 58 mole % cationic lipid, 30 mole % cholesterol, 10 mole % DSPC, and 2 mole % PEG-2000 DMG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Multivalent Vaccines

The RSV vaccines, as provided herein, may include an RNA (e.g. mRNA) or multiple RNAs encoding two or more antigens of the same or different RSV species. In some embodiments, an RSV vaccine includes an RNA or multiple RNAs encoding two or more antigens selected from glycoprotein G (G), glycoprotein F (F), matrix protein (M), small hydrophobic protein (SH), nonstructural protein 1 (NS1), and nonstructural protein 2 (NS2). In some embodiments, the RNA (at least one RNA) of an RSV vaccine may encode 1, 2, 3, 4, 5, 6, 7, 8, 9, 10, 11, 12, or more antigens.

In some embodiments, an RSV vaccine includes an RNA or multiple RNAs encoding two or more antigens selected from glycoprotein G and glycoprotein F. In some embodiments, an RSV vaccine includes an RNA or multiple RNAs encoding two or more antigens selected from glycoprotein G and matrix protein. In some embodiments, an RSV vaccine includes an RNA or multiple RNAs encoding two or more antigens selected from glycoprotein F and matrix protein.

In some embodiments, two or more different RNA (e.g., mRNA) encoding antigens may be formulated in the same lipid nanoparticle. In other embodiments, two or more different RNA encoding antigens may be formulated in separate lipid nanoparticles (each RNA formulated in a single lipid nanoparticle). The lipid nanoparticles may then be combined and administered as a single vaccine composition (e.g., comprising multiple RNA encoding multiple antigens) or may be administered separately.

Combination Vaccines

The RSV vaccines, as provided herein, may include an RNA or multiple RNAs encoding two or more antigens of the same or different RSV strains. Also provided herein are combination vaccines that include RNA encoding one or more RSV antigen(s) and one or more antigen(s) of a different organisms (e.g., bacterial and/or viral organism). Thus, the vaccines of the present disclosure may be combination vaccines that target one or more antigens of the same strain/species, or one or more antigens of different strains/species, e.g., antigens which induce immunity to organisms which are found in the same geographic areas where the risk of RSV infection is high or organisms to which an individual is likely to be exposed to when exposed to RSV.

Dosing/Administration

Provided herein are compositions (e.g., pharmaceutical compositions), methods, kits and reagents for prevention and/or treatment of RSV in humans and other mammals. RSV RNA vaccines can be used as therapeutic or prophylactic agents. In some aspects, the RNA vaccines of the disclosure are used to provide prophylactic protection from RSV. In some aspects, the RNA vaccines of the disclosure are used to treat an RSV infection. In some embodiments, the RSV vaccines of the present disclosure are used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, the RSV vaccines are administered to a subject (e.g., a mammalian subject, such as a human subject) in an effective amount to induce an antigen-specific immune response. The RNA encoding the RSV antigen is expressed and translated in vivo to produce the antigen, which then stimulates an immune response in the subject.

Prophylactic protection from RSV can be achieved following administration of an RSV RNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against RSV is provided in aspects of the present disclosure. The method involves administering to the subject an RSV RNA vaccine comprising at least one RNA (e.g., mRNA) comprising an open reading frame encoding at least one RSV antigen, thereby inducing in the subject an immune response specific to RSV antigen, wherein anti-antigen antibody titer in the subject is increased following vaccination relative to anti-antigen antibody titer in a subject vaccinated with a prophylactically effective dose of a traditional vaccine against the RSV. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the RSV or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the RSV or an unvaccinated subject.

A method of eliciting an immune response in a subject against an RSV is provided in other aspects of the disclosure. The method involves administering to the subject an RSV RNA vaccine comprising at least one RNA polynucleotide comprising an open reading frame encoding at least one RSV antigen, thereby inducing in the subject an immune response specific to RSV antigen, wherein the immune response in the subject is equivalent to an immune response in a subject vaccinated with a traditional vaccine against the RSV at 2 times to 100 times the dosage level relative to the RNA vaccine.

In some embodiments, the immune response in the subject is equivalent to an immune response in a subject vaccinated with a traditional vaccine at twice the dosage level relative to the RSV RNA vaccine. In some embodiments, the immune response in the subject is equivalent to an immune response in a subject vaccinated with a traditional vaccine at three times the dosage level relative to the RSV RNA vaccine. In some embodiments, the immune response in the subject is equivalent to an immune response in a subject vaccinated with a traditional vaccine at 4 times, 5 times, 10 times, 50 times, or 100 times the dosage level relative to the RSV RNA vaccine. In some embodiments, the immune response in the subject is equivalent to an immune response in a subject vaccinated with a traditional vaccine at 10 times to 1000 times the dosage level relative to the RSV RNA vaccine. In some embodiments, the immune response in the subject is equivalent to an immune response in a subject vaccinated with a traditional vaccine at 100 times to 1000 times the dosage level relative to the RSV RNA vaccine.

In other embodiments, the immune response is assessed by determining antibody titer in the subject. In other embodiments, the ability of serum or antibody from an immunized subject is tested for its ability to neutralize viral uptake or reduce RSV transformation of human B lymphocytes. In other embodiments, the ability to promote a robust T cell response(s) is measured using art recognized techniques.

Other aspects the disclosure provide methods of eliciting an immune response in a subject against an RSV by administering to the subject an RSV RNA vaccine comprising at least one RNA polynucleotide comprising an open reading frame encoding at least one RSV antigen, thereby inducing in the subject an immune response specific to RSV antigen, wherein the immune response in the subject is induced 2 days to 10 weeks earlier relative to an immune response induced in a subject vaccinated with a prophylactically effective dose of a traditional vaccine against the RSV. In some embodiments, the immune response in the subject is induced in a subject vaccinated with a prophylactically effective dose of a traditional vaccine at 2 times to 100 times the dosage level relative to the RNA vaccine.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against an RSV by administering to the subject an RSV RNA vaccine comprising an open reading frame encoding a first antigen, wherein the RNA polynucleotide does not include a stabilization element, and wherein an adjuvant is not co-formulated or co-administered with the vaccine.

RSV RNA (e.g., mRNA) vaccines may be administered by any route which results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. RSV RNA (e.g., mRNA) vaccines compositions are typically formulated in dosage unit form for ease of administration and uniformity of dosage. It will be understood, however, that the total daily usage of RSV RNA (e.g., mRNA) vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of an RSV vaccine, as provided herein, may be as low as 20 µg, administered for example as a single dose or as two 10 µg doses. In some embodiments, the effective amount is a total dose of 20 µg-200 µg. For example, the effective amount may be a total dose of 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 160 µg, 170 µg, 180 µg, 190 µg or 200 µg. In some embodiments, the effective amount is a total dose of 25 µg-200 µg. In some embodiments, the effective amount is a total dose of 50 µg-200 µg.

In some embodiments, RSV RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013/078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, RSV RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, RSV RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, RSV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, an RSV RNA (e.g., mRNA) vaccine composition may be administered three or four times.

In some embodiments, RSV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the RSV RNA (e.g., mRNA) vaccine for use in a method of vaccinating a subject is administered the subject a single dosage of between 10 µg/kg and 400 µg/kg of the nucleic acid vaccine in an effective amount to vaccinate the subject. In some embodiments, the RNA vaccine for use in a method of vaccinating a subject is administered the subject a single dosage of between 10 µg and 400 µg of the nucleic acid vaccine in an effective amount to vaccinate the subject. In some embodiments, an RSV RNA (e.g., mRNA) vaccine for use in a method of vaccinating a subject is administered to the subject as a single dosage of 25-1000 µg (e.g., a single dosage of mRNA encoding an RSV antigen). In some embodiments, an RSV RNA vaccine is administered to the subject as a single dosage of 25, 50, 100, 150, 200, 250, 300, 350, 400, 450, 500, 550, 600, 650, 700, 750, 800, 850, 900, 950 or 1000 µg. For example, an RSV RNA vaccine may be administered to a subject as a single dose of 25-100, 25-500, 50-100, 50-500, 50-1000, 100-500, 100-1000, 250-500, 250-1000, or 500-1000 µg. In some embodiments, an RSV RNA (e.g., mRNA) vaccine for use in a method of vaccinating a subject is administered to the subject as two dosages, the combination of which equals 25-1000 µg of the RSV RNA (e.g., mRNA) vaccine.

An RSV RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Vaccine Efficacy

Some aspects of the present disclosure provide formulations of the RSV RNA (e.g., mRNA) vaccine, wherein the RSV RNA vaccine is formulated in an effective amount to produce an antigen specific immune response in a subject (e.g., production of antibodies specific to an anti-RSV antigen). "An effective amount" is a dose of an RSV RNA (e.g., mRNA) vaccine effective to produce an antigen-specific immune response. Also provided herein are methods of inducing an antigen-specific immune response in a subject.

As used herein, an immune response to a composition (e.g., mRNA formulated with or without LNP) of the present disclosure is the development in a subject of a humoral and/or a cellular immune response to a (one or more) RSV protein(s) present in the composition. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function, and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-RSV antigen antibody titer produced in a subject administered an RSV RNA (e.g., mRNA) vaccine as provided herein. An antibody titer is a measurement of the amount of antibodies within a subject, for example, antibodies that are specific to a particular antigen (e.g., an anti-RSV antigen) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the RSV RNA (e.g., mRNA) vaccine.

In some embodiments, an anti-RSV antigen antibody titer produced in a subject is increased by at least 1 log relative to a control. For example, anti-RSV antigen antibody titer produced in a subject may be increased by at least 1.5, at least 2, at least 2.5, or at least 3 log relative to a control. In some embodiments, the anti-RSV antigen antibody titer produced in the subject is increased by 1, 1.5, 2, 2.5 or 3 log relative to a control. In some embodiments, the anti-RSV antigen antibody titer produced in the subject is increased by 1-3 log relative to a control. For example, the anti-RSV antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-RSV antigen antibody titer produced in a subject is increased at least 2 times relative to a control. For example, the anti-RSV antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-RSV antigen antibody titer produced in the subject is increased 2, 3, 4, 5, 6, 7, 8, 9, or 10 times relative to a control. In some embodiments, the anti-RSV antigen antibody titer produced in a subject is increased 2-10 times relative to a control. For example, the anti-RSV antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-RSV antigen antibody titer produced in a subject who has not been administered an RSV RNA (e.g., mRNA) vaccine. In some embodiments, a control is an anti-RSV antigen antibody titer produced in a subject administered a recombinant or purified RSV protein vaccine. Recombinant protein vaccines typically include protein antigens that either have been produced in a heterologous expression system (e.g., bacteria or yeast) or purified from large amounts of the pathogenic organism.

In some embodiments, the ability of an RSV vaccine to be effective is measured in a murine model. For example, the RSV vaccines may be administered to a murine model and the murine model assayed for induction of neutralizing antibody titers. Viral challenge studies may also be used to assess the efficacy of a vaccine of the present disclosure. For example, the RSV vaccines may be administered to a murine model, the murine model challenged with RSV, and the murine model assayed for survival and/or immune response (e.g., neutralizing antibody response).

In some embodiments, the ability of an RSV vaccine to be effective is measured in a non-human primate (e.g., African green monkey) model. For example, the RSV vaccines may be administered to a non-human primate model and the murine model assayed for induction of neutralizing antibody titers. Viral challenge studies may also be used to assess the efficacy of a vaccine of the present disclosure. For example, the RSV vaccines may be administered to a non-human primate model, the non-human primate model challenged with RSV, and the non-human primate model assayed for survival and/or immune response (e.g., neutralizing antibody response).

In some embodiments, an effective amount of an RSV RNA (e.g., mRNA) vaccine is a dose that is reduced compared to the standard of care dose of a recombinant RSV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified RSV protein vaccine, or a live attenuated or inactivated RSV vaccine, or an RSV VLP vaccine, that a physician/clinician or other medical professional would administer to a subject to treat or prevent RSV, or an RSV-related condition, while following the standard of care guideline for treating or preventing RSV, or an RSV-related condition.

In some embodiments, the anti-RSV antigen antibody titer produced in a subject administered an effective amount of an RSV RNA vaccine is equivalent to an anti-RSV antigen antibody titer produced in a control subject administered a standard of care dose of a recombinant or purified RSV protein vaccine, or a live attenuated or inactivated RSV vaccine, or an RSV VLP vaccine.

In some embodiments, an effective amount of an RSV RNA (e.g., mRNA) vaccine is a dose equivalent to an at least 2-fold reduction in a standard of care dose of a recombinant or purified RSV protein vaccine. For example, an effective amount of an RSV RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified RSV protein vaccine. In some embodiments, an effective amount of an RSV RNA vaccine is a dose equivalent to an at least 100-fold, at least 500-fold, or at least 1000-fold reduction in a standard of care dose of a recombinant or purified RSV protein vaccine. In some embodiments, an effective amount of an RSV RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified RSV protein vaccine. In some embodiments, the anti-RSV antigen antibody titer produced in a subject administered an effective amount of an RSV RNA vaccine is equivalent to an anti-RSV antigen antibody titer produced in a control subject administered the standard of care dose of a recombinant or protein RSV protein vaccine, or a live attenuated or inactivated RSV vaccine, or an RSV VLP vaccine. In some embodiments, an effective amount of an RSV RNA (e.g., mRNA) vaccine is a dose equivalent to a 2-fold to 1000-fold (e.g., 2-fold to 100-fold, 10-fold to 1000-fold) reduction in the standard of care dose of a recombinant or purified RSV protein vaccine, wherein the anti-RSV antigen antibody titer produced in the subject is equivalent to an anti-RSV antigen antibody titer produced in a control subject administered the standard of care dose of a recombinant or purified RSV protein vaccine, or a live attenuated or inactivated RSV vaccine, or an RSV VLP vaccine.

In some embodiments, the effective amount of an RSV RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 300-, 4 to 200-, 4 to 100-, 4 to 90-, 4 to 80-, 4 to 70-, 4 to 60-, 4 to 50, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant RSV protein vaccine. In some embodiments, such as the foregoing, the anti-RSV antigen antibody titer produced in the subject is equivalent to an anti-RSV antigen antibody titer produced in a control subject administered the standard of care dose of a recombinant or purified RSV protein vaccine, or a live attenuated or inactivated RSV vaccine, or an RSV VLP vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 460-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant RSV protein vaccine. In some embodiments, such as the foregoing, an anti-RSV antigen antibody titer produced in the subject is equivalent to an anti-RSV antigen antibody titer produced in a control subject administered the standard of care dose of a recombinant or purified RSV protein vaccine, or a live attenuated or inactivated RSV vaccine, or an RSV VLP vaccine.

In some embodiments, the effective amount of an RSV RNA (e.g., mRNA) vaccine is a total dose of 50-1000 g. In some embodiments, the effective amount of an RSV RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 g. In some embodiments, the effective amount of an RSV RNA (e.g., mRNA) vaccine is a total dose of 50, 100, 150, 200, 250, 300, 350, 400, 450, 500, 550, 600, 650, 700, 750, 800, 850, 900, 950 or 1000 μg. In some embodiments, the effective amount is a dose of 25-500 g administered to the subject a total of two times. In some embodiments, the effective amount of an RSV RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 g administered to the subject a total of two times. In some embodiments, the effective amount of an RSV RNA (e.g., mRNA) vaccine is a total dose of 25, 50, 100, 150, 200, 250, 300, 350, 400, 450, or 500 g administered to the subject a total of two times.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

Efficacy=(ARU−ARV)/ARU×100; and

Efficacy=(1−RR)×100.

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

Effectiveness=(1−OR)×100.

In some embodiments, efficacy of the RSV vaccine is at least 60% relative to unvaccinated control subjects. For example, efficacy of the RSV vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of an RSV vaccine of the present disclosure is sufficient to provide sterilizing immunity in the subject for at least 1 year. For example, the effective amount of an RSV vaccine of the present disclosure is sufficient to provide sterilizing immunity in the subject for at least 2 years, at least 3 years, at least 4 years, or at least 5 years. In some embodiments, the effective amount of an RSV vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of an RSV vaccine of the present disclosure is sufficient to produce detectable levels of RSV antigen as measured in serum of the subject at 1-72 hours post administration.

Titer. An antibody titer is a measurement of the amount of antibodies within a subject, for example, antibodies that are specific to a particular antigen (e.g., an anti-RSV antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of an RSV vaccine of the present disclosure is sufficient to produce a 1,000-10,000 neutralizing antibody titer produced by neutralizing antibody against the RSV antigen as measured in serum of the subject at 1-72 hours post administration. In some embodiments, the effective amount is sufficient to produce a 1,000-5,000 neutralizing antibody titer produced by neutralizing antibody against the RSV antigen as measured in serum of the subject at 1-72 hours post administration. In some embodiments, the effective amount is sufficient to produce a 5,000-10,000 neutralizing antibody titer produced by neutralizing antibody against the RSV antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-RSV antigen antibody titer produced in the subject is increased by at least 1 log relative to a control. For example, an anti-RSV antigen antibody titer produced in the subject may be increased by at least 2, 3, 4, 5, 6, 7, 8, 9 or 10 log relative to a control.

In some embodiments, an anti-RSV antigen antibody titer produced in the subject is increased at least 2 times relative to a control. For example, an anti-RSV antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated RSV vaccine, an inactivated RSV vaccine, or a protein subunit RSV vaccine.

EXAMPLES

Example 1: Cotton Rat Immunogenicity and Efficacy

In this example, assays were carried out to test the immunogenicity and efficacy of mRNA/LNP vaccines in the cotton rat RSV challenge model. More specifically, female

*Sigmodon hispidus* cotton rats were used and immunizations began at 6-7 weeks of age. The mRNA vaccines used were generated and formulated in lipid nanoparticles (e.g the LNP comprises 58 mole % (13Z,16Z)—N,N-dimethyl-2-nonyl-henicosa-12,15-dien-1-amine, 30 mole % cholesterol, 10 mole % DSPC, and 2 mole % PEG-2000 DMG). The mRNA vaccines evaluated in this study included:

MRK-04 membrane-bound DS-Cav1 (stabilized prefusion F protein) (SEQ ID NO: 90)

MRK-04_nopolyA_3mut membrane-bound DS-Cav1 (stabilized prefusion F protein) (SEQ ID NO: 92)

mVRC-1 (v2) membrane-bound single chain sc9 mDS-Cav1, A149C, Y458C (stabilized prefusion F protein) (SEQ ID NO: 21)

mLZF-111 membrane-bound single chain mDS-Cav1, D486C, D489C (stabilized prefusion F protein) (SEQ ID NO: 74)

Groups of 8 cotton rats were immunized intramuscularly with 100 μL of vaccine, delivered with 50 μL injections into each quadriceps. The groups were vaccinated with the following vaccines:

TABLE 1

Vaccine Formulations Tested for Cotton Rats

| Group | Vaccine | SEQ ID NO: | Conc (μg/ml) | Dose (μg) |
|---|---|---|---|---|
| 1 | None | n/a | NA | NA |
| 2 | MRK-04, I.M. | 90 | 250 | 25 |
| 3 | MRK-04_nopolyA_3mut, I.M. | 92 | 250 | 25 |
| 4 | MRK-04_nopolyA_3mut, I.M. | 92 | 50 | 5 |
| 5 | MRK-04_nopolyA_3mut, I.M.. | 92 | 10 | 1 |
| 6 | mVRC-1 (v2), I.M. | 21 | 250 | 25 |
| 7 | mVRC-1 (v2), I.M. | 21 | 50 | 5 |
| 8 | mVRC-1 (v2), I.M. | 21 | 10 | 1 |
| 9 | mLZF-111, I.M. | 74 | 250 | 25 |
| 10 | mLZF-111, I.M. | 74 | 50 | 5 |
| 11 | mLZF-111, I.M. | 74 | 10 | 1 |

The animals were immunized on day 0 and day 28 of the experiment. On days 28 and 56, blood was drawn from each animal and used for serological assays. On day 56, the cotton rats were challenged intranasally with $1 \times 10^{5.5}$ PFU RSV A2. Four days post inoculation animals were sacrificed by $CO_2$ inhalation and lung (left lobes) and nasal turbinates were removed and homogenized in 10 volumes of Hanks Balanced Salt Solution (Lonza) containing SPG on wet ice. The samples were clarified by centrifugation at 2000 rpm for 10 minutes, aliquoted, flash frozen, and immediately stored frozen at −70° C.

A. RSV Neutralization Assay:

Cotton rat sera from each animal was evaluated for neutralization of RSV-A (Long strain) using the following procedures:

1. All sera samples were heat inactivated by placing in dry bath incubator set at 56° C. for 30 minutes. Samples and control sera were then diluted 1:3 in virus diluent (2% FBS in EMEM) and duplicate samples were added to an assay plate and serially diluted.
2. RSV-Long stock virus was removed from the freezer and quickly thawed in 37° C. water bath. Viruses were diluted to 2000 pfu/mL in virus diluent
3. 50 μL of diluted virus was added to each well of the 96-well plate, with the exception of one column of cells, which used as a "no-virus" control
4. HEp-2 cells were trypsinized, washed, resuspended at $1.5 \times 10^5$ cells/ml in virus diluent, and 100 mL of the suspended cells were added to each well of the 96-well plate. The plates were then incubated for 72 hours at 37° C., 5% $CO_2$.
5. Following the 72 hour incubation, the cells were washed with PBS, and fixed using 80% acetone dissolved in PBS for 10-20 minutes at 16-24° C. The fixative was removed and the plates were allowed to air-dry.
6. Plates were then washed thoroughly with PBS+0.05% Tween™ (polysorbate). The detections monoclonal antibodies, 143-F3-1B8 and 34C9 were diluted to 2.5 μg/mL in assay diluent (1% BSA-PBS-0.1% Tween), and 50 μL of the diluted antibodies were added to each well of the 96-well plate. The plates were then incubated in a humid chamber at 16-24° C. for 60-75 minutes on rocker.
7. Following the incubation, the plates were thoroughly washed.
8. Biotinylated horse anti-mouse IgG was diluted 1:200 in assay diluent and added to each well of the 96-well plate. Plates were incubated as above and washed.
9. A cocktail of IRDye 800CW Streptavidin (1:1000 final dilution), Sapphire 700 (1:1000 dilution) and 5 mM DRAQ5 solution (1:10,000 dilution) was prepared in assay diluent and 50 mL of the cocktail was added to each well of the 96-well plate. Plates were incubated as above in the dark, washed, and allowed to air dry.
10. Plates were then read using an Aerius Imager. Serum neutralizing titers were then calculated using a 4 parameter curve fit in Graphpad Prism.

The titers determined post dose 1 (day 28) and post dose 2 (day 56) are shown in FIG. 1. It was found that the neutralizing titers were elicited in a dose dependent manner for all mRNA vaccines. All mRNA vaccines resulted in increased titers after a second dose regardless of the dose evaluated. Both mVRC-1 (v2) and mLVF111 induced higher titers then MRK-04 and MRK-04_nopolyA_3mut demonstrating superior or similar serum neutralizing titers at a 5-fold lower dose.

B. Competition alphaLISA:

The immune response to specific epitopes on RSV F-protein for neutralizing antibodies was characterized. The antigenic site II is the binding site for palivizumab, a monoclonal antibody developed for the prevention of lower respiratory infection with RSV in at risk infants and toddlers. Antigenic site Ø is a binding site for more potent neutralizing antibodies that are elicited by natural infection with RSV. Additionally, we have generated an antibody (4D7) that targets site I, an epitope not presented in the prefusion conformation. Therefore, in contrast to D25, elicitation of 4D7-competing antibodies would suggest the in vivo generation of postF-like proteins. A competition alphaLTSA was developed to characterize the antigenic site 0, antigenic site I and antigenic site II response to the various mRNA-based vaccines.

To measure competing antibody titers, 10 μl of samples serially diluted in HiBlock buffer (PerkinElmer) are placed in a 384 well alphaLISA plate. Diluted samples are mixed with 5 μl of AlphaLISA acceptor beads (100 μg/ml) that has been previously conjugated to a prefusion-stabilized RSV F protein (DS-Cav1) or a postfusion RSV F protein (RSV F wt). After 30 min incubation at room temperature, 10 μl of biotinylated D25, palimizumab, or 4D7 antibody diluted in Hiblock buffer is added to every well. After additional 30 min incubation, 25 μl of streptavidin-donor beads (20 μg/ml)

in HiBlock buffer is added to each well and incubated for 30 min in the dark. Plate is then read on an EnVision_Alpha Reader (615 nm detection).

Figure 2:
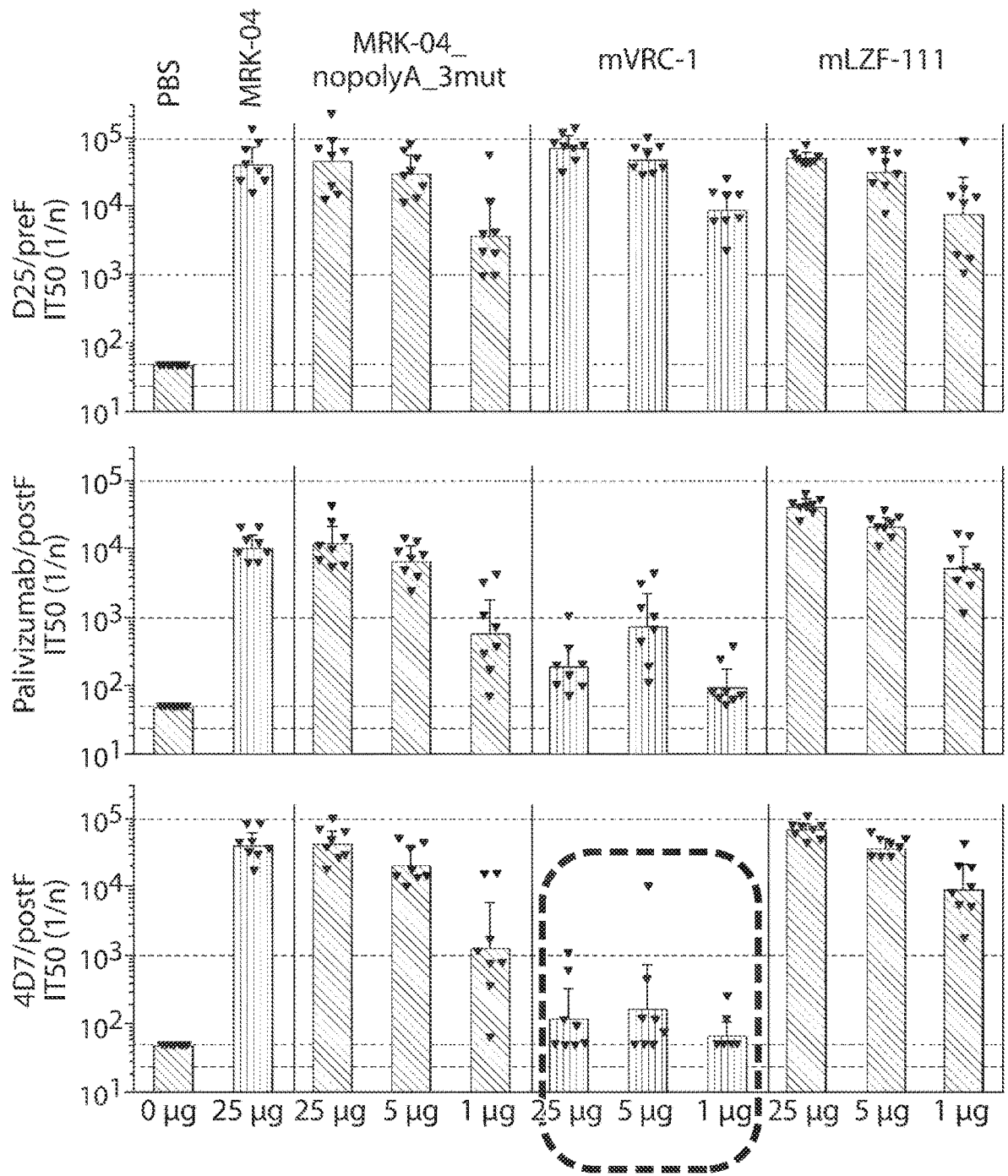
FIG. 2 shows a graph of serum antibody competition ELISA Titers ($IT_{50}$ Individual and GMT with 95% confidence intervals) against D25 (site Ø), palivizumab (site II), and 4D7 (site I) measured at Day 56 (4 weeks PD2).

The palivizumab, D25 and 4D7 competing antibody titers measured on Day 56 (4 weeks PD2) are presented in FIG. 2. The competition data revealed that mVRC-1 (v2) induced lower levels of 4D7-postfusion F competing antibodies, while D25-prefusion titers and palivizumab titers are not affected. This different competition profile correlates with mVRC-1 (v2) mRNA expressing a more prefusion stabilized protein then MRK-04_nopolyA_3mut and mLZF-111.

C. Cotton Rat Challenge Results

Procedures for measuring RSV titers in the cotton rat Lung and nose homogenates are described below. Lung and nose homogenates were clarified by centrifugation and diluted 1:10 and 1:100 in EMEM. Confluent HEp-2 monolayers were infected in duplicates with 50 µl per well starting with undiluted (neat) samples followed by diluted homogenates in 24-well plates. After one hour incubation at 37° C. in a 5% $CO_2$ incubator, wells were overlaid with 0.75% methylcellulose medium and plates restored into the 37° C. incubator. After 4 days of incubation the overlay was removed and the cells were fixed with 0.1% crystal violet stain for one hour, then rinsed, and air-dried. Plaques were counted and virus titers were expressed as plaque forming units per gram of tissue.

Figure 3:
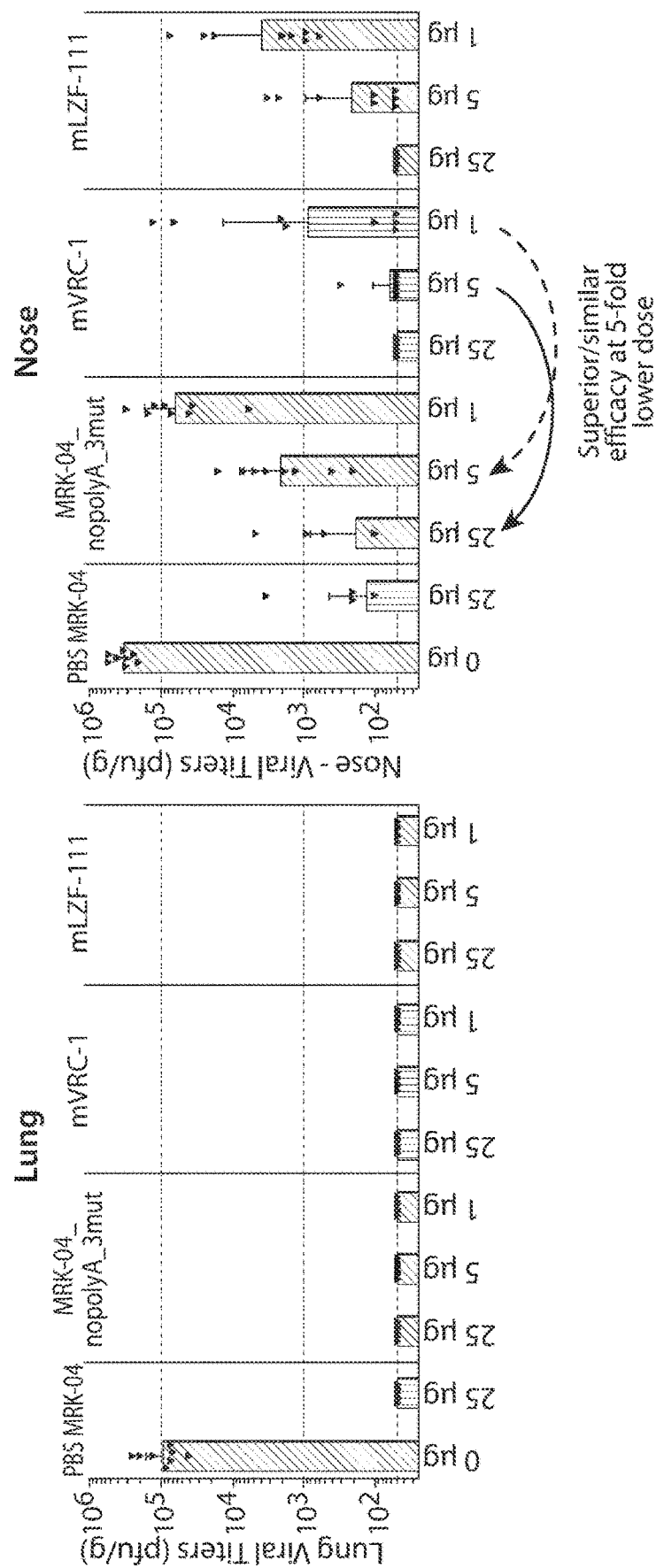
FIG. 3 shows graphs of RSV content in lung and nose after challenge of cotton rats with RSV A.

To assess vaccine-mediated protection, viral titers were measured in lung and nose 5 days after challenge. All mRNA vaccines achieved total protection in the lung, but mVRC-1 (v2) and mLZF-111 showed improved protection in the nose, demonstrating superior or similar efficacy to MRK-04 and MRK-04nopolyA_3mut, at a 5-fold lower dose (FIG. 3).

Example 2: African Green Monkey Immunogenicity and Efficacy

In this example, assays were carried out to test the immunogenicity and efficacy of mRNA/LNP vaccines in the African Green Monkey RSV challenge model.

More specifically, male and female adult African Green Monkeys with body weights ranging from 1.6 to 2.65 kg, which were confirmed to be RSV-negative by neutralizing antibody titer, were used. The mRNA vaccines used were generated and formulated in lipid nanoparticles (e.g the LNP comprises 58 mole % (13Z,16Z)—N,N-dimethyl-2-nonyl-henicosa-12,15-dien-1-amine, 30 mole % cholesterol, 10 mole % DSPC, and 2 mole % PEG-2000 DMG). The mRNA vaccines evaluated in this study included:

MRK-04_nopolyA_3mut membrane-bound DS-Cav1 (stabilized prefusion F protein) (SEQ ID NO: 92)

mVRC-1 (v2) membrane-bound single chain sc9 mDS-Cav1, A149C, Y458C (stabilized prefusion F protein) (SEQ ID NO: 21)

mLZF-111 membrane-bound single chain mDS-Cav1, D486C, D489C (stabilized prefusion F protein) (SEQ ID NO: 74)

Groups of 4 African Green Monkeys were immunized intramuscularly with 500 µL of vaccine into one deltoid. The groups were vaccinated with the following vaccines as out in

TABLE 2

Vaccine Formulations Tested for Immunogenicity in African Green Monkeys

| Group | Vaccine | Conc (µg/ml) | Dose (µg) |
|---|---|---|---|
| 1 | MRK-04_nopolyA_3mut, I.M. | 50 | 25 |
| 2 | MRK-04_nopolyA_3mut, I.M. | 10 | 5 |
| 3 | mVRC-1 (v2) | 50 | 25 |
| 4 | mVRC-1 (v2) | 10 | 5 |
| 5 | mLZF-111 | 50 | 25 |
| 6 | mLZF-111 | 10 | 5 |
| 7 | RSV A2 5.5log10pfu, I.N. | NA | NA |
| 8 | None | NA | NA |

The animals were immunized on day 0, day 28, and day 56 of the experiment. On days 0, 14, 28, 42, 56, and 70, blood was drawn from each animal and used for serological assays. On day 70, the African Green Monkeys were challenged intranasally with $1\times10^5$. PFU RSV A2. Nasopharyngeal swabs were collected on days 1-14 post challenge, and lung lavage samples were collected on days 3, 5, 7, 9, 12 and 14 post challenge to test for viral replication.

Figure 4:
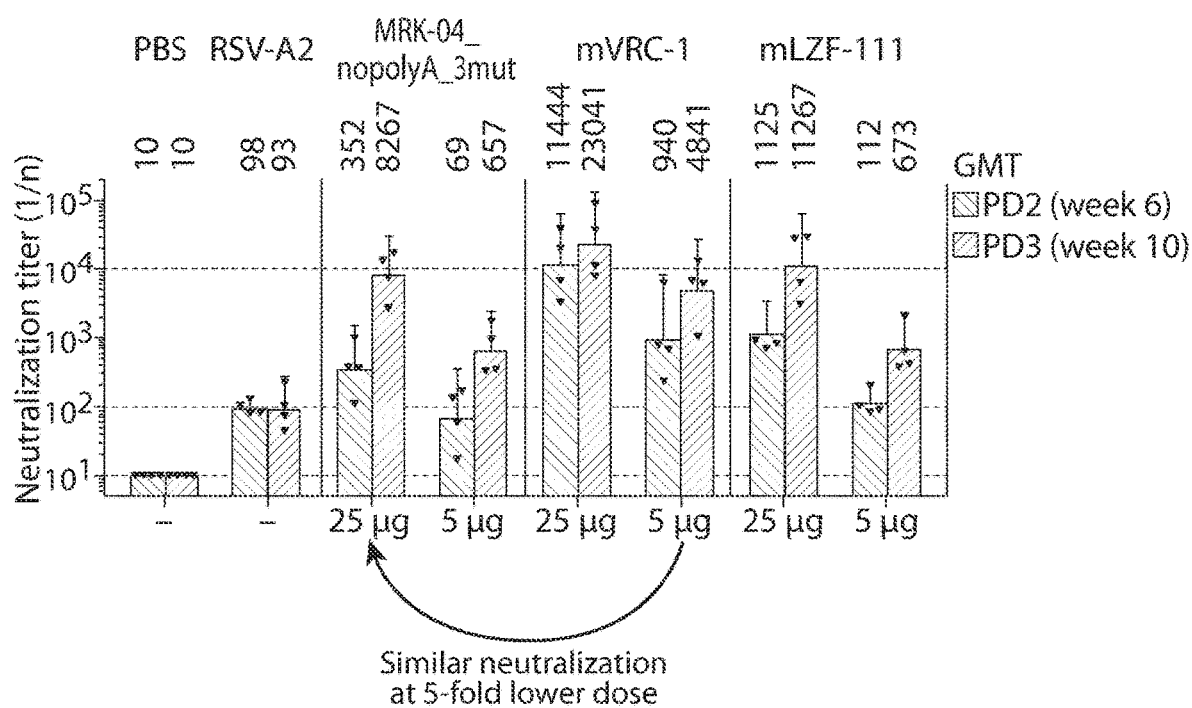
FIG. 4 shows serum neutralizing antibody titers ($NT_{50}$ Individual and GMT with 95% confidence Iintervals) to RSV A induced in African green monkeys by mRNA vaccines and control Formulations.

A. RSV Neutralization Assay:

Monkey sera from each animal were evaluated for neutralization of RSV-A (Long strain) as described above. The $NT_{50}$ titers determined post dose 1 and post dose 2 are shown in FIG. 4. Titers were seen to increase after each dose all groups receiving mRNA vaccines. The GMTs obtained with mRNA vaccines at week 10 (2 weeks post-dose 3) were 1 to 2 orders of magnitude higher than in the animals that received RSV A2 depending on the dose and mRNA being tested. Serum samples from mVRC-1 (v2) immunized animals exhibited the highest neutralization titers, demonstrating a five-fold higher potency relative to MRK-04_nopolyA_3mut.

B. Competition ELISA

Competition ELISA titers were determined for palivizumab, D25 and 4D7 to characterize the antigenic site 0, antigenic site I and antigenic site II response to the various mRNA-based vaccines as described above.

Figure 5:
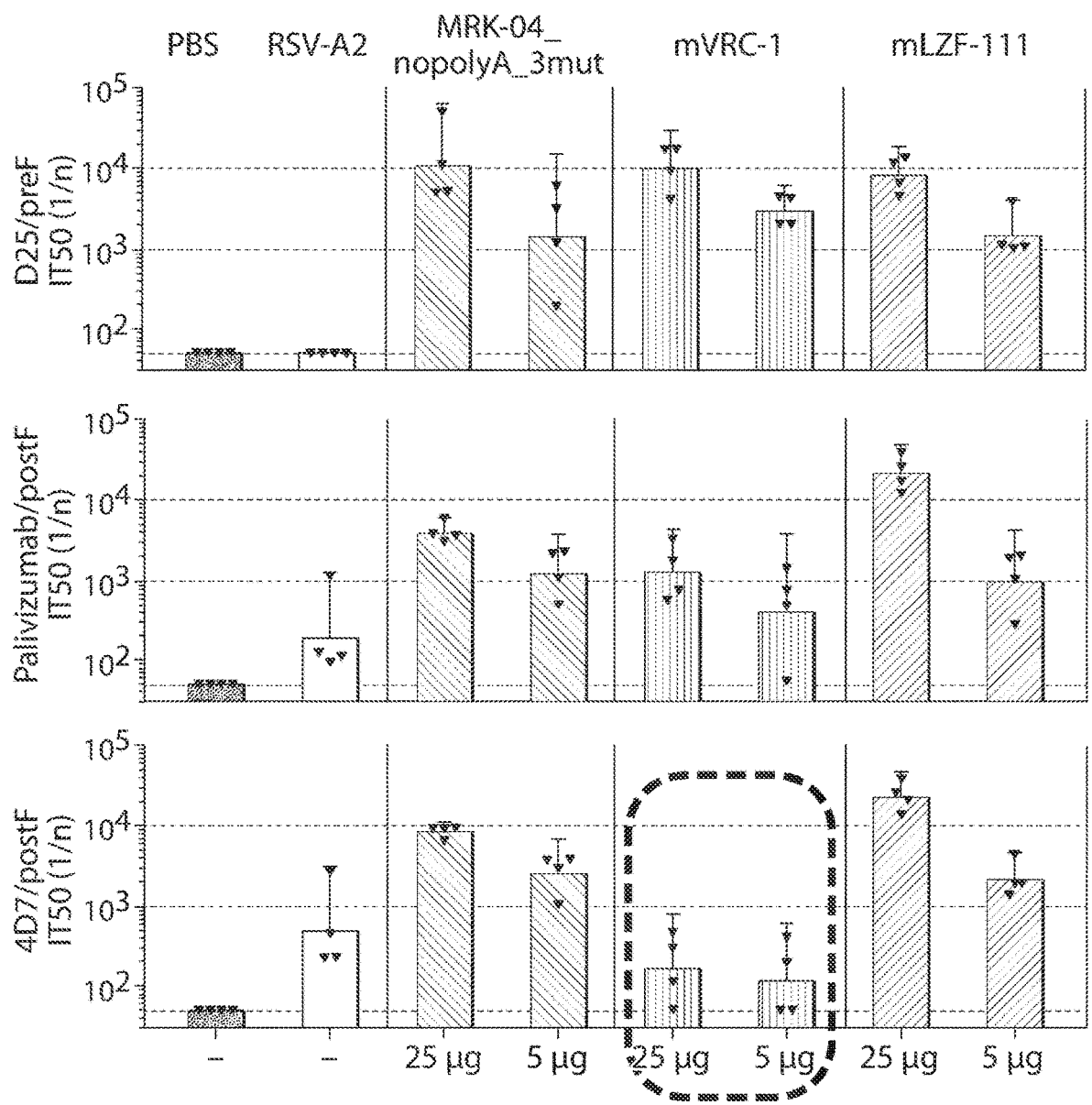
FIG. 5 shows serum antibody competition ELISA titers ($IT_{50}$ Individual and GMT with 95% confidence intervals) against D25 (site 0), palivizumab (site II), and 4D7 (site I) measured at week 10 (2 weeks PD3).

The palivizumab, D25 and 4D7 competing antibody titers measured at week 10 (2 weeks PD3) are presented in FIG. 5. The competition data revealed that mVRC-1 (v2) induced lower levels of 4D7-postfusion F competing antibodies, while D25-prefusion titers and palivizumab titers are not affected. This different competition profile correlates with mVRC-1 (v2) mRNA expressing a more prefusion stabilized protein then MRK-04_nopolyA_3mut and mLZF-111.

C. African Green Monkey Challenge Results

As mentioned above, in order to evaluate vaccine efficacy African Green Monkeys were challenged intranasally with $1\times10^5$ PFU RSV A2 on day 70 post vaccination and nasopharyngeal swabs and lung lavage samples were collected post challenge to test for the presence of virus.

Figure 6A:
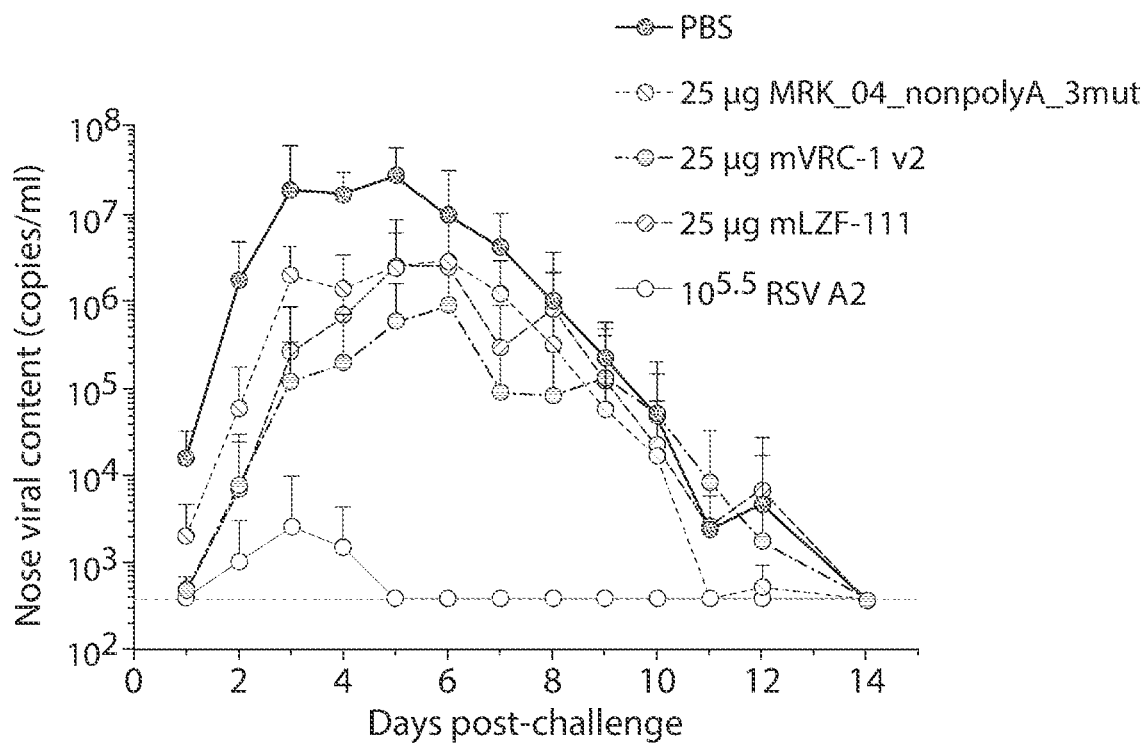
FIGS. 6A-6C shows RSV content in bronchoalveolar (BAL) fluid after challenge of AGMs
Figure 6B:
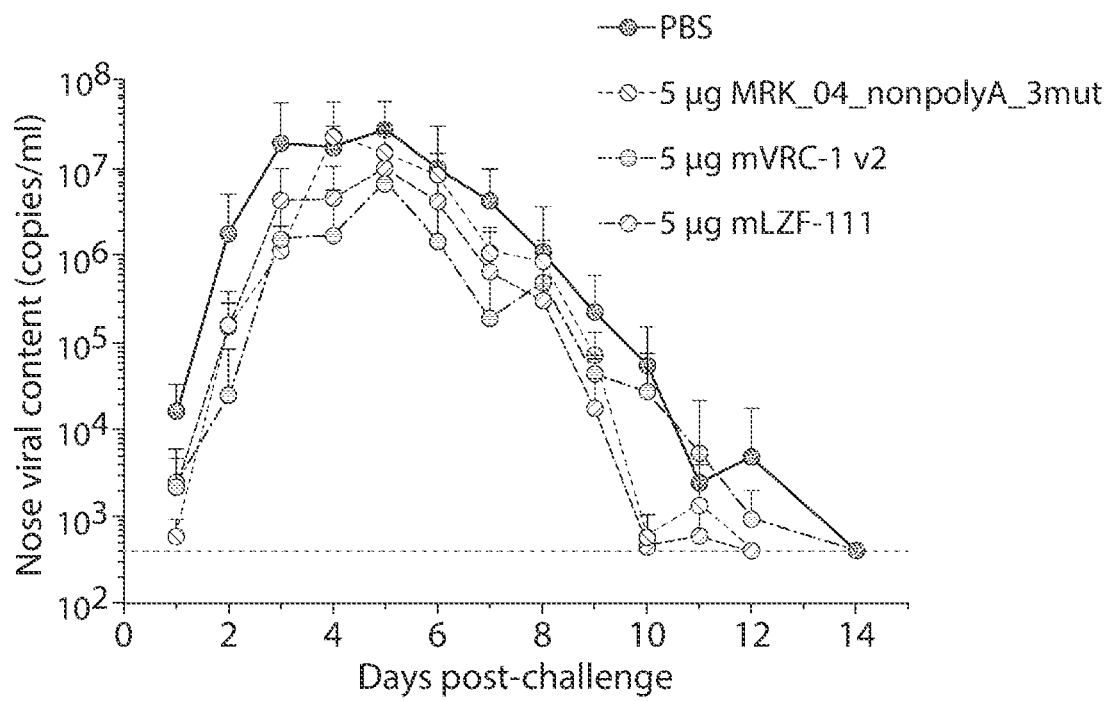
Figure 6C:
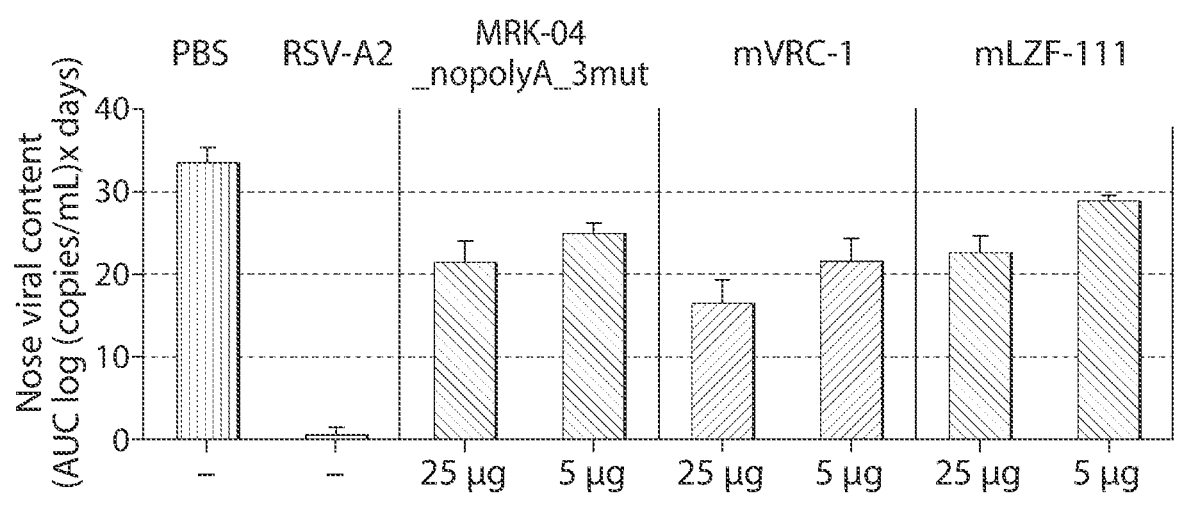

In order to measure RSV titers in the African Green Monkey lung lavage samples a viral plaque assay procedure for measuring viral titers was followed as outlined below. Briefly, samples were diluted and added in duplicate to 24-well plates containing confluent HEp-2 cell monolayers. The plates were incubated at 37° C. for one hour. Following the one hour incubation, sample inoculum was aspirated and 1 ml of overlay containing 0.75% methylcellulose was added. The plates were incubated at 37° C. for 5 days. Following the 5 day incubation, the cells were fixed and stained with crystal violet/glutaraldehyde solution. Plaques were counted and titers were expressed as pfu/ml. Analysis of viral content in bronchoalveolar lavage (BAL) fluid (FIGS. 6A-6C) revealed that only mVRC-1 (v2) (25 µg) conferred total protection in the lung, and it afforded the best protection at a lower dose (5 µg).

In order to measure RSV titers in the African Green Monkey nasopharyngeal swabs an RSV RT-qPCR assay to detect RSV A was carried out as follows:

1) Equipment and Materials:
A. Equipment
 1. Stratagene Mx3005P Real Time PCR system and MxPro Software
 2. Jouan GR422 centrifuge or equivalent
 3. Jouan Plate carriers or equivalent
B. Reagents
 1. Quantitect® Probe Rt-PCR kit (1000) catalog #204445
 2. Water, Molecular Biology Grade DNAase-free and Protease free, 5 Prime, catalog #2900136
 3. TE buffer, 10 mM Tris 1 mM EDTA ph 8.0, Fisher Bioreagents, catalog #BP2473-100
 4. Viral primers: RSV A Forward and Reverse primers, Sigma custom, HPLC purified. Primer stocks are reconstituted to 100 uM in Molecular grade water and stored at −20° C.
 5. RSV dual labeled probe, Sigma custom, HPLC purified. Probe stocks are reconstituted to 100 uM in TE buffer and stored at −20° C. protected from light.
 6. RSV A standard were generated in-house and stored at −20° C. Standards for the assay were generated by designing primer pairs to the N gene of RSV A. The product length for the RSV A standard is 885 bp. QIAGEN OneStep RT-PCR was used to generate this standard.

TABLE 3

Primer Sequences

| Primers | Sequences |
|---|---|
| RSV A F N gene | 5' CTC AAT TTC CTC ACT TCT CCA GTG T (SEQ ID NO: 93) |
| RSV A R N gene | 5' CTT GAT TCC TCG TGT ACT CTG T (SEQ ID NO: 94) |
| RSV A FAM N gene | 5'FAM-TCC CAT TAT GCC TAG GCC AGC AGC A(BHQ1) (SEQ ID NO: 95) |

7. Promega, Maxwell® 16 Viral Total Nucleic Acid Purification Kit (Product #AS1150
C. Supplies
 1. Stratagene Optical cap 8× strip, catalog #401425
 2. Stratagene Mx3000P 96 well plates, skirted, catalog #401334
 3. ART filtered pipet tips
2) RT-PCR Reactions and set up
A. Preparation of Complete Master Mix
 1. Prepare complete Master Mix following the set up below for a final reaction volume of 50 µL. The following table is volume per well. Final primer concentration is 300 nM and final probe concentration is 200 nM.

TABLE 4

| Reagents | |
|---|---|
| Reagent | µL |
| 2X Master Mix | 25 |
| RSV A F 100 uM | 0.2 |
| RSV A R 100 uM | 0.2 |
| RSV A FAM 100 uM | 0.1 |
| RT enzyme mix | 0.5 |
| Water | 19 |

2. Add 45 µL of complete master mix to each well. Cover plate with plate cover and wrap in aluminum foil to protect from light.
B. Preparation of Standard curve
 1. Remove standard from −20° C.
 2. Dilute standards to final concentrations of 1e6 copy/5 µL to 1 copy/5 L using 10-fold dilutions.
C. Sample preparation
 1. Nasopharyngeal swab and lung lavage samples are prepared for the RT-PCR reaction using the Maxwell® 16 Viral Total Nucleic Acid Purification Kit (Promega, product #AS1150)
 2. 200 µL of sample is extracted following the manufactures protocol and eluted into 50 µL to be used in PCR reactions.
D. Additions of samples
 1. Add 5 µL of extracted samples to appropriate wells. After addition of samples, carefully cap sample wells before adding standard curves.
 2. Add 5 µL of diluted standard to appropriate wells and cap.
 3. Add 5 µL of molecular grade water to No Template Control (NTC) wells.
 4. Wrap plates in aluminum foil and transfer plates to centrifuge.
 5. Spin plates for 2 mins at 100 rpm to pull down any samples or master mix that may be on the sides of well.
 6. Wrap plates in aluminum foil and transfer to Stratagene instrument.
E. Thermo cycler: Stratagene MX 3005P
 1. Place plates in Stratagene Mx3005P and set thermal profile conditions to:

TABLE 5

| PCR Conditions | | |
|---|---|---|
| Step | Time | Temperature |
| Reverse Transcription | 30 min | 50 |
| PCR intial activation step | 15 min | 95 |
| 2-step cycling: | | |
| Denaturation | 16 sec | 94 |
| Combined annealing/extension | 60 sec | 62 |
| Number of cycles | 40 | |

2. Analyze results using the Stratagene Mx3005p software

Figure 7:
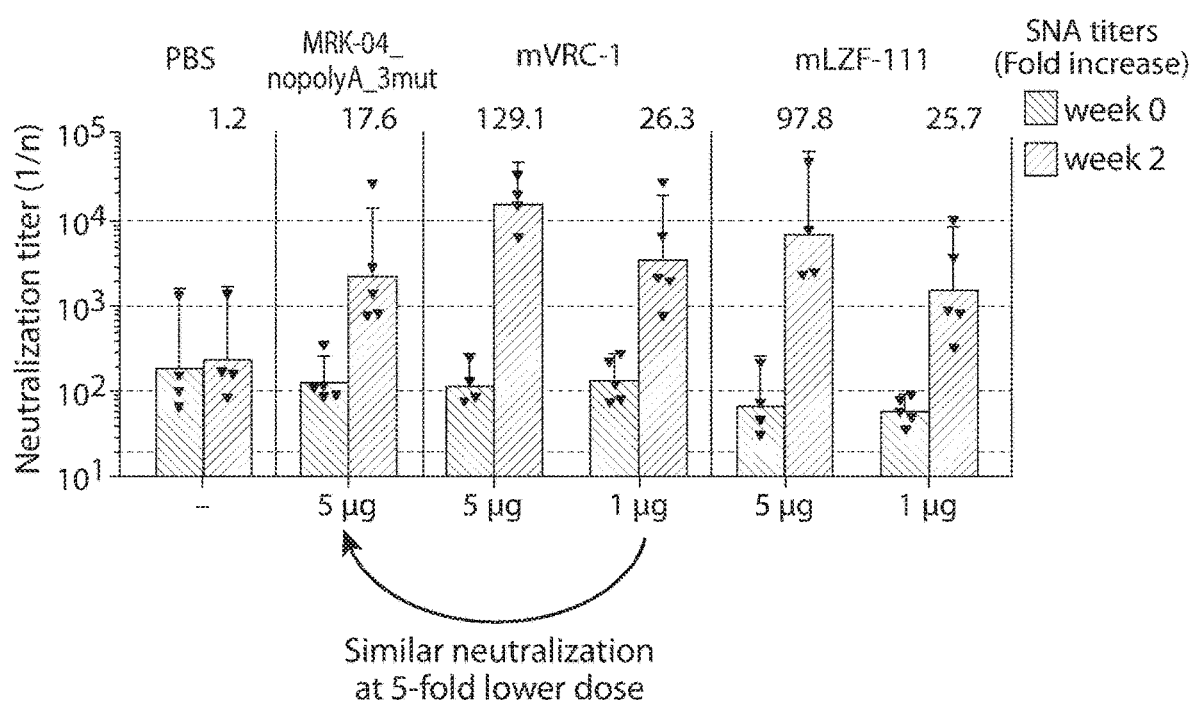
FIG. 7 shows serum neutralizing antibody titers ($NT_{50}$ Individual and GMT with 95% confidence intervals) to RSV A induced in RSV experienced African green monkeys by mRNA vaccines and control formulations.

The mean RNA copy number detected in the nose samples are presented in FIG. 7. The protective effect of all mRNA-based vaccines was less apparent in the nose, but again mVRC-1 (v2) demonstrated a 5-fold higher efficacy over MRK-04_nopolyA_3mut. mLZF-111 demonstrated decreased protection efficacy in lung and nose of AGMs relative to MRK-04_nopolyA_3mut.

Example 3: Immunogenicity in RSV-Experienced African Green Monkeys

The immunogenicity of mRNA vaccines formulated in LNP was tested in RSV-experienced African Green Monkeys.

Healthy adult, African Green Monkeys of either sex (n=4 or 5/group), with body weights ranging from 2.85 to 4.65 kg, that were confirmed to be RSV seropositive by ELISA and neutralizing antibody titers, were selected for the study. The pool of animals selected for this study had been experimentally infected with RSV in previous vaccine studies and were distributed across study groups based on their pre study RSV neutralization titers so that all groups would have similar group GMTs at study start. RSV experienced animals provide a model of immune memory recall response to vaccination that may reflect the responses that can be anticipated in seropositive human adults, with the caveat that the antibody response in AGMs following RSV exposure is more biased towards postfusion F protein epitopes than the human immune repertoire.

A single vaccine dose was administered to each animal at week 0 by the intramuscular (IM) route. A control group receiving only PBS was also included in the study design. Vaccines were administered as described in Table 6. After vaccination, the animals were observed daily for any changes at the inoculation site or other changes in activity or feeding habits that might indicate an adverse reaction to the vaccine but none were noted. Serum samples were collected for assessment of RSV neutralizing antibody titers, as well as palivizumab (site II), D25 (site 0) and 4D7 (site I) competing antibody titers. PBMC samples were collected to assess cell mediated immune responses.

TABLE 6

Vaccine Formulations Tested for Immunogenicity in RSV Seropositive African Green Monkeys

| Group | Vaccine | Conc (µg/ml) | Dose (µg) |
|---|---|---|---|
| 1 | MRK-04_nopolyA_3mut, I.M. | 10 | 5 |
| 2 | mVRC-1 (v2), I.M. | 10 | 5 |
| 3 | mVRC-1 (v2), I.M | 2 | 1 |
| 4 | mLZF-111 | 10 | 5 |
| 5 | mLZF-111 | 2 | 1 |
| 6 | None (PBS) | NA | NA |

Individual animal $NT_{50}$ titers were measured in serum samples collected at baseline and 2 weeks post vaccination using methods described above and the results are shown in FIG. 8. All vaccines were found to be highly immunogenic as demonstrated by the increase in levels of serum antibodies binding RSV F proteins (both prefusion and postfusion RSV F, data not shown) and increases in serum neutralizing antibody levels. mVRC-1 (v2) induced the highest boost in neutralizing titers (>100 fold at the highest dose), and exhibited similar potency at a 5-fold lower dose relative to MRK-04_nopolyA_3mut. Similarly, mLZF-111 also demonstrated increased potency relative to MRK-04_nopolyA_3mut. No increase in titers was observed in the PBS control group. As this study is still ongoing the durability of these immune responses will continue to be evaluated over the next several months.

Figure 8:
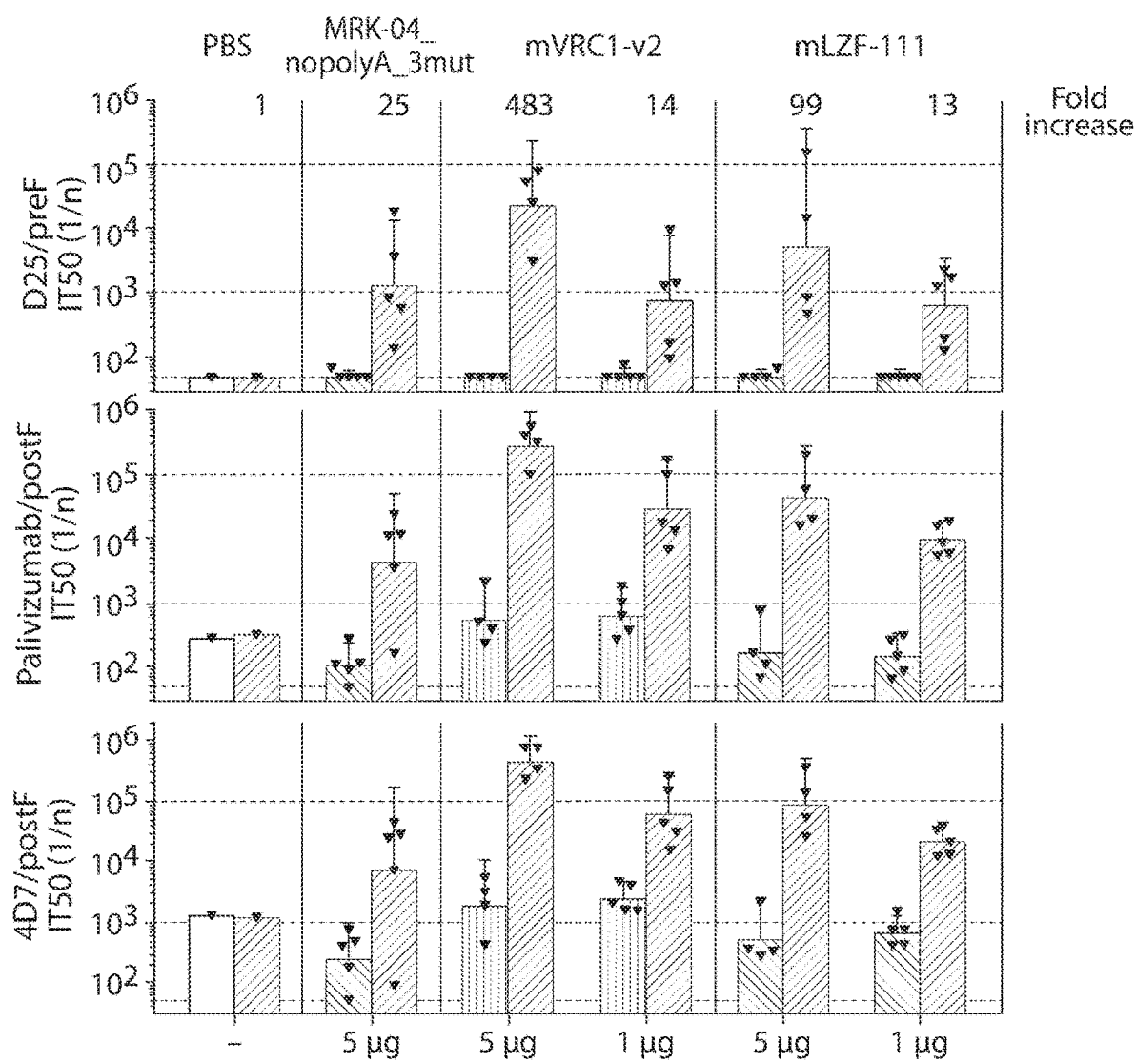
FIG. 8 shows serum antibody competition ELISA titers ($IT_{50}$ Individual and GMT with 95% confidence intervals) against D25 (site 0), palivizumab (site II), and 4D7 (site I) measured at week 2 (2 weeks PD).

To evaluate the quality of the boosted responses in the vaccinated animals, palivizumab (site II), D25 (site Ø) and 4D7 (site I) competing antibody titers were determined in serum collected at 2 weeks post vaccination (FIG. 8). As described above, antigenic site II is a neutralization epitope found on both the prefusion and the postfusion conformation of the F protein, site Ø is a prefusion specific neutralization epitope and 4D7 is a postfusion specific neutralization epitope. Due to the baseline immune bias to the postfusion conformation, RSV-experienced AGMs do not have detectable D25-competing antibody titers prior to immunization. However, all three mRNA antigens induced high competing antibodies titers, demonstrating that AGMs do mount an antigenic site 0 immune response after RSV infection that can be boosted by immunization. The boost in D25 competing antibody titers following mVRC-1 (v2) immunization were the highest (>450 fold), and demonstrating again similar potency at a 5-fold lower dose than the MRK-04_nopolyA_3mut. In contrast to naïve animals (cotton rats and AGMs) we observed a high boost of 4D7/post-F specific antibodies in RSV-experienced AGMs in the mVRC-1 (v2) group, demonstrating that the baseline antibody pool can determine the outcome of the epitope-specific antibody profile after immunization. Since the B cell memory pool from natural RSV infection in humans is thought to be strongly biased towards the prefusion conformation, we speculate mVRC-1 (v2) immunization in humans will boost preferentially antibodies against these epitopes, known to have more potent neutralizing activity, leading to increased efficacy over MRK-04_nopolyA_3mut.

SEQUENCE LISTING

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a polyA tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

(SEQ ID NO: 2)
5' UTR:
GGGAAAUAAGAGAGAAAAGAAGAGUAAGAAGAAAUAUAAGAGCCACC (SEQ ID NO: 77)
5' UTR:
GGGAAAUAAGAGAGAAAAGAAGAGUAAGAAGAAAUAUAAGACCCCGGCGC

CGCCACC (SEQ ID NO: 4)
3' UTR:
UGAUAAUAGGCUGGAGCCUCGGUGGCCAUGCUUCUUGCCCCUUGGGCCUC

CCCCCAGCCCCUCCUCCCCUUCCUGCACCCGUACCCCGUGGUCUUUGAA

UAAAGUCUGAGUGGGCGGC (SEQ ID NO: 78)
3' UTR:
UGAUAAUAGGCUGGAGCCUCGGUGGCCUAGCUUCUUGCCCCUUGGGCCUC

CCCCCAGCCCCUCCUCCCCUUCCUGCACCCGUACCCCGUGGUCUUUGAA

UAAAGUCUGAGUGGGCGGC

TABLE 7

| | mVRC-1 | |
|---|---|---|
| SEQ ID NO: 1 consists of from 5' end to 3' end: 5' UTR SEQ ID NO: 2, mRNA ORF SEQ ID NO: 3, and 3' UTR SEQ ID NO: 4. | | 1 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAAAACGCUGUGACC GAGCUGCAGUUAUUGAUGCAGAGUACACCUGCCACCGGG UCGGGCUCUGCCAUUUGCUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAAAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUGCGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGCAUAACGUGAAUGCUGGGAAA UCUAACAACCAACAUCAUGAUCACUACCAUCAUUAUUGUG AUUAUCGUAAUUCUGCUAUCCUUGAUUGCUGUCGGGCUG CUUCUGUACUGUAAGGCCAGAUCGACGCCUGUGACCCUU UCAAAAGACCAACUUAGCGGUAUCAAUAAUAUUGCCUUU AGCAAU | 3 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAICSGVAVCKVLHLEGEVNKIK SALLSTNKAVVSLSNGVSVLTFKVLDLKNYIDKQLLPILNKQS CSISNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGKSLYV KGEPIINFYDPLVFPSDEFDASISQVNEKINQSLAFIRKSDELLH NVNAGKSTTNIMITTIIIVIIVILLSLIAVGLLLYCKARSTPVTLS KDQLSGINNIAFSN | 5 |
| PolyA tail | 100 nt | |

TABLE 7-continued

| mVRC-2 | | |
|---|---|---|
| SEQ ID NO: 6 consists of from 5' end to 3' end: 5' UTR SEQ ID NO: 2, mRNA ORF SEQ ID NO: 7, and 3' UTR SEQ ID NO: 4. | | 6 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUAAGUAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAAAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCGUGUUGGAAGCUGCAUACCAGUCCACUCUGCACCACUA<br>ACACAAAGGAAGGGAGCAAUAUUUGCCUCACUCGAACCG<br>ACAGGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCAAAUCCCUUU<br>AUGUAAAGGGCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGCAUAACGUGAAUGCUGGGA<br>AAUCUACAACCAACAUCAUGAUCACUACCAUCAUUAUUG<br>UGAUUAUCGUAAUUCUGCUAUCCUUGAUUGCUGUCGGGC<br>UGCUUCUGUACUGUAAGGCCAGAUCGACGCCUGUGACCC<br>UUUCAAAAGACCAACUUAGCGGUAUCAAUAAUAUUGCCU<br>UUAGCAAU | 7 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAIASGVAVCKVLHLEGEVNKIK<br>SALLSTNKAVVSLSGCGVSVLTFKVLDLKNYIDKQLLPILNKQ<br>SCSISNIETVIEFQQKNNRLLEITREFSVNAGVTTPVSTYMLTNS<br>ELLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTFSNGCDYVSNKGVDTVSVGNTLYYVNKQEGKSLYV<br>KGEPIINFYDPLVFPSDEFDASISQVNEKINQSLAFIRKSDELLH<br>NVNAGKSTTNIMITTIIIVIIVILLSLIAVGLLLYCKARSTPVTLS<br>KDQLSGINNIAFSN | 8 |
| PolyA tail | 100 nt | |

TABLE 7-continued mVRC-3

| | | |
|---|---|---|
| SEQ ID NO: 9 consists of from 5' end to 3' end: 5' UTR SEQ ID NO: 2, mRNA ORF SEQ ID NO: 10, and 3' UTR SEQ ID NO: 4. | | 9 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCAAU<br>AACGGGUCGGGCUCUGCCAUUGCUUCCGGCGUGGCUGUA<br>UGUAAAGUUCUCCACCUCGAGGGAGAGGUUAAUAAGAUU<br>AAGUCGGCCCUGCUGAGUACUAACAAAGCAGUGGUGUCG<br>CUGAGUAACGGAGUAAGUGUGUUAACAUUUAAGGUGCUG<br>GACCUCAAGAAUUAUAUUGACAAACAGUUGCUUCCUAUU<br>CUAAACAAACAGAGCUGUUCAAUAAGUAAUAUUGAAACU<br>GUUAUUGAGUUUCAGCAGAAGAACAACAGGCUUCUUGAG<br>AUUACACGCGAGUUCAGUGUCAAUGCCGGCGUUACAACA<br>CCCGUGUCUACCUACAUGCUGACGAAUUCUGAGCUUCUC<br>UCUCUCAUAAACGACAUGCCCAUUACGAAUGACCAAAAA<br>AAACUUAUGUCCAACAACGUGCAGAUUGUGCGACAGCAA<br>UCCUAUAGCAUUAUGUGUAUCAUCAAGGAAGAGGUACUC<br>GCUUAUGUUGUGCAGCUACCACUCUAUGGUGUGAUUGAC<br>ACCCCCUGUUGGAAGCUGCAUACCAGUCCACUCUGCACCA<br>CUAACACAAAGGAAGGGAGCAAUAUUUGCCUCACUCGAA<br>CCGACAGGGGUGGUAUUGCGAUAAUGCGGGCUCCGUGU<br>CCUUCUUUCCACAGGCUGAAACUUGUAAGGUACAGUCAA<br>ACCGCGUGUUCUGUGAUACUAUGAAUUCUCGUACUCUUC<br>CCAGCGAGGUUAAUCUCUGCAACGUCGACAUUUUCAAUC<br>CUAAAUAUGACUGCAAGAUCAUGACCAGCAAGACCGACG<br>UCUCCAGCUCAGUAAUCACUAGCCUAGGGGCCAUUGUAA<br>GCUGCUAUGGCAAAACCAAGUGUACUGCCUCUAAUAAGA<br>ACAGAGGCAUAAUUAAAACCUUUUCAAAUGGCUGUGACU<br>AUGUGUCGAAUAAGGGCGUCGACACGGUCUCAGUAGGGA<br>AUACCCUCUACUACGUUAACAAACAGGAAGGCAAAUCCC<br>UUUAUGUAAAGGGCGAGCCCAUCAUAAAUUUCUACGACC<br>CACUUGUGUUCCCCAGUGAUGAAUUCGAUGCAUCAAUCU<br>CCCAGGUGAACGAAAAGAUCAAUCAAUCCCUUGCUUUUA<br>UACGAAAGUCAGAUGAACUCCUGCAUAACGUGAAUGCUG<br>GGAAAUCUACAACCAACAUCAUGAUCACUACCAUCAUUA<br>UUGUGAUUAUCGUAAUUCUGCUAUCCUUGAUUGCUGUCG<br>GGCUGCUUCUGUACUGUAAGGCCAGAUCGACGCCUGUGA<br>CCCUUUCAAAAGACCAACUUAGCGGUAUCAAUAAUAUUG<br>CCUUUAGCAAU | 10 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSPATNNGSGSAIASGVAVCKVLHLEGEVNK<br>IKSALLSTNKAVVSLSNGVSVLTFKVLDLKNYIDKQLLPILNK<br>QSCSISNIETVIEFQQKNNRLLEITREFSVNAGVTTPVSTYMLT<br>NSELLSLINDMPITNDQKKLMSNNVQIVRQQSYSIMCIIKEEVL<br>AYVVQLPLYGVIDTPCWKLHTSPLCTTNTKEGSNICLTRTDRG<br>WYCDNAGSVSFFPQAETCKVQSNRVFCDTMNSRTLPSEVNLC<br>NVDIFNPKYDCKIMTSKTDVSSSVITSLGAIVSCYGKTKCTASN<br>KNRGIIKTFSNGCDYVSNKGVDTVSVGNTLYYVNKQEGKSLY<br>VKGEPIINFYDPLVFPSDEFDASISQVNEKINQSLAFIRKSDELL<br>HNVNAGKSTTNIMITTIIVIIVILLSLIAVGLLLYCKARSTPVTL<br>SKDQLSGINNIAFSN | 11 |
| PolyA tail | 100 nt | |

TABLE 7-continued

| VRC-1 | | |
|---|---|---|
| SEQ ID NO: 12 consists of from 5' end to 3' end: 5' UTR SEQ ID NO: 2, mRNA ORF SEQ ID NO: 13, and 3' UTR SEQ ID NO: 4. | | 12 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAAACGCUGUGACC GAGCUGCAGUUAUUGAUGCAGAGUACACCUGCCACCGGG UCGGGCUCUGCCAUUUGCUCCGGCUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAAAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUGCGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGUCCGCCAUCGGUGGCUAUAUC CCAGAAGCCCCAAGAGACGGACAAGCGUACGUCCGGAAA GAUGGUGAGUGGGUCCUCCUCUCUACCUUUCUU | 13 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAICSGVAVCKVLHLEGEVNKIK SALLSTNKAVVSLSNGVSVLTFKVLDLKNYIDKQLLPILNKQS CSISNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGKSLYV KGEPIINFYDPLVFPSDEFDASISQVNEKINQSLAFIRKSDELLS AIGGYIPEAPRDGQAYVRKDGEWVLLSTFL | 14 |
| PolyA tail | 100 nt | |

TABLE 7-continued

| VRC-2 | | |
|---|---|---|
| SEQ ID NO: 15 consists of from 5' end to 3' end: 5' UTR SEQ ID NO: 2, mRNA ORF SEQ ID NO: 16, and 3' UTR SEQ ID NO: 4. | | 15 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUUGCUUCCUAUUCUA<br>AACAAACAGAGCUGUUCAAUAAGUAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAAAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCGUGUUGGAAGCUGCAUACCAGUCCACUCUGCACCACUA<br>ACACAAAGGAAGGGAGCAAUAUUUGCCUCACUCGAACCG<br>ACAGGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCAAAUCCCUUU<br>AUGUAAAGGGCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGUCCGCCAUCGGUGGCUAUA<br>UCCCAGAAGCCCCAAGAGACGGACAAGCGUACGUCCGGA<br>AAGAUGGUGAGUGGGUCCUCCUCUCUACCUUUCUU | 16 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAIASGVAVCKVLHLEGEVNKIK<br>SALLSTNKAVVSLSGCGVSVLTFKVLDLKNYIDKQLLPILNKQ<br>SCSISNIETVIEFQQKNNRLLEITREFSVNAGVTTPVSTYMLTNS<br>ELLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTFSNGCDYVSNKGVDTVSVGNTLYYVNKQEGKSLYV<br>KGEPIINFYDPLVFPSDEFDASISQVNEKINQSLAFIRKSDELLS<br>AIGGYIPEAPRDGQAYVRKDGEWVLLSTFL | 17 |
| PolyA tail | 100 nt | |

TABLE 7-continued

VRC-3

| | | |
|---|---|---|
| SEQ ID NO: 18 consists of from 5' end to 3' end: 5' UTR SEQ ID NO: 2, mRNA ORF SEQ ID NO: 19, and 3' UTR SEQ ID NO: 4. | | 18 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAAAACGCUGUGACC<br>GAGCUGCAGUUAUUGAUGCAGAGUACACCUGCCACCAAU<br>AACGGGUCGGGCUCUGCCAUUGCUUCCGGCGUGGCUGUA<br>UGUAAAGUUCUCCACCUCGAGGGAGAGGUUAAUAAGAUU<br>AAGUCGGCCCUGCUGAGUACUAACAAAGCAGUGGUGUCG<br>CUGAGUAACGGAGUAAGUGUGUUAACAUUUAAGGUGCUG<br>GACCUCAAGAAUUAUAUUGACAAACAGUUGCUUCCUAUU<br>CUAAACAAACAGAGCUGUUCAAUAAGUAAUAUUGAAACU<br>GUUAUUGAGUUUCAGCAGAAGAACAACAGGCUUCUUGAG<br>AUUACACGCGAGUUCAGUGUCAAUGCCGGCGUUACAACA<br>CCCGUGUCUACCUACAUGCUGACGAAUUCUGAGCUUCUC<br>UCUCUCAUAAACGACAUGCCCAUUACGAAUGACCAAAAA<br>AAACUUAUGUCCAACAACGUGCAGAUUGUGCGACAGCAA<br>UCCUAUAGCAUUAUGUGUAUCAUCAAGGAAGAGGUACUC<br>GCUUAUGUUGUGCAGCUACCACUCUAUGGUGUGAUUGAC<br>ACCCCCUGUUGGAAGCUGCAUACCAGUCCACUCUGCACCA<br>CUAACACAAAGGAAGGGAGCAAUAUUUGCCUCACUCGAA<br>CCGACAGGGGUGGUAUUGCGAUAAUGCGGGCUCCGUGU<br>CCUUCUUUCCACAGGCUGAAACUUGUAAGGUACAGUCAA<br>ACCGCGUGUUCUGUGAUACUAUGAAUUCUCGUACUCUUC<br>CCAGCGAGGUUAAUCUCUGCAACGUCGACAUUUUCAAUC<br>CUAAAUAUGACUGCAAGAUCAUGACCAGCAAGACCGACG<br>UCUCCAGCUCAGUAAUCACUAGCCUAGGGGCCAUUGUAA<br>GCUGCUAUGGCAAAACCAAGUGUACUGCCUCUAAUAAGA<br>ACAGAGGCAUAAUUAAAACCUUUUCAAAUGGCUGUGACU<br>AUGUGUCGAAUAAGGGCGUCGACACGGUCUCAGUAGGGA<br>AUACCCUCUACUACGUUAACAAACAGGAAGGCAAAUCCC<br>UUUAUGUAAAGGGCGAGCCCAUCAUAAAUUUCUACGACC<br>CACUUGUGUUCCCCAGUGAUGAAUUCGAUGCAUCAAUCU<br>CCCAGGUGAACGAAAAGAUCAAUCAAUCCCUUGCUUUUA<br>UACGAAAGUCAGAUGAACUCCUGUCCGCCAUCGGUGGCU<br>AUAUCCCAGAAGCCCCAAGAGACGGACAAGCGUACGUCC<br>GGAAAGAUGGUGAGUGGGUCCUCCUCUCUACCUUUCUU | 19 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATNNGSGSAIASGVAVCKVLHLEGEVNK<br>IKSALLSTNKAVVSLSNGVSVLTFKVLDLKNYIDKQLLPILNK<br>QSCSISNIETVIEFQQKNNRLLEITREFSVNAGVTTPVSTYMLT<br>NSELLSLINDMPITNDQKKLMSNNVQIVRQQSYSIMCIIKEEVL<br>AYVVQLPLYGVIDTPCWKLHTSPLCTTNTKEGSNICLTRTDRG<br>WYCDNAGSVSFFPQAETCKVQSNRVFCDTMNSRTLPSEVNLC<br>NVDIFNPKYDCKIMTSKTDVSSSVITSLGAIVSCYGKTKCTASN<br>KNRGIIKTFSNGCDYVSNKGVDTVSVGNTLYYVNKQEGKSLY<br>VKGEPIINFYDPLVFPSDEFDASISQVNEKINQSLAFIRKSDELL<br>SAIGGYIPEAPRDGQAYVRKDGEWVLLSTFL | 20 |
| PolyA tail | 100 nt | |

TABLE 7-continued

| mVRC-1 (v2) | | |
|---|---|---|
| SEQ ID NO: 21 consists of from 5' end to 3' end: 5' UTR SEQ ID NO: 2, mRNA ORF SEQ ID NO: 22, and 3' UTR SEQ ID NO: 4. | | 21 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCGGG UCGGGCUCUGCCAUUUGCUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUGCGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGCAGAUGAACUCCUGCAUAACGUGAAUGCUGGGAAA UCUACAACCAACAUCAUGAUCACUACCAUCAUUAUUGUG AUUAUCGUAAUUCUGCUAUCCUUGAUUGCUGUCGGGCUG CUUCUGUACUGUAAGGCCAGAUCGACGCCUGUGACCCUU UCAAAAGACCAACUUAGCGGUAUCAAUAAUAUUGCCUUU AGCAAU | 22 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAICSGVAVCKVLHLEGEVNKIK SALLSTNKAVVSLSNGVSVLTFKVLDLKNYIDKQLLPILNKQS CSISNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGKSLYV KGEPIINFYDPLVFPSDEFDASISQVNEKINQSLAFIRKSDELLH NVNAGKSTTNIMITTIIIVIIVILLSLIAVGLLLYCKARSTPVTLS KDQLSGINNIAFSN | 5 |
| PolyA tail | 100 nt | |

TABLE 7-continued

| mVRC-2 (v2) | | |
|---|---|---|
| SEQ ID NO: 23 consists of from 5' end to 3' end: 5' UTR SEQ ID NO: 2, mRNA ORF SEQ ID NO: 24, and 3' UTR SEQ ID NO: 4. | | 23 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCGGG UCGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU GGCUGCGGAGUAAGUGUGUUAACAUUUAAGGUGCUGGAC CUCAAGAAUUAUAUUGACAAACAGUUGCUUCCUAUUCUA AACAAACAGAGCUGUUCAAUAAGUAAUAUUGAAACUGUU AUUGAGUUUCAGCAGAAGAACAACAGGCUUCUUGAGAUU ACACGCGAGUUCAGUGUCAAUGCCGGCGUUACAACACCC GUGUCUACCUACAUGCUGACGAAUUCUGAGCUUCUCUCU CUCAUAAACGACAUGCCCAUUACGAAUGACCAAAAGAAA CUUAUGUCCAACAACGUGCAGAUUGUGCGACAGCAAUCC UAUAGCAUUAUGUGUAUCAUCAAGGAAGAGGUACUCGCU UAUGUUGUGCAGCUACCACUCUAUGGUGUGAUUGACACC CCCUGUUGGAAGCUGCAUACCAGUCCACUCUGCACCACUA ACACAAAGGAAGGGAGCAAUAUUUGCCUCACUCGAACCG ACAGGGGGUGGUAUUGCGAUAAUGCCGGGCUCCGUGUCCU UCUUUCCACAGGCUGAAACUUGUAAGGUACAGUCAAACC GCGUGUUCUGUGAUACUAUGAAUUCUCGUACUCUUCCCA GCGAGGUUAAUCUCUGCAACGUCGACAUUUUCAAUCCUA AAUAUGACUGCAAGAUCAUGACCAGCAAGACCGACGUCU CCAGCUCAGUAAUCACUAGCCUAGGGGCCAUUGUAAGCU GCUAUGGCAAAACCAAGUGUACUGCCUCUAAUAAGUGCA GAGGCAUAAUUAAAACCUUUUCAAAUGGCUGUGACUAUG UGUCGAAUAAGGGCGUCGACACGGUCUCAGUAGGGAAUA CCCUCUACUACGUUAACAAACAGGAAGGCAAAUCCCUUU AUGUAAAGGGCGAGCCCAUCAUAAAUUUCUACGACCCAC UUGUGUUCCCCAGUGAUGAAUUCGAUGCAUCAAUCUCCC AGGUGAACGAAAAGAUCAAUCAAUCCCUUGCUUUUAUAC GAAAGUCAGAUGAACUCCUGCAUAACGUGAAUGCUGGGA AAUCUACAACCAACAUCAUGAUCACUACCAUCAUUAUUG UGAUUAUCGUAAUUCUGCUAUCCUUGAUUGCUGUCGGGC UGCUUCUGUACUGUAAGGCCAGAUCGACGCCUGUGACCC UUUCAAAAGACCAACUUAGCGGUAUCAAUAAUAUUGCCU UUAGCAAU | 24 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAIASGVAVCKVLHLEGEVNKIK SALLSTNKAVVSLSGCGVSVLTFKVLDLKNYIDKQLLPILNKQ SCSISNIETVIEFQQKNNRLLEITREFSVNAGVTTPVSTYMLTNS ELLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK CRGIIKTFSNGCDYVSNKGVDTVSVGNTLYYVNKQEGKSLYV KGEPIINFYDPLVFPSDEFDASISQVNEKINQSLAFIRKSDELLH NVNAGKSTTNIMITTIIIVIIVILLSLIAVGLLLYCKARSTPVTLS KDQLSGINNIAFSN | 8 |
| PolyA tail | 100 nt | |

TABLE 7-continued

| mVRC-3 (v2) | | |
|---|---|---|
| SEQ ID NO: 25 consists of from 5' end to 3' end: 5' UTR SEQ ID NO: 2, mRNA ORF SEQ ID NO: 26, and 3' UTR SEQ ID NO: 4. | | 25 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCAAU AACGGGUCGGGCUCUGCCAUUGCUUCCGGCGUGGCUGUA UGUAAAGUUCUCCACCUCGAGGGAGAGGUUAAUAAGAUU AAGUCGGCCCUGCUGAGUACUAACAAAGCAGUGGUGUCG CUGAGUAACGGAGUAAGUGUGUUAACAUUUAAGGUGCUG GACCUCAAGAAUUAUAUUGACAAACAGUUGCUUCCUAUU CUAAACAAACAGAGCUGUUCAAUAAGUAAUAUUGAAACU GUUAUUGAGUUUCAGCAGAAGAACAACAGGCUUCUUGAG AUUACACGCGAGUUCAGUGUCAAUGCCGGCGUUACAACA CCCGUGUCUACCUACAUGCUGACGAAUUCUGAGCUUCUC UCUCUCAUAAACGACAUGCCCAUUACGAAUGACCAAAAG AAACUUAUGUCCAACAACGUGCAGAUUGUGCGACAGCAA UCCUAUAGCAUUAUGUGUAUCAUCAAGGAAGAGGUACUC GCUUAUGUUGUGCAGCUACCACUCUAUGGUGUGAUUGAC ACCCCCUGUUGGAAGCUGCAUACCAGUCCACUCUGCACCA CUAACACAAAGGAAGGGAGCAAUAUUUGCCUCACUCGAA CCGACAGGGGUGGUAUUGCGAUAAUGCGGGCUCCGUGU CCUUCUUUCCACAGGCUGAAACUUGUAAGGUACAGUCAA ACCGCGUGUUCUGUGAUACUAUGAAUUCUCGUACUCUUC CCAGCGAGGUUAAUCUCUGCAACGUCGACAUUUUCAAUC CUAAAUAUGACUGCAAGAUCAUGACCAGCAAGACCGACG UCUCCAGCUCAGUAAUCACUAGCCUAGGGGCCAUUGUAA GCUGCUAUGGCAAAACCAAGUGUACUGCCUCUAAUAAGA ACAGAGGCAUAAUUAAAACCUUUUCAAAUGGCUGUGACU AUGUGUCGAAUAAGGGCGUCGACACGGUCUCAGUAGGGA AUACCCUCUACUACGUUAACAAACAGGAAGGCAAAUCCC UUUAUGUAAAGGGCGAGCCCAUCAUAAAUUUCUACGACC CACUUGUGUUCCCCAGUGAUGAAUUCGAUGCAUCAAUCU CCCAGGUGAACGAAAAGAUCAAUCAAUCCCUUGCUUUUA UACGAAAGUCAGAUGAACUCCUGCAUAACGUGAAUGCUG GGAAAUCUACAACCAACAUCAUGAUCACUACCAUCAUUA UUGUGAUUAUCGUAAUUCUGCUAUCCUUGAUUGCUGUCG GGCUGCUUCUGUACUGUAAGGCCAGAUCGACGCCUGUGA CCCUUUCAAAAGACCAACUUAGCGGUAUCAAUAAUAUUG CCUUUAGCAAU | 26 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATNNGSGSAIASGVAVCKVLHLEGEVNK IKSALLSTNKAVVSLSNGVSVLTFKVLDLKNYIDKQLLPILNK QSCSISNIETVIEFQQKNNRLLEITREFSVNAGVTTPVSTYMLT NSELLSLINDMPITNDQKKLMSNNVQIVRQQSYSIMCIIKEEVL AYVVQLPLYGVIDTPCWKLHTSPLCTTNTKEGSNICLTRTDRG WYCDNAGSVSFFPQAETCKVQSNRVFCDTMNSRTLPSEVNLC NVDIFNPKYDCKIMTSKTDVSSSVITSLGAIVSCYGKTKCTASN KNRGIIKTFSNGCDYVSNKGVDTVSVGNTLYYVNKQEGKSLY VKGEPIINFYDPLVFPSDEFDASISQVNEKINQSLAFIRKSDELL HNVNAGKSTTNIMITTIIVIIVILLSLIAVGLLLYCKARSTPVTL SKDQLSGINNIAFSN | 11 |
| PolyA tail | 100 nt | |

TABLE 7-continued

| VRC-1 (v2) | | |
|---|---|---|
| SEQ ID NO: 27 consists of from 5' end to 3' end: 5' UTR SEQ ID NO: 2, mRNA ORF SEQ ID NO: 28, and 3' UTR SEQ ID NO: 4. | | 27 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCGGG UCGGGCUCUGCCAUUUGCUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGUCUCAGUAGGGAAUACC CUCUACUGCGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGUCCGCCAUCGGUGGCUAUAUC CCAGAAGCCCCAAGAGACGGACAAGCGUACGUCCGGAAA GAUGGUGAGUGGGUCCUCCUCUCUACCUUUCUU | 28 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAICSGVAVCKVLHLEGEVNKIK SALLSTNKAVVSLSNGVSVLTFKVLDLKNYIDKQLLPILNKQS CSISNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGKSLYV KGEPIINFYDPLVFPSDEFDASISQVNEKINQSLAFIRKSDELLS AIGGYIPEAPRDGQAYVRKDGEWVLLSTFL | 14 |
| PolyA tail | 100 nt | |

TABLE 7-continued

| VRC-2 (v2) | | |
|---|---|---|
| SEQ ID NO: 29 consists of from 5' end to 3' end: 5' UTR SEQ ID NO: 2, mRNA ORF SEQ ID NO: 30, and 3' UTR SEQ ID NO: 4. | | 29 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAAUAAGUAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAGAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCUGUUGGAAGCUGCAUACCAGUCCACUCUGCACCACUA<br>ACACAAAGGAAGGGAGCAAUAUUUGCCUCACUCGAACCG<br>ACAGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCAAAUCCCUUU<br>AUGUAAAGGGCGAGCCCAUCAUAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGUCCGCCAUCGGUGGCUAUA<br>UCCCAGAAGCCCCAAGAGACGGACAAGCGUACGUCCGGA<br>AAGAUGGUGAGUGGGUCCUCCUCUCUACCUUUCUU | 30 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAIASGVAVCKVLHLEGEVNKIK<br>SALLSTNKAVVSLSGCGVSVLTFKVLDLKNYIDKQLLPILNKQ<br>SCSISNIETVIEFQQKNNRLLEITREFSVNAGVTTPVSTYMLTNS<br>ELLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTFSNGCDYVSNKGVDTVSVGNTLYYVNKQEGKSLYV<br>KGEPIINFYDPLVFPSDEFDASISQVNEKINQSLAFIRKSDELLS<br>AIGGYIPEAPRDGQAYVRKDGEWVLLSTFL | 17 |
| PolyA tail | 100 nt | |

TABLE 7-continued

| VRC-3 (v2) | | |
|---|---|---|
| SEQ ID NO: 31 consists of from 5' end to 3' end: 5' UTR SEQ ID NO: 2, mRNA ORF SEQ ID NO: 32, and 3' UTR SEQ ID NO: 4. | | 31 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCAAU AACGGGUCGGGCUCUGCCAUUGCUUCCGGCGUGGCUGUA UGUAAAGUUCUCCACCUCGAGGGAGAGGUUAAUAAGAUU AAGUCGGCCCUGCUGAGUACUAACAAAGCAGUGGUGUCG CUGAGUAACGGAGUAAGUGUGUUAACAUUUAAGGUGCUG GACCUCAAGAAUUAUAUUGACAAACAGUUGCUUCCUAUU CUAAACAAACAGAGCUGUUCAAUAAGUAAUAUUGAAACU GUUAUUGAGUUUCAGCAGAAGAACAACAGGCUUCUUGAG AUUACACGCGAGUUCAGUGUCAAUGCCGGCGUUACAACA CCCGUGUCUACCUACAUGCUGACGAAUUCUGAGCUUCUC UCUCUCAUAAACGACAUGCCCAUUACGAAUGACCAAAAG AAACUUAUGUCCAACAACGUGCAGAUUGUGCGACAGCAA UCCUAUAGCAUUAUGUGUAUCAUCAAGGAAGAGGUACUC GCUUAUGUUGUGCAGCUACCACUCUAUGGUGUGAUUGAC ACCCCCUGUUGGAAGCUGCAUACCAGUCCACUCUGCACCA CUAACACAAAGGAAGGGAGCAAUAUUUGCCUCACUCGAA CCGACAGGGGGUGGUAUUGCGAUAAUGCGGGCUCCGUGU CCUUCUUUCCACAGGCUGAAACUUGUAAGGUACAGUCAA ACCGCGUGUUCUGUGAUACUAUGAAUUCUCGUACUCUUC CCAGCGAGGUUAAUCUCUGCAACGUCGACAUUUUCAAUC CUAAAUAUGACUGCAAGAUCAUGACCAGCAAGACCGACG UCUCCAGCUCAGUAAUCACUAGCCUAGGGGCCAUUGUAA GCUGCUAUGGCAAAACCAAGUGUACUGCCUCUAAUAAGA ACAGAGGCAUAAUUAAAACCUUUUCAAAUGGCUGUGACU AUGUGUCGAAUAAGGGCGUCGACACGGUCUCAGUAGGGA AUACCCUCUACUACGUUAACAAACAGGAAGGCAAAUCCC UUUAUGUAAAGGGCGAGCCCAUCAUAAAUUUCUACGACC CACUUGUGUUCCCCAGUGAUGAAUUCGAUGCAUCAAUCU CCCAGGUGAACGAAAAGAUCAAUCAAUCCCUUGCUUUUA UACGAAAGUCAGAUGAACUCCUGUCCGCCAUCGGUGGCU AUAUCCCAGAAGCCCCAAGAGACGGACAAGCGUACGUCC GGAAAGAUGGUGAGUGGGUCCUCCUCUCUACCUUUCUU | 32 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATNNGSGSAIASGVAVCKVLHLEGEVNK IKSALLSTNKAVVSLSNGVSVLTFKVLDLKNYIDKQLLPILNK QSCSISNIETVIEFQQKNNRLLEITREFSVNAGVTTPVSTYMLT NSELLSLINDMPITNDQKKLMSNNVQIVRQQSYSIMCIIKEEVL AYVVQLPLYGVIDTPCWKLHTSPLCTTNTKEGSNICLTRTDRG WYCDNAGSVSFFPQAETCKVQSNRVFCDTMNSRTLPSEVNLC NVDIFNPKYDCKIMTSKTDVSSSVITSLGAIVSCYGKTKCTASN KNRGIIKTFSNGCDYVSNKGVDTVSVGNTLYYVNKQEGKSLY VKGEPIINFYDPLVFPSDEFDASISQVNEKINQSLAFIRKSDELL SAIGGYIPEAPRDGQAYVRKDGEWVLLSTFL | 20 |
| PolyA tail | 100 nt | |

TABLE 7-continued mVRC-4

| | | |
|---|---|---|
| SEQ ID NO: 33 consists of from 5' end to 3' end: 5' UTR SEQ ID NO: 2, mRNA ORF SEQ ID NO: 34, and 3' UTR SEQ ID NO: 4. | | 33 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGGGCGCGCUCCGCACAGGAUGG UACACCUCCGUGAUCACCAUCGAGCUCAGCAAUAUUAAA GAGAUUAAGUGCAAUGGUACCGACGCUAAAGUCAAACUU AUCAAGCAGGAACUCGACAAAUAUAAGAACGCUGUGACC GACCUGCAGUUAUUGAUGCAGAGUACACCUGCCACCGGG UCGGGCUCUGCCAUUUGCUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUACCCAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUGCGUUAACAAACAGGAAGGCCAGUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGCAUAACGUGAAUGCUGGGAAA UCUACAACCAACAUCAUGAUCACUACCAUCAUUAUUGUG AUUAUCGUAAUUCUGCUAUCCUUGAUUGCUGUCGGGCUG CUUCUGUACUGUAAGGCCAGAUCGACGCCUGUGACCCUU UCAAAAGACCAACUUAGCGGUAUCAAUAAUAUUGCCUUU AGCAAU | 34 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LGALRTGWYTSVITIELSNIKEIKCNGTDAKVKLIKQELDKYK NAVTDLQLLMQSTPATGSGSAICSGVAVCKVLHLEGEVNKIK SALLSTNKAVVSLSNGVSVLTFKVLDLKNYIDKQLLPILNKQS CSIPNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGQSLYV KGEPIINFYDPLVFPSDEFDASISQVNEKINQSLAFIRKSDELLH NVNAGKSTTNIMITTIIIVIIVILLSLIAVGLLLYCKARSTPVTLS KDQLSGINNIAFSN | 35 |
| PolyA tail | 100 nt | |

TABLE 7-continued mVRC-5

| | | |
|---|---|---|
| SEQ ID NO: 36 consists of from 5' end to 3' end: 5' UTR SEQ ID NO: 2, mRNA ORF SEQ ID NO: 37, and 3' UTR SEQ ID NO: 4. | | 36 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGGGCGCGCUCCGCACAGGAUGG UACACCUCCGUGAUCACCAUCGAGCUCAGCAAUAUUAAA GAGAUUAAGUGCAAUGGUACCGACGCUAAAGUCAAACUU AUCAAGCAGGAACUCGACAAAUAUAAGAACGCUGUGACC GACCUGCAGUUAUUGAUGCAGAGUACACCUGCCACCGGG UCGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU GGCUGCGGAGUAAGUGUGUUAACAUUUAAGGUGCUGGAC CUCAAGAAUUAUAUUGACAAACAGUUGCUUCCUAUUCUA AACAAACAGAGCUGUUCAAUACCCAAUAUUGAAACUGUU AUUGAGUUUCAGCAGAAGAACAACAGGCUUCUUGAGAUU ACACGCGAGUUCAGUGUCAAUGCCGGCGUUACAACACCC GUGUCUACCUACAUGCUGACGAAUUCUGAGCUUCUCUCU CUCAUAAACGACAUGCCCAUUACGAAUGACCAAAAGAAA CUUAUGUCCAACAACGUGCAGAUUGUGCGACAGCAAUCC UAUAGCAUUAUGUGUAUCAUCAAGGAAGAGGUACUCGCU UAUGUUGUGCAGCUACCACUCUAUGGUGUGAUUGACACC CCCUGUUGGAAGCUGCAUACCAGUCCACUCUGCACCACUA ACACAAAGGAAGGGAGCAAUAUUUGCCUCACUCGAACCG ACAGGGGGUGGUAUUGCGAUAAUGCGGGCUCCGUGUCCU UCUUUCCACAGGCUGAAACUUGUAAGGUACAGUCAAACC GCGUGUUCUGUGAUACUAUGAAUUCUCGUACUCUUCCCA GCGAGGUUAAUCUCUGCAACGUCGACAUUUUCAAUCCUA AAUAUGACUGCAAGAUCAUGACCAGCAAGACCGACGUCU CCAGCUCAGUAAUCACUAGCCUAGGGGCCAUUGUAAGCU GCUAUGGCAAAACCAAGUGUACUGCCUCUAAUAAGUGCA GAGGCAUAAUUAAAACCUUUUCAAAUGGCUGUGACUAUG UGUCGAAUAAGGGCGUCGACACGGUCUCAGUAGGGAAUA CCCUCUACUACGUUAACAAACAGGAAGGCCAGUCCCUUU AUGUAAAGGGCGAGCCCAUCAUAAAUUUCUACGACCCAC UUGUGUUCCCCAGUGAUGAAUUCGAUGCAUCAAUCUCCC AGGUGAACGAAAAGAUCAAUCAAUCCCUUGCUUUUAUAC GAAAGUCAGAUGAACUCCUGCAUAACGUGAAUGCUGGGA AAUCUACAACCAACAUCAUGAUCACUACCAUCAUUAUUG UGAUUAUCGUAAUUCUGCUAUCCUUGAUUGCUGUCGGGC UGCUUCUGUACUGUAAGGCCAGAUCGACGCCUGUGACCC UUUCAAAAGACCAACUUAGCGGUAUCAAUAAUAUUGCCU UUAGCAAU | 37 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LGALRTGWYTSVITIELSNIKEIKCNGTDAKVKLIKQELDKYK NAVTDLQLLMQSTPATGSGSAIASGVAVCKVLHLEGEVNKIK SALLSTNKAVVSLSGCGVSVLTFKVLDLKNYIDKQLLPILNKQ SCSIPNIETVIEFQQKNNRLLEITREFSVNAGVTTPVSTYMLTNS ELLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK CRGIIKTFSNGCDYVSNKGVDTVSVGNTLYYVNKQEGQSLYV KGEPIINFYDPLVFPSDEFDASISQVNEKINQSLAFIRKSDELLH NVNAGKSTTNIMITTIIIVIIVILLSLIAVGLLLYCKARSTPVTLS KDQLSGINNIAFSN | 38 |
| PolyA tail | 100 nt | |

TABLE 7-continued mVRC-6

| | | |
|---|---|---|
| SEQ ID NO: 39 consists of from 5' end to 3' end: 5' UTR SEQ ID NO: 2, mRNA ORF SEQ ID NO: 40, and 3' UTR SEQ ID NO: 4. | | 39 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCGGG UCGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUACGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGCAUAACGUGAAUGCUGGGAAA UCUACAACCAACAUCAUGAUCACUACCAUCAUUAUUGUG AUUAUCGUAAUUCUGCUAUCCUUGAUUGCUGUCGGGCUG CUUCUGUACUGUAAGGCCAGAUCGACGCCUGUGACCCUU UCAAAAGACCAACUUAGCGGUAUCAAUAAUAUUGCCUUU AGCAAU | 40 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAIASGVAVCKVLHLEGEVNKIK SALLSTNKAVVSLSNGVSVLTFKVLDLKNYIDKQLLPILNKQS CSISNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYYVNKQEGKSLYV KGEPIINFYDPLVFPSDEFDASISQVNEKINQSLAFIRKSDELLH NVNAGKSTTNIMITTIIVIIVILLSLIAVGLLLYCKARSTPVTLS KDQLSGINNIAFSN | 41 |
| PolyA tail | 100 nt | |

TABLE 7-continued

| VRC-4 | | |
|---|---|---|
| SEQ ID NO: 42 consists of from 5' end to 3' end: 5' UTR SEQ ID NO: 2, mRNA ORF SEQ ID NO: 43, and 3' UTR SEQ ID NO: 4. | | 42 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGGGCGCGCUCCGCACAGGAUGG UACACCUCCGUGAUCACCAUCGAGCUCAGCAAUAUUAAA GAGAUUAAGUGCAAUGGUACCGACGCUAAAGUCAAACUU AUCAAGCAGGAACUCGACAAAUAUAAGAACGCUGUGACC GACCUGCAGUUAUUGAUGCAGAGUACACCUGCCACCGGG UCGGGCUCUGCCAUUUGCUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUACCCAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGUCUCAGUAGGGAAUACC CUCUACUGCGUUAACAAACAGGAAGGCCAGUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGUCCGCCAUCGGUGGCUAUAUC CCAGAAGCCCCAAGAGACGGACAAGCGUACGUCCGGAAA GAUGGUGAGUGGGUCCUCCUCUCUACCUUUCUU | 43 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LGALRTGWYTSVITIELSNIKEIKCNGTDAKVKLIKQELDKYK NAVTDLQLLMQSTPATGSGSAICSGVAVCKVLHLEGEVNKIK SALLSTNKAVVSLSNGVSVLTFKVLDLKNYIDKQLLPILNKQS CSIPNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGQSLYV KGEPIINFYDPLVFPSDEFDASISQVNEKINQSLAFIRKSDELLS AIGGYIPEAPRDGQAYVRKDGEWVLLSTFL | 44 |
| PolyA tail | 100 nt | |

TABLE 7-continued

| VRC-5 | | |
|---|---|---|
| SEQ ID NO: 45 consists of from 5' end to 3' end: 5' UTR SEQ ID NO: 2, mRNA ORF SEQ ID NO: 46, and 3' UTR SEQ ID NO: 4. | | 45 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGGGCGCGCUCCGCACAGGAUGG UACACCUCCGUGAUCACCAUCGAGCUCAGCAAUAUUAAA GAGAUUAAGUGCAAUGGUACCGACGCUAAAGUCAAACUU AUCAAGCAGGAACUCGACAAAUAUAAGAACGCUGUGACC GACCUGCAGUUAUUGAUGCAGAGUACACCUGCCACCGGG UCGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU GGCUGCGGAGUAAGUGUGUUAACAUUUAAGGUGCUGGAC CUCAAGAAUUAUAUUGACAAACAGUUGCUUCCUAUUCUA AACAAACAGAGCUGUUCAAUCCCAAUAUUGAAACUGUU AUUGAGUUUCAGCAGAAGAACAACAGGCUUCUUGAGAUU ACACGCGAGUUCAGUGUCAAUGCCGGCGUUACAACACCC GUGUCUACCUACAUGCUGACGAAUUCUGAGCUUCUCUCU CUCAUAAACGACAUGCCCAUUACGAAUGACCAAAAGAAA CUUAUGUCCAACAACGUGCAGAUUGUGCGACAGCAAUCC UAUAGCAUUAUGUGUAUCAUCAAGGAAGAGGUACUCGCU UAUGUUGUGCAGCUACCACUCUAUGGUGUGAUUGACACC CCCUGUUGGAAGCUGCAUACCAGUCCACUCUGCACCACUA ACACAAAGGAAGGGAGCAAUAUUUGCCUCACUCGAACCG ACAGGGGUGGUAUUGCGAUAAUGCGGGCUCCGUGUCCU UCUUUCCACAGGCUGAAACUUGUAAGGUACAGUCAAACC GCGUGUUCUGUGAUACUAUGAAUUCUCGUACUCUUCCCA GCGAGGUUAAUCUCUGCAACGUCGACAUUUUCAAUCCUA AAUAUGACUGCAAGAUCAUGACCAGCAAGACCGACGUCU CCAGCUCAGUAAUCACUAGCCUAGGGGCCAUUGUAAGCU GCUAUGGCAAAACCAAGUGUACUGCCUCUAAUAAGUGCA GAGGCAUAAUUAAAACCUUUUCAAAUGGCUGUGACUAUG UGUCGAAUAAGGGCGUCGACACGGUCUCAGUAGGGAAUA CCCUCUACUACGUUAACAAACAGGAAGGCCAGUCCCUUU AUGUAAAGGGCGAGCCCAUCAUAAAUUUCUACGACCCAC UUGUGUUCCCCAGUGAUGAAUUCGAUGCAUCAAUCUCCC AGGUGAACGAAAAGAUCAAUCAAUCCCUUGCUUUUAUAC GAAAGUCAGAUGAACUCCUGUCCGCCAUCGGUGGCUAUA UCCCAGAAGCCCCAAGAGACGGACAAGCGUACGUCCGGA AAGAUGGUGAGUGGGUCCUCCUCUCUACCUUUCUU | 46 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LGALRTGWYTSVITIELSNIKEIKCNGTDAKVKLIKQELDKYK NAVTDLQLLMQSTPATGSGSAIASGVAVCKVLHLEGEVNKIK SALLSTNKAVVSLSGCGVSVLTFKVLDLKNYIDKQLLPILNKQ SCSIPNIETVIEFQQKNNRLLEITREFSVNAGVTTPVSTYMLTNS ELLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK CRGIIKTFSNGCDYVSNKGVDTVSVGNTLYYVNKQEGQSLYV KGEPIINFYDPLVFPSDEFDASISQVNEKINQSLAFIRKSDELLS AIGGYIPEAPRDGQAYVRKDGEWVLLSTFL | 47 |
| PolyA tail | 100 nt | |

TABLE 7-continued

| VRC-6 | | |
|---|---|---|
| SEQ ID NO: 48 consists of from 5' end to 3' end: 5' UTR SEQ ID NO: 2, mRNA ORF SEQ ID NO: 49, and 3' UTR SEQ ID NO: 4. | | 48 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCGGG UCGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGUCUCAGUAGGGAAUACC CUCUACUACGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGUCCGCCAUCGGUGGCUAUAUC CCAGAAGCCCCAAGAGACGGACAAGCGUACGUCCGGAAA GAUGGUGAGUGGGUCCUCCUCUCUACCUUUCUU | 49 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAIASGVAVCKVLHLEGEVNKIK SALLSTNKAVVSLSNGVSVLTFKVLDLKNYIDKQLLPILNKQS CSISNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYYVNKQEGKSLYV KGEPIINFYDPLVFPSDEFDASISQVNEKINQSLAFIRKSDELLS AIGGYIPEAPRDGQAYVRKDGEWVLLSTFL | 50 |
| PolyA tail | 100 nt | |

TABLE 7-continued

| RSVF mVRC1(v2) UTR v1.1 | | |
|---|---|---|
| SEQ ID NO: 51 consists of from 5' end to 3' end: 5' UTR SEQ ID NO: 77, mRNA ORF SEQ ID NO: 52, and 3' UTR SEQ ID NO: 78. | | 51 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGACCCCGGCGCCGCCACC | 77 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCGGG UCGGGCUCUGCCAUUUGCUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUGCGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGCAUAACGUGAAUGCUGGGAAA UCUACAACCAACAUCAUGAUCACUACCAUCAUUAUUGUG AUUAUCGUAAUUCUGCUAUCCUUGAUUGCUGUCGGGCUG CUUCUGUACUGUAAGGCCAGAUCGACGCCUGUGACCCUU UCAAAAGACCAACUUAGCGGUAUCAAUAAUAUUGCCUUU AGCAAU | 52 |
| 3' UTR | UGAUAAUAGGCUGGAGCCUCGGUGGCCUAGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 78 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAICSGVAVCKVLHLEGEVNKIK SALLSTNKAVVSLSNGVSVLTFKVLDLKNYIDKQLLPILNKQS CSISNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGKSLYV KGEPIINFYDPLVFPSDEFDASISQVNEKINQSLAFIRKSDELLH NVNAGKSTTNIMITTIIIVIIVILLSLIAVGLLLYCKARSTPVTLS KDQLSGINNIAFSN | 5 |
| PolyA tail | 100 nt | |

TABLE 7-continued

MRK_RSVF mVRC1(v2)_SE_001

| | | |
|---|---|---|
| SEQ ID NO: 53 consists of from 5' end to 3' end: 5' UTR SEQ ID NO: 77, mRNA ORF SEQ ID NO: 54, and 3' UTR SEQ ID NO: 78. | | 53 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 77 |
| ORF of mRNA Construct (excluding the stop codon) | AUGGAGCUGCUGAUCCUCAAGGCUAACGCCAUCACCACC<br>AUCCUGACCGCCGUGACCUUCUGCUUCGCCAGCGGGCAGA<br>ACAUCACCGAGGAGUUCUACCAGAGCACUUGCAGCGCCG<br>UGAGCAAGGGCUACCUGUCAGCCCUGCGGACCGGCUGGU<br>ACACCAGCGUGAUCACCAUCGAGCUGAGCAACAUCAAGG<br>AGAACAAGUGCAACGGCACCGACGCCAAGGUGAAGCUGA<br>UCAAGCAGGAGCUGGACAAGUACAAGAACGCCGUGACCG<br>AGCUGCAGCUGCUGAUGCAGUCCACGCCCGCUACCGGGUC<br>AGGCAGCGCCAUCUGCUCCGGCGUGGCCGUGUGCAAGGU<br>GCUGCACCUGGAGGGCGAGGUGAACAAGAUCAAGAGCGC<br>CCUGCUGAGCACCAACAAGGCCGUGGUGAGCCUGAGCAA<br>CGGCGUGAGCGUGCUGACCUUCAAGGUGCUGGACCUGAA<br>GAACUACAUCGACAAGCAGCUGCUGCCCAUCCUGAACAA<br>GCAGUCCUGCUCCAUCUCCAACAUCGAAACUGUGAUCGA<br>GUUCCAGCAGAAGAACAACCGCCUGCUGGAGAUCACCCG<br>CGAGUUCAGCGUGAACGCCGGCGUGACCACCCCAGUGAG<br>CACCUACAUGCUGACCAACAGCGAGCUGCUGAGCCUGAU<br>CAACGACAUGCCCAUCACCAACGACCAGAAGAAGCUGAU<br>GAGCAACAACGUGCAGAUCGUGCGCCAGCAGUCCUACUC<br>UAUCAUGUGCAUCAUCAAGGAGGAGGUGCUGGCCUACGU<br>GGUGCAGCUGCCCCUGUACGGCGUGAUCGACACACCCUGC<br>UGGAAGCUGCACACCUCCCCUCUGUGCACCACUAACACCA<br>AGGAGGGGAGCAACAUCUGCCUGACCCGGACCGACCGCG<br>GCUGGUACUGCGACAACGCCGGCAGCGUGAGCUUCUUCC<br>CUCAGGCCGAAACCUGCAAGGUGCAGAGCAACAGGGUGU<br>UCUGCGACACCAUGAACUCCCGGACCCUGCCCAGCGAGGU<br>GAACCUGUGCAACGUGGACAUCUUCAACCCCAAGUACGA<br>UUGCAAGAUCAUGACCUCCAAGACCGACGUGAGCAGCUC<br>CGUGAUCACCUCCCUGGGCGCCAUCGUGAGUUGCUACGG<br>CAAGACCAAGUGCACCGCCAGCAACAAGAACCGCGGCAUC<br>AUCAAGACCUUCAGCAACGGCUGCGACUACGUGUCCAAC<br>AAGGGCGUGGACACCGUGAGCGUGGGCAACACCCUGUAC<br>UGCGUGAACAAGCAGGAGGGCAAGAGCCUGUACGUGAAG<br>GGCGAGCCCAUCAUCAACUUCUACGAUCCGCUGGUGUUC<br>CCCUCCGACGAGUUCGACGCCUCCAUCAGCCAGGUGAACG<br>AGAAGAUCAACCAGAGCCUGGCCUUCAUCCGCAAGUCCG<br>ACGAGCUGCUGCACAACGUCAACGCCGGUAAGAGCACCA<br>CCAACAUCAUGAUCACCACAAUCAUCAUCGUGAUCAUUG<br>UGAUCUUGCUCUCCUUAAUCGCCGUGGGCCUGCUGCUGU<br>ACUGCAAGGCCCGGAGCACCCCAGUGACCCUGAGCAAAG<br>AUCAGCUGUCCGGCAUCAACAACAUCGCCUUCUCCAAC | 54 |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 78 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLTNSE<br>LLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTFSNGCDYVSNKGVDTVSVGNTLYCVNKQEGKSLYV<br>KGEPIINFYDPLVFPSDEFDASISQVNEKINQSLAFIRKSDELLH<br>NVNAGKSTTNIMITTIIIVIIVILLSLIAVGLLLYCKARSTPVTLS<br>KDQLSGINNIAFSN | 5 |
| PolyA tail | 100 nt | |

TABLE 7-continued

| MRK_RSVF mVRC1(v2)_SE_002 | | |
|---|---|---|
| SEQ ID NO: 55 consists of from 5' end to 3' end: 5' UTR SEQ ID NO: 77, mRNA ORF SEQ ID NO: 56, and 3' UTR SEQ ID NO: 78. | | 55 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 77 |
| ORF of mRNA Construct (excluding the stop codon) | AUGGAGCUGCUGAUUCUGAAGGCCAACGCCAUUACCACC<br>AUUCUGACCGCCGUGACCUUCUGCUUCGCCAGCGGCCAGA<br>AUAUUACCGAGGAGUUCUACCAGUCAACCUGCAGCGCCG<br>UGAGCAAGGGCUACCUGAGCGCCCUACGGACCGGGUGGU<br>ACACCUCCGUGAUCACCAUUGAGCUGAGCAAUAUUAAGG<br>AGAAUAAGUGCAACGGGACCGACGCCAAGGUGAAGCUCA<br>UCAAGCAGGAGCUGGAUAAGUACAAGAACGCCGUGACCG<br>AGCUGCAGCUGCUGAUGCAGAGCACACCGGCCACGGGCU<br>CCGGCAGCGCCAUUUGCUCAGGCGUGGCCGUGUGCAAGG<br>UGCUGCACCUCGAGGGCGAGGUCAAUAAGAUUAAGAGCG<br>CCCUGUUGAGCACCAAUAAGGCCGUGGUGAGCCUGAGCA<br>ACGGCGUGAGCGUGCUGACCUUCAAGGUGCUGGAUCUCA<br>AGAAUUACAUUGAUAAGCAGCUGCUGCCAAUUCUCAAUA<br>AGCAGAGCUGCAGCAUUAGCAAUAUCGAAACCGUGAUUG<br>AGUUCCAGCAGAAGAAUAAUCGCCUGCUGGAGAUUACCC<br>GCGAGUUCAGCGUCAACGCCGGGGUGACCACCCCAGUCA<br>GCACCUACAUGCUGACCAAUAGCGAGCUGCUGAGCCUGA<br>UUAACGAUAUGCCCAUUACCAACGACCAGAAGAAGCUGA<br>UGAGCAAUAACGUGCAGAUUGUGCGCCAGCAGAGCUACA<br>GCAUUAUGUGCAUUAUUAAGGAGGAGGUGCUGGCCUACG<br>UGGUGCAGCUGCCCCUCUACGGCGUGAUUGAUACGCCCU<br>GCUGGAAGCUGCACACCAGCCCACUGUGCACCACCAAUAC<br>CAAGGAGGGCAGCAAUAUUUGCCUGACCCGCACCGAUCG<br>CGGGUGGUACUGCGAUAACGCCGGCAGCGUGAGCUUCUU<br>CCCACAGGCCGAAACAUGCAAGGUGCAGUCCAAUCGCGU<br>GUUCUGCGAUACCAUGAACAGCCGCACCCUGCCCAGCGAG<br>GUGAAUCUCUGCAACGUGGAUAUUUUCAAUCCAAAGUAC<br>GAUUGCAAGAUUAUGACCAGCAAGACCGACGUGAGCUCC<br>AGCGUGAUUACCUCACUCGGCGCCAUUGUGAGCUGCUAC<br>GGCAAGACCAAGUGCACCGCCUCAAAUAAGAAUCGCGGC<br>AUUAUUAAGACCUUCAGCAACGGCUGCGAUUACGUGAGC<br>AAUAAGGGCGUGGAUACCGUGAGCGUGGGAAAUACCCUG<br>UACUGCGUGAAUAAGCAGGAGGGCAAGAGCCUGUACGUG<br>AAGGGCGAGCCAAUUAUUAAUUUCUACGAUCCCCUGGUG<br>UUCCCCAGCGACGAGUUCGACGCCAGCAUUAGCCAGGUG<br>AACGAGAAGAUUAAUCAGAGCCUGGCCUUCAUUCGCAAG<br>UCCGACGAGCUCCUGCACAACGUGAACGCCGGCAAGAGC<br>ACCACCAACAUCAUGAUUACCACCAUCAUCAUUGUGAUU<br>AUCGUGAUCCUCCUCAGCCUCAUUGCCGUGGGCCUCCUCC<br>UGUACUGCAAGGCCCGCAGCACUCCUGUGACCCUCAGCAA<br>GGAUCAGCUGAGCGGCAUCAAUAAUAUCGCCUUCAGCAA<br>U | 56 |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 78 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATGSGSAICSGVAVCKVLHLEGEVNKIK<br>SALLSTNKAVVSLSNGVSVLTFKVLDLKNYIDKQLLPILNKQS<br>CSISNIETVIEFQQKNNRLLEITREFSVNAGVTTPVSTYMLTNSE<br>LLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>NRGIIKTFSNGCDYVSNKGVDTVSVGNTLYCVNKQEGKSLYV | 5 |

TABLE 7-continued

KGEPIINFYDPLVFPSDEFDASISQVNEKINQSLAFIRKSDELLH
NVNAGKSTTNIMITTIIIVIIVILLSLIAVGLLLYCKARSTPVTLS
KDQLSGINNIAFSN

| PolyA tail | 100 nt |  |
|---|---|---|

MRK_RSVF mVRC1(v2)_SE_003

| | | |
|---|---|---|
| SEQ ID NO: 57 consists of from 5' end to 3' end: 5' UTR SEQ ID NO: 77, mRNA ORF SEQ ID NO: 58, and 3' UTR SEQ ID NO: 78. | | 57 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGACCCCGGCGCCGCCACC | 77 |
| ORF of mRNA Construct (excluding the stop codon) | AUGGAGCUGCUGAUCCUGAAGGCCAACGCCAUCACCACC AUCCUGACCGCCGUGACCUUCUGCUUCGCCAGCGGCCAGA ACAUUACCGAGGAGUUCUACCAGUCCACCUGCAGCGCCG UGAGCAAGGGCUACCUGAGCGCCCUGCGCACCGGGUGGU ACACCAGCGUGAUCACCAUCGAGCUGUCCAACAUCAAGG AGAACAAGUGCAACGGCACAGACGCCAAGGUGAAGCUGA UCAAGCAGGAGCUGGACAAGUACAAGAACGCCGUGACCG AGCUCCAGCUGCUGAUGCAGUCCACCCCGGCCACCGGCAG UGGAAGUGCUAUCUGCAGCGGGGUGGCCGUGUGCAAGGU GCUGCACCUGGAGGGCGAGGUGAACAAGAUCAAGAGCGC CCUGCUGAGCACCAACAAGGCCGUGGUGAGCCUGAGCAA CGGGGUGUCCGUGCUGACAUUCAAGGUGCUGGACCUGAA GAACUACAUCGACAAGCAGCUGCUGCCCAUCCUCAACAA GCAGAGCUGCUCCAUCUCCAAUAUCGAAACCGUGAUCGA GUUUCAGCAGAAGAACAACCGGCUGCUGGAGAUCACCCG GGAGUUCUCCGUGAACGCCGGGGUGACCACCCCAGUGAG CACCUACAUGCUGACCAACUCCGAGCUGCUGAGCCUGAUC AACGAUAUGCCAAUCACAAACGAUCAGAAGAAGCUGAUG AGCAACAACGUGCAGAUCGUGCGGCAGCAGUCCUACAGC AUCAUGUGCAUCAUCAAGGAGGAGGUGCUGGCCUACGUG GUGCAGCUGCCCCUGUACGGCGUGAUCGACACUCCUUGC UGGAAGCUGCACACCUCACCGCUGUGCACCACGAACACUA AGGAGGGCAGCAACAUCUGCCUGACCCGGACCGACCGAG GCUGGUACUGCGACAACGCCGGCAGCGUCUCUUUCUUUC CGCAGGCCGAGACGUGCAAGGUGCAGUCCAACGGGUGU UCUGCGACACCAUGAACUCCCGGACCCUGCCCUCCGAGGU GAACCUGUGCAACGUGGACAUUUUCAACCCCAAGUACGA CUGCAAGAUCAUGACCAGUAAGACCGACGUGUCCAGCUC CGUAAUCACCAGCCUGGGCGCCAUCGUGUCCUGUUACGG CAAGACCAAGUGUACCGCCUCCAACAAGAACCGAGGUAU CAUCAAGACCUUCUCCAACGGGUGCGACUACGUGUCCAA CAAGGGCGUGGACACCGUGAGCGUGGGAAAUACCCUCUA CUGCGUGAACAAGCAGGAGGGGAAGUCCCUGUACGUGAA GGGUGAGCCCAUCAUCAACUUUUACGAUCCCCUGGUGUU CCCCAGCGACGAGUUCGACGCAUCCAUUAGCCAGGUGAA CGAGAAGAUCAACCAGAGUCUGGCCUUCAUCCGCAAGUC CGACGAGCUGCUGCACAACGUGAACGCUGGCAAGUCAAC AACCAACAUCAUGAUCACGACCAUCAUUAUCGUGAUCAU CGUGAUCCUGCUGUCCCUGAUCGCAGUGGGCCUGCUCCU GUACUGCAAGGCCCGCAGCACACCCGUGACCCUCAGCAAG GAUCAGCUCAGCGGCAUCAACAACAUCGCCUUCAGCAAC | 58 |
| 3' UTR | UGAUAAUAGGCUGGAGCCUCGGUGGCCUAGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 78 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATGSGSAICSGVAVCKVLHLEGEVNKIK SALLSTNKAVVSLSNGVSVLTFKVLDLKNYIDKQLLPILNKQS CSISNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGKSLYV | 5 |

TABLE 7-continued

|  |  |  |
|---|---|---|
|  | KGEPIINFYDPLVFPSDEFDASISQVNEKINQSLAFIRKSDELLH<br>NVNAGKSTTNIMITTIIIVIIVILLSLIAVGLLLYCKARSTPVTLS<br>KDQLSGINNIAFSN |  |
| PolyA tail | 100 nt |  |

MRK_sLZF129

SEQ ID NO: 59 consists of from 5' end to 3' end: 5' UTR SEQ ID NO: 2, mRNA ORF SEQ ID NO: 60, and 3' UTR SEQ ID NO: 4.    59

| | | |
|---|---|---|
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGGGAGGCGGUAGCGGUGGCGGA<br>UCCGGCGGUGGAAGCGGCUCUGCCAUUGCUUCCGGCGUG<br>GCUGUAUGUAAAGUUCUCCACCUCGAGGGAGAGGUUAAU<br>AAGAUUAAGUCGGCCCUGCUGAGUACUAACAAAGCAGUG<br>GUGUCGCUGAGUAACGGAGUAAGUGUGUUAACAUUUAAG<br>GUGCUGGACCUCAAGAAUUAUAUUGACAAACAGUUGCUU<br>CCUAUUCUAAACAAACAGAGCUGUUCAAUAAGUAAUAUU<br>GAAACUGUUAUUGAGUUUCAGCAGAAGAACAACAGGCUU<br>CUUGAGAUUACACGCGAGUUCAGUGUCAAUGCCGGCGUU<br>ACAACACCCGUGUCUACCUACAUGCUGACGAAUUCUGAG<br>CUUCUCUCUCUCAUAAACGACAUGCCCAUUACGAAUGAC<br>CAAAAGAAACUUAUGUCCAACAACGUGCAGAUUGUGCGA<br>CAGCAAUCCUAUAGCAUUAUGUGUAUCAUCAAGGAAGAG<br>GUACUCGCUUAUGUUGUGCAGCUACCACUCUAUGGUGUG<br>AUUGACACCCCCUGUUGGAAGCUGCAUACCAGUCCACUC<br>UGCACCACUAACACAAAGGAAGGGAGCAAUAUUUGCCUC<br>ACUCGAACCGACAGGGGGUGGUAUUGCGAUAAUGCGGGC<br>UCCGUGUCCUUCUUUCCACAGGCUGAAACUUGUAAGGUA<br>CAGUCAAACCGCGUGUUCUGUGAUACUAUGAAUUCUCUG<br>ACUCUUCCCAGCGAGGUUAAUCUCUGCAACGUCGACAUU<br>UUCAAUCCUAAAUAUGACUGCAAGAUCAUGACCAGCAAG<br>ACCGACGUCUCCAGCUCAGUAAUCACUAGCCUAGGGGCC<br>AUUGUAAGCUGCUAUGGCAAAACCAAGUGUACUGCCUCU<br>AAUAAGAACAGAGGCAUAAUUAAAACCUUUUCAAAUGGC<br>UGUGACUAUGUGUCGAAUAAGGGCGUCGACACGGUCUCA<br>GUAGGGAAUACCCUCUACUACGUUAACAAACAGGAAGGC<br>AAAUCCCUUUAUGUAAAGGGCGAGCCCAUCAUAAAUUUC<br>UACGACCCACUUUCCGCCAUCGGUGGCUAUAUCCCAGAA<br>GCCCCAAGAGACGGACAAGCGUACGUCCGGAAAGAUGGU<br>GAGUGGGUCCUCCUCUCUACCUUUCUU | 60 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMGGGSGGGSGGGSGSAIASGVAVCKVLHLEGE<br>VNKIKSALLSTNKAVVSLSNGVSVLTFKVLDLKNYIDKQLLPI<br>LNKQSCSISNIETVIEFQQKNNRLLEITREFSVNAGVTTPVSTY<br>MLTNSELLSLINDMPITNDQKKLMSNNVQIVRQQSYSIMCIIKE<br>EVLAYVVQLPLYGVIDTPCWKLHTSPLCTTNTKEGSNICLTRT<br>DRGWYCDNAGSVSFFPQAETCKVQSNRVFCDTMNSLTLPSEV<br>NLCNVDIFNPKYDCKIMTSKTDVSSSVITSLGAIVSCYGKTKCT<br>ASNKNRGIIKTFSNGCDYVSNKGVDTVSVGNTLYYVNKQEGK<br>SLYVKGEPIINFYDPLSAIGGYIPEAPRDGQAYVRKDGEWVLL<br>STFL | 61 |
| PolyA tail | 100 nt | |

TABLE 7-continued

MRK_sLZF128

| | | |
|---|---|---|
| SEQ ID NO: 62 consists of from 5' end to 3' end: 5' UTR SEQ ID NO: 2, mRNA ORF SEQ ID NO: 63, and 3' UTR SEQ ID NO: 4. | | 62 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGAGUGCGCUCCGCACAGGAUGG<br>UACACCUCCGUGAUCACCAUCGAGCUCAGCAAUAUUAAA<br>GAGAACAAGUGCAAUGGUACCGACGCUAAAGUCAAACUU<br>AUCAAGCAGGAACUCGACAAAUAUAAGAACGCUGUGACC<br>GAGCUGCAGUUAUUGAUGCAGAGUACACCUGCCACCAAU<br>AACAGAGCUAGGAGGGAGUUGCCUAGGUUUAUGAACUAC<br>ACUCUCAACAACGCGAAGAAAACCAAUGUGACGCUAUCC<br>AAGAAACGGAAGAGGAGGUUCCUGGGGUUUCUUUUAGGG<br>GUGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>AACGGAGUAAGUGUGUUAACAUUUAAGGUGCUGGACCUC<br>AAGAAUUAUAUUGACAAACAGUUGCUUCCUAUUCUAAAC<br>AAACAGAGCUGUUCAAUAAGUAAUAUUGAAACUGUUAUU<br>GAGUUUCAGCAGAAGAACAACAGGCUUCUUGAGAUUACA<br>CGCGAGUUCAGUGUCAAUGCCGGCGUUACAACACCCGUG<br>UCUACCUACAUGCUGACGAAUUCUGAGCUUCUCUCUCUC<br>AUAAACGACAUGCCCAUUACGAAUGACCAAAAGAAACUU<br>AUGUCCAACAACGUGCAGAUUGUGCGACAGCAAUCCUAU<br>AGCAUUAUGUGUAUCAUCAAGGAAGAGGUACUCGCUUAU<br>GUUGUGCAGCUACCACUCUAUGGUGUGAUUGACACCCCC<br>UGUUGGAAGCUGCAUACCAGUCCACUCUGCACCACUAAC<br>ACAAAGGAAGGGAGCAAUAUUUGCCUCACUCGAACCGAC<br>AGGGGGUGGUAUUGCGAUAAUGCGGGCUCCGUGUCCUUC<br>UUUCCACAGGCUGAAACUUGUAAGGUACAGUCAAACCGC<br>GUGUUCUGUGAUACUAUGAAUUCUCUGACUCUUCCCAGC<br>GAGGUUAAUCUCUGCAACGUCGACAUUUUCAAUCCUAAA<br>UAUGACUGCAAGAUCAUGACCAGCAAGACCGACGUCUCC<br>AGCUCAGUAAUCACUAGCCUAGGGGCCAUUGUAAGCUGC<br>UAUGGCAAAACCAAGUGUACUGCCUCUAAUAAGAACAGA<br>GGCAUAAUUAAAACCUUUUCAAAUGGCUGUGACUAUGUG<br>UCGAAUAAGGGCGUCGACACGGUCUCAGUAGGGAAUACC<br>CUCUACUACGUUAACAAACAGGAAGGCAAAUCCCUUUAU<br>GUAAAGGGCGAGCCCAUCAUAAAUUUCUACGACCCACUU<br>UCCGCCAUCGGUGGCUAUAUCCCAGAAGCCCCAAGAGAC<br>GGACAAGCGUACGUCCGGAAAGAUGGUGAGUGGGUCCUC<br>CUCUCUACCUUUCUU | 63 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MELLILKANAITTILTAVTFCFASGQNITEEFYQSTCSAVSKGY<br>LSALRTGWYTSVITIELSNIKENKCNGTDAKVKLIKQELDKYK<br>NAVTELQLLMQSTPATNNRARRELPRFMNYTLNNAKKTNVT<br>LSKKRKRRFLGFLLGVGSAIASGVAVCKVLHLEGEVNKIKSAL<br>LSTNKAVVSLSNGVSVLTFKVLDLKNYIDKQLLPILNKQSCSIS<br>NIETVIEFQQKNNRLLEITREFSVNAGVTTPVSTYMLTNSELLS<br>LINDMPITNDQKKLMSNNVQIVRQQSYSIMCIIKEEVLAYVVQ<br>LPLYGVIDTPCWKLHTSPLCTTNTKEGSNICLTRTDRGWYCD<br>NAGSVSFFPQAETCKVQSNRVFCDTMNSLTLPSEVNLCNVDIF<br>NPKYDCKIMTSKTDVSSSVITSLGAIVSCYGKTKCTASNKNRG<br>IIKTFSNGCDYVSNKGVDTVSVGNTLYYVNKQEGKSLYVKGE<br>PIINFYDPLSAIGGYIPEAPRDGQAYVRKDGEWVLLSTFL | 64 |
| PolyA tail | 100 nt | |

TABLE 7-continued

MRK_sLZF125

| | | |
|---|---|---|
| SEQ ID NO: 65 consists of from 5' end to 3' end: 5' UTR SEQ ID NO: 2, mRNA ORF SEQ ID NO: 66, and 3' UTR SEQ ID NO: 4. | | 65 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCAAU AACAGAGCUAGGAGGGAGUUGCCUAGGUUUAUGAACUAC ACUCUCAACAACGCGAAGAAAACCAAUGUGACGCUAUCC AAGAAACGGAAGAGGAGGUUCCUGGGGUUUCUUUUAGGG GUGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCUGACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUACGUUAACAAACAGGAAGGCAAAUCCCUUUAU GUAAAGGGCGAGCCCAUCAUAAAUUUCUACGACCCACUU GUGUUCCCCAGUUGCGAAUUCUGCGCAUCAAUCUCCCAG GUGAACGAAAAGAUCAAUCAAUCCCUUGCUUUUAUACGA AAGUCAGAUGAACUCCUGUCCGCCAUCGGUGGCUAUAUC CCAGAAGCCCCAAGAGACGGACAAGCGUACGUCCGGAAA GAUGGUGAGUGGGUCCUCCUCUCUACCUUUCUU | 66 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATNNRARRELPRFMNYTLNNAKKTNVT LSKKRKRRFLGFLLGVGSAIASGVAVCKVLHLEGEVNKIKSAL LSTNKAVVSLSNGVSVLTFKVLDLKNYIDKQLLPILNKQSCSIS NIETVIEFQQKNNRLLEITREFSVNAGVTTPVSTYMLTNSELLS LINDMPITNDQKKLMSNNVQIVRQQSYSIMCIIKEEVLAYVVQ LPLYGVIDTPCWKLHTSPLCTTNTKEGSNICLTRTDRGWYCD NAGSVSFFPQAETCKVQSNRVFCDTMNSLTLPSEVNLCNVDIF NPKYDCKIMTSKTDVSSSVITSLGAIVSCYGKTKCTASNKNRG IIKTFSNGCDYVSNKGVDTVSVGNTLYYVNKQEGKSLYVKGE PIINFYDPLVFPSCEFCASISQVNEKINQSLAFIRKSDELLSAIGG YIPEAPRDGQAYVRKDGEWVLLSTFL | 67 |
| PolyA tail | 100 nt | |

TABLE 7-continued

MRK_sLZF111

| | | |
|---|---|---|
| SEQ ID NO: 68 consists of from 5' end to 3' end: 5' UTR SEQ ID NO: 2, mRNA ORF SEQ ID NO: 69, and 3' UTR SEQ ID NO: 4. | | 68 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGGGAGGCGGUAGCGGUGGCGGA UCCGGCGGUGGAAGCGGCUCUGCCAUUGCUUCCGGCGUG GCUGUAUGUAAAGUUCUCCACCUCGAGGGAGAGGUUAAU AAGAUUAAGUCGGCCCUGCUGAGUACUAACAAAGCAGUG GUGUCGCUGAGUAACGGAGUAAGUGUGUUAACAUUUAAG GUGCUGGACCUCAAGAAUUAUAUUGACAAACAGUUGCUU CCUAUUCUAAACAAACAGAGCUGUUCAAUAAGUAAUAUU GAAACUGUUAUUGAGUUUCAGCAGAAGAACAACAGGCUU CUUGAGAUUACACGCGAGUUCAGUGUCAAUGCCGGCGUU ACAACACCCGUGUCUACCUACAUGCUGACGAAUUCUGAG CUUCUCUCUCUCAUAAACGACAUGCCCAUUACGAAUGAC CAAAAGAAACUUAUGUCCAACAACGUGCAGAUUGUGCGA CAGCAAUCCUAUAGCAUUAUGUGUAUCAUCAAGGAAGAG GUACUCGCUUAUGUUGUGCAGCUACCACUCUAUGGUGUG AUUGACACCCCCUGUUGGAAGCUGCAUACCAGUCCACUC UGCACCACUAACACAAAGGAAGGGAGCAAUAUUUGCCUC ACUCGAACCGACAGGGGUGGUAUUGCGAUAAUGCGGGC UCCGUGUCCUUCUUUCCACAGGCUGAAACUUGUAAGGUA CAGUCAAACCGCGUGUUCUGUGAUACUAUGAAUUCUCUG ACUCUUCCCAGCGAGGUUAAUCUCUGCAACGUCGACAUU UUCAAUCCUAAAUAUGACUGCAAGAUCAUGACCAGCAAG ACCGACGUCUCCAGCUCAGUAAUCACUAGCCUAGGGGCC AUUGUAAGCUGCUAUGGCAAAACCAAGUGUACUGCCUCU AAUAAGAACAGAGGCAUAAUUAAAACCUUUUCAAAUGGC UGUGACUAUGUGUCGAAUAAGGGCGUCGACACGGUCUCA GUAGGGAAUACCCUCUACUACGUUAACAAACAGGAAGGC AAAUCCCUUUAUGUAAAGGGCGAGCCCAUCAUAAAUUUC UACGACCCACUUGUGUUCCCCAGUUGCGAAUUCUGCGCA UCAAUCUCCCAGGUGAACGAAAAGAUCAAUCAAUCCCUU GCUUUUAUACGAAAGUCAGAUGAACUCCUGUCCGCCAUC GGUGGCUAUAUCCCAGAAGCCCCAAGAGACGGACAAGCG UACGUCCGGAAAGAUGGUGAGUGGGUCCUCCUCUCUACC UUUCUU | 69 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMGGGSGGGSGGGSGSAIASGVAVCKVLHLEGE VNKIKSALLSTNKAVVSLSNGVSVLTFKVLDLKNYIDKQLLPI LNKQSCSISNIETVIEFQQKNNRLLEITREFSVNAGVTTPVSTY MLTNSELLSLINDMPITNDQKKLMSNNVQIVRQQSYSIMCIIKE EVLAYVVQLPLYGVIDTPCWKLHTSPLCTTNTKEGSNICLTRT DRGWYCDNAGSVSFFPQAETCKVQSNRVFCDTMNSLTLPSEV NLCNVDIFNPKYDCKIMTSKTDVSSSVITSLGAIVSCYGKTKCT ASNKNRGIIKTFSNGCDYVSNKGVDTVSVGNTLYYVNKQEGK SLYVKGEPIINFYDPLVFPSCEFCASISQVNEKINQSLAFIRKSD ELLSAIGGYIPEAPRDGQAYVRKDGEWVLLSTFL | 70 |
| PolyA tail | 100 nt | |

TABLE 7-continued

| MRK_mLZF125 | | |
|---|---|---|
| SEQ ID NO: 71 consists of from 5' end to 3' end: 5' UTR SEQ ID NO: 2, mRNA ORF SEQ ID NO: 72, and 3' UTR SEQ ID NO: 4. | | 71 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCAAU AACAGAGCUAGGAGGGAGUUGCCUAGGUUUAUGAACUAC ACUCUCAACAACGCGAAGAAAACCAAUGUGACGCUAUCC AAGAAACGGAAGAGGAGGUUCCUGGGGUUUCUUUUAGGG GUGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCUGACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUACGUUAACAAACAGGAAGGCAAAUCCCUUUAU GUAAAGGGCGAGCCCAUCAUAAAUUUCUACGACCCACUU GUGUUCCCCAGUUGCGAAUUCUGCGCAUCAAUCUCCCAG GUGAACGAAAAGAUCAAUCAAUCCCUUGCUUUUAUACGA AAGUCAGAUGAACUCCUGCAUAACGUGAAUGCUGGGAAA UCUACAACCAACAUCAUGAUCACUACCAUCAUUAUUGUG AUUAUCGUAAUUCUGCUAUCCUUGAUUGCUGUCGGGCUG CUUCUGUACUGUAAGGCCAGAUCGACGCCUGUGACCCUU UCAAAAGACCAACUUAGCGGUAUCAAUAAUAUUGCCUUU AGCAAU | 72 |
| 3' UTR | UGAUAAUAGGCUGGAGCCUCGGUGGCCAUGCUUCUUGCC CCUUGGGCCUCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATNNRARRELPRFMNYTLNNAKKTNVT LSKKRKRRFLGFLLGVGSAIASGVAVCKVLHLEGEVNKIKSAL LSTNKAVVSLSNGVSVLTFKVLDLKNYIDKQLLPILNKQSCSIS NIETVIEFQQKNNRLLEITREFSVNAGVTTPVSTYMLTNSELLS LINDMPITNDQKKLMSNNVQIVRQQSYSIMCIIKEEVLAYVVQ LPLYGVIDTPCWKLHTSPLCTTNTKEGSNICLTRTDRGWYCD NAGSVSFFPQAETCKVQSNRVFCDTMNSLTLPSEVNLCNVDIF NPKYDCKIMTSKTDVSSSVITSLGAIVSCYGKTKCTASNKNRG IIKTFSNGCDYVSNKGVDTVSVGNTLYYVNKQEGKSLYVKGE PIINFYDPLVFPSCEFCASISQVNEKINQSLAFIRKSDELLHNVN AGKSTTNIMITTIIIVIIVILLSLIAVGLLLYCKARSTPVTLSKDQ LSGINNIAFSN | 73 |
| PolyA tail | 100 nt | |

TABLE 7-continued

| MRK_mLZF111 | | |
|---|---|---|
| SEQ ID NO: 74 consists of from 5' end to 3' end: 5' UTR SEQ ID NO: 2, mRNA ORF SEQ ID NO: 75, and 3' UTR SEQ ID NO: 4. | | 74 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGGGAGGCGGUAGCGGUGGCGGA UCCGGCGGUGGAAGCGGCUCUGCCAUUGCUUCCGGCGUG GCUGUAUGUAAAGUUCUCCACCUCGAGGGAGAGGUUAAU AAGAUUAAGUCGGCCCUGCUGAGUACUAACAAAGCAGUG GUGUCGCUGAGUAACGGAGUAAGUGUGUUAACAUUUAAG GUGCUGGACCUCAAGAAUUAUAUUGACAAACAGUUGCUU CCUAUUCUAAACAAACAGAGCUGUUCAAUAAGUAAUAUU GAAACUGUUAUUGAGUUUCAGCAGAAGAACAACAGGCUU CUUGAGAUUACACGCGAGUUCAGUGUCAAUGCCGGCGUU ACAACACCCGUGUCUACCUACAUGCUGACGAAUUCUGAG CUUCUCUCUCUCAUAAACGACAUGCCCAUUACGAAUGAC CAAAAGAAACUUAUGUCCAACAACGUGCAGAUUGUGCGA CAGCAAUCCUAUAGCAUUAUGUGUAUCAUCAAGGAAGAG GUACUCGCUUAUGUUGUGCAGCUACCACUCUAUGGUGUG AUUGACACCCCCUGUUGGAAGCUGCAUACCAGUCCACUC UGCACCACUAACACAAAGGAAGGGAGCAAUAUUUGCCUC ACUCGAACCGACAGGGGGUGGUAUUGCGAUAAUGCGGGC UCCGUGUCCUUCUUUCCACAGGCUGAAACUUGUAAGGUA CAGUCAAACCGCGUGUUCUGUGAUACUAUGAAUUCUCUG ACUCUUCCCAGCGAGGUUAAUCUCUGCAACGUCGACAUU UUCAAUCCUAAAUAUGACUGCAAGAUCAUGACCAGCAAG ACCGACGUCUCCAGCUCAGUAAUCACUAGCCUAGGGGCC AUUGUAAGCUGCUAUGGCAAAACCAAGUGUACUGCCUCU AAUAAGAACAGAGGCAUAAUUAAAACCUUUUCAAAUGGC UGUGACUAUGUGUCGAAUAAGGGCGUCGACACGGUCUCA GUAGGGAAUACCCUCUACUACGUUAACAAACAGGAAGGC AAAUCCUUUAUGUAAAGGGCGAGCCCAUCAUAAAUUUC UACGACCCACUUGUGUUCCCCAGUUGCGAAUUCUGCGCA UCAAUCUCCCAGGUGAACGAAAAGAUCAAUCAAUCCCUU GCUUUUAUACGAAAGUCAGAUGAACUCCUGCAUAACGUG AAUGCUGGGAAAUCUACAACCAACAUCAUGAUCACUACC AUCAUUAUUGUGAUUAUCGUAAUUCUGCUAUCCUUGAUU GCUGUCGGGCUGCUUCUGUACUGUAAGGCCAGAUCGACG CCUGUGACCCUUUCAAAAGACCAACUUAGCGGUAUCAAU AAUAUUGCCUUUAGCAAU | 75 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMGGGSGGGSGGGSAIASGVAVCKVLHLEGE VNKIKSALLSTNKAVVSLSNGVSVLTFKVLDLKNYIDKQLLPI LNKQSCSISNIETVIEFQQKNNRLLEITREFSVNAGVTTPVSTY MLTNSELLSLINDMPITNDQKKLMSNNVQIVRQQSYSIMCIIKE EVLAYVVQLPLYGVIDTPCWKLHTSPLCTTNTKEGSNICLTRT DRGWYCDNAGSVSFFPQAETCKVQSNRVFCDTMNSLTLPSEV NLCNVDIFNPKYDCKIMTSKTDVSSSVITSLGAIVSCYGKTKCT ASNKNRGIIKTFSNGCDYVSNKGVDTVSVGNTLYYVNKQEGK SLYVKGEPIINFYDPLVFPSCEFCASISQVNEKINQSLAFIRKSD ELLHNVNAGKSTTNIMITTIIIVIIVILLSLIAVGLLLYCKARSTP VTLSKDQLSGINNIAFSN | 76 |
| PolyA tail | 100 nt | |

TABLE 7-continued

| MRK-04 membrane-bound DS-CAV1 (stabilized prefusion F protein) | | |
|---|---|---|
| SEQ ID NO: 90 consists of from 5' end to 3' end: 5' UTR SEQ ID NO: 2, mRNA ORF SEQ ID NO: 88, and 3' UTR SEQ ID NO: 4. | | 90 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAAAACGCUGUGACC GAGCUGCAGUUAUUGAUGCAGAGUACACCUGCCACCAAU AACAGAGCUAGGAGGGAGUUGCCUAGGUUUAUGAACUAC ACUCUCAACAACGCGAAAAAAACCAAUGUGACGCUAUCC AAGAAACGGAAGAGGAGGUUCCUGGGGUUUCUUUUAGGG GUGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAAAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCUGACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUACGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGCAUAACGUGAAUGCUGGGAAA UCUACAACCAACAUCAUGAUCACUACCAUCAUUAUUGUG AUUAUCGUAAUUCUGCUAUCCUUGAUUGCUGUCGGGCUG CUUCUGUACUGUAAGGCCAGAUCGACGCCUGUGACCCUU UCAAAAGACCAACUUAGCGGUAUCAAUAAUAUUGCCUUU AGCAAU | 88 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATNNRARRELPRFMNYTLNNAKKTNVT LSKKRKRRFLGFLLGVGSAIASGVAVCKVLHLEGEVNKIKSAL LSTNKAVVSLSNGVSVLTFKVLDLKNYIDKQLLPILNKQSCSIS NIETVIEFQQKNNRLLEITREFSVNAGVTTPVSTYMLTNSELLS LINDMPITNDQKKLMSNNVQIVRQQSYSIMCIIKEEVLAYVVQ LPLYGVIDTPCWKLHTSPLCTTNTKEGSNICLTRTDRGWYCD NAGSVSFFPQAETCKVQSNRVFCDTMNSLTLPSEVNLCNVDIF NPKYDCKIMTSKTDVSSSVITSLGAIVSCYGKTKCTASNKNRG IIKTFSNGCDYVSNKGVDTVSVGNTLYYVNKQEGKSLYVKGE PIINFYDPLVFPSDEFDASISQVNEKINQSLAFIRKSDELLHNVN AGKSTTNIMITTIIIVIIVILLSLIAVGLLLYCKARSTPVTLSKDQ LSGINNIAFSN | 89 |
| PolyA tail | 100 nt | |

TABLE 7-continued

MRK_04_nopolyA_3mut

| | | |
|---|---|---|
| SEQ ID NO: 92 consists of from 5' end to 3' end: 5' UTR SEQ ID NO: 2, mRNA ORF SEQ ID NO: 91, and 3' UTR SEQ ID NO: 4. | | 92 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGAGUGCGCUCCGCACAGGAUGG UACACCUCCGUGAUCACCAUCGAGCUCAGCAAUAUUAAA GAGAACAAGUGCAAUGGUACCGACGCUAAAGUCAAACUU AUCAAGCAGGAACUCGACAAAUAUAAGAACGCUGUGACC GAGCUGCAGUUAUUGAUGCAGAGUACACCUGCCACCAAU AACAGAGCUAGGAGGGAGUUGCCUAGGUUUAUGAACUAC ACUCUCAACAACGCGAAGAAAACCAAUGUGACGCUAUCC AAGAAACGGAAGAGGAGGUUCCUGGGGUUUCUUUUAGGG GUGGGCUCUGCCAUUGCUUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUAAGUAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCUGACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGGUCUCAGUAGGGAAUACC CUCUACUACGUUAACAAACAGGAAGGCAAAUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAGAUCAAUCAAUCCCUUGCUUUUUAUACGA AAGUCAGAUGAACUCCUGCAUAACGUGAAUGCUGGGAAA UCUACAACCAACAUCAUGAUCACUACCAUCAUUAUUGUG AUUAUCGUAAUUCUGCUAUCCUUGAUUGCUGUCGGGCUG CUUCUGUACUGUAAGGCCAGAUCGACGCCUGUGACCCUU UCAAAAGACCAACUUAGCGGUAUCAAUAAUAUUGCCUUU AGCAAU | 91 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LSALRTGWYTSVITIELSNIKENKCNGTDAKVKLIKQELDKYK NAVTELQLLMQSTPATNNRARRELPRFMNYTLNNAKKTNVT LSKKRKRRFLGFLLGVSAIASGVAVCKVLHLEGEVNKIKSAL LSTNKAVVSLSNGVSVLTFKVLDLKNYIDKQLLPILNKQSCSIS NIETVIEFQQKNNRLLEITREFSVNAGVTTPVSTYMLTNSELLS LINDMPITNDQKKLMSNNVQIVRQQSYSIMCIIKEEVLAYVVQ LPLYGVIDTPCWKLHTSPLCTTNTKEGSNICLTRTDRGWYCD NAGSVSFFPQAETCKVQSNRVFCDTMNSLTLPSEVNLCNVDIF NPKYDCKIMTSKTDVSSSVITSLGAIVSCYGKTKCTASNKNRG IIKTFSNGCDYVSNKGVDTVSVGNTLYYVNKQEGKSLYVKGE PIINFYDPLVFPSDEFDASISQVNEKINQSLAFIRKSDELLHNVN AGKSTTNIMITTIIIVIIVILLSLIAVGLLLYCKARSTPVTLSKDQ LSGINNIAFSN | 89 |

TABLE 7-continued

VRC-4A

| | | |
|---|---|---|
| SEQ ID NO: 98 consists of from 5' end to 3' end: 5' UTR SEQ ID NO: 2, mRNA ORF SEQ ID NO: 96, and 3' UTR SEQ ID NO: 4. | | 98 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA AGAGCCACC | 2 |
| ORF of mRNA Construct (excluding the stop codon) | AUGGAACUGCUCAUUUUGAAGGCAAACGCUAUCACGACA AUACUCACUGCAGUGACCUUCUGUUUUGCCUCAGGCCAG AACAUAACCGAGGAGUUUUAUCAAUCUACAUGCAGCGCU GUAUCUAAAGGCUACCUGGGCGCGCUCCGCACAGGAUGG UACACCUCCGUGAUCACCAUCGAGCUCAGCAAUAUUAAA GAGAUCAAGUGCAAUGGUACCGACGCUAAAGUCAAACUU AUCAAGCAGGAACUCGACAAAUAUAAGAACGCUGUGACC GACCUGCAGUUAUUGAUGCAGAGUACACCUGCCACCGGG UCGGGCUCUGCCAUUUGCUCCGGCGUGGCUGUAUGUAAA GUUCUCCACCUCGAGGGAGAGGUUAAUAAGAUUAAGUCG GCCCUGCUGAGUACUAACAAAGCAGUGGUGUCGCUGAGU AACGGAGUAAGUGUGUUAACAUUUAAGGUGCUGGACCUC AAGAAUUAUAUUGACAAACAGUUGCUUCCUAUUCUAAAC AAACAGAGCUGUUCAAUACCCAAUAUUGAAACUGUUAUU GAGUUUCAGCAGAAGAACAACAGGCUUCUUGAGAUUACA CGCGAGUUCAGUGUCAAUGCCGGCGUUACAACACCCGUG UCUACCUACAUGCUGACGAAUUCUGAGCUUCUCUCUCUC AUAAACGACAUGCCCAUUACGAAUGACCAAAAGAAACUU AUGUCCAACAACGUGCAGAUUGUGCGACAGCAAUCCUAU AGCAUUAUGUGUAUCAUCAAGGAAGAGGUACUCGCUUAU GUUGUGCAGCUACCACUCUAUGGUGUGAUUGACACCCCC UGUUGGAAGCUGCAUACCAGUCCACUCUGCACCACUAAC ACAAAGGAAGGGAGCAAUAUUUGCCUCACUCGAACCGAC AGGGGGUGGUAUUGCGAUAAUGCGGGCUCCGUGUCCUUC UUUCCACAGGCUGAAACUUGUAAGGUACAGUCAAACCGC GUGUUCUGUGAUACUAUGAAUUCUCGUACUCUUCCCAGC GAGGUUAAUCUCUGCAACGUCGACAUUUUCAAUCCUAAA UAUGACUGCAAGAUCAUGACCAGCAAGACCGACGUCUCC AGCUCAGUAAUCACUAGCCUAGGGGCCAUUGUAAGCUGC UAUGGCAAAACCAAGUGUACUGCCUCUAAUAAGAACAGA GGCAUAAUUAAAACCUUUUCAAAUGGCUGUGACUAUGUG UCGAAUAAGGGCGUCGACACGUCUCAGUAGGGAAUACC CUCUACUGCGUUAACAAACAGGAAGGCCAGUCCCUUUAU GUAAAGGGCGAGCCCAUCAUAAAUUUCUACGACCCACUU GUGUUCCCCAGUGAUGAAUUCGAUGCAUCAAUCUCCCAG GUGAACGAAAAGAUCAAUCAAUCCCUUGCUUUUAUACGA AAGUCAGAUGAACUCCUGUCCGCCAUCGGUGGCUAUAUC CCAGAAGCCCCAAGAGACGGACAAGCGUACGUCCGGAAA GAUGGUGAGUGGGUCCUCCUCUCUACCUUUCUU | 96 |
| 3' UTR | UGAUAAUAGGCUGGAGCCUCGGUGGCCAUGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MELLILKANAITTILTAVTFCFASGQNITEEFYQSTCSAVSKGY LGALRTGWYTSVITIELSNIKEIKCNGTDAKVKLIKQELDKYK NAVTDLQLLMQSTPATGSGSAICSGVAVCKVLHLEGEVNKIK SALLSTNKAVVSLSNGVSVLTFKVLDLKNYIDKQLLPILNKQS CSIPNIETVIEFQQKNNRLLEITREFSVNAGVTTPVSTYMLTNSE LLSLINDMPITNDQKKLMSNNVQIVRQQSYSIMCIIKEEVLAY VVQLPLYGVIDTPCWKLHTSPLCTTNTKEGSNICLTRTDRGW YCDNAGSVSFFPQAETCKVQSNRVFCDTMNSRTLPSEVNLCN VDIFNPKYDCKIMTSKTDVSSSVITSLGAIVSCYGKTKCTASNK NRGIIKTFSNGCDYVSNKGVDTVSVGNTLYCVNKQEGQSLYV KGEPIINFYDPLVFPSDEFDASISQVNEKINQSLAFIRKSDELLS AIGGYIPEAPRDGQAYVRKDGEWVLLSTFL | 44 |
| PolyA tail | 100 nt | |

TABLE 7-continued

VRC-5A

| | | |
|---|---|---|
| SEQ ID NO: 99 consists of from 5' end to 3' end: 5' UTR SEQ ID NO: 2, mRNA ORF SEQ ID NO: 97, and 3' UTR SEQ ID NO: 4. | | 99 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGAGCCACC | 2 |
| ORF of mRNA Construct (excluding the stop codon) | AUGGAACUGCUCAUUUUGAAGGCAAACGCUAUCACGACA<br>AUACUCACUGCAGUGACCUUCUGUUUUGCCUCAGGCCAG<br>AACAUAACCGAGGAGUUUUAUCAAUCUACAUGCAGCGCU<br>GUAUCUAAAGGCUACCUGGGCGCGCUCCGCACAGGAUGG<br>UACACCUCCGUGAUCACCAUCGAGCUCAGCAAUAUUAAA<br>GAGAUCAAGUGCAAUGGUACCGACGCUAAAGUCAAACUU<br>AUCAAGCAGGAACUCGACAAAUAUAAGAACGCUGUGACC<br>GACCUGCAGUUAUUGAUGCAGAGUACACCUGCCACCGGG<br>UCGGGCUCUGCCAUUGCUUCCGGCGUGGCUGUAUGUAAA<br>GUUCUCCACCUCGAGGGAGAGGUUAAUAAGAUUAAGUCG<br>GCCCUGCUGAGUACUAACAAAGCAGUGGUGUCGCUGAGU<br>GGCUGCGGAGUAAGUGUGUUAACAUUUAAGGUGCUGGAC<br>CUCAAGAAUUAUAUUGACAAACAGUUGCUUCCUAUUCUA<br>AACAAACAGAGCUGUUCAUACCCAAUAUUGAAACUGUU<br>AUUGAGUUUCAGCAGAAGAACAACAGGCUUCUUGAGAUU<br>ACACGCGAGUUCAGUGUCAAUGCCGGCGUUACAACACCC<br>GUGUCUACCUACAUGCUGACGAAUUCUGAGCUUCUCUCU<br>CUCAUAAACGACAUGCCCAUUACGAAUGACCAAAAGAAA<br>CUUAUGUCCAACAACGUGCAGAUUGUGCGACAGCAAUCC<br>UAUAGCAUUAUGUGUAUCAUCAAGGAAGAGGUACUCGCU<br>UAUGUUGUGCAGCUACCACUCUAUGGUGUGAUUGACACC<br>CCCGUUGGAAGCUGCAUACCAGUCCACUCUGCACCACUA<br>ACACAAAGGAAGGGAGCAAUAUUUGCCUCACUCGAACCG<br>ACAGGGGUGGUAUUGCGAUAAUGCGGGCUCCGUGUCCU<br>UCUUUCCACAGGCUGAAACUUGUAAGGUACAGUCAAACC<br>GCGUGUUCUGUGAUACUAUGAAUUCUCGUACUCUUCCCA<br>GCGAGGUUAAUCUCUGCAACGUCGACAUUUUCAAUCCUA<br>AAUAUGACUGCAAGAUCAUGACCAGCAAGACCGACGUCU<br>CCAGCUCAGUAAUCACUAGCCUAGGGGCCAUUGUAAGCU<br>GCUAUGGCAAAACCAAGUGUACUGCCUCUAAUAAGUGCA<br>GAGGCAUAAUUAAAACCUUUUCAAAUGGCUGUGACUAUG<br>UGUCGAAUAAGGGCGUCGACACGGUCUCAGUAGGGAAUA<br>CCCUCUACUACGUUAACAAACAGGAAGGCCAGUCCCUUU<br>AUGUAAAGGGCGAGCCCAUCAUAAAAUUUCUACGACCCAC<br>UUGUGUUCCCCAGUGAUGAAUUCGAUGCAUCAAUCUCCC<br>AGGUGAACGAAAAGAUCAAUCAAUCCCUUGCUUUUAUAC<br>GAAAGUCAGAUGAACUCCUGUCCGCCAUCGGUGGCUAUA<br>UCCCAGAAGCCCCAAGAGACGGACAAGCGUACGUCCGGA<br>AAGAUGGUGAGUGGGUCCUCCUCUCUACCUUUCUU | 97 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | <u>MELLILKANAITTILTAVTFCFASG</u>QNITEEFYQSTCSAVSKGY<br>LGALRTGWYTSVITIELSNIKEIKCNGTDAKVKLIKQELDKYK<br>NAVTDLQLLMQSTPATGSGSAIASGVAVCKVLHLEGEVNKIK<br>SALLSTNKAVVSLSGCGVSVLTFKVLDLKNYIDKQLLPILNKQ<br>SCSIPNIETVIEFQQKNNRLLEITREFSVNAGVTTPVSTYMLTNS<br>ELLSLINDMPITNDQKKLMSNNVQIVRQQSYSIMCIIKEEVLAY<br>VVQLPLYGVIDTPCWKLHTSPLCTTNTKEGSNICLTRTDRGW<br>YCDNAGSVSFFPQAETCKVQSNRVFCDTMNSRTLPSEVNLCN<br>VDIFNPKYDCKIMTSKTDVSSSVITSLGAIVSCYGKTKCTASNK<br>CRGIIKTFSNGCDYVSNKGVDTVSVGNTLYYVNKQEGQSLYV<br>KGEPIINFYDPLVFPSDEFDASISQVNEKINQSLAFIRKSDELLS<br>AIGGYIPEAPRDGQAYVRKDGEWVLLSTFL | 47 |
| PolyA tail | 100 nt | |

*The underlined sequences above are signal sequences. It should be understood that any one of the open reading frames and/or corresponding amino acid sequences described in Table 7 may include or exclude the underlined signal sequence. It should also be understood that the underlined sequence may be replaced by a different signal sequence, for example, any one of SEQ ID NOs: 79-84.

EQUIVALENTS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

The entire contents of International Application Nos. PCT/US2015/02740, PCT/US2016/043348, PCT/US2016/043332, PCT/US2016/058327, PCT/US2016/058324, PCT/US2016/058314, PCT/US2016/058310, PCT/US2016/058321, PCT/US2016/058297, PCT/US2016/058319, and PCT/US2016/058314 are incorporated herein by reference.

What is claimed is:

1. A respiratory syncytial virus (RSV) messenger ribonucleic acid (mRNA) vaccine composition, comprising:
   an mRNA that comprises an open reading frame (ORF) encoding an RSV F protein comprising an amino acid sequence having at least 95% identity to the amino acid sequence of SEQ ID NO: 5, wherein identity defines the percentage of amino acid residues in the RSV F protein that are identical to residues of SEQ ID NO: 5 after introducing any necessary gaps to align the two full-length sequences; and
   a lipid nanoparticle comprising 20-60 mol % ionizable cationic lipid, 5-25 mol % neutral lipid, 25-55 mol % sterol, and 0.5-15 mol % PEG-modified lipid.

2. The RSV mRNA vaccine composition of claim 1, wherein the RSV F protein comprises an F1 domain linked to an F2 subunit through a GS linker.

3. The RSV mRNA vaccine composition of claim 1, wherein the mRNA is chemically modified.

4. The RSV mRNA vaccine composition of claim 3, wherein the ORF of the mRNA comprises uracil and at least 80% of the uracil in the ORF of the mRNA comprises 1-methyl-pseudouridine.

5. The RSV mRNA vaccine composition of claim 4, wherein 100% of the uracil in the ORF of the mRNA comprises 1-methyl-pseudouridine.

6. The RSV mRNA vaccine composition of claim 1, wherein the lipid nanoparticle comprises 40-50 mol % ionizable cationic lipid, 10-20 mol % neutral lipid, 35-45 mol % cholesterol, and 1-5 mol % PEG-modified lipid.

7. The RSV mRNA vaccine composition of claim 6, wherein the ionizable cationic lipid is a compound of Formula (I):

$$\left( \begin{array}{c} R_4 \diagdown N \diagup R_1 \\ R_5 \diagdown \diagup \\ R_6 \end{array} \right)_m \begin{array}{c} R_2 \\ M \diagdown R_7, \\ R_3 \end{array} \quad (I)$$

or a salt or isomer thereof, wherein:
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_n$Q, —$(CH_2)_n$CHQR, —CHQR, —CO(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

8. The RSV mRNA vaccine composition of claim 7, wherein:

$R_1$ is R"M'R'; $R_2$ and $R_3$ are each independently $C_{1-14}$ alkyl; $R_4$ is —(CH$_2$)$_n$Q, wherein Q is OH and n is 4; M and M' are each independently —OC(O)—; $R_5$, $R_6$, and $R_7$ are each H; R' is $C_{1-12}$ alkyl substituted with $C_{6-9}$ alkyl; R" is $C_{3-14}$ alkyl; and m is 6.

9. The RSV mRNA vaccine composition of claim 7, wherein:

$R_1$ is $C_{5-20}$ alkenyl; $R_2$ and $R_3$ are each independently $C_{1-14}$ alkyl; $R_4$ is —(CH$_2$)$_n$Q, wherein Q is OH and n is 3; M is —C(O)O—; $R_5$, $R_6$, and $R_7$ are each H; and m is 6.

10. The RSV mRNA vaccine composition of claim 7, wherein the compound of Formula (I) is Compound 1:

(Compound 1)

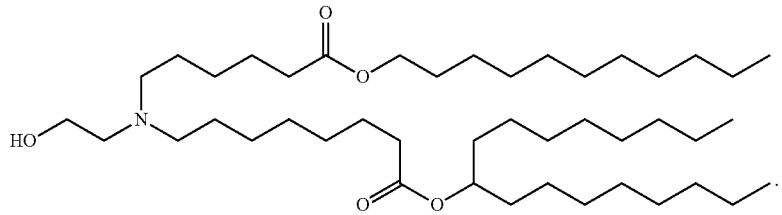

11. The RSV mRNA vaccine composition of claim 7, wherein the neutral lipid is 1,2 distearoyl-sn-glycero-3-phosphocholine (DSPC) and the PEG-modified lipid is 1,2 dimyristoyl-sn-glycerol, methoxypolyethyleneglycol (PEG-2000 DMG).

12. A method comprising administering to a subject the RSV mRNA vaccine composition of claim 1 in a therapeutically effective amount to induce in the subject an RSV F protein neutralizing antibody titer.

13. The method of claim 12, wherein the vaccine is administered intramuscularly.

* * * * *

```
                            SEQUENCE LISTING

<160> NUMBER OF SEQ ID NOS: 100

<210> SEQ ID NO 1
<211> LENGTH: 1771
<212> TYPE: RNA
<213> ORGANISM: Artificial Sequence
<220> FEATURE:
<223> OTHER INFORMATION: Synthetic Polynucleotide

<400> SEQUENCE: 1
gggaaauaag agagaaaaga agaguaagaa gaaauauaag agccaccaug gaacugcuca      60
uuuugaaggc aaacgcuauc acgacaauac ucacugcagu gaccuucugu uuugccucag    120
gccagaacau aaccgaggag uuuuaucaau cuacaugcag cgcuguaucu aaaggcuacc    180
ugagugcgcu ccgcacagga agguacaccu ccgugaucac caucgagcuc agcaauauua    240
aagagaacaa gugcaauggu accgacgcua aagucaaacu uaucaagcag gaacucgaca    300
aauauaaaaa cgcugugacc gagcugcagu uauugaugca gaguacaccu gccaccgggu    360
cgggcucugc cauuugcucc ggcguggcug uauguaaagu ucuccaccuc gagggagagg    420
uuaauaagau uaagucggcc cugcugagua cuaacaaagc aguggucgcg cugaguaacg    480
gaguaagugu guuaacauuu aaggugcugg accucaagaa uuauauugac aaacaguugc    540
uuccuauucu aaacaaacag agcuguucaa uaaguaauau ugaaacuguu auugaguuuc    600
agcagaagaa caacaggcuu cuugagauua cacgcgaguu cagugucaau gccggcguua    660
caacacccgu gucuaccuac augcugacga auucugagcu ucucucucuc auaaacgaca    720
ugcccauuac gaaugaccaa aaaaaacuua uguccaacaa cgugcagauu gugcgacagc    780
aauccuauag cauuaugugu aucaucaagg aagagguacu cgcuuauguu gugcagcuac    840
cacucuaugg ugugauugac accccccuguu ggaagcugca uaccaguccca cucugcacca    900 cuaacacaaa ggaagggagc aauauuugcc ucacucgaac cgacagggggg ugguauugcg    960 auaaugcggg cuccguguc uucuuccac aggcugaaac uuguaaggua cagucaaacc   1020
gcguguucug ugauacuaug aauucgcua cucuuccag cgagguuaau cucugcaacg   1080
ucgacauuuu caauccuaaa uaugacugca agaucaugac cagcaagacc gacgucuca   1140 gcucaguaau cacuagccua ggggccauug uaagcugcua uggcaaaacc aaguguacug   1200
ccucuaauaa gaacagaggc auaauuaaaa ccuuucaaa uggcugugac uauguucga   1260 auaagggcgu cgacacgguc ucaguaggga auacccucua cugcguuaac aaacaggaag   1320
```

| | |
|---|---|
| gcaaaucccu uuauguaaag ggcgagccca ucauaaauuu cuacgaccca cuuguguucc | 1380 |
| ccagugauga auucgaugca ucaaucuccc aggugaacga aaagaucaau caaucccuug | 1440 |
| cuuuuauacg aaagucagau gaacuccugc auaacgugaa ugcugggaaa ucuacaacca | 1500 |
| acaucaugau cacuaccauc auuauguga uuaucguaau ucugcuaucc uugauugcug | 1560 |
| ucgggcugcu ucuguacugu aaggccagau cgacgccugu gacccuuuca aaagaccaac | 1620 |
| uuagcgguau caauaauauu gccuuuagca auugauaaua ggcuggagcc ucgguggcca | 1680 |
| ugcuucuugc cccuugggcc ucccccagc cccuccuccc cuuccugcac ccguacccc | 1740 |
| guggucuuug aauaaagucu gagugggcgg c | 1771 |

<210> SEQ ID NO 2
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 2

| | |
|---|---|
| gggaaauaag agagaaaaga agaguaagaa gaaauauaag agccacc | 47 |

<210> SEQ ID NO 3
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 3

| | |
|---|---|
| auggaacugc ucauuuugaa ggcaaacgcu aucacgacaa uacucacugc agugaccuuc | 60 |
| uguuuugccu caggccagaa cauaaccgag gaguuuauc aaucuacaug cagcgcugua | 120 |
| ucuaaaggcu accgagugc gcuccgcaca ggaugguaca ccuccgugau caccaucgag | 180 |
| cucagcaaua uuaagagaa caagugcaau gguaccgacg cuaaagucaa acuuaucaag | 240 |
| caggaacucg acaaauauaa aaacgcugug accgagcugc aguuauugau gcagaguaca | 300 |
| ccugccaccg ggucgggcuc ugccauuugc uccggcgugg cuguauguaa aguucuccac | 360 |
| cucgagggag agguuaauaa gauuaagucg gcccugcuga guacuaacaa agcaguggug | 420 |
| ucgcugagua acgaguaag uguguuaaca uuuaaggugc uggaccucaa gaauuauauu | 480 |
| gacaaacagu ugcuuccuau ucuaaacaaa cagagcuguu caauaaguaa uauugaaacu | 540 |
| guuauugagu uucagcagaa gaacaacagg cuucuugaga uuacgcgcga guucagguc | 600 |
| aaugccggcg uuacaacacc cgugucuacc uacaugcuga cgaauucuga gcuucucucu | 660 |
| cucauaaacg acaugcccau uacgaaugac caaaaaaaac uuaugccaa caacgugcag | 720 |
| auugugcgac agcaauccua uagcauuaug uguaucauca aggaagaggu acucgcuuau | 780 |
| guugugcagc uaccacucua ugguguaauu gacaccccu guggaagcu gcauaccagu | 840 |
| ccacucugca ccacuaacac aaaggaaggg agcaauauuu gccucacucg aaccgacagg | 900 |
| ggugguauu gcgauaaugc gggcuccgug uccuucuuuc cacaggcuga aacuuguaag | 960 |
| guacagucaa accgcguguu cugugauacu augaauucuc guacucuucc cagcgagguu | 1020 |
| aaucucugca acgucgacau uuucaauccu aaauaugacu gcaagaucau gaccagcaag | 1080 |
| accgacgucu ccagcucagu aaucacuagc cuaggggcca uguaagcug cuauggcaaa | 1140 |
| accaagugua cugccucuaa uaagaacaga ggcauaauua aaaccuuuuc aaauggcugu | 1200 |
| gacuaugugu cgaauaaggg cgucgacacg gucucaguag ggaauacccu cuacugcguu | 1260 |

-continued

```
aacaaacagg aaggcaaauc ccuuuaugua aagggcgagc ccaucauaaa uuucuacgac     1320
ccacuugugu uccccaguga ugaauucgau gcaucaaucu cccaggugaa cgaaaagauc     1380
aaucaauccc uugcuuuuau acgaaaguca gaugaacucc ugcauaacgu gaaugcuggg     1440
aaaucuacaa ccaacaucau gaucacuacc aucauuauug ugauuaucgu aauucugcua     1500
uccuugauug cugucgggcu gcuucuguac uguaaggcca gaucgacgcc ugugacccuu     1560
ucaaaagacc aacuuagcgg uaucaauaau auugccuuua gcaau                    1605

<210> SEQ ID NO 4
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 4
ugauaauagg cuggagccuc gguggccaug cuucuugccc cuugggccuc ccccccagccc     60 cuccucccu uccugcaccc guaccccgu ggucuuugaa uaaagucuga gugggcggc       119

<210> SEQ ID NO 5
<211> LENGTH: 535
<212> TYPE: PRT
<213> ORGANISM: Artificial Sequence
<220> FEATURE:
<223> OTHER INFORMATION: Synthetic Polypeptide

<400> SEQUENCE: 5
```

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
            245                 250                 255

Val Leu Ala Tyr Val Val Gln Leu Pro Leu Tyr Gly Val Ile Asp Thr
        260                 265                 270

Pro Cys Trp Lys Leu His Thr Ser Pro Leu Cys Thr Thr Asn Thr Lys
    275                 280                 285

Glu Gly Ser Asn Ile Cys Leu Thr Arg Thr Asp Arg Gly Trp Tyr Cys
290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
450                 455                 460

Ala Phe Ile Arg Lys Ser Asp Glu Leu Leu His Asn Val Asn Ala Gly
465                 470                 475                 480

Lys Ser Thr Thr Asn Ile Met Ile Thr Thr Ile Ile Ile Val Ile Ile
                485                 490                 495

Val Ile Leu Leu Ser Leu Ile Ala Val Gly Leu Leu Leu Tyr Cys Lys
            500                 505                 510

Ala Arg Ser Thr Pro Val Thr Leu Ser Lys Asp Gln Leu Ser Gly Ile
        515                 520                 525

Asn Asn Ile Ala Phe Ser Asn
530                 535

<210> SEQ ID NO 6
<211> LENGTH: 1774
<212> TYPE: RNA
<213> ORGANISM: Artificial Sequence
<220> FEATURE:
<223> OTHER INFORMATION: Synthetic Polynucleotide

<400> SEQUENCE: 6
gggaaauaag agagaaaaga agaguaagaa gaaauauaag agccaccaug gaacugcuca      60
uuuugaaggc aaacgcuauc acgacaauac ucacugcagu gaccuucugu uuugccucag     120
gccagaacau aaccgaggag uuuuaucaau cuacaugcag cgcuguaucu aaaggcuacc     180
ugagugcgcu ccgcacagga ugguacaccu ccgugaucac caucgagcuc agcaauauua     240
aagagaacaa gugcaauggu accgacgcua aagucaaacu uaucaagcag gaacucgaca     300

-continued

```
aauauaaaaa cgcugugacc gagcugcagu uauugaugca gaguacaccu gccaccgggu      360
cgggcucugc cauugcuucc ggcguggcug uauguaaagu ucccaccuc gagggagagg       420 uuaauaagau uaagucggcc cugcugagua cuaacaaagc aguggugucg cugaguggcu      480
gcggaguaag uguguuaaca uuuaaggugc uggaccucaa gaauuauauu gacaaacagu      540
ugcuuccuau ucuaaacaaa cagagcuguu caauaaguaa uauugaaacu guuauugagu      600
uucagcagaa gaacaacagg cuucuugaga uuacacgcga guucagucc aaugccggcg      660 uuacaacacc cgucuacc uacaugcuga cgaauucuga gcuucucucu cucauaaacg       720
acaugcccau uacgaaugac caaaaaaaac uuauguccaa caacgugcag auugugcgac    780
agcaauccua uagcauuaug uguaucauca aggaagaggu acucgcuuau guugugcagc    840
uaccacucua uggugugauu gacacccccu guuggaagcu gcauaccagu ccacucugca    900
ccacuaacac aaaggaaggg agcaauauuu gccucacucg aaccgacagg ggguggguauu   960 gcgauaaugc gggcuccgug uccuucuuuc cacaggcuga aacuuguaag guacagucaa   1020
accgcguguu cugugauacu augaauucuc guacucuucc cagcgagguu aaucucugca   1080
acgucgacau uuucaauccu aaauaugacu gcaagaucau gaccagcaag accgacgucu   1140
ccagcucagu aaucacuagc cuaggggcca uguaagcug cuauggcaaa accaagugua    1200
cugccucuaa uaagucaga ggcauaauua aaaccuuuuc aaauggcugu gacuauaugu   1260
cgaauaaggg cgucgacacg gucucaguag ggaauacccu cuacacguu aacaaacagg    1320 aaggcaaauc ccuuuauguu aaggggcgagc ccaucauaaa uuucuacgac ccacuugugu   1380
uccccaguga ugaauucgau gcaucaaucu cccaggugaa cgaaaagauc aaucaauccc   1440
uugcuuuuau acgaaaguca gaugaacucc ugcauaacgu gaaugcuggg aaaucuacaa    1500
ccaacaucau gaucacuacc aucauuauug ugauuaucgu aauucugcua ccuugauug    1560 cgucgggcu gcuucuguac uguaaggcca gaucgacgcc ugugacccuu caaaagacc    1620 aacuuagcgg uaucaauaau auugccuuua gcaauugaua auaggcugga gccucggugg    1680
ccaugcuucu ugcccuugg gccuccccc agccccuccu ccccuuccug cacccgaccc    1740
cccguggucu uugaauaaag ucugagugg cggc                               1774
```

<210> SEQ ID NO 7
<211> LENGTH: 1608
<212> TYPE: RNA
<213> ORGANISM: Artificial Sequence
<220> FEATURE:
<223> OTHER INFORMATION: Synthetic Polynucleotide

<400> SEQUENCE: 7

```
auggaacugc ucauuuugaa ggcaaacgcu aucacgacaa uacucacugc agugaccuuc      60
uguuuugccu caggccagaa cauaaccgag gaguuuuauc aaucuacaug cagcgcugua    120
ucuaaaggcu accugagugc gcuccgcaca ggauggauaca ccuccgugau caccaucgag    180
cucagcaaua uuaagagaa caagugcaau gguaccgacg cuaaagucaa acuuaucaag    240
caggaacucg acaaauauaa aaacgcugug accgagcugc aguuauugau gcagaguaca    300
ccugccaccg ggucgggcuc ugccauugcu uccggcgugg cuguauguaa aguucuccac    360
cucgagggag agguuaauaa gauuaagucg gcccugcuga guacuaacaa agcaguggug    420
ucgcugagug cgcggagu aaguguguuc acauuuaagg ugcuggaccu caagaauuau    480
auugacaaac aguugcuucc uauucuaaac aaacagagcu guucaauaag uaauauugaa    540
```

| | |
|---|---|
| acuguuauug aguuucagca gaagaacaac aggcuucuug agauuacacg cgaguucagu | 600 |
| gucaaugccg gcguuacaac acccgugucu accuacaugc ugacgaauuc ugagcuucuc | 660 |
| ucucucauaa acgacaugcc cauuacgaau gaccaaaaaa aacuuauguc caacaacgug | 720 |
| cagauugugc gacagcaauc cuauagcauu auguguauca ucaaggaaga gguacucgcu | 780 |
| uauguugugc agcuaccacu cuauggugug auugacaccc ccuguuggaa gcugcauacc | 840 |
| aguccacucu gcaccacuaa cacaaaggaa gggagcaaua uuugccucac ucgaaccgac | 900 |
| aggggguggu auugcgauaa ugcgggcucc gugaccuucu uccacaggc ugaaacuugu | 960 |
| aagguacagu caaaccgcgu guucugugau acuaugaauu cucguacucu ucccagcgag | 1020 |
| guuaaucucu gcaacgucga cauuuucaau ccuaaauaug acugcaagau caugaccagc | 1080 |
| aagaccgacg ucuccagcuc aguaaucacu agccuagggg ccauuguaag cugcuauggc | 1140 |
| aaaaccaagu guacugccuc uaauaagugc agaggcauaa uuaaaaccuu ucaaauggc | 1200 |
| ugugacuaug ugucgaauaa gggcgucgac acggucucag uagggaauac ccucuacuac | 1260 |
| guuaacaaac aggaaggcaa aucccuuuau guaaagggcg agcccaucau aaauuucuac | 1320 |
| gacccacuug uguucccag ugaugaauuc gaugcaucaa ucucccaggu gaacgaaaag | 1380 |
| aucaaucaau cccuugcuuu auacgaaag ucagaugaac uccugcauaa cgugaaugcu | 1440 |
| gggaaaucua caaccaacau caugaucacu accaucauua uugugauuau cguaauucug | 1500 |
| cuauccuuga uugcugucgg gcugcuucug uacuguaagg ccagaucgac gccugugacc | 1560 |
| cuuucaaaag accaacuuag cgguaucaau aauauugccu uuagcaau | 1608 |

```
<210> SEQ ID NO 8
<211> LENGTH: 536
<212> TYPE: PRT
<213> ORGANISM: Artificial Sequence
<220> FEATURE:
<223> OTHER INFORMATION: Synthetic Polypeptide

<400> SEQUENCE: 8

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175
```

Ser Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu His Asn Val Asn Ala
465                 470                 475                 480

Gly Lys Ser Thr Thr Asn Ile Met Ile Thr Thr Ile Ile Ile Val Ile
                485                 490                 495

Ile Val Ile Leu Leu Ser Leu Ile Ala Val Gly Leu Leu Leu Tyr Cys
            500                 505                 510

Lys Ala Arg Ser Thr Pro Val Thr Leu Ser Lys Asp Gln Leu Ser Gly
        515                 520                 525

Ile Asn Asn Ile Ala Phe Ser Asn
    530                 535

<210> SEQ ID NO 9
<211> LENGTH: 1777
<212> TYPE: RNA
<213> ORGANISM: Artificial Sequence
<220> FEATURE:
<223> OTHER INFORMATION: Synthetic Polynucleotide

<400> SEQUENCE: 9

| | |
|---|---|
| gggaaauaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugagugcgcu ccgcacagga ugguacaccu ccgugaucac caucgagcuc agcaauauua | 240 |
| aagagaacaa gugcaauggu accgacgcua aagucaaacu uaucaagcag gaacucgaca | 300 |
| aauauaaaaa cgcugugacc gagcugcagu uauugaugca gaguacaccu gccaccaaua | 360 |
| acgggucggg cucugccauu gcuuccggcg uggcuguaug uaaaguucuc caccucgagg | 420 |
| gagagguuaa uaagauuaag ucggcccugc ugaguacuaa caaagcagug gugucgcuga | 480 |
| guaacggagu aagugguguua acauuuaagg ugcuggaccu caagaauuau auugacaaac | 540 |
| aguugcuucc uauucuaaac aaacagagcu guucaauaag uaauauugaa acuguuauug | 600 |
| aguuucagca gaagaacaac aggcuucuug agauuacacg cgaguucagu gucaaugccg | 660 |
| gcguuacaac acccgugucu accuacaugc ugacgaauuc ugagcuucuc ucucucauaa | 720 |
| acgacaugcc cauuacgaau gaccaaaaaa aacuuaugu caacaacgug cagauugugc | 780 |
| gacagcaauc cuauagcauu augugauca ucaaggaaga gguacucgcu uauguugugc | 840 |
| agcuaccacu cuauggugug auugacaccc ccguuggaa gcugcauacc aguccacucu | 900 |
| gcaccacuaa cacaaaggaa gggagcaaua uuugccucac ucgaaccgac agggggugu | 960 |
| auugcgauaa ugcgggcucc guguccuucu uccacaggc ugaaacuugu aaguacagu | 1020 |
| caaaccgcgu guucugugau acuaugaauu cucguacucu ucccagcgag guuaaucucu | 1080 |
| gcaacgucga cauuucaau ccuaaauaug acugcaagau caugaccagc aagaccgacg | 1140 |
| ucuccagcuc aguaaucacu agccuagggg ccauuguaag cugcuauggc aaaaccaagu | 1200 |
| guacugcuc uaauaagaac agaggcauaa uuaaaaccuu ucaaauggc ugugacuaug | 1260 |
| ugucgaauaa gggcgucgac acggucucag uagggaauac ccucuacuac guuaacaaac | 1320 |
| aggaaggcaa aucccuuuau guaaagggcg agcccaucau aaauuucuac gacccacuug | 1380 |
| uguucccag ugaugaauuc gaugcaucaa ucucccaggu gaacgaaaag aucaaucaau | 1440 |
| cccuugcuuu uauacgaaag ucagaugaac uccugcauaa cgugaaugcu gggaaaucua | 1500 |
| caaccaacau caugaucacu accaucauua uugugauuau cguaauucug cuauccuuga | 1560 |
| uugcugucgg gcugcuucug uacuguaagg ccagaucgac gccugugacc cuuucaaaag | 1620 |
| accaacuuag cgguaucaau aauauugccu uuagcaauug auaauaggcu ggagccucgg | 1680 |
| uggccaugcu ucuugcccu ugggccuccc cccagcccu ccuccccuuc cugcacccgu | 1740 |
| accccgugg ucuuugaaua aagucugagu gggcggc | 1777 |

<210> SEQ ID NO 10
<211> LENGTH: 1611
<212> TYPE: RNA
<213> ORGANISM: Artificial Sequence
<220> FEATURE:
<223> OTHER INFORMATION: Synthetic Polynucleotide

<400> SEQUENCE: 10

| | |
|---|---|
| auggaacugc ucauuugaa ggcaaacgcu aucacgacaa uacucacugc agugaccuuc | 60 |
| uguuuugccu caggccagaa cauaaccgag gaguuuuauc aaucuacaug cagcgcugua | 120 |
| ucuaaaggcu accugagugc gcuccgcaca ggaugguaca ccuccgugau caccaucgag | 180 |
| cucagcaaua uuaagagaa caagugcaau ggguaccgacg cuaaagucaa acuuaucaag | 240 |
| caggaacucg acaaauauaa aaacgcugug accgagcugc aguuauugau gcagaguaca | 300 |

```
ccugccacca auaacggguc gggcucugcc auugcuuccg gcguggcugu auguaaaguu    360
cuccaccucg agggagaggu uaauaagauu aagucggccc ugcugaguac uaacaaagca    420
guggugucgc ugaguaacgg aguaagugug uuaacauuua aggugcugga ccucaagaau    480
uauauugaca aacaguugcu uccuauucua aacaaacaga gcuguucaau aaguaauauu    540
gaaacuguua uugaguuuca gcagaagaac aacaggcuuc uugagauuac acgcgaguuc    600
agugucaaug ccggcguuac aacacccgug ucuaccuaca ugcugacgaa uucugagcuu    660
cucucucuca uaaacgacau gcccauuacg aaugaccaaa aaaaacuuau guccaacaac    720
gugcagauug ugcgacagca auccuauagc auuaugugua ucaucaagga agagguacuc    780
gcuuauguug ugcagcuacc acucuauggu gugauugaca cccccuguug gaagcugcau    840
accaguccac ucugcaccac uaacacaaag gaagggagca auauuugccu cacucgaacc    900
gacagggggu gguauugcga uaaugcgggc uccguguccu ucuuuccaca ggcugaaacu    960
uguaagguac agucaaaccg cguguucugu gauacuauga auucucguac ucuucccagc   1020
gagguuaauc ucugcaacgu cgacauuuuc aauccuaaau augacugcaa gaucaugacc   1080
agcaagaccg acgucuccag cucaguaauc acuagccuag gggccauugu aagcugcuau   1140
ggcaaaacca aguguacugc cucuaauaag aacagaggca uaauuaaaac cuuuucaaau   1200
ggcugugacu augugucgaa uaagggcguc gacacggucu caguagggaa uacccucuac   1260
uacguuaaca aacaggaagg caaaucccuu uauguaaagg gcgagcccau cauaaauuuc   1320
uacgacccac uuguguuccc cagugaugaa uucgaugcau caaucuccca ggugaacgaa   1380
aagaucaauc aaucccuugc uuuuauacga aagucagaug aacuccugca uaacgugaau   1440
gcugggaaau cuacaaccaa caucaugauc acuaccauca uuauugugau uaucguaauu   1500
cugcuauccu ugauugcugu cgggcugcuu cuguacugua aggccagauc gacgccugug   1560
acccuuucaa aagaccaacu uagcgguauc aauaauauug ccuuuagcaa u            1611
```

<210> SEQ ID NO 11
<211> LENGTH: 537
<212> TYPE: PRT
<213> ORGANISM: Artificial Sequence
<220> FEATURE:
<223> OTHER INFORMATION: Synthetic Polypeptide

<400> SEQUENCE: 11

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gly Ser Gly Ser Ala Ile Ala
            100                 105                 110

Ser Gly Val Ala Val Cys Lys Val Leu His Leu Glu Gly Glu Val Asn
        115                 120                 125
```

```
Lys Ile Lys Ser Ala Leu Leu Ser Thr Asn Lys Ala Val Val Ser Leu
130                 135                 140

Ser Asn Gly Val Ser Val Leu Thr Phe Lys Val Leu Asp Leu Lys Asn
145                 150                 155                 160

Tyr Ile Asp Lys Gln Leu Leu Pro Ile Leu Asn Lys Gln Ser Cys Ser
                165                 170                 175

Ile Ser Asn Ile Glu Thr Val Ile Glu Phe Gln Gln Lys Asn Asn Arg
            180                 185                 190

Leu Leu Glu Ile Thr Arg Glu Phe Ser Val Asn Ala Gly Val Thr Thr
        195                 200                 205

Pro Val Ser Thr Tyr Met Leu Thr Asn Ser Glu Leu Leu Ser Leu Ile
210                 215                 220

Asn Asp Met Pro Ile Thr Asn Asp Gln Lys Lys Leu Met Ser Asn Asn
225                 230                 235                 240

Val Gln Ile Val Arg Gln Gln Ser Tyr Ser Ile Met Cys Ile Ile Lys
                245                 250                 255

Glu Glu Val Leu Ala Tyr Val Val Gln Leu Pro Leu Tyr Gly Val Ile
            260                 265                 270

Asp Thr Pro Cys Trp Lys Leu His Thr Ser Pro Leu Cys Thr Thr Asn
        275                 280                 285

Thr Lys Glu Gly Ser Asn Ile Cys Leu Thr Arg Thr Asp Arg Gly Trp
290                 295                 300

Tyr Cys Asp Asn Ala Gly Ser Val Ser Phe Phe Pro Gln Ala Glu Thr
305                 310                 315                 320

Cys Lys Val Gln Ser Asn Arg Val Phe Cys Asp Thr Met Asn Ser Arg
                325                 330                 335

Thr Leu Pro Ser Glu Val Asn Leu Cys Asn Val Asp Ile Phe Asn Pro
            340                 345                 350

Lys Tyr Asp Cys Lys Ile Met Thr Ser Lys Thr Asp Val Ser Ser Ser
        355                 360                 365

Val Ile Thr Ser Leu Gly Ala Ile Val Ser Cys Tyr Gly Lys Thr Lys
370                 375                 380

Cys Thr Ala Ser Asn Lys Asn Arg Gly Ile Ile Lys Thr Phe Ser Asn
385                 390                 395                 400

Gly Cys Asp Tyr Val Ser Asn Lys Gly Val Asp Thr Val Ser Val Gly
                405                 410                 415

Asn Thr Leu Tyr Tyr Val Asn Lys Gln Glu Gly Lys Ser Leu Tyr Val
            420                 425                 430

Lys Gly Glu Pro Ile Ile Asn Phe Tyr Asp Pro Leu Val Phe Pro Ser
        435                 440                 445

Asp Glu Phe Asp Ala Ser Ile Ser Gln Val Asn Glu Lys Ile Asn Gln
450                 455                 460

Ser Leu Ala Phe Ile Arg Lys Ser Asp Glu Leu Leu His Asn Val Asn
465                 470                 475                 480

Ala Gly Lys Ser Thr Thr Asn Ile Met Ile Thr Thr Ile Ile Ile Val
                485                 490                 495

Ile Ile Val Ile Leu Leu Ser Leu Ile Ala Val Gly Leu Leu Leu Tyr
            500                 505                 510

Cys Lys Ala Arg Ser Thr Pro Val Thr Leu Ser Lys Asp Gln Leu Ser
        515                 520                 525

Gly Ile Asn Asn Ile Ala Phe Ser Asn
530                 535
```

<210> SEQ ID NO 12
<211> LENGTH: 1681
<212> TYPE: RNA
<213> ORGANISM: Artificial Sequence
<220> FEATURE:
<223> OTHER INFORMATION: Synthetic Polynucleotide

<400> SEQUENCE: 12

```
gggaaauaag agagaaaaga agaguaagaa gaaauauaag agccaccaug gaacugcuca     60
uuuugaaggc aaacgcuauc acgacaauac ucacugcagu gaccuucugu uuugccucag    120
gccagaacau aaccgaggag uuuuaucaau cuacaugcag cgcuguaucu aaaggcuacc    180
ugagugcgcu ccgcacagga ugguacaccu ccgugaucac caucgagcuc agcaauauua    240
aagagaacaa gugcaauggu accgacgcua aagucaaacu uaucaagcag gaacucgaca    300
aauauaaaaa cgcugugacc gagcugcagu uauugaugca gaguacaccu gccaccgggu    360
cgggcucugc cauuugcucc ggcguggcug uauguaaagu ucuccaccuc gagggagagg    420
uuaauaagau uaagucggcc cugcugagua cuaacaaagc aguggugucg cugaguaacg    480
gaguaagugu guuaacauuu aaggugcugg accuaagaa uuauauugac aaacaguugc    540
uuccuauucu aaacaaacag agcuguucaa uaaguaauau ugaaacuguu auugaguuuc    600
agcagaagaa caacaggcuu cuugagauua cacgcgaguu cagugucaau gccggcguua    660
caacacccgu gucuaccuac augcugacga auucugagcu ucucucucuc auaaacgaca    720
ugcccauuac gaaugaccaa aaaaaacuua ugccaacaa cgugcagauu gugcgacagc    780
aauccuauag cauuaugugu aucaucaagg aagagguacu cgcuuauguu gugcagcuac    840
cacucuaugg ugugauugac accccguu ggaagcugca uaccagucca cucugcacca    900
cuaacacaaa ggaagggagc aauauuugcc ucacucgaac cgacaggggg ugguauugcg    960
auaaugcggg cuccgugucc uucuuccac aggcugaaac uuguaaggua cagucaaacc   1020
gcguguucug uguauacuaug aauucucgua cucuucccag cgagguuaau cucugcaacg   1080
ucgacauuuu caauccuaaa uaugacugca agaucaugac cagcaagacc gacgucucca   1140
gcucaguaau cacuagccua ggggccauug uaagcugcua uggcaaaaacc aagguacug   1200
ccucuaauaa gaacagaggc auaauuaaaa ccuuuucaaa uggcugugac uauguguccga   1260
auaagggcgu cgacacgguc ucaguaggga uacccucua cugcguuaac aaacaggaag   1320
gcaaaucccu uuauguaaag ggcgagccca ucauaaauuu cuacgaccca cuuguguucc   1380
ccagugauga auucgaugca ucaaucuccc aggugaacga aaagaucaau caaucccuug   1440
cuuuuauacg aaagucagau gaacccugu ccgccaucgg uggcuauauc ccagaagccc   1500
caagagacgg acaagcguac guccggaaag augugagug ggucccucuc ucuaccuuc   1560
uuugauaaua ggcuggagcc ucgguggcca ugcuucuugc cccuugggcc uccccccagc   1620
cccuccuccc cuuccugcac ccguaccccc guggucuuug aauaaagucu gagugggcgg   1680
c                                                                  1681
```

<210> SEQ ID NO 13
<211> LENGTH: 1515
<212> TYPE: RNA
<213> ORGANISM: Artificial Sequence
<220> FEATURE:
<223> OTHER INFORMATION: Synthetic Polynucleotide

<400> SEQUENCE: 13

```
auggaacugc ucauuuugaa ggcaaacgcu aucacgacaa uacucacugc agugaccuuc     60
```

|  |  |
|---|---|
| uguuuugccu caggccagaa cauaaccgag gaguuuuauc aaucuacaug cagcgcugua | 120 |
| ucuaaaggcu accugagugc gcuccgcaca ggaugguaca ccuccgugau caccaucgag | 180 |
| cucagcaaua uuaaagagaa caagugcaau gguaccgacg cuaaagucaa acuuaucaag | 240 |
| caggaacucg acaaauauaa aaacgcugug accgagcugc aguuauugau gcagaguaca | 300 |
| ccugccaccg ggucgggcuc ugccauuugc uccggcgugg cuguauguaa aguucuccac | 360 |
| cucgagggag agguuaauaa gauuaagucg gcccugcuga guacuaacaa agcagggug | 420 |
| ucgcugagua acggaguaag uguguuaaca uuuaaggugc uggaccucaa gaauuauauu | 480 |
| gacaaacagu ugcuuccuau ucuaaacaaa cagagcuguu caauaaguaa uauugaaacu | 540 |
| guuauugagu uucagcagaa gaacaacagg cuucuugaga uuacacgcga guucaguguc | 600 |
| aaugccggcg uuacaacacc cgugucuacc uacaugcuga cgaauucuga gcuucucucu | 660 |
| cucauaaacg acaugcccau uacgaaugac caaaaaaaac uuaugccaa caacgugcag | 720 |
| auugugcgac agcaauccua uagcauuaug uguaucauca aggaagaggu acucgcuuau | 780 |
| guugugcagc uaccacucua uggugugauu gacaccccu guuggaagcu gcauaccagu | 840 |
| ccacucugca ccacuaaacac aaaggaaggg agcaauauuu gccucacucg aaccgacagg | 900 |
| ggugguauu gcgauaaugc gggcuccgug ccuucuuuc cacaggcuga aacuugaag | 960 |
| guacagucaa accgcguguu cugugauacu augaauucuc guacucuucc cagcgaggu | 1020 |
| aaucucugca acgucgacau uuucaauccu aaauaugacu gcaagaucau gaccagcaag | 1080 |
| accgacgucu ccagcucagu aaucacuagc cuaggggcca uguaagcug cuauggcaaa | 1140 |
| accaagugua cugccucuaa uaagaacaga ggcauaauua aaaccuuuuc aaauggcugu | 1200 |
| gacuaugugu cgaauaaggg cgucgacacg gucucaguag ggaauacccu cuacugcguu | 1260 |
| aacaaacagg aaggcaaauc ccuuuaugua aagggcgagc ccaucauaaa uuucuacgac | 1320 |
| ccacuugugu uccccaguga ugaauucgau gcaucaaucu cccaggugaa cgaaaagauc | 1380 |
| aaucaauccc uugcuuuuau acgaaagucu gaugaacucc uguccgccau cgguggcuau | 1440 |
| aucccagaag ccccaagaga cggacaagcg uacguccgga agaugguga gugggucccuc | 1500 |
| cucucuaccu uucuu | 1515 |

<210> SEQ ID NO 14
<211> LENGTH: 505
<212> TYPE: PRT
<213> ORGANISM: Artificial Sequence
<220> FEATURE:
<223> OTHER INFORMATION: Synthetic Polypeptide

<400> SEQUENCE: 14

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
```

100                 105                 110
Val Ala Val Cys Lys Val Leu His Leu Glu Gly Glu Val Asn Lys Ile
            115                 120                 125

Lys Ser Ala Leu Leu Ser Thr Asn Lys Ala Val Val Ser Leu Ser Asn
130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
            195                 200                 205

Ser Thr Tyr Met Leu Thr Asn Ser Glu Leu Leu Ser Leu Ile Asn Asp
        210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
            275                 280                 285

Glu Gly Ser Asn Ile Cys Leu Thr Arg Thr Asp Arg Gly Trp Tyr Cys
        290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
            355                 360                 365

Thr Ser Leu Gly Ala Ile Val Ser Cys Tyr Gly Lys Thr Lys Cys Thr
        370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
            435                 440                 445

Phe Asp Ala Ser Ile Ser Gln Val Asn Glu Lys Ile Asn Gln Ser Leu
        450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu
            500                 505

<210> SEQ ID NO 15

<211> LENGTH: 1684
<212> TYPE: RNA
<213> ORGANISM: Artificial Sequence
<220> FEATURE:
<223> OTHER INFORMATION: Synthetic Polynucleotide

<400> SEQUENCE: 15

| | | | | | |
|---|---|---|---|---|---|
| gggaauuaag | agagaaaaga | agaguaagaa | gaaauauaag | agccaccaug | gaacugcuca | 60 |
| uuuugaaggc | aaacgcuauc | acgacaauac | ucacugcagu | gaccuucugu | uuugccucag | 120 |
| gccagaacau | aaccgaggag | uuuuaucaau | cuacaugcag | cgcuguaucu | aaaggcuacc | 180 |
| ugagugcgcu | ccgcacagga | ugguacaccu | ccgugaucac | caucgagcuc | agcaauauua | 240 |
| aagagaacaa | gugcaauggu | accgacgcua | aagucaaacu | uaucaagcag | gaacucgaca | 300 |
| aauauaaaaa | cgcugugacc | gagcugcagu | uauugaugca | gaguacaccu | gccaccgggu | 360 |
| cgggcucugc | cauugcuucc | ggcguggcug | uauguaaagu | ucuccaccuc | gagggagagg | 420 |
| uuaauaagau | uaagucggcc | cugcugagua | cuaacaaagc | aguggugucg | cugaguggcu | 480 |
| gcggaguaag | uguguuaaca | uuuaaggugc | uggaccucaa | gaauuauauu | gacaaacagu | 540 |
| ugcuuccuau | ucuaaacaaa | cagagcuguu | caauaaguaa | uauugaaacu | guuauugagu | 600 |
| uucagcagaa | gaacaacagg | cuucuugaga | uuacacgcga | guucagugcu | aaugccggcg | 660 |
| uuacaacacc | cgugucuacc | uacaugcuga | cgaauucuga | gcuucucucu | cucauaaacg | 720 |
| acaugcccau | uacgaaugac | caaaaaaaac | uuaugccaa | caacgugcag | auugugcgac | 780 |
| agcaauccua | uagcauuaug | uguaucauca | aggaagaggu | acucgcuuau | guugugcagc | 840 |
| uaccacucua | uggugugauu | gacaccccu | guuggaagcu | gcauaccagu | ccacucugca | 900 |
| ccacuaacac | aaaggaaggg | agcaauauuu | gccucacucg | aaccgacagg | gggugguauu | 960 |
| gcgauaaugc | gggcuccgug | uccuucuuuc | cacaggcuga | aacuuguaag | guacagucaa | 1020 |
| accgcguguu | cugugauacu | augaauucuc | guacucuucc | cagcgagguu | aaucucugca | 1080 |
| acgucgacau | uuucaauccu | aaauaugacu | gcaagaucau | gaccagcaag | accgacgucu | 1140 |
| ccagcucagu | aaucacuagc | cuaggggcca | uguaagcug | cuauggcaaa | accaagugua | 1200 |
| cugccucuaa | uaagugcaga | ggcauaauua | aaaccuuuuc | aaauggcugu | gacuaugugu | 1260 |
| cgaauaaggg | cgucgacacg | gucucaguag | ggaauacccu | cuacuacguu | aacaaacagg | 1320 |
| aaggcaaauc | ccuuuaugua | aagggcgagc | ccaucauaaa | uuucuacgac | ccacuugugu | 1380 |
| uccccaguga | ugaauucgau | gcaucaaucu | cccaggugaa | cgaaaagauc | aaucaauccc | 1440 |
| uugcuuuuau | acgaaaguca | gaugaacucc | uguccgccau | cgguggcuau | aucccagaag | 1500 |
| ccccaagaga | cggacaagcg | uacguccgga | aagaugguga | gugggccuc | cucucuaccu | 1560 |
| uucuuugaua | auaggcugga | gccucggugg | ccaugcuucu | ugccccuugg | gccucccccc | 1620 |
| agccccuccu | ccccuuccug | cacccguacc | cccgguggucu | uugaauaaag | ucugaguggg | 1680 |
| cggc | | | | | | 1684 |

<210> SEQ ID NO 16
<211> LENGTH: 1518
<212> TYPE: RNA
<213> ORGANISM: Artificial Sequence
<220> FEATURE:
<223> OTHER INFORMATION: Synthetic Polynucleotide

<400> SEQUENCE: 16

| | | | | | |
|---|---|---|---|---|---|
| auggaacugc | ucauuugaa | ggcaaacgcu | aucacgacaa | uacucacugc | agugaccuuc | 60 |
| uguuuugccu | caggccagaa | cauaaccgag | gaguuuuauc | aauucuacaug | cagcgcugua | 120 |

```
ucuaaaggcu accugagugc gcuccgcaca ggaugguaca ccuccgugau caccaucgag    180
cucagcaaua uuaaagagaa caagugcaau gguaccgacg cuaaagucaa acuuaucaag    240
caggaacucg acaaauauaa aaacgcugug accgagcugc aguuauugau gcagaguaca    300
ccugccaccg ggucgggcuc ugccauugcu uccggcgugg cuguauguaa aguucuccac    360
cucgagggag agguuaauaa gauuaagucg gcccugcuga guacuaacaa agcaguggug    420
ucgcugagug gcugcggagu aagugucuua cauuuaagg ugcuggaccu caagaauuau    480
auugacaaac aguugcuucc uauucuaaac aaacagagcu guucaauaag uaauauugaa    540
acuguuauug aguucagca gaagaacaac aggcuucuug agauuacacg cgaguucagu    600
gucaaugccg gcguuacaac acccgugucu accacaugc ugacgaauuc ugagcuucuc     660
ucucucauaa acgacaugcc cauuacgaau gaccaaaaaa aacuuaugc caacaacgug     720
cagauugugc gacagcaauc cuauagcauu augeguauca ucaaggaaga gguacucgcu    780
uauguugugc agcuaccacu cuauggugug auugacaccc ccuguuggaa gcugcauacc    840
aguccacucu gcaccacuaa cacaaaggaa gggagcaaua uuugccucac ucgaaccgac    900
aggggguggu auugcgauaa ugcgggcucc guguccuucu uuccacaggc ugaaacuugu    960
aagguacagu caaaccgcgu guucugugau acuaugaauu cucguacucu ucccagcgag   1020
guuaaucucu gcaacgucga cauuuucaau ccuaaauaug acugcaagau caugaccagc   1080
aagaccgacg ucuccagcuc aguaaucacu agccaggggg ccauuguaag cugcuauggc   1140
aaaaccaagu guacugccuc uaauaagugc agaggcauaa uuaaaaccuu uucaaauggc   1200
ugugacuaug ugucgaauaa gggcgucgac acggucucag uagggaauac ccucuacuac   1260
guuaacaaac aggaaggcaa aucccuuuau guaaagggcg agcccaucau aaauuucuac   1320
gacccacuug uguuccccag ugaugaauuc gaugcaucaa ucucccaggu gaacgaaaag   1380
aucaaucaau ccccuugcuuu uauacgaaag ucagaugaac uccugccgc caucggugc    1440
uauaucccag aagccccaag agacggacaa gcguacgucc ggaaagaugg ugaguggguc   1500
cuccucucua ccuuucuu                                                 1518
```

<210> SEQ ID NO 17
<211> LENGTH: 506
<212> TYPE: PRT
<213> ORGANISM: Artificial Sequence
<220> FEATURE:
<223> OTHER INFORMATION: Synthetic Polypeptide

<400> SEQUENCE: 17

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110
```

```
Val Ala Val Cys Lys Val Leu His Leu Glu Gly Glu Val Asn Lys Ile
        115                 120                 125
Lys Ser Ala Leu Leu Ser Thr Asn Lys Ala Val Val Ser Leu Ser Gly
        130                 135                 140
Cys Gly Val Ser Val Leu Thr Phe Lys Val Leu Asp Leu Lys Asn Tyr
145                 150                 155                 160
Ile Asp Lys Gln Leu Leu Pro Ile Leu Asn Lys Gln Ser Cys Ser Ile
                165                 170                 175
Ser Asn Ile Glu Thr Val Ile Glu Phe Gln Gln Lys Asn Asn Arg Leu
                180                 185                 190
Leu Glu Ile Thr Arg Glu Phe Ser Val Asn Ala Gly Val Thr Thr Pro
                195                 200                 205
Val Ser Thr Tyr Met Leu Thr Asn Ser Glu Leu Leu Ser Leu Ile Asn
        210                 215                 220
Asp Met Pro Ile Thr Asn Asp Gln Lys Lys Leu Met Ser Asn Asn Val
225                 230                 235                 240
Gln Ile Val Arg Gln Gln Ser Tyr Ser Ile Met Cys Ile Ile Lys Glu
                245                 250                 255
Glu Val Leu Ala Tyr Val Val Gln Leu Pro Leu Tyr Gly Val Ile Asp
                260                 265                 270
Thr Pro Cys Trp Lys Leu His Thr Ser Pro Leu Cys Thr Thr Asn Thr
        275                 280                 285
Lys Glu Gly Ser Asn Ile Cys Leu Thr Arg Thr Asp Arg Gly Trp Tyr
        290                 295                 300
Cys Asp Asn Ala Gly Ser Val Ser Phe Phe Pro Gln Ala Glu Thr Cys
305                 310                 315                 320
Lys Val Gln Ser Asn Arg Val Phe Cys Asp Thr Met Asn Ser Arg Thr
                325                 330                 335
Leu Pro Ser Glu Val Asn Leu Cys Asn Val Asp Ile Phe Asn Pro Lys
                340                 345                 350
Tyr Asp Cys Lys Ile Met Thr Ser Lys Thr Asp Val Ser Ser Ser Val
        355                 360                 365
Ile Thr Ser Leu Gly Ala Ile Val Ser Cys Tyr Gly Lys Thr Lys Cys
        370                 375                 380
Thr Ala Ser Asn Lys Cys Arg Gly Ile Ile Lys Thr Phe Ser Asn Gly
385                 390                 395                 400
Cys Asp Tyr Val Ser Asn Lys Gly Val Asp Thr Val Ser Val Gly Asn
                405                 410                 415
Thr Leu Tyr Tyr Val Asn Lys Gln Glu Gly Lys Ser Leu Tyr Val Lys
                420                 425                 430
Gly Glu Pro Ile Ile Asn Phe Tyr Asp Pro Leu Val Phe Pro Ser Asp
        435                 440                 445
Glu Phe Asp Ala Ser Ile Ser Gln Val Asn Glu Lys Ile Asn Gln Ser
        450                 455                 460
Leu Ala Phe Ile Arg Lys Ser Asp Glu Leu Leu Ser Ala Ile Gly Gly
465                 470                 475                 480
Tyr Ile Pro Glu Ala Pro Arg Asp Gly Gln Ala Tyr Val Arg Lys Asp
                485                 490                 495
Gly Glu Trp Val Leu Leu Ser Thr Phe Leu
                500                 505

<210> SEQ ID NO 18
<211> LENGTH: 1687
```

```
<212> TYPE: RNA
<213> ORGANISM: Artificial Sequence
<220> FEATURE:
<223> OTHER INFORMATION: Synthetic Polynucleotide

<400> SEQUENCE: 18
gggaauaaag agagaaaaga agaguaagaa gaaauauaag agccaccaug gaacugcuca      60
uuuugaaggc aaacgcuauc acgacaauac ucacugcagu gaccuucugu uuugccucag     120
gccagaacau aaccgaggag uuuuaucaau cuacaugcag cgcuguaucu aaaggcuacc     180
ugagugcgcu ccgcacagga ugguacaccu ccgugaucac caucgagcuc agcaauauua     240
aagagaacaa gugcaauggu accgacgcua aagucaaacu uaucaagcag gaacucgaca     300
aauauaaaaa cgcugugacc gagcugcagu auugaugca gaguacaccu gccaccaaua      360 acggguucggg cucugccauu gcuuccggcg uggcuguaug uaaaguucuc caccucgagg     420
gagagguuaa uaagauuaag ucggcccugc ugaguacuaa caaagcagug gugucgcuga     480
guaacggagu aagugucguua acauuuaagg ugcuggaccu caagaauuau auugacaaac     540
aguugcuucc uauucuaaac aaacagagcu guucaauaag uaauauugaa acuguuauug     600
aguuucagca gaagaacaac aggcuucuug agauuuacg cgaguucagu gucaaugccg      660
gcguuacaac acccgugucu accuacaugc ugacgaauuc ugagcuucuc ucucucauaa     720
acgacaugcc cauuacgaau gaccaaaaaa aacuuaugac caacaacgug cagauugugc     780
gacagcaauc cuauagcauu auguguauca ucaaggaaga gguacucgcu uauguugugc     840
agcuaccacu cuauggugug auugacaccc ccguuggaa gcugcauacc aguccacucu      900
gcaccacuaa cacaaaggaa gggagcaaua uuugccucac ucgaaccgac aggggguggu     960
auugcgauaa ugcgggcucc guguccuucu uccacaggc ugaaacuugu aagguacagu     1020
caaaccgcgu guucugugau acaugaauu cucgacucu ucccagcgag guuaaucucu      1080
gcaacgucga cauuuucaau ccuaaauaug acugcaagau caugaccagc aagaccgacg     1140
ucuccagcuc aguaaucacu agccagggg ccauuguaag cugcuauggc aaaaccaagu      1200
guacugccuc uaauaagaac agaggcauaa uuaaaaaccuu ucaaauggc ugugacuaug     1260 ugucgaauaa gggcgucgac acggucucag uaggaauac ccucuacuac guuaacaaac      1320
aggaaggcaa auccuuuuau guaaagggcg agcccaucau aaauuucuac gacccacuug     1380
uguuccccag ugaugaauuc gaugcaucaa ucucccaggu gaacgaaaag aucaaucaau     1440
cccuugcuuu uauacgaaag ucagaugaac uccugccgc caucgguggc uauauccag      1500 aagccccaag agacggacaa gcguacgucc ggaaagaugg ugagugggu cucccucucua     1560 ccuuucuuug auaauaggcu ggagccucgg uggccaugcu ucuugccccu ugggccuccc     1620
cccagccccu ccucccuuc cugcacccgu accccgugg ucuuugaaua aagucugagu      1680
gggcggc                                                              1687

<210> SEQ ID NO 19
<211> LENGTH: 1521
<212> TYPE: RNA
<213> ORGANISM: Artificial Sequence
<220> FEATURE:
<223> OTHER INFORMATION: Synthetic Polynucleotide

<400> SEQUENCE: 19
auggaacugc ucauuuugaa ggcaaacgcu aucacgacaa uacucacugc agugaccuuc      60
uguuuugccu caggccagaa cauaaccgag gaguuuuauc aaucuacaug cagcgcugua     120
```

-continued

| | |
|---|---|
| ucuaaaggcu accugagugc gcuccgcaca ggaugguaca ccuccgugau caccaucgag | 180 |
| cucagcaaua uuaaagagaa caagugcaau gguaccgacg cuaaagucaa acuuaucaag | 240 |
| caggaacucg acaaauauaa aaacgcugug accgagcugc aguuauugau gcagaguaca | 300 |
| ccugccacca auaacgqquc gggcucugcc auugcuuccg gcguggcugu auguaaaguu | 360 |
| cuccaccucg agggagaggu uaauaagauu aagucggccc ugcugaguac uaacaaagca | 420 |
| guggugucgc ugaguaacgg aguaagugug uuaacauuua aggugcugga ccucaagaau | 480 |
| uauauugaca aacaguugcu uccuauucua aacaaacaga gcuguucaau aaguaauauu | 540 |
| gaaacuguua uugaguuuca gcagaagaac aacaggcuuc uugagauuac acgcgaguuc | 600 |
| aguucaaug ccggcguuac aacacccgug ucuaccuaca ugcugacgaa ucugagcuu | 660 |
| cucucucuca uaaacgacau gcccauuacg aaugaccaaa aaaaacuuau guccaacaac | 720 |
| gugcagauug ugcgacagca auccuauagc auuaugugua ucaucaagga agagguacuc | 780 |
| gcuuauguug ugcagcuacc acucuauggu gugauugaca cccccuguug gaagcugcau | 840 |
| accaguccac ucugcaccac uaacacaaag gaagggagca auauuugccu cacucgaacc | 900 |
| gacaggqgqu gguauugcga uaaugcggqc uccgugaccu ucuuccaca ggcugaaacu | 960 |
| uguaaggauc agucaaaccg cguguucugu gauacuauga auucucaguac ucuucccagc | 1020 |
| gagguuaauc ucugcaacgu cgacauuuuc aauccuaaau augacugcaa gaucaugacc | 1080 |
| agcaagaccg acgucuccag cucaguaauc acuagccuag ggccauugu aagcugcuau | 1140 |
| ggcaaaacca agugacugc cucuaauaag aacagaggca uaauuaaaac cuuucaaau | 1200 |
| ggcugugacu augugucgaa uaagggcguc gacacggucu caguagggaa uacccucuac | 1260 |
| uacguuaaca aacaggaagg caaauccuu uauguaaagg gcgagcccau cauaaauuuc | 1320 |
| uacgacccac uuguguuccc cagugaugaa uucgaugcau caaucucca ggugaacgaa | 1380 |
| aagaucaauc aauccuuugc uuuuauacga aagucagaug aacuccuguc cgccaucggu | 1440 |
| ggcuauaucc cagaagcccc aagagacgga caagcguacg uccggaaaga uggugagugg | 1500 |
| guccuccucu cuaccuuucu u | 1521 |

<210> SEQ ID NO 20
<211> LENGTH: 507
<212> TYPE: PRT
<213> ORGANISM: Artificial Sequence
<220> FEATURE:
<223> OTHER INFORMATION: Synthetic Polypeptide

<400> SEQUENCE: 20

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gly Ser Gly Ser Ala Ile Ala
            100                 105                 110

-continued

```
Ser Gly Val Ala Val Cys Lys Val Leu His Leu Glu Gly Glu Val Asn
            115                 120                 125
Lys Ile Lys Ser Ala Leu Leu Ser Thr Asn Lys Ala Val Val Ser Leu
        130                 135                 140
Ser Asn Gly Val Ser Val Leu Thr Phe Lys Val Leu Asp Leu Lys Asn
145                 150                 155                 160
Tyr Ile Asp Lys Gln Leu Leu Pro Ile Leu Asn Lys Gln Ser Cys Ser
                165                 170                 175
Ile Ser Asn Ile Glu Thr Val Ile Glu Phe Gln Gln Lys Asn Asn Arg
            180                 185                 190
Leu Leu Glu Ile Thr Arg Glu Phe Ser Val Asn Ala Gly Val Thr Thr
        195                 200                 205
Pro Val Ser Thr Tyr Met Leu Thr Asn Ser Glu Leu Leu Ser Leu Ile
    210                 215                 220
Asn Asp Met Pro Ile Thr Asn Asp Gln Lys Lys Leu Met Ser Asn Asn
225                 230                 235                 240
Val Gln Ile Val Arg Gln Gln Ser Tyr Ser Ile Met Cys Ile Ile Lys
                245                 250                 255
Glu Glu Val Leu Ala Tyr Val Val Gln Leu Pro Leu Tyr Gly Val Ile
            260                 265                 270
Asp Thr Pro Cys Trp Lys Leu His Thr Ser Pro Leu Cys Thr Thr Asn
        275                 280                 285
Thr Lys Glu Gly Ser Asn Ile Cys Leu Thr Arg Thr Asp Arg Gly Trp
    290                 295                 300
Tyr Cys Asp Asn Ala Gly Ser Val Ser Phe Phe Pro Gln Ala Glu Thr
305                 310                 315                 320
Cys Lys Val Gln Ser Asn Arg Val Phe Cys Asp Thr Met Asn Ser Arg
                325                 330                 335
Thr Leu Pro Ser Glu Val Asn Leu Cys Asn Val Asp Ile Phe Asn Pro
            340                 345                 350
Lys Tyr Asp Cys Lys Ile Met Thr Ser Lys Thr Asp Val Ser Ser Ser
        355                 360                 365
Val Ile Thr Ser Leu Gly Ala Ile Val Ser Cys Tyr Gly Lys Thr Lys
    370                 375                 380
Cys Thr Ala Ser Asn Lys Asn Arg Gly Ile Ile Lys Thr Phe Ser Asn
385                 390                 395                 400
Gly Cys Asp Tyr Val Ser Asn Lys Gly Val Asp Thr Val Ser Val Gly
                405                 410                 415
Asn Thr Leu Tyr Tyr Val Asn Lys Gln Glu Gly Lys Ser Leu Tyr Val
            420                 425                 430
Lys Gly Glu Pro Ile Ile Asn Phe Tyr Asp Pro Leu Val Phe Pro Ser
        435                 440                 445
Asp Glu Phe Asp Ala Ser Ile Ser Gln Val Asn Glu Lys Ile Asn Gln
    450                 455                 460
Ser Leu Ala Phe Ile Arg Lys Ser Asp Glu Leu Leu Ser Ala Ile Gly
465                 470                 475                 480
Gly Tyr Ile Pro Glu Ala Pro Arg Asp Gly Gln Ala Tyr Val Arg Lys
                485                 490                 495
Asp Gly Glu Trp Val Leu Leu Ser Thr Phe Leu
            500                 505

<210> SEQ ID NO 21
<211> LENGTH: 1771
<212> TYPE: RNA
```

<213> ORGANISM: Artificial Sequence
<220> FEATURE:
<223> OTHER INFORMATION: Synthetic Polynucleotide

<400> SEQUENCE: 21

```
gggaaauaag agagaaaaga agaguaagaa gaaauauaag agccaccaug gaacugcuca      60
uuuugaaggc aaacgcuauc acgacaauac ucacugcagu gaccuucugu uuugccucag     120
gccagaacau aaccgaggag uuuuaucaau cuacaugcag cgcuguaucu aaaggcuacc     180
ugagugcgcu ccgcacagga ugguacaccu ccgugaucac caucgagcuc agcaauauua     240
aagagaacaa gugcaauggu accgacgcua aagucaaacu uaucaagcag gaacucgaca     300
aauauaagaa cgcugugacc gagcugcagu uauugaugca gaguacaccu gccaccgggu     360
cgggcucugc cauuugcucc ggcguggcug uauguaaagu ucccaccuc gagggagagg      420
uuaauaagau uaagucggcc cugcugagua cuaacaaagc aguggugucg cugaguaacg     480
gaguaagugu guuaacauuu aaggugcugg accuaagaa uuauauugac aaacaguugc      540
uuccuauucu aaacaaacag agcuguucaa uaaguaauau ugaaacuguu auugaguuuc     600
agcagaagaa caacaggcuu cuugagauua cacgcgaguu cagugucaau gccggcguua     660
caacacccgu gucuaccuac augcugacga auucugagcu ucucucucuc auaaacgaca     720
ugcccauuac gaaugaccaa aagaaacuua uguccaacaa cgugcagauu gugcgacagc     780
aauccuauag cauuaugugu aucaucaagg aagaggacu cgcuuauguu gugcagcuac      840
cacucuaugg ugugauugac accccccuguu ggaagcugca uaccagucca cucugcacca    900
cuaacacaaa ggaagggagc aauauuugcc ucacucgaac cgacaggggg ugguauugcg     960
auaaugcggg cuccgugucc uucuuccac aggcugaaac uguaaggua cagucaaacc       1020
gcguguucug ugauacuaug aauucucgua cucuucccag cgagguuaau cucugcaacg     1080
ucgacauuuu caauccuaaa uaugacugca agaucaugac cagcaagacc gacgucucca     1140
gcucaguaau cacuagccua ggggccauug uaagcugcua uggcaaaacc aaguguacug     1200
ccucuaauaa gaacagaggc auaauuaaaa ccuuuucaaa uggcugugac uaugugucga     1260
auaagggcgu cgacacgguc ucaguaggga auccccucua cugcguuaac aaacaggaag     1320
gcaaauccu uuauguaaag ggcgagccca ucauaaauuu cuacgaccca cuugugeucc      1380
ccagugauga auucgaugca ucaaucuccc aggugaacga aaagaucaau caacccuug     1440
cuuuuauacg aaagucagau gaacuccugc auaacgugaa ugcugggaaa ucuacaaccca   1500
acaucaugau cacuaccauc auuauuguga uuaucguaau ucugcuaucc uugauugcug     1560
ucgggcugcu ucuguacugu aaggccagau cgacgccugu gacccuuuca aaagaccaac     1620
uuagcgguau caauaauauu gccuuuagca auugauaaua ggcuggagcc ucgguggcca     1680
ugcuucuugc cccuugggcc uccccccagc cccuccuccc cuuccugcac ccguaccccc     1740
guggucuuug aauaaagucu gaguggggcgg c                                    1771
```

<210> SEQ ID NO 22
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 22

```
auggaacugc ucauuuugaa ggcaaacgcu aucacgacaa uacucacugc agugaccuuc      60
uguuuugccu caggccagaa cauaaccgag gaguuuuauc aaucuacaug cagcgcugua     120
```

| | | |
|---|---|---|
| ucuaaaggcu accugagugc gcuccgcaca ggaugguaca ccuccgugau caccaucgag | 180 | |
| cucagcaaua uuaaagagaa caagugcaau gguaccgacg cuaaagucaa acuuaucaag | 240 | |
| caggaacucg acaaauauaa gaacgcugug accgagcugc aguuauugau gcagaguaca | 300 | |
| ccugccaccg ggucgggcuc ugccauuugc uccggcgugg cuguauguaa aguucuccac | 360 | |
| cucgagggag agguuaauaa gauuaagucg gcccugcuga guacuaacaa agcagguggug | 420 | |
| ucgcugagua acggagcaag uguguuaaca uuuaaggugc uggaccucaa gaauuauauu | 480 | |
| gacaaacagu ugcuuccuau ucuaaacaaa cagagcuguu caauaaguaa uauugaaacu | 540 | |
| guuauugagu uucagcagaa gaacaacagg cuucuugaga uuacacgcga guucagguguc | 600 | |
| aaugccggcg uuacaacacc cgugucuacc uacaugcuga cgaauucuga gcuucucucu | 660 | |
| cucauaaacg acaugcccau uacgaaugac caaaagaaac uuaugccaa caacgugcag | 720 | |
| auugugcgac agcaauccua uagcauuaug uguaucauca aggaagaggu acucgcuuau | 780 | |
| guugugcagc uaccacucua ugguguugauu gacaccccccu guuggaagcu gcauaccagu | 840 | |
| ccacucugca ccacuaacac aaaggaaggg agcaauauuu gccucacucg aaccgacagg | 900 | |
| ggguggauauu gcgauaaugc gggcuccgug uccuucuuuc cacaggcuga aacuuguaag | 960 | |
| guacagucaa accgcguguu cugugauacu augaauucuc guacucuucc cagcgagguu | 1020 | |
| aaucucugca acgucgacau uuucaauccu aaauaugacu gcaagaucau gaccagcaag | 1080 | |
| accgacgucu ccagcucagu aaucacuagc uaggggcca uguaagcug cuauggcaaa | 1140 | |
| accaagugua cugccucuaa uaagaacaga ggcauaauua aaaccuuuuc aaauggcugu | 1200 | |
| gacuaugugu cgaauaaggg cgucgacacg gucagguag ggaauacccu cuacugcguu | 1260 | |
| aacaaacagg aaggcaaauc ccuuuaugua aagggcgagc ccaucauaaa uuucuacgac | 1320 | |
| ccacuugugu uccccaguga ugaauucgau gcaucaaucu cccaggugaa cgaaaagauc | 1380 | |
| aaucaauccc uugcuuuuau acgaaaguca gaugaacucc ugcauaacgu gaaugcuggg | 1440 | |
| aaaucuacaa ccaacaucau gaucacuacc aucauuauug ugauuaucgu aauucugcua | 1500 | |
| uccuugauug cugucgggcu gcuucuguac uguaaggcca gaucgacgcc ugugacccuu | 1560 | |
| ucaaaagacc aacuuagcgg uaucaauaau auugccuuua gcaau | 1605 | |

<210> SEQ ID NO 23
<211> LENGTH: 1774
<212> TYPE: RNA
<213> ORGANISM: Artificial Sequence
<220> FEATURE:
<223> OTHER INFORMATION: Synthetic Polynucleotide

<400> SEQUENCE: 23

| | | |
|---|---|---|
| gggaaauaag agagaaaaga agaguaagaa gaaauauaag agccaccaug gaacugcuca | 60 | |
| uuuugaaggc aaacgcuauc acgacaauac ucacugcagu gaccuucugu uuugccucag | 120 | |
| gccagaacau aaccgaggag uuuuaucaau cuacaugcag cgcuguaucu aaaggcuacc | 180 | |
| ugagugcgcu ccgcacagga ugguacaccu ccgugaucac caucgagcuc agcaauauua | 240 | |
| aagagaacaa gugcaauggu accgacgcua aagucaaacu uaucaagcag gaacucgaca | 300 | |
| aauauaagaa cgcugugacc gagcugcagu auugaugca gaguacaccu gccaccgggu | 360 | |
| cgggcucugc cauugcuucc ggcguggcug uauguaaagu ucuccaccuc gagggagagg | 420 | |
| uuaauaagau uaagucggcc cugcuguagua cuaacaaagc agguggucg cugaguggcu | 480 | |
| gcggaguaag uguguuaaca uuuaaggugc uggaccucaa gaauuauauu gacaaacagu | 540 | |

| | |
|---|---|
| ugcuuccuau ucuaaacaaa cagagcuguu caauaaguaa uauugaaacu guuauugagu | 600 |
| uucagcagaa gaacaacagg cuucuugaga uuacacgcga guucaguguc aaugccggcg | 660 |
| uuacaacacc cgugucuacc uacaugcuga cgaauucuga gcuucucucu cucauaaacg | 720 |
| acaugcccau uacgaaugac caaaagaaac uuauguccaa caacgugcag auugugcgac | 780 |
| agcaauccua uagcauuaug uguaucauca aggaagaggu acucgcuuau guugugcagc | 840 |
| uaccacucua uggugugauu gacaccccu guuggaagcu gcauaccagu ccacucugca | 900 |
| ccacuaacac aaaggaaggg agcaauauuu gccucacucg aaccgacagg ggugguauu | 960 |
| gcgauaaugc gggcuccgug uccuucuuuc cacaggcuga aacuguaag guacagucaa | 1020 |
| accgcguguu cugugauacu augaauucuc guacucuucc cagcgagguu aaucucugca | 1080 |
| acgucgacau uuucaauccu aaauaugacu gcaagaucau gaccagcaag accgacgucu | 1140 |
| ccagcucagu aaucacuagc cuaggggcca uguaagcug cuaggcaaa accaagugua | 1200 |
| cugccucuaa uaagugcaga ggcauaauua aaaccuuuuc aaauggcugu gacuaugugu | 1260 |
| cgaauaaggg cgucgacacg gucucaguag ggaauacccu cuacuacguu aacaaacagg | 1320 |
| aaggcaaauc ccuuuaugua aagggcgagc ccaucauaaa uuucuacgac ccacuugugu | 1380 |
| uccccaguga ugaauucgau gcaucaaucu cccaggugaa cgaaaagauc aaucaauccc | 1440 |
| uugcuuuuau acgaaaguca gaugaacucc ugcauaacgu gaaugcuggg aaaucuacaa | 1500 |
| ccaacaucau gaucacuacc aucauuauug ugauuaucgu aauucugcua ccuugauuu | 1560 |
| cgucgggcu gcuucuguac uguaaggcca gaucgacgcc ugugacccuu caaaagacc | 1620 |
| aacuuagcgg uaucaauaau auugccuuua gcaauugaua auaggcugga gccucggugg | 1680 |
| ccaugcuucu ugcccuuugg gccucccccc agccccuccu ccccuuccug cacccguacc | 1740 |
| cccguggucu uugaauaaag ucugaguggg cggc | 1774 |

<210> SEQ ID NO 24
<211> LENGTH: 1608
<212> TYPE: RNA
<213> ORGANISM: Artificial Sequence
<220> FEATURE:
<223> OTHER INFORMATION: Synthetic Polynucleotide

<400> SEQUENCE: 24

| | |
|---|---|
| auggaacugc ucauuuugaa ggcaaacgcu aucacgacaa uacucacugc agugaccuuc | 60 |
| uguuuugccu caggccagaa cauaaccgag gaguuuauc aaucuacaug cagcgcugua | 120 |
| ucuaaaggcu accugagugc gcuccgcaca ggauggauaca ccccgugau caccaucgag | 180 |
| cucagcaaua uuaagagaa caagugcaau gguaccgacg cuaaagucaa acuuaucaag | 240 |
| caggaacucg acaaauauaa gaacgcgug accgagcugc aguuauugau gcagaguaca | 300 |
| ccugccaccg ggucgggcuc ugccauugcu uccggcgugg cuguauguaa aguucuccac | 360 |
| cucgagggag agguuaauaa gauuaagucg gcccugcuga guacuaacaa agcaguggug | 420 |
| ucgcugagug gcugcggagu aagugugua acauuuaagg ugcuggaccu caagaauuau | 480 |
| auugacaaac aguugcuucc uauucuaaac aaacagagcu guucaauaag uauauugaa | 540 |
| acuguuauug aguucagca gaagaacaac aggcuucuug agauuacacg cgaguucagu | 600 |
| gucaaugccg gcguuacaac acccgugucu accuacaugc ugacgaauuc ugagcuucuc | 660 |
| ucucucauaa acgacaugcc cauuacgaau gaccaaaaga aacuuauguc caacaacgug | 720 |
| cagauugugc gacagcaauc cuauagcauu augugaucaau caaggaagag guacucgcu | 780 |
| uauguugugc agcuaccacu cuauggugug auugacaccc ccuguuggaa gcugcauacc | 840 |

| | |
|---|---:|
| aguccacucu gcaccacuaa cacaaaggaa gggagcaaua uuugccucac ucgaaccgac | 900 |
| aggggguggu auugcgauaa ugcgggcucc guguccuucu uuccacaggc ugaaacuugu | 960 |
| aagguacagu caaaccgcgu guucugugau acaugaauu cucguacucu ucccagcgag | 1020 |
| guuaaucucu gcaacgucga cauuuucaau ccuaaauaug acugcaagau caugaccagc | 1080 |
| aagaccgacg ucuccagcuc aguaaucacu agccagggg ccauuguaag cugcuauggc | 1140 |
| aaaaccaagu guacugccuc uaauaagugc agaggcauaa uuaaaaccuu ucaaauggc | 1200 |
| ugugacuaug ugucgaauaa gggcgucgac acggucucag uagggaauac ccucuacuac | 1260 |
| guuaacaaac aggaaggcaa auccccuuuau guaaagggcg agcccaucau aaauuucuac | 1320 |
| gacccacuug uguucccccag ugaugaauuc gaugcaucaa ucucccaggu gaacgaaaag | 1380 |
| aucaaucaau cccuugcuuu auacgaaagu cagaugaac uccugcauaa cgugaaugcu | 1440 |
| gggaaaucua caaccaacau caugaucacu accaucauua uugugauuau cguaauucug | 1500 |
| cuauccuuga uugcgucgg gcugcuucug uacuguaagg ccagaucgac gccugugacc | 1560 |
| cuuucaaaag accaacuuag cgguaucaau aauauugccu uuagcaau | 1608 |

<210> SEQ ID NO 25
<211> LENGTH: 1777
<212> TYPE: RNA
<213> ORGANISM: Artificial Sequence
<220> FEATURE:
<223> OTHER INFORMATION: Synthetic Polynucleotide

<400> SEQUENCE: 25

| | |
|---|---:|
| gggaauaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugagugcgcu ccgcacagga ugguacaccu ccgugaucac caucgagcuc agcaauauua | 240 |
| aagagaacaa gugcaauggu accgacgcua aagucaaacu uaucaagcag gaacucgaca | 300 |
| aauauaagaa cgcugugacc gagcugcagu uauugaugca gauacaccu gccaccaaua | 360 |
| acgggucggg cucugccauu gcuuccggcg uggcuguaug uaaaguucuc caccucgagg | 420 |
| gagagguuaa uaagauuaag ucggcccugc ugaguacuaa caaagcagug gugucgcuga | 480 |
| guaacggagu aagugugua acauuuaagg ugcuggaccu caagaauuau auugacaaac | 540 |
| aguugcuucc uauucuaaac aaacagagcu guucaauaag uaauauugaa acuguuauug | 600 |
| aguucagca gaagaacaac aggcuucuug agauuacacg cgaguucagu gucaaugccg | 660 |
| gcguuacaac acccgugucu accuacaugc ugacgaauuc ugagcuucuc ucucucauaa | 720 |
| acgacaugcc cauuacgaau gaccaaaaga acuuaugic caacaacgug cagauugugc | 780 |
| gacagcaauc cuauagcauu auguguauca ucaaggaaga ggauacgcu auguugugc | 840 |
| agcuaccacu cuauggugug auugacaccc ccguuggaa gcugcauacc aguccacucu | 900 |
| gcaccacuaa cacaaaggaa gggagcaaua uuugccucac ucgaaccgac agggguggu | 960 |
| auugcgauaa ugcgggcucc guguccuucu uuccacaggc ugaaacuugu aagguacagu | 1020 |
| caaaccgcgu guucugugau acaugaauu cucguacucu ucccagcgag guuaaucucu | 1080 |
| gcaacgucga cauuuucaau ccuaaauaug acugcaagau caugaccagc aagaccgacg | 1140 |
| ucuccagcuc aguaaucacu agccagggg ccauuguaag cugcuauggc aaaaccaagu | 1200 |
| guacugccuc uaauaagaac agaggcauaa uuaaaaccuu ucaaauggc ugugacuaug | 1260 |

| | |
|---|---:|
| ugucgaauaa gggcgucgac acggucucag uagggaauac ccucuacuac guuaacaaac | 1320 |
| aggaaggcaa aucccuuuau guaaagggcg agcccaucau aaauuucuac gacccacuug | 1380 |
| uguucccag ugaugaauuc gaugcaucaa ucucccaggu gaacgaaaag aucaaucaau | 1440 |
| cccuugcuuu uauacgaaag ucagaugaac uccugcauaa cgugaaugcu gggaaaucua | 1500 |
| caaccaacau caugaucacu accaucauua ugugauuau cguaauucug cuauccuuga | 1560 |
| uugcugucgg gcugcuucug uacguaagg ccagaucgac gccugugacc cuuucaaaag | 1620 |
| accaacuuag cgguaucaau aauauugccu uuagcaauug auaauaggcu ggagccucgg | 1680 |
| uggccaugcu ucuugccccu ugggccuccc ccagccccu ccuccccuuc cugcacccgu | 1740 |
| acccccgugg ucuuugaaua aagucugagu gggcggc | 1777 |

<210> SEQ ID NO 26
<211> LENGTH: 1611
<212> TYPE: RNA
<213> ORGANISM: Artificial Sequence
<220> FEATURE:
<223> OTHER INFORMATION: Synthetic Polynucleotide

<400> SEQUENCE: 26

| | |
|---|---:|
| auggaacugc ucauuuugaa ggcaaacgcu aucacgacaa uacucacugc agugaccuuc | 60 |
| uguuuugccu caggccagaa cauaaccgag gaguuuuauc aaucuacaug cagcgcugua | 120 |
| ucuaaaggcu accugagugc gcuccgcaca ggaugguaca ccccgugau caccaucgag | 180 |
| cucagcaaua uuaaagagaa caagugcaau gguaccgacg cuaaagucaa acuuaucaag | 240 |
| caggaacucg acaaauauaa gaacgcugug accgagcugc aguuauugau gcagaguaca | 300 |
| ccugccacca auaacggguc gggcucugcc auugcuuccg gcguggcugu auguaaaguu | 360 |
| cuccaccucg agggagaggu uaauaagauu aagucggccc ugcugaguac uaacaaagca | 420 |
| guggugucgc ugaguaacgg aguaagugug uuaacauuua aggugcugga ccucaagaau | 480 |
| uauauugaca aacaguugcu uccuauucua aacaaacaga gcuguucaau aaguaauauu | 540 |
| gaaacuguua uugaguuuca gcagaagaac aacaggcuuc uugagauuac acgcgaguuc | 600 |
| agugucaaug ccggcguuac aacacccgug ucuaccuaca ugcugacgaa uucgagcuu | 660 |
| cucucucuca uaaacgacau gcccauuacg aaugaccaaa agaaacuuau guccaacaac | 720 |
| gugcagauug ugcgacagca auccuauagc auuaugugua ucaucaagga agagguacuc | 780 |
| gcuuauguug ugcagcuacc acucuauggu ugauugaca cccccguuug gaagcugcau | 840 |
| accaguccac ucugcaccac uaacacaaag gaagggagca auauuugccu cacucgaacc | 900 |
| gacaggggu gguauugcga uaaugcgggc uccgugucu ucuuccaca ggcugaaacu | 960 |
| uguaagguac agucaaaccg cguuucugu gauacuauga uucucguac ucuucccagc | 1020 |
| gagguuaauc ucugcaacgu cgacauuuc aauccuaaau ugacugcaa gaucaugacc | 1080 |
| agcaagaccg acgucuccag cucaguaauc acuagccuag ggccauugu aagcugcuau | 1140 |
| ggcaaaacca aguguacugc cucuaauaag aacagaggca uaauuaaaac cuuucaaau | 1200 |
| ggcugugacu auguguaa uaagggcguc gacacggucu caguagggaa uacccucuac | 1260 |
| uacguuaaca aacaggaagg caaaucccu uauguaaagg gcgagcccau caaaauuuc | 1320 |
| uacgacccac uuguguuccc cagugaugaa uucgaugcau caaucuccca ggugaacgaa | 1380 |
| aagaucaauc aaucccuugc uuuuauacga aagucagaug aacuccugca uaacgugaau | 1440 |
| gcugggaaau cuacaaccaa caucaugauc acuaccauca uuauguguau uaucguaauu | 1500 |
| cugcuauccu ugauugcugu cgggcugcuu cuguacugua aggccagauc gacgccugug | 1560 |

<210> SEQ ID NO 27
<211> LENGTH: 1681
<212> TYPE: RNA
<213> ORGANISM: Artificial Sequence
<220> FEATURE:
<223> OTHER INFORMATION: Synthetic Polynucleotide

<400> SEQUENCE: 27

| | |
|---|---:|
| gggaaauaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugagugcgcu ccgcacagga ugguacaccu ccgugaucac caucgagcuc agcaauauua | 240 |
| aagagaacaa gugcaauggu accgacgcua aagucaaacu uaucaagcag gaacucgaca | 300 |
| aauauaagaa cgcugugacc gagcugcagu uauugaugca gaguacaccu gccaccgggu | 360 |
| cgggcucugc cauuugcucc ggcguggcug uauguaaagu ucuccaccuc gagggagagg | 420 |
| uuaauaagau uaagucggcc cugcugagua cuaacaaagc aguggugucg cugaguaacg | 480 |
| gaguaagugu guuaacauuu aaggugcugg accuaagaa uuauauugac aaacaguugc | 540 |
| uuccuauucu aaacaaacag agcuguucaa uaaguaauau ugaacuguu auugaguuuc | 600 |
| agcagaagaa caacaggcuu cuugagauua cacgcgaguu cagugucaau gccggcguua | 660 |
| caacacccgu gucuaccuac augcugacga auucugagcu ucucucucuc auaaacgaca | 720 |
| ugcccauuac gaaugaccaa aagaaacuua ugccaacaa cgugcagauu gugcgacagc | 780 |
| aauccuauag cauuaugugu aucaucaagg aagaggacu cgcuuauguu gugcagcuac | 840 |
| cacucuaugg ugugauugac accccuguu ggaagcugca uaccaguca cucugcacca | 900 |
| cuaacacaaa ggaagggagc aauauuugcc ucacucgaac cgacagggg ugguauugcg | 960 |
| auaaugcggg cuccgugucc uucuuccac aggcugaaac uuguaaggua cagucaaacc | 1020 |
| gcguguucug ugauacuaug aauucucgua cucuucccag cgagguuaau cucugcaacg | 1080 |
| ucgacauuuu caauccuaaa uaugacgca agaucaugc cagcaagacc gacgucucca | 1140 |
| gcucaguaau cacuagccua ggggccauug uaagcugcua uggcaaaacc aaguguacug | 1200 |
| ccucuaauaa gaacagaggc auaauuaaaa ccuuuucaaa uggcugugac uauguugcga | 1260 |
| auaagggcgu cgacacgguc ucaguaggga uacccucua cugcguuaac aaacaggaag | 1320 |
| gcaaaucccu uuauguaaag ggcgagccca ucauaaauuu cuacgaccca cuuguguucc | 1380 |
| ccagugauga auucgaugca ucaaucuccc aggugaacga aaagaucaau caauccuug | 1440 |
| cuuuuauacg aaagucagau gaacuccugu ccgccaucgg uggcuauauc ccagaagccc | 1500 |
| caagagacgg acaagcguac guccggaaag augguagug gguccuccuc ucuaccuuuc | 1560 |
| uuugauaaua ggcuggagcc ucgguggcca ugcuucuugc cccuugggcc uccccccagc | 1620 |
| cccuccuccc cuuccugcac ccguacccc guggucuuug aauaaagucu gagugggcgg | 1680 |
| c | 1681 |

<210> SEQ ID NO 28
<211> LENGTH: 1515
<212> TYPE: RNA
<213> ORGANISM: Artificial Sequence
<220> FEATURE:
<223> OTHER INFORMATION: Synthetic Polynucleotide

<400> SEQUENCE: 28

```
auggaacugc ucauuuugaa ggcaaacgcu aucacgacaa uacucacugc agugaccuuc      60
uguuuugccu caggccagaa cauaaccgag gaguuuuauc aaucuacaug cagcgcugua     120
ucuaaaggcu accugagugc gcuccgcaca ggaugguaca ccuccgugau caccaucgag     180
cucagcaaua uuaagagaa caagugcaau gguaccgacg cuaaagucaa acuuaucaag      240
caggaacucg acaaauauaa gaacgcugug accgagcugc aguuauugau gcagaguaca     300
ccugccaccg ggucgggcuc ugccauuugc uccggcgugg cuguauguaa aguucuccac     360
cucgagggag agguuaauaa gauuaagucg gcccugcuga guacuaacaa agcaguggug     420
ucgcugagua acggaguaag uguguuaaca uuuaaggugc uggaccucaa gaauuauauu     480
gacaaacagu ugcuuccuau ucuaaacaaa cagagcuguu caauaaguaa uauugaaacu     540
guuauugagu uucagcagaa gaacaacagg cuucuugaga uuacacgcga guucagugug     600
aaugccggcg uuacaacacc cgugucuacc uacaugcuga cgaauucuga gcuucucucu     660
cucauaaacg acaugcccau uacgaaugac caaagaaaac uuaugccaa caacgugcag     720
auugugcgac agcaauccua uagcauuaug uguaucauca aggaagaggu acucgcuuau     780
guugugcagc uaccacucua ugguguuauu gacaccccu guuggaagcu gcauaccagu     840
ccacucugca ccacuaaacac aaaggaaggg agcaauauuu gccucacucg aaccgacagg     900
ggguguauu gcgauaaugc gggcuccgug ccuucuuuc acaggcuga aacuuguaag      960
guacagucaa accgcguguu cugugauacu augaauucuc guacucuucc cagcgagguu    1020
aaucucugca cgucgacauu uucaauccu aaauaugacu gcaagaucau gaccagcaag    1080
accgacgucu ccagcucagu aaucacuagc cuaggggcca uguaagcug cuauggcaaa    1140
accaaguguua cugccucuaa uaagaacaga ggcauaauua aaaccuuuuc aaauggcugu    1200
gacuaugugu cgaauaaggg cgucgacacg gucucaguag gaauacccu cuacugcguu    1260
aacaaacagg aaggcaaauc ccuuuaugua aagggcgagc ccaucauaaa uuucuacgac    1320
ccacuugugu uccccaguga ugaauucgau gcaucaaucu cccaggugaa cgaaaagauc    1380
aaucaauccc uugcuuuuau acgaaaguca gaugaacucc uguccgccau cgguggcuau    1440
aucccagaag ccccaagaga cggacaagcg uacguccgga agaugguga gugggccuc     1500
cucucuaccu uucuu                                                    1515
```

<210> SEQ ID NO 29
<211> LENGTH: 1684
<212> TYPE: RNA
<213> ORGANISM: Artificial Sequence
<220> FEATURE:
<223> OTHER INFORMATION: Synthetic Polynucleotide

<400> SEQUENCE: 29

```
gggaauaag agagaaaaga agaguaagaa gaaauauaag agccaccaug gaacugcuca      60
uuuugaaggc aaacgcuauc acgacaauac ucacugcagu gaccuucugu uuugccucag     120
gccagaacau aaccgaggag uuuuaucaau cuacaugcag cgcuaucu aaaggcuacc      180
ugagugcgcu ccgcacagga ugguacaccu ccgugaucac caucgagcuc agcaauauua     240
aagagaacaa gugcaauggu accgacgcua agucaaacu auaucaagcag gaacucgaca     300
aauauaagaa cgcugugacc gagcugcagu uauugaugca gaguacaccu gccaccgggu     360
cgggcucugc cauugcuucc ggcgguggcug uauguaaagu ucuccaccuc gagggagagg     420
uuaauaagau uaagucggcc cugcugagua cuaacaaagc aguggugucg cugaguggcu     480
```

| | | |
|---|---|---|
| gcggaguaag uguguuaaca uuuaaggugc uggaccucaa gaauuauauu gacaaacagu | 540 |
| ugcuuccuau ucuaaacaaa cagagcuguu caauaaguaa uauugaaacu guuauugagu | 600 |
| uucagcagaa gaacaacagg cuucuugaga uuacacgcga guucagugue aaugccggcg | 660 |
| uuacaacacc cgugucuacc uacaugcuga cgaauucuga gcuucucucu ucauaaacg | 720 |
| acaugcccau uacgaaugac caaaagaaac uuaugccaa caacgugcag auugugcgac | 780 |
| agcaauccua uagcauuaug uguaucauca aggaagaggu acucgcuuau guugugcagc | 840 |
| uaccacucua ugguguugauu gacaccccu guuggaagcu gcauaccagu ccacucugca | 900 |
| ccacuaaacac aaaggaaggg agcaauauuu gccucacucg aaccgacagg ggugguauu | 960 |
| gcgauaaugc gggcuccgug uccuucuuuc acaggcuga aacuguaag guacagucaa | 1020 |
| accgcguguu cugugauacu augaauucuc guacucuucc cagcgagguu aaucucugca | 1080 |
| acgucgacau uuucaauccu aaauaugacu gcaagaucau gaccagcaag accgacgucu | 1140 |
| ccagcucagu aaucacuagc cuaggggcca uguaagcug cuauggcaaa accaagugua | 1200 |
| cugccucuaa uaagugcaga ggcauaauua aaaccuuuuc aaauggcugu gacuaugugu | 1260 |
| cgaauaaggg cgucgacacg gucucaguag ggaauacccu cuacuacguu aacaaacagg | 1320 |
| aaggcaaauc ccuuuaugua aagggcgagc ccaucauaaa uuucuacgac ccacuugugu | 1380 |
| ucccagcuga ugaauucgau gcaucaaucu cccaggugaa cgaaaagauc aaucaauccc | 1440 |
| uugcuuuuau acgaaaguca gaugaacucc uguccgccau cgguggcuau auccccagaag | 1500 |
| ccccaagaga cggacaagcg uacguccgga aagaugguga gugggucccuc cucucuaccu | 1560 |
| uucuuugaua uaggcugga gccucgguugg ccaugcuucu ugcccuugg gccucccccc | 1620 |
| agccccuccu ccccuuccug caccccguacc cccgugguucu uugaauaaag ucgaguggg | 1680 |
| cggc | 1684 |

<210> SEQ ID NO 30
<211> LENGTH: 1518
<212> TYPE: RNA
<213> ORGANISM: Artificial Sequence
<220> FEATURE:
<223> OTHER INFORMATION: Synthetic Polynucleotide

<400> SEQUENCE: 30

| | | |
|---|---|---|
| auggaacugc ucauuuugaa ggcaaacgcu aucacgacaa uacucacugc agugaccuuc | 60 |
| uguuuugccu caggccagaa cauaaccgag gaguuuuauc aaucuacaug cagcgcugua | 120 |
| ucuaaaggcu accgagugc gcuccgcaca ggaugguaca cuccgugau caccaucgag | 180 |
| cucagcaaua uuaagagaa caagugcaau gguaccgacg cuaaagucaa acuuaucaag | 240 |
| caggaacucg acaaauauaa gaacgcugug accgagcugc aguuauugau gcagaguaca | 300 |
| ccugccaccg ggucgggcuc ugccauugcu uccggcgugg cuguaugcuaa aguucuccac | 360 |
| cucgagggag agguuaauaa gauuaagucg gcccugcuga guacuaacaa agcagggug | 420 |
| ucgcugagug gcugcggagu aaguguguua acauuuaagg ugcuggaccu caagaauuau | 480 |
| auugacaaac aguugcuucc uauucuaaac aaacagagcu guucaauaag uaauauugaa | 540 |
| acuguuauug aguucagca gaagaacaac aggcuucuug agauuacacg cgaguucagu | 600 |
| gucaaugccg gcguuacaac acccgugucu accuacaugc ugacgaauuc ugagcuucuc | 660 |
| ucucucauaa acgacaugcc cauuacgaau gaccaaaaga aacuuaugcc caacaacgug | 720 |
| cagauugugc gacagcaauc cuauagcauu auguguauca ucaaggaaga gguacucgcu | 780 |

| | |
|---|---|
| uauguugugc agcuaccacu cuauggugug auugacaccc ccuguuggaa gcugcauacc | 840 |
| aguccacucu gcaccacuaa cacaaaggaa gggagcaaua uuugccucac ucgaaccgac | 900 |
| aggggguggu auugcgauaa ugcgggcucc guguccuucu uuccacaggc ugaaacuugu | 960 |
| aagguacagu caaaccgcgu guucugugau acuaugaauu cucguacucu ucccagcgag | 1020 |
| guuaaucucu gcaacgucga cauuuucaau ccuaaauaug acugcaagau caugaccagc | 1080 |
| aagaccgacg ucuccagcuc aguaaucacu agccuagggg ccauuguaag cugcuauggc | 1140 |
| aaaaccaagu guacugccuc uaauaagugc agaggcauaa uuaaaaccuu ucaauggc | 1200 |
| ugugacuaug ugucgaauaa gggcgucgac acggucucag uagggaauac ccucuacuac | 1260 |
| guuaacaaac aggaaggcaa aucccuuuau guaaagggcg agcccaucau aaauuucuac | 1320 |
| gacccacuug uguccccag ugaugaauuc gaugcaucaa ucccaggu gaacgaaaag | 1380 |
| aucaaucaau cccuugcuuu uauacgaaag ucagaugaac uccugccgc caucgguggc | 1440 |
| uauaucccag aagccccaag agacggacaa gcguacgucc ggaaagaugg ugaguggguc | 1500 |
| cuccucucua ccuuucuu | 1518 |

<210> SEQ ID NO 31
<211> LENGTH: 1687
<212> TYPE: RNA
<213> ORGANISM: Artificial Sequence
<220> FEATURE:
<223> OTHER INFORMATION: Synthetic Polynucleotide

<400> SEQUENCE: 31

| | |
|---|---|
| gggaaauaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugagugcgcu ccgcacagga ugguacaccu ccgugaucac caucgagcuc agcaauauua | 240 |
| aagagaacaa gugcaauggu accgacgcua aagucaaacu uaucaagcag gaacucgaca | 300 |
| aauauaagaa cgcugugacc gagcugcagu auugaugca gaguacaccu gccaccaaua | 360 |
| acgggucggg cucugccauu gcuuccggcg uggcuguau uaaaguucuc caccucgagg | 420 |
| gagagguuaa uaagauuaag ucggcccugc ugaguacuaa caaagcagug gugucgcuga | 480 |
| guaacggagu aagugugüua acauuuaagg ugcuggaccu caagaauuau auugacaaac | 540 |
| aguugcuucc uauucuaaac aaacagagcu guucaauaag uaauauugaa acuguuauug | 600 |
| aguuucagca gaagaacaac aggcuucuug agauuacacg cgaguucagu gucaaugccg | 660 |
| gcguuacaac acccguguc uaccacaugc ugacgaauuc ugagcuucuc ucucucauaa | 720 |
| acgacaugcc cauuacgaau gaccaaaaga aacuuaugu caacaacgug cagauugugc | 780 |
| gacagcaauc cuauagcauu augguauca ucaaggaaga gguacucgcu uauguuugc | 840 |
| agcuaccacu cuaugugug auugacaccc ccguuggaa gcugcauacc aguccacucu | 900 |
| gcaccacuaa cacaaaggaa gggagcaaua uuugccucac ucgaaccgac aggggguggu | 960 |
| auugcgauaa ugcgggcucc guguccuucu uuccacaggc ugaaacuugu aagguacagu | 1020 |
| caaaccgcgu guucugugau acuaugaauu cucguacucu ucccagcgag guuaaucucu | 1080 |
| gcaacgucga cauuuucaau ccuaaauaug acugcaagau caugaccagc aagaccgacg | 1140 |
| ucuccagcuc aguaaucacu agccuagggg ccauuguaag cugcuauggc aaaaccaagu | 1200 |
| guacugccuc uaauaagaac agaggcauaa uuaaaaccuu ucaauggc ugugacuaug | 1260 |
| ugucgaauaa gggcgucgac acggucucag uagggaauac ccucuacuac guuaacaaac | 1320 |

```
aggaaggcaa aucccuuuau guaaagggcg agcccaucau aaauuucuac gacccacuug      1380 uguucccag ugaugaauuc gaugcaucaa ucucccaggu gaacgaaaag aucaaucaau       1440
cccuugcuuu uauacgaaag ucagaugaac uccuguccgc caucggUggc uauaucccag      1500 aagcccaag agacggacaa gcguacgucc ggaaagaugg ugagggguc cuccucucua        1560 ccuuucuuug uaaauaggcu ggagccucgg uggccaugcu ucuugcsccu ugggccuccc      1620 cccagcccu ccucccuuc cugcacccgu accccgugg ucuuugaaua aagucugagu         1680
gggcggc                                                                1687
```

<210> SEQ ID NO 32
<211> LENGTH: 1521
<212> TYPE: RNA
<213> ORGANISM: Artificial Sequence
<220> FEATURE:
<223> OTHER INFORMATION: Synthetic Polynucleotide

<400> SEQUENCE: 32

```
auggaacugc ucauuuugaa ggcaaacgcu aucacgacaa uacucacugc agugaccuuc        60
uguuuugccu caggccagaa cauaaccgag gaguuuuauc aaucuacaug cagcgcugua       120
ucuaaaggcu accugagugc gcuccgcaca ggaugguaca ccuccgugau caccaucgag       180
cucagcaaua uuaaagagaa caagugcaau gguaccgacg cuaaagucaa acuuaucaag       240
caggaacucg acaaauauaa gaacgcugug accgagcugc aguuauugau gcagaguaca       300
ccugccacca auaacgdgguc gggcucugcc auugcuuccg gcguggcugu auguaaaguu       360
cuccaccucg agggagaggu uaauaagauu aagucggccc ugcugaguac uaacaaagca       420 gugugucgc ugaguaacgg aguaagugug uuaacauuua aggucugga ccucaagaau        480 uauauugaca aacaguugcu uccuauucua aacaaacaga gcuguucaau aaguaauauu       540
gaaacuguua uugaguuuca gcagaagaac aacaggcuuc uugagauuac acgcgaguuc       600
agugucaaug ccggcguuac aacacccgug ucuaccuaca ugcugacgaa uucugagcuu       660
cucucucuca uaaacgacau gcccauuacg aaugaccaaa agaaacuuau guccaacaac       720
gugcagauug ugcgacagca auccuauagc auuaugugua ucaucaagga agagguacuc       780
gcuuauguug ugcagcuacc acucuauggu ugauugaca cccccuguug gaagcugcau       840
accaguccac ucugcaccac uaacacaaag gaagggagca auauuugccu cacucgaacc       900
gacagggggu gguauugcga uaaugcgggc uccgugaccu ucuuccaca ggcugaaacu       960 uguaagguac agucaaaccg cguguucugu gauacuauga auucucgauac ucuucccagc       1020 gagguuaauc ucucgaacgu cgacauuuuc aauccuaaau augacugcaa gaucaugacc       1080
agcaagaccg acgucuccag cucaguaauc acuagccuag gggccauugu aagcugcuau       1140
ggcaaaacca aguguacugc cucuaauaag aacagaggca uaauuaaaac cuuuucaaau       1200
ggcugugacu augugucgaa uaagggcguc gacacgguCu caguagggaa uacccucuac       1260
uacguuaaca aacaggaagg caaauccuu uauguaaagg gcgagcccau cauaaauuuc       1320
uacgacccac uuguguuccc cagugaugaa uucgaugcau caaucucccca ggugaacgaa       1380 aagaucaauc aaucccuugc uuuuauacga aagucagaug aacuccuguc cgccaucggu       1440
ggcuauaucc cagaagccc aagagacgga caagcguacg uccggaaaga ugggugaggg       1500 ucCucucu cuaccuuucu u                                                  1521
```

<210> SEQ ID NO 33

<211> LENGTH: 1771
<212> TYPE: RNA
<213> ORGANISM: Artificial Sequence
<220> FEATURE:
<223> OTHER INFORMATION: Synthetic Polynucleotide

<400> SEQUENCE: 33

```
gggaaauaag agagaaaaga agaguaagaa gaaauauaag agccaccaug gaacugcuca     60
uuuugaaggc aaacgcuauc acgacaauac ucacugcagu gaccuucugu uuugccucag    120
gccagaacau aaccgaggag uuuuaucaau cuacaugcag cgcuguaucu aaaggcuacc    180
ugggcgcgcu ccgcacagga ugguacaccu ccgugaucac caucgagcuc agcaauauua    240
aagagauuaa gugcaauggu accgacgcua aagucaaacu uaucaagcag gaacucgaca    300
aauauaagaa cgcugugacc gaccugcagu uauugaugca gaguacaccu gccaccgggu    360
cgggcucugc cauuugcucc ggcguggcug uauguaaagu cuccaccuc gagggagagg     420
uuaauaagau uaagucggcc cugcugagua cuaacaaagc aguggugucg cugaguaacg    480
gaguaagugu guuaacauuu aaggugcugg accuaagaa uuauauugac aaacaguugc     540
uuccuauucu aaacaaacag agcuguucaa uacccaauau ugaaacuguu auugaguuuc    600
agcagaagaa caacaggcuu cuugagauua cacgcgaggu cagugucaau gccggcguua    660
caacacccgu gucuaccuac augcugacga uucugagcu ucucucucuc auaaacgaca     720
ugcccauuac gaaugaccaa aagaaacuua ugaccaacaa cgugcagauu gugcgacagc    780
aauccuauag cauuaugugu aucaucaagg aagagguacu cgcuuauguu gugcagcuac    840
cacucuaugg ugugauugac accccccuguu ggaagcugca uaccagucca cucugcacca    900
cuaacacaaa ggaagggagc aauauuugcc ucacucgaac cgacagggg ugguauugcg      960
auaaugcggg cuccguguc uucuuccac aggcugaaac uuguaaggua cagucaaacc     1020
gcguguucug ugauacuaug aauucucgua cucuucccag cgagguuaau cucugcaacg   1080
ucgacauuuu caauccuaaa uaugacgcca agaucaugac cagcaagacc gacgucucca   1140
gcucaguaau cacuagccua ggggccauug uaagcugcua uggcaaaaac aagucuacug   1200
ccucuaauaa gaacagaggc auaauuaaa cuuuucaaa uggcugugac uaugugucga     1260
auaagggcgu cgacacgguc ucaguaggga auacccucua cugcguuaac aaacaggaag   1320
gccaguccu uuuaugaaag ggcgagccca ucauaaauuu cuacgaccca cuuguguucc   1380
ccagugauga auucgaugca ucaaucuccc aggugaacga aaagaucaau caaucccuug   1440
cuuuuauacg aaagucagau gaacuccugc auaacgugaa ugcugggaaa ucuacaacca   1500
acaucaugau cacuaccauc auuauuguga uuaucguaau ucugcuaucc uugauugcug   1560
ucgggcugcu ucuguacugu aaggccagau cgacgccgu gacccuuuca aaagaccaac   1620
uuagcgguau caauaauauu gccuuuagca auugauaaua ggcuggagcc ucgguggcca   1680
ugcuucuugc cccuugggcc uccccccagc cccuccuccc cuuccugcac ccguaccccc   1740
guggucuuug aauaaagucu gaguggggcgg c                                  1771
```

<210> SEQ ID NO 34
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 34

```
auggaacugc ucauuuugaa ggcaaacgcu aucacgacaa uacucacugc agugaccuuc     60
```

```
uguuuugccu caggccagaa cauaaccgag gaguuuuauc aaucuacaug cagcgcugua    120
ucuaaaggcu accgggcgc gcuccgcaca ggaugguaca ccuccgugau caccaucgag    180
cucagcaaua uuaaagagau uaagugcaau gguaccgacg cuaaagucaa acuuaucaag    240
caggaacucg acaaauauaa gaacgcugug accgaccugc aguuauugau gcagaguaca    300
ccugccaccg ggucgggcuc ugccauuugc uccggcgugg cuguauguaa aguuccac     360 cucgagggag agguuaauaa gauuaagucg cccugcuga guacuaacaa agcagggug     420 ucgcugagua acggaguaag uguguuaaca uuuaaggugc uggaccucaa gaauuauauu    480
gacaaacagu ugcuuccuau ucuaaacaaa cagagcuguu caauacccaa uauugaaacu    540
guuauugagu uucagcagaa gaacaacagg cuucuugaga uuacgcgcga guucagugu     600 aaugccggcg uuacaacacc cgugucuacc uacaugcuga cgaauucuga gcuucucucu    660
cucauaaacg acaugcccau uacgaaugac caaagaaac uuaugccaa caacgugcag     720 auugugcgac agcaauccua uagcauuaug uguaucauca aggaagaggu acucgcuuau    780
guugugcagc uaccacucua uggugugauu gacacccccu guuggaagcu gcauaccagu    840
ccacucugca ccacuaacac aaaggaaggg agcaauauu gccucacucg aaccgacagg     900 ggugguauu gcgauaaugc gggccuucgug uccuucuuc acaggcuga aacuuguaag     960 guacagucaa accgcguguu cuguaauacu augaauucuc guacucucc cagcgagguu   1020 aucucgca acgucgacau uuucaauccu aaauaugacu gcaagaucau gaccagcaag    1080
accgacgucu ccagcucagu aaucacucgc cuagggggca uuguaagcug cuauggcaaa   1140 accaaguguua cugccucuaa uaagaacaga ggcauaauua aaaccuuuuc aaauggcugu   1200
gacuaugugu cgaauaaggg cgucgacacg gucucaguag ggaauacccu cuacugcguu   1260
aacaaacagg aaggccaguc ccuuuaugua aagggcgagc ccaucauaaa uuucuacgac   1320
ccacuugugu ucccagugua ugaauucgau gcaucaaucu cccagugaa cgaaaagauc    1380 aaucaauccc uugcuuuuau acgaaaguca gaugaacucc ugcauaacgu gaaugcuggg   1440
aaaucuacaa ccaacaucau gaucacuacc aucauuauug gauuaucgu aauucugcua   1500 uccuugauug cugucgggcu gcuucuguac uguaaggcca gaucgacgcc ugugacccuu    1560
ucaaaagacc aacuuagcgg uaucaauaau auugccuuua gcaau                  1605
```

<210> SEQ ID NO 35
<211> LENGTH: 535
<212> TYPE: PRT
<213> ORGANISM: Artificial Sequence
<220> FEATURE:
<223> OTHER INFORMATION: Synthetic Polypeptide

<400> SEQUENCE: 35

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
```

```
            85                  90                  95
Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
            115                 120                 125

Lys Ser Ala Leu Leu Ser Thr Asn Lys Ala Val Val Ser Leu Ser Asn
            130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
            165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
            195                 200                 205

Ser Thr Tyr Met Leu Thr Asn Ser Glu Leu Leu Ser Leu Ile Asn Asp
            210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Lys Glu Glu
            245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
            275                 280                 285

Glu Gly Ser Asn Ile Cys Leu Thr Arg Thr Asp Arg Gly Trp Tyr Cys
            290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
            325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
            355                 360                 365

Thr Ser Leu Gly Ala Ile Val Ser Cys Tyr Gly Lys Thr Lys Cys Thr
            370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
            405                 410                 415

Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
            435                 440                 445

Phe Asp Ala Ser Ile Ser Gln Val Asn Glu Lys Ile Asn Gln Ser Leu
            450                 455                 460

Ala Phe Ile Arg Lys Ser Asp Glu Leu Leu His Asn Val Asn Ala Gly
465                 470                 475                 480

Lys Ser Thr Thr Asn Ile Met Ile Thr Thr Ile Ile Val Ile Ile
            485                 490                 495

Val Ile Leu Leu Ser Leu Ile Ala Val Gly Leu Leu Leu Tyr Cys Lys
            500                 505                 510
```

```
Ala Arg Ser Thr Pro Val Thr Leu Ser Lys Asp Gln Leu Ser Gly Ile
        515                 520                 525

Asn Asn Ile Ala Phe Ser Asn
        530                 535

<210> SEQ ID NO 36
<211> LENGTH: 1774
<212> TYPE: RNA
<213> ORGANISM: Artificial Sequence
<220> FEATURE:
<223> OTHER INFORMATION: Synthetic Polynucleotide

<400> SEQUENCE: 36
gggaaauaag agagaaaaga agaguaagaa gaaauauaag agccaccaug gaacugcuca    60
uuuugaaggc aaacgcuauc acgacaauac ucacugcagu gaccuucugu uuugccucag   120
gccagaacau aaccgaggag uuuuaucaau cuacaugcag cgcuguaucu aaaggcuacc   180
ugggcgcgcu ccgcacagga ugguacaccu ccgugaucac caucgagcuc agcaauauua   240
aagagauuaa gugcaauggu accgacgcua aagucaaacu uaucaagcag gaacucgaca   300
aauauaagaa cgcugugacc gaccugcagu uauugaugca gaguacaccu gccaccgggu   360
cgggcucugc cauugcuucc ggcguggcug uauguaaagu ucuccaccuc gagggagagg   420
uuaauaagau uaagucggcc cugcugagua cuaacaaagc aguggugucg cugaguggcu   480
gcggaguaag uguguuaaca uuuaaggugc uggaccucaa gaauuauauu gacaaacagu   540
ugcuuccuau ucuaaacaaa cagagcuguu caauacccaa uauugaaacu guuauugagu   600
uucagcagaa gaacaacagg cuucuugaga uuacacgcga guucaguguc aaugccggcg   660
uuacaacacc cgugucuacc uacaugcuga cgaauucuga gcuucucucu cucauaaacg   720
acaugcccau uacgaaugac caaagagaac uuaugugccc ugacgugcag auugugcgac   780
agcaauccua uagcauuaug uguaucauca aggaagaggu acucgcuuau guugugcagc   840
uaccacucua ugguggugauu gacaccccccu guuggaagcu gcauaccagu ccacucugca   900
ccacuaacac aaaggaaggg agcaauauuu gccucacucg aaccgacagg ggugguauu    960
gcgauaaugc gggcuccgug uccuucuuuc cacaggcuga acuuguaagg guacagucaa  1020
accgcguguu cuguqauacu augaauucuc guacucuucc cagcgagguu aaucucugca  1080
acgucgacau uuucaauccu aaauaugacu gcaagaucau gaccagcaag accgacgucu  1140
ccagcucagu aaucacuagc cuaggggcca uguaagcug cuauggcaaa accaaguagua  1200
cugccucuaa uaagugcaga ggcauaauua aaccuuuuc aaauggcugu gacuaugugu  1260
cgaauaaggg cgucgacacg gucucaguag ggaauacccu cuacacguu aacaaacagg  1320
aaggccaguc ccuuuaugua aagggcgagc ccaucauaaa uuucuacgac ccacuugugu  1380
uccccaguga ugaauucgau gcaucaaucu cccaggugaa cgaaaagauc aaucaauccc  1440
uugcuuuuau acgaaaguca gaugaacucc ugcauaacgu gaaugcuggg aaaucuacaa  1500
ccaacaucau gaucacuacc aucauuauug ugauuaucgu aauucugcua ccuugauug   1560
cugucgggcu gcuucuguac uguaaggcca gaucgacgcc ugugacccuu ucaaaagacc  1620
aacuuagcgg uaucaauaau auugccuuua gcaauugaua auaggcugga gcucggugug  1680
ccaugcuucu ugcccuuggg gccucccccc agccccuccu cccuuccug cacccguacc   1740
cccguggucu uugaauaaag ucugaguggg cggc                              1774

<210> SEQ ID NO 37
```

<211> LENGTH: 1608
<212> TYPE: RNA
<213> ORGANISM: Artificial Sequence
<220> FEATURE:
<223> OTHER INFORMATION: Synthetic Polynucleotide

<400> SEQUENCE: 37

| | | | | | |
|---|---|---|---|---|---|
| auggaacugc | ucauuuugaa | ggcaaacgcu | aucacgacaa | uacucacugc | agugaccuuc | 60 |
| uguuuugccu | caggccagaa | cauaaccgag | gaguuuuauc | aaucuacaug | cagcgcugua | 120 |
| ucuaaaggcu | accugggcgc | gcuccgcaca | ggaugguaca | ccuccgugau | caccaucgag | 180 |
| cucagcaaua | uuaaagagau | uaagugcaau | gguaccgacg | cuaaagucaa | acuuaucaag | 240 |
| caggaacucg | acaaauauaa | gaacgcugug | accgaccugc | aguuauugau | gcagaguaca | 300 |
| ccugccaccg | ggucgggcuc | ugccauugcu | uccggcgugg | cuguauguaa | aguucuccac | 360 |
| cucgagggag | agguuaauaa | gauuaagucg | gcccugcuga | guacuaacaa | agcaguggug | 420 |
| ucgcugagug | gcugcggagu | aagugguuua | acauuuaagg | ugcuggaccu | caagaauuau | 480 |
| auugacaaac | aguugcuucc | uauucuaaac | aaacagagcu | uucaauacc | caauauugaa | 540 |
| acuguuauug | aguuucagca | gaagaacaac | aggcuucuug | agauuacacg | cgaguucagu | 600 |
| gucaaugccg | gcguuacaac | acccgugucu | accuacaugc | ugacgaauuc | ugagcuucuc | 660 |
| ucucucauaa | acgacaugcc | cauuacgaau | gaccaaaaga | aacuuaugug | caacaacgug | 720 |
| cagauugugc | gacagcaauc | cuauagcauu | augugguauca | ucaaggaaga | gguacucgcu | 780 |
| uauguugugc | agcuaccacu | cuaugguguug | auugacaccc | ccuguuggaa | gcugcauacc | 840 |
| aguccacucu | gcaccacuaa | cacaaaggaa | gggagcaaua | uuugcccac | ucgaaccgac | 900 |
| agggggugu | auugcgauaa | ugcgggcucc | guguccuucu | uuccacaggc | ugaaacuugu | 960 |
| aagguacagu | caaaccgcgu | guucugugau | acuaugaauu | ucgacucu | ucccagcgag | 1020 |
| guuaaucucu | gcaacgucga | cauuuucaau | ccuaaauaug | acgcaagau | caugaccagc | 1080 |
| aagaccgacg | ucccagcuc | aguaaucacu | agccuagggg | ccauuguaag | cugcuauggc | 1140 |
| aaaaccaagu | guacugccuc | uaauaagugc | agaggcauaa | uuaaaaccuu | ucaaauggc | 1200 |
| ugugacuaug | ugucgaauaa | gggcgucgac | acggucucag | uagggaauac | ccucuacuac | 1260 |
| guuaacaaac | aggaaggcca | guccccuuuau | guaaagggcg | agcccaucau | aaauuucuac | 1320 |
| gacccacuug | uguccccag | ugaugaauuc | gaugcaucaa | ucucccaggu | gaacgaaaag | 1380 |
| aucaaucaau | cccuugcuuu | uauacgaaag | ucagaugaac | uccugcauaa | cgugaaugcu | 1440 |
| gggaaaucua | caaccaacau | caugaucacu | accaucauua | uugugauuau | cguaauucug | 1500 |
| cuauccuuga | uugcugucgg | gcugcuucug | uacuguaagg | ccagaucgac | gccugugacc | 1560 |
| cuuucaaaag | accaacuuag | cgguaucaau | aauauugccu | uuagcaau | | 1608 |

<210> SEQ ID NO 38
<211> LENGTH: 536
<212> TYPE: PRT
<213> ORGANISM: Artificial Sequence
<220> FEATURE:
<223> OTHER INFORMATION: Synthetic Polypeptide

<400> SEQUENCE: 38

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu

```
            35                  40                  45
Arg Thr Gly Trp Tyr Thr Ser Val Ile Thr Ile Glu Leu Ser Asn Ile
 50                  55                  60
Lys Glu Ile Lys Cys Asn Gly Thr Asp Ala Lys Val Lys Leu Ile Lys
 65                  70                  75                  80
Gln Glu Leu Asp Lys Tyr Lys Asn Ala Val Thr Asp Leu Gln Leu Leu
                 85                  90                  95
Met Gln Ser Thr Pro Ala Thr Gly Ser Gly Ser Ala Ile Ala Ser Gly
             100                 105                 110
Val Ala Val Cys Lys Val Leu His Leu Glu Gly Glu Val Asn Lys Ile
             115                 120                 125
Lys Ser Ala Leu Leu Ser Thr Asn Lys Ala Val Val Ser Leu Ser Gly
130                 135                 140
Cys Gly Val Ser Val Leu Thr Phe Lys Val Leu Asp Leu Lys Asn Tyr
145                 150                 155                 160
Ile Asp Lys Gln Leu Leu Pro Ile Leu Asn Lys Gln Ser Cys Ser Ile
                165                 170                 175
Pro Asn Ile Glu Thr Val Ile Glu Phe Gln Gln Lys Asn Asn Arg Leu
            180                 185                 190
Leu Glu Ile Thr Arg Glu Phe Ser Val Asn Ala Gly Val Thr Thr Pro
            195                 200                 205
Val Ser Thr Tyr Met Leu Thr Asn Ser Glu Leu Leu Ser Leu Ile Asn
            210                 215                 220
Asp Met Pro Ile Thr Asn Asp Gln Lys Lys Leu Met Ser Asn Asn Val
225                 230                 235                 240
Gln Ile Val Arg Gln Gln Ser Tyr Ser Ile Met Cys Ile Ile Lys Glu
                245                 250                 255
Glu Val Leu Ala Tyr Val Val Gln Leu Pro Leu Tyr Gly Val Ile Asp
            260                 265                 270
Thr Pro Cys Trp Lys Leu His Thr Ser Pro Leu Cys Thr Thr Asn Thr
            275                 280                 285
Lys Glu Gly Ser Asn Ile Cys Leu Thr Arg Thr Asp Arg Gly Trp Tyr
            290                 295                 300
Cys Asp Asn Ala Gly Ser Val Ser Phe Phe Pro Gln Ala Glu Thr Cys
305                 310                 315                 320
Lys Val Gln Ser Asn Arg Val Phe Cys Asp Thr Met Asn Ser Arg Thr
                325                 330                 335
Leu Pro Ser Glu Val Asn Leu Cys Asn Val Asp Ile Phe Asn Pro Lys
            340                 345                 350
Tyr Asp Cys Lys Ile Met Thr Ser Lys Thr Asp Val Ser Ser Ser Val
            355                 360                 365
Ile Thr Ser Leu Gly Ala Ile Val Ser Cys Tyr Gly Lys Thr Lys Cys
            370                 375                 380
Thr Ala Ser Asn Lys Cys Arg Gly Ile Ile Lys Thr Phe Ser Asn Gly
385                 390                 395                 400
Cys Asp Tyr Val Ser Asn Lys Gly Val Asp Thr Val Ser Val Gly Asn
                405                 410                 415
Thr Leu Tyr Tyr Val Asn Lys Gln Glu Gly Gln Ser Leu Tyr Val Lys
            420                 425                 430
Gly Glu Pro Ile Ile Asn Phe Tyr Asp Pro Leu Val Phe Pro Ser Asp
            435                 440                 445
Glu Phe Asp Ala Ser Ile Ser Gln Val Asn Glu Lys Ile Asn Gln Ser
            450                 455                 460
```

```
Leu Ala Phe Ile Arg Lys Ser Asp Glu Leu Leu His Asn Val Asn Ala
465                 470                 475                 480

Gly Lys Ser Thr Thr Asn Ile Met Ile Thr Thr Ile Ile Val Ile
            485                 490                 495

Ile Val Ile Leu Leu Ser Leu Ile Ala Val Gly Leu Leu Leu Tyr Cys
500                 505                 510

Lys Ala Arg Ser Thr Pro Val Thr Leu Ser Lys Asp Gln Leu Ser Gly
        515                 520                 525

Ile Asn Asn Ile Ala Phe Ser Asn
    530                 535

<210> SEQ ID NO 39
<211> LENGTH: 1771
<212> TYPE: RNA
<213> ORGANISM: Artificial Sequence
<220> FEATURE:
<223> OTHER INFORMATION: Synthetic Polynucleotide

<400> SEQUENCE: 39
gggaaauaag agagaaaaga agaguaagaa gaaauauaag agccaccaug gaacugcuca    60
uuuugaaggc aaacgcuauc acgacaauac ucacugcagu gaccuucugu uuugccucag   120
gccagaacau aaccgaggag uuuuaucaau cuacaugcag cgcuguaucu aaaggcuacc   180
ugagugcgcu ccgcacagga ugguacaccu ccgugaucac caucgagcuc agcaauauua   240
aagagaacaa gugcaauggu accgacgcua aagucaaacu uaucaagcag gaacucgaca   300
aauauaagaa cgcugugacc gagcugcagu uauugaugca gaguacaccu gccaccgggu   360
cgggcucugc cauugcuucc ggcguggcug uauguaaagu ucuccaccuc gagggagagg   420
uuaauaagau uaagucgggc cugcugagua cuaacaaagc aguggugucg cugaguaacg   480
gaguaagugu guuaacauuu aaggugcugg accuaagaa uuauauugac aaacaguugc   540
uuccuauucu aaacaaacag agcuguucaa uaaguaauau ugaaacuguu auugaguuuc   600
agcagaagaa caacaggcuu cuugagauua cacgcgaguu cagugucaau gccggcguua   660
caacacccgu gucuaccuac augcugacga auucugagcu ucucucucuc auaaacgaca   720
ugcccauuac gaaugaccaa aagaaacuua ugccaacaa cgugcagauu gugcgacagc   780
aauccauaag cauuaugugu aucaucaagg aagagguacu cgcuuauguu gugcagcuac   840
cacucuaugg ugugauugac accccguu ggaagcugca uaccaguca cucugcacca   900
cuaacacaaa ggaagggagc aauauuugcc ucacucgaac cgacaggggg ugguauugcg   960
auaaugcggg cuccgugucc uucuuccac aggcugaaac uuguaaggua cagucaaacc  1020
gcguguucug uguauacuag aauucucgua cucuucccag cgagguuaau cucgcaacg  1080
ucgacauuuu caauccuaaa uaugacugca agaucaugac cagcaagacc gacgucucca  1140
gcucaguaau cacuagccua ggggccauug uaagcgcua uggcaaaacc aaguguacug  1200
ccucuaauaa gaacagaggc auaauuaaaa ccuuucaaa uggcugugac uaugucga  1260
auaagggcgu cgacacgguc ucaguaggga uacccucua cuacguuaac aaacaggaag  1320
gcaaaucccu uuauguaaag ggcgageeca ucauaaauuu cuacgaccca cuuguguucc  1380
ccagugauga auucgaugca ucaaucuccc aggugaacga aaagaucaau caauccuug  1440
cuuuuauacg aaagucagau gaacuccugc auaacgugaa ugcugggaaa ucuacaacca  1500
acaucaugau cacuaccauc auuauguga uuucguaa  cugcuaucc uugauugcug  1560
ucgggcugcu ucuguacugu aaggccagau cgacgccugu gacccuuuca aaagaccaac  1620
```

| | |
|---|---|
| uuagcgguau caauaauauu gccuuuagca auugauaaua ggcuggagcc ucgguggcca | 1680 |
| ugcuucuugc cccuugggcc uccccccagc cccuccuccc cuuccugcac ccguaccccc | 1740 |
| guggucuuug aauaaagucu gagugggcgg c | 1771 |

<210> SEQ ID NO 40
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 40

| | |
|---|---|
| auggaacugc ucauuuugaa ggcaaacgcu aucacgacaa uacucacugc agugaccuuc | 60 |
| uguuuugccu caggccagaa cauaaccgag gaguuuuauc aaucuacaug cagcgcugua | 120 |
| ucuaaaggcu accgagugc gcuccgcaca ggauggauaca ccuccgugau caccaucgag | 180 |
| cucagcaaua uuaaagagaa caagugcaau gguaccgacg cuaaagucaa acuuaucaag | 240 |
| caggaacucg acaaauauaa gaacgcugug accgagcugc aguuauugau gcagaguaca | 300 |
| ccugccaccg ggucgggcuc ugccauugcu uccggcgugg cuguauguaa aguucuccac | 360 |
| cucgagggag agguuaauaa gauuaagucg gcccugcuga guacuaacaa agcaguggug | 420 |
| ucgcugagua acgagauaag ugguguuaaca uuuaaggugc uggaccucaa gaauuauauu | 480 |
| gacaaacagu ugcuuccuau ucuaaacaaa cagagcuguu caauaaguaa uauugaaacu | 540 |
| guuauugagu ucagcagaa gaacaacagg cuucuugaga uuacgcgca guucagagagu | 600 |
| aaugccggcg uuacaacacc cgugucuacc uacaugcuga cgaauucuga gcuucucucu | 660 |
| cucauaaacg acaugcccau uacgaaugac caaagaaac uuaugccaa caacgugcag | 720 |
| auugugcgac agcaauccua uagcauuaug uguaucauca aggaagaggu acucgcuuau | 780 |
| guugugcagc uaccacucua uggugugauu gacaccccu guuggaagcu gcauaccagu | 840 |
| ccacucugca ccacuaaacac aaaggaaggg agcaauauuu gccucacucg aaccgacagg | 900 |
| gggugguauu gcgauaaugc gggcucccgug uccuucuuuc cacaggcuga acuuguaag | 960 |
| guacagucaa accgcguguu cugugauacu augaauucuc guacucuucc cagcgagguu | 1020 |
| aaucucugca acgucgacau uuucaauccu aaauaugacu gcaagaucau gaccagcaag | 1080 |
| accgacgucu ccagcucagu aaucacuagc cuaggggcca uguaagcug cuauggcaaa | 1140 |
| accaagugua cugccucuaa uaagaacaga ggcauaauua aaaccuuuuc aaauggcugu | 1200 |
| gacuaugugu cgauuaaggg cgucgacacg gucucaguag ggauacccu cuacuacguu | 1260 |
| aacaaacagg aaggcaaauc ccuuuaugua aagggcgagc ccaucauaaa uuucuacgac | 1320 |
| ccacuugugu uccccaguga ugaauucgau gcaucaaucu cccaggugaa cgaaaagauc | 1380 |
| aaucaauccc uugcuuuuau acgaaaguca gaugaacucc ugcauaacgu gaaugcuggg | 1440 |
| aaaucuacaa ccaacaucau gaucacuacc aucauuauug gauuaucgu aauucugcua | 1500 |
| uccuugauug cugucgggcu gcuucuguac uguaaggcca gaucgacgcc ugugacccuu | 1560 |
| ucaaaagacc aacuuagcgg uaucaauaau auugccuuua gcaau | 1605 |

<210> SEQ ID NO 41
<211> LENGTH: 535
<212> TYPE: PRT
<213> ORGANISM: Artificial Sequence
<220> FEATURE:
<223> OTHER INFORMATION: Synthetic Polypeptide

```
<400> SEQUENCE: 41

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415
```

Leu Tyr Val Asn Lys Gln Glu Gly Lys Ser Leu Tyr Val Lys Gly
        420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
450                 455                 460

Ala Phe Ile Arg Lys Ser Asp Glu Leu Leu His Asn Val Asn Ala Gly
465                 470                 475                 480

Lys Ser Thr Thr Asn Ile Met Ile Thr Thr Ile Ile Val Ile Ile
                485                 490                 495

Val Ile Leu Leu Ser Leu Ile Ala Val Gly Leu Leu Leu Tyr Cys Lys
        500                 505                 510

Ala Arg Ser Thr Pro Val Thr Leu Ser Lys Asp Gln Leu Ser Gly Ile
        515                 520                 525

Asn Asn Ile Ala Phe Ser Asn
        530                 535

<210> SEQ ID NO 42
<211> LENGTH: 1681
<212> TYPE: RNA
<213> ORGANISM: Artificial Sequence
<220> FEATURE:
<223> OTHER INFORMATION: Synthetic Polynucleotide

<400> SEQUENCE: 42
gggaauaaag agagaaaaga agaguaagaa gaaauauaag agccaccaug gaacugcuca      60
uuuugaaggc aaacgcuauc acgacaauac ucacugcagu gaccuucugu uuugccucag    120
gccagaacau aaccgaggag uuuuaucaau cuacaugcag cgcuguaucu aaaggcuacc    180
ugggcgcgcu ccgcacagga ugguacaccu ccgugaucac caucgagcuc agcaauauua    240
aagagauuaa gugcaauggu accgacgcua aagucaaacu uaucaagcag gaacucgaca    300
aauauaagaa cgcugugacc gaccugcagu auugaugca gaguacaccu gccaccgggu    360
cgggcucugc cauuugcucc ggcguggcug uauguaaagu ucccaccuc gagggagagg    420
uuaauaagau uaagucggcc cugcugagua cuaacaaagc aguggugucg cugaguaacg    480
gaguaagugu guuaacauuu aaggugcugg accuaagaa uuauauugac aaacaguugc    540
uuccuauucu aaacaaacag agcuguucaa uacccaauau ugaaacuguu auugaguuc    600
agcagaagaa caacaggcuu cuugagauua cacgcgaguu caguguaau gccggcguua    660
caacacccgu gucuaccuac augcugacga auucugagcu ucucucucuc auaaacgaca    720
ugcccauuac gaaugaccaa agaaacuua uguccaacaa cgugcagauu gugcgacagc    780
aauccuauag cauuaugugu aucaucaagg aagagguacu cgcuuauguu gugcagcuac    840
cacucuaugg ugugauugac accccccuguu ggaagcugca uaccagucca cucugcacca    900
cuaacacaaa ggaagggagc aauauuugcc ucacucgaac cgacagggggg ugguauugcg    960
auaaugcggg cuccgugucc uucuuccac aggcugaaac uuguaaggua cagucaaacc   1020
gcguguucug uguauacuaug aauucucgua cucuucccag cgagguuaau cucugcaacg   1080
ucgacauuuu caauccuaaa auguacgca agaucaugca cagcaagacc gacgucuca   1140
gcucaguaau cacuagccua ggggccauug uaagcugcua uggcaaaacc aaguguacug   1200
ccucuaauaa gaacagaggc auaauuaaaa ccuuuucaaa uggcugugac uauguucga   1260
auaagggcgu cgacacgguc ucaguaggga auacccucua cugcguuaac aaacaggaag   1320

| | |
|---|---:|
| gccagucccu uuauguaaag ggcgagccca ucauaaauuu cuacgaccca cuuguguucc | 1380 |
| ccagugauga auucgaugca ucaaucuccc aggugaacga aaagaucaau caaucccuug | 1440 |
| cuuuuauacg aaagucagau gaacuccugu ccgccaucgg uggcuauauc ccagaagccc | 1500 |
| caagagacgg acaagcguac guccggaaag auggugagug gguccuccuc ucuaccuuuc | 1560 |
| uuugauaaua ggcuggagcc ucgguggcca ugcuucuugc cccuugggcc uccccccagc | 1620 |
| cccuccuccc cuuccugcac ccguaccccc guggucuuug aauaaagucu gagugggcgg | 1680 |
| c | 1681 |

<210> SEQ ID NO 43
<211> LENGTH: 1515
<212> TYPE: RNA
<213> ORGANISM: Artificial Sequence
<220> FEATURE:
<223> OTHER INFORMATION: Synthetic Polynucleotide

<400> SEQUENCE: 43

| | |
|---|---:|
| auggaacugc ucauuuugaa ggcaaacgcu aucacgacaa uacucacugc agugaccuuc | 60 |
| uguuuugccu caggccagaa cauaaccgag gaguuuuauc aaucuacaug cagcgcugua | 120 |
| ucuaaaggcu accugggcgc gcuccgcaca ggauggauaca ccuccgugau caccaucgag | 180 |
| cucagcaaua uuaaagagau uaagugcaau gguaccgacg cuaaagucaa acuuaucaag | 240 |
| caggaacucg acaaauauaa gaacgcgugu accgaccugc aguuauugau gcagaguaca | 300 |
| ccugccaccg ggucgggcuc ugccauuugc uccggcgugg cuguauguaa aguucuccac | 360 |
| cucgagggag agguuaauaa gauuaagucg gcccugcuga guacuaacaa agcaguggug | 420 |
| ucgcugagua acggaguaag uguguuaaca uuuaaggugc uggaccucaa gaauuauauu | 480 |
| gacaaacagu ugcuuccuau ucuaaacaaa cagagcuguu caauacccaa uauugaaacu | 540 |
| guuauugagu uucagcagaa gaacaacagg cuucuugaga uuacacgcga guucaguguc | 600 |
| aaugccggcg uuacaacacc cgugucuacc uacaugcuga cgaauucuga gcuucucucu | 660 |
| cucauaaacg acaugcccau acgaaugac caaagaaac uuaugccaa caacgugcag | 720 |
| auugugcgac agcaauccua uagcauuaug uguaucauca aggaagaggu acucgcuuau | 780 |
| guugugcagc uaccacucua uggugugauu gacacccccu guuggaagcu gcauaccagu | 840 |
| ccacucugca ccacuaacac aaaggaaggg agcaauauuu gccucacucg aaccgacagg | 900 |
| ggguggauau gcgauaaugc gggcuccgug ccuucucuuc cacaggcuga aacuuguaag | 960 |
| guacagucaa accgcguguu cuguauacu augaauucuc guacucuucc cagcgagguu | 1020 |
| aaucucugca acgucgacau uuucaauccu aaauaugacu gcaagaucau gaccagcaag | 1080 |
| accgacgucu ccagcucagu aaucacuagc cuaggggcca uuguaagcug cuauggcaaa | 1140 |
| accaagugua cugccucuaa uaagaacaga ggcauaauua aaaccuuuuc aaauggcugu | 1200 |
| gacuaugugu cgaauaaggg cgucgacacg gucuuaguag ggauacccu cuacugcguu | 1260 |
| aacaaacagg aaggccaguc ccuuuaugua aagggcgagc ccaucauaaa uuucuacgac | 1320 |
| ccacuugugu uccccaguga ugaauucgau gcaucaaucu cccaggugaa cgaaaagauc | 1380 |
| aaucaauccc uugcuuuuau acgaaaguca gaugaacucc uguccgccau cgguggcuau | 1440 |
| aucccagaag ccccaagaga cggacaagcg uacguccgga agaugguga gugggccuuc | 1500 |
| cucucuaccu uucuu | 1515 |

<210> SEQ ID NO 44
<211> LENGTH: 505

<212> TYPE: PRT
<213> ORGANISM: Artificial Sequence
<220> FEATURE:
<223> OTHER INFORMATION: Synthetic Polypeptide

<400> SEQUENCE: 44

| | | | | | | | | | | | | | | |
|---|---|---|---|---|---|---|---|---|---|---|---|---|---|---|
| Met | Glu | Leu | Leu | Ile | Leu | Lys | Ala | Asn | Ala | Ile | Thr | Thr | Ile | Leu | Thr |
| 1 | | | | 5 | | | | | 10 | | | | | 15 | |

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
                35                  40                  45

Arg Thr Gly Trp Tyr Thr Ser Val Ile Thr Ile Glu Leu Ser Asn Ile
 50                  55                  60

Lys Glu Ile Lys Cys Asn Gly Thr Asp Ala Lys Val Lys Leu Ile Lys
 65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
            115                 120                 125

Lys Ser Ala Leu Leu Ser Thr Asn Lys Ala Val Val Ser Leu Ser Asn
130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
            195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
            275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
            355                 360                 365

Thr Ser Leu Gly Ala Ile Val Ser Cys Tyr Gly Lys Thr Lys Cys Thr
    370                 375                 380

```
Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
            405                 410                 415

Leu Tyr Cys Val Asn Lys Gln Glu Gly Gln Ser Leu Tyr Val Lys Gly
        420                 425                 430

Glu Pro Ile Ile Asn Phe Tyr Asp Pro Leu Val Phe Pro Ser Asp Glu
            435                 440                 445

Phe Asp Ala Ser Ile Ser Gln Val Asn Glu Lys Ile Asn Gln Ser Leu
        450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
            485                 490                 495

Glu Trp Val Leu Leu Ser Thr Phe Leu
            500                 505
```

<210> SEQ ID NO 45
<211> LENGTH: 1684
<212> TYPE: RNA
<213> ORGANISM: Artificial Sequence
<220> FEATURE:
<223> OTHER INFORMATION: Synthetic Polynucleotide

<400> SEQUENCE: 45

```
gggaauaaag agagaaaaga agaguaagaa gaaauauaag agccaccaug gaacugcuca      60
uuuugaaggc aaacgcuauc acgacaauac ucacugcagu gaccuucugu uuugccucag     120
gccagaacau aaccgaggag uuuuaucaau cuacaugcag cgcuguaucu aaaggcuacc     180
ugggcgcgcu ccgcacagga ugguacaccu ccgugaucac caucgagcuc agcaauauua     240
aagagauuaa gugcaauggu accgacgcua agucaaacu uaucaagcag aacucgaca      300
aauauaagaa cgcugugacc gaccugcagu auugaugca gaguacaccu gccaccgggu      360
cgggcucugc cauugcuucc ggcguggcug uauguaaagu ucuccaccuc gagggagagg      420
uuaauaagau uaagucggcc cugcugagua cuaacaaagc aguggugucg cugaguggcu      480
gcggagaag uguguuaaca uuuaaggugc uggaccucaa gaauuauauu gacaaacagu      540
ugcuuccuau ucuaaacaaa cagagcuguu caauacccaa uauugaaacu guuauugagu      600
uucagcagaa gaacaacagg cuucuugaga uuacacgcga guucagugc aaugccggcg      660
uuacaacacc cgugucuacc uacaugcuga cgaauucuga gcuucucucu ucauaaaacg      720
acaugcccau uacgaaugac caaaagaaac uuaugccaa caacgugcag auugugcgac      780
agcaauccua uagcauuaug uguaucauca aggaagaggu acucgcuuau guugugcagc      840
uaccacucua ugguguggauu gacaccccu guuggaagcu gcauaccagu ccacucugca      900
ccacuaacac aaaggaaggg agcaauauuu gccucacucg aaccgacagg ggguggauuu      960
gcgauaaguc gggcucccug uccuucuuuc cacaggcuga acuuguaag guacagucaa     1020
accgcguguu cugugauacu augaauucuc guacucuucc cagcgagguu aaucuccucga    1080
acgucgacau uuucaauccu aaauaugacu gcaagaucau gaccagcaag accgacgucu     1140
ccagcucagu aaucacuagc cuaggggcca uguaagcug cuauggcaaa accaaguguu      1200
cugccucuaa uaaagcaga ggcauaauua aaccuuuuc aaauggcugu gacuaugugu     1260
cgaauaaggg cgucgacacg gucucaguag ggaauacccu cuacacguu aacaaacagg       1320
aaggccaguc ccuuuaugua aagggcgagc ccaucauaaa uuucuacgac ccacuugugu     1380
```

```
ucccccaguga ugaauucgau gcaucaaucu cccaggugaa cgaaaagauc aaucaauccc    1440
uugcuuuuau acgaaaguca gaugaacucc uguccgccau cgguggcuau aucccagaag    1500
ccccaagaga cggacaagcg uacguccgga agaugguga gugggccuc cucucuaccu     1560 uucuuugaua auaggcugga gccucggugg ccaugcuucu ugccccuugg gccucccccc    1620
agccccuccu ccccuuccug cacccguacc cccguggucu ugaauaaag ucugagugg     1680 cggc                                                                 1684

<210> SEQ ID NO 46
<211> LENGTH: 1518
<212> TYPE: RNA
<213> ORGANISM: Artificial Sequence
<220> FEATURE:
<223> OTHER INFORMATION: Synthetic Polynucleotide

<400> SEQUENCE: 46
auggaacugc ucauuuugaa ggcaaacgcu aucacgacaa uacucacugc agugaccuuc      60
uguuuugccu caggccagaa cauaaccgag gaguuuuauc aaucuacaug cagcgcugua    120
ucuaaaggcu accugggcgc gcuccgcaca ggaugguaca ccuccgugau caccaucgag    180
cucagcaaua uuaaagagau uaagugcaau gguaccgacg cuaaagucaa acuuaucaag    240
caggaacucg acaaauauaa gaacgcugug accgaccugc aguuauugau gcagagcaca    300
ccugccaccg ggucgggcuc ugccauugcu uccggcgugg cuguauguaa aguucuccac    360
cucgagggag agguuaauaa gauuaagucg gcccugcuga guacuaacaa agcagguguc    420
ucgcugagug gcugcggagu aagugguguua acauuuaagg ugcuggaccu caagaauuau    480
auugacaaac aguugcuucc uauucuaaac aaacagagcu guucaauacc caauauugaa    540
acuguuauug aguucagca aagaacaac aggcuucuug agauuacacg cgaguucagu    600
gucaaugccg gcguuacaac acccgugucu accacaugc ugacgaauuc ugagcuucuc    660
ucucucauaa acgacaugcc cauuacgaau gaccaaaaga acuuaugue caacaacgug    720 cagauugugc gacagcaauc cuauagcauu auguguauca ucaaggaaga gguacucgcu    780
uauguugugc agcuaccacu cuauggugug auugacaccc ccuguuggaa gcugcauacc    840
aguccacucu gcaccacuaa cacaaaggaa gggagcaaua uuugccucac ucgaaccgac    900
aggggguggu auugcgauaa ucgggcucc guguccuucu uuccacaggc ugaaacuugu    960
aagguacagu caaaccgcgu guucugugau acuaugaauu ucgacucucu ucccagcgag   1020
guuaaucucu gcaacgucga cauuuucaau ccuaaauaug acugaagau caugaccagc    1080 aagaccgacg ucuccagcuc aguaaucacu agccaggggg ccauguaag cugcuauggc    1140 aaaaccaagu gacugccuc uaauaagugc agaggcauaa uuaaaaccuu ucaaauggc    1200 ugugacuaug ugucgaauaa gggcgucgac acggucucag uagggaauac ccucuacuac    1260
guuaacaaac aggaaggcca gucccuuuau guaaagggcg agcccaucau aaauuucuac    1320
gacccacuug uguccccag ugaugaauuc gaugcaucaa ucucccaggu gaacgaaaag    1380
aucaaucaau cccuugcuuu uaucgaaag ucagaugaac uccugucgc caucgguggc    1440 uauaucccag aagccccaag agacggacaa gcguacgucc ggaaagaugg ugagugggu   1500 cuccucucua ccuuucuu                                                 1518

<210> SEQ ID NO 47
<211> LENGTH: 506
<212> TYPE: PRT
```

<213> ORGANISM: Artificial Sequence
<220> FEATURE:
<223> OTHER INFORMATION: Synthetic Polypeptide

<400> SEQUENCE: 47

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
370                 375                 380

Thr Ala Ser Asn Lys Cys Arg Gly Ile Ile Lys Thr Phe Ser Asn Gly
```

```
                385                 390                 395                 400
Cys Asp Tyr Val Ser Asn Lys Gly Val Asp Thr Val Ser Val Gly Asn
                    405                 410                 415

Thr Leu Tyr Tyr Val Asn Lys Gln Glu Gly Gln Ser Leu Tyr Val Lys
                420                 425                 430

Gly Glu Pro Ile Ile Asn Phe Tyr Asp Pro Leu Val Phe Pro Ser Asp
            435                 440                 445

Glu Phe Asp Ala Ser Ile Ser Gln Val Asn Glu Lys Ile Asn Gln Ser
        450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu
                500                 505

<210> SEQ ID NO 48
<211> LENGTH: 1681
<212> TYPE: RNA
<213> ORGANISM: Artificial Sequence
<220> FEATURE:
<223> OTHER INFORMATION: Synthetic Polynucleotide

<400> SEQUENCE: 48
gggaauuaag agagaaaaga agaguaagaa gaaauauaag agccaccaug gaacugcuca      60
uuuugaaggc aaacgcuauc acgacaauac ucacugcagu gaccuucugu uuugccucag    120
gccagaacau aaccgaggag uuuuaucaau cuacaugcag cgcuguaucu aaaggcuacc    180
ugagugcgcu ccgcacagga ugguacaccu ccgugaucac caucgagcuc agcaauauua    240
aagagaacaa gugcaauggu accgacgcua aagucaaacu uaucaagcag gaacucgaca    300
aauauaagaa cgcugugacc gagcugcagu uauugaugca gaguacaccu gccaccgggu    360
cgggcucugc cauugcuucc ggcgugcug uauguaaagu cuccaccuc gagggagagg       420 uuaauaagau uaagucggcc cugcugagua cuaacaaagc aguggugucg cugaguaacg    480
gaguaagugu guuaacauuu aaggugcugg accuaagaa uuauauugac aaacaguugc     540
uuccuauucu aaacaaacag agcuguucaa uaaguaauau ugaaacuguu auugaguuuc    600
agcagaagaa caacaggcuu cuugagauua cacgcgaguu cagugucaau gccggcguua    660
caacacccgu gucuaccuac augcugacga auucugagcu ucucucucuc auaaacgaca    720
ugcccauuac gaaugaccaa aagaaacuua uguccaacaa cgugcagauu gugcgacagc    780
aauccuauag cauuauguga ucaucaagg aagagguacu cgcuuauguu gugcagcuac      840
cacucuaugg ugugauugac accccuguu ggaagcugca uaccaguccca cucugcacca    900 cuaacacaaa ggaagggagc aauauuugcc ucacucgaac cgacagggg uggauuugcg     960 auaaugcggg cuccguguc uucuuccac aggcugaaac uuguaaggua cagucaaacc     1020
gcguguucug ugauacuaug aauucucgua cucuucccag cgagguuaau ucugcaacg    1080 ucgacauuuu caauccuaaa uaugacugca agaucaugac cagcaagacc gacgucucca    1140
gcucaguaau cacuagccua ggggccauug uaagcugcua uggcaaaacc aaguuacug     1200 ccucuaauaa gaacagaggc auaauuaaaa ccuuuucaaa uggcugugac uauguggucga   1260 auaagggcgu cgacacgguc ucaguaggga uacccucua cuacguuaac aaacaggaag    1320
gcaaaucccu uuauguaaag ggcgagccca ucauaaauuu cuacgaccca cuuguguucc    1380
```

| | | |
|---|---|---|
| ccagugauga auucgaugca ucaaucuccc aggugaacga aaagaucaau caaucccuug | 1440 | |
| cuuuuauacg aaagucagau gaacuccugu ccgccaucgg uggcuauauc ccagaagccc | 1500 | |
| caagagacgg acaagcguac guccggaaag auggugagug gguccuccuc ucuaccuuuc | 1560 | |
| uuugauaaua ggcuggagcc ucgguggcca ugcuucuugc cccuugggcc ucccccagc | 1620 | |
| cccuccuccc cuuccugcac ccguacccc guggucuuug aauaaagucu gagugggcgg | 1680 | |
| c | 1681 | |

<210> SEQ ID NO 49
<211> LENGTH: 1515
<212> TYPE: RNA
<213> ORGANISM: Artificial Sequence
<220> FEATURE:
<223> OTHER INFORMATION: Synthetic Polynucleotide

<400> SEQUENCE: 49

| | | |
|---|---|---|
| auggaacugc ucauuuugaa ggcaaacgcu aucacgacaa uacucacugc agugaccuuc | 60 | |
| uguuuugccu caggccagaa cauaaccgag gaguuuuauc aaucuacaug cagcgcugua | 120 | |
| ucuaaaggcu accugagugc gcuccgcaca ggaugguaca ccuccgugau caccaucgag | 180 | |
| cucagcaaua uuaagagaa caagugcaau gguaccgacg cuaaagucaa acuuaucaag | 240 | |
| caggaacucg acaaauauaa gaacgcugug accgagcugc aguuauugau gcagaguaca | 300 | |
| ccugccaccg ggucgggcuc ugccauugcu uccggcgugg cuguauguaa aguucuccac | 360 | |
| cucgagggag agguuaauaa gauuaagucg gcccugcuga guacuaacaa agcaguggug | 420 | |
| ucgcugagua acgagguaag uguguuaaca uuuaagguc uggaccucaa gaauuauauu | 480 | |
| gacaaacagu ugcuuccuau ucuaaacaaa cagagcuguu caauaaguaa uauugaaacu | 540 | |
| guuauugagu uucagcagaa gaacaacagg cuucuugaga uuacgcgca guucagguc | 600 | |
| aaugccggcg uuacaacacc cgugucuacc uacaugcuga cgaauucuga gcuucucucu | 660 | |
| cucauaaacg acaugcccau uacgaaugac caaaagaaac uuaugccaa caacgugcag | 720 | |
| auugugcgac agcaauccua uagcauuaug uguaucauca aggaagaggu acucgcuuau | 780 | |
| guugugcagc uaccacucua uggugugauu gacacccccu guuggaagcu gcauaccagu | 840 | |
| ccacucugca ccacuaacac aaaggaaggg agcaauauuu gccucacucg aaccgacagg | 900 | |
| ggguggguauu gcgauaaugc gggcuccgug uccuucuuuc cacaggcuga aacuugaag | 960 | |
| guacagucaa accgcguguu cugugauacu augaauucuc guacucuucc cagcgagguu | 1020 | |
| aaucucugca acgucgacau uuucaauccu aaauaugacu gcaagaucau gaccagcaag | 1080 | |
| accgacgucu ccagcucagu aaucacuagc cuaggggcca uguaagcug cuauggcaaa | 1140 | |
| accaagugua cugccucuaa uaagaacaga ggcauaauua aaaccuuuuc aaugggcugu | 1200 | |
| gacuaugugu cgaauaaggg cgucgacacg gucucaguag ggaauacccu cuacuacguu | 1260 | |
| aacaaacagg aaggcaaauc ccuuuaugua aagggcgagc ccaucauaaa uuucuacgac | 1320 | |
| ccacugugu uccccaguga ugaauucgau gcaucaaucu cccaggugaa cgaaaagauc | 1380 | |
| aaucaauccc uugcuuuuau acgaaaguca gaugaacucc uguccgccau cgguggcuau | 1440 | |
| aucccagaag ccccaagaga cggacaagcg uacguccgga agaugguga gugggucuc | 1500 | |
| cucucuaccu uucuu | 1515 | |

<210> SEQ ID NO 50
<211> LENGTH: 505
<212> TYPE: PRT
<213> ORGANISM: Artificial Sequence
<220> FEATURE:
<223> OTHER INFORMATION: Synthetic Polypeptide

<400> SEQUENCE: 50

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400
```

```
Asp Tyr Val Ser Asn Lys Gly Val Asp Thr Val Ser Val Gly Asn Thr
            405                 410                 415

Leu Tyr Tyr Val Asn Lys Gln Glu Gly Lys Ser Leu Tyr Val Lys Gly
        420                 425                 430

Glu Pro Ile Ile Asn Phe Tyr Asp Pro Leu Val Phe Pro Ser Asp Glu
            435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
            485                 490                 495

Glu Trp Val Leu Leu Ser Thr Phe Leu
            500                 505

<210> SEQ ID NO 51
<211> LENGTH: 1781
<212> TYPE: RNA
<213> ORGANISM: Artificial Sequence
<220> FEATURE:
<223> OTHER INFORMATION: Synthetic Polynucleotide

<400> SEQUENCE: 51
gggaauaaag agagaaaaga agaguaagaa gaaauauaag accccggcgc cgccaccaug        60
gaacugcuca uuuugaaggc aaacgcuauc acgacaauac ucacugcagu gaccuucugu       120
uuugccucag gccagaacau aaccgaggag uuuuaucaau cuacaugcag cgcuguaucu       180
aaaggcuacc ugagugcgcu ccgcacagga ugguacaccu ccgugaucac caucgagcuc       240
agcaauauua aagagaacaa gugcaauggu accgacgcua agucaaaacu uaucaagcag       300
gaacucgaca auauaagaa cgcugugacc gagcugcagu auugaugca gaguacaccu         360 gccaccgggu cgggcucugc cauuugcucc ggcguggcug uauguaaagu ucuccaccuc       420
gagggagagg uuaauaagau uagucggcc cugcugagua cuaacaaagc aguggugucg        480
cugaguaacg gaguaagugu guuaacauuu aaggucuggg accucaagaa uuauauugac       540
aaacaguugc uuccuauucu aaacaaacag agcuguucaa uaaguaauau ugaaacuguu       600
auugaguuuc agcagaagaa caacaggcuu cuugagauua cacgcgaguu cagugucaau       660
gccggcguua caacacccgu gucuaccuac augcugacga uucugagcu ucucucucuc        720 auaaacgaca ugcccauuac gaaugaccaa agaaacuua uguccaacaa cgugcagauu        780
gugcgacagc aauccuauag cauuaugugu aucaucaagg aagagguacu cgcuuauguu       840
gugcagcuac cacucuaugg ugugauugac accccuguu ggaagcugca uaccaguca         900 cucugcacca cuaacacaaa ggaagggagc aauauuugcc ucacucgaac cgacaggggg       960
ugguauugcg auaaugcggg ucccgugucc uucuuccac aggcugaaac uuguaaggua      1020
cagucaaacc gcguguucug ugauacuaug aauucucgua cucuucccag cgagguuaau      1080
cucugcaacg ucgacauuuu caauccuaaa uaugacugca gaucaugac cagcaagacc      1140 gacgucucca gcucaguaau cacuagccua ggggccauug uaagcugcua uggcaaaaacc    1200 aagugaccug ccucuaauaa gaacagaggc auaauuaaaa ccuuuucaaa uggcugugac      1260 uauguguga auaaggcgu cgacacgguc cagauaggga uaccucuua cugcguuaac        1320 aaacaggaag gcaaaucccu uuauguaaag ggcgagccca ucauaaauuu cuacgaccca    1380 cuugugguucc ccagugauga auucgaugca ucaaucuccc aggugaacga aaagaucaau     1440
```

```
caaucccuug cuuuuauacg aaagucagau gaacuccugc auaacgugaa ugcugggaaa    1500
ucuacaacca acaucaugau cacuaccauc auuauuguga uuaucguaau ucugcuaucc    1560
uugauugcug ucgggcugcu ucuguacugu aaggccagau cgacgccugu gacccuuuca    1620
aaagaccaac uuagcgguau caauaauauu gccuuuagca auugauaaua ggcuggagcc    1680
ucgguggccu agcuucuugc cccuugggcc ucccccagc cccuccuccc cuuccugcac     1740
ccguaccccc guggucuuug aauaaagucu gagugggcgg c                       1781
```

<210> SEQ ID NO 52
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 52

```
auggaacugc ucauuuugaa ggcaaacgcu aucacgacaa uacucacugc agugaccuuc      60
uguuuugccu caggccagaa cauaaccgag gaguuuuauc aaucuacaug cagcgcugua    120
ucuaaaggcu accgagugc gcuccgcaca ggauggauaca ccuccgugau caccaucgag    180
cucagcaaua uuaagagaa caagugcaau gguaccgacg cuaaagucaa acuuaucaag    240
caggaacucg acaaauauaa gaacgcgugu accgagcugc aguuauugau gcagaguaca    300
ccugccaccg ggucgggcuc ugccauuugc uccggcgugg cuguauguaa aguucccac     360 cucgagggag agguuaauaa gauuaagucg gcccugcuga guacuaacaa agcagguggug   420 ucgcugagua acggaguaag uguguuaaca uuuaaggugc uggaccucaa gaauuauauu    480
gacaaacagu ugcuuccuau ucuaaacaaa cagagcuguu caauaaguaa uauugaaacu    540
guuauugagu uucagcagaa gaacaacagg cuucuugaga uuacacgcga guucagugue    600 aaugccggcg uuacaacacc cgugucuacc uacaugcuga cgaauucuga gcuucucucu    660
cucauaaacg acaugcccau uacgaaugac caaaagaaac uuaugccaa caacgugcag     720 auugugcgac agcaauccua uagcauuaug uguaucauca aggaagaggu acucgcuuau    780
guugugcagc uaccacucua ugguguaauu gacacccccu guuggaagcu gcauaccagu    840
ccacucugca ccacuaaacac aaaggaaggg agcaauauuu gccucacucg aaccgacagg    900 ggugguauu gcgauaaugc gggcuccgug uccuucuuuc cacaggcuga acuuguaag     960 guacagucaa accgcguguu cugugauacu augaauucuc guacucuucc cagcgagguu   1020
aaucucugca acgucgacau uuucaauccu aaauaugacu gcaagaucau gaccagcaag   1080
accgacgucu ccagcucagu aaucacuagc cuagggccaa uguaagcug cuauggcaaa   1140 accaagugua cugccucuaa uaagaacaga ggcauaauua aaaccuuuuc aaauggcugu   1200
gacuaugugu cgaauaaggg cgucgacacg gucucaguag ggaauacccu cuacugcguu   1260
aacaaacagg aaggcaaauc ccuuuaugua aagggcgagc caucauaaa uuucuacgac    1320 ccacuugugu uccccaguga ugaauucgau gcaucaaucu cccaggugaa cgaaaagauc    1380
aaucaauccc uugcuuuuau acgaaaguca gaugaacucc ugcauaacgu gaaugcuggg    1440
aaaucuacaa ccaacaucau gaucacuacc aucauuauug gauuaucgu aauucugcua    1500 uccuugauug cugucgggcu gcuucuguac uguaaggcca gaucgacgcc ugugacccuu    1560
ucaaaagacc aacuuagcgg uaucaauaau auugccuuua gcaau                    1605
```

<210> SEQ ID NO 53

```
<211> LENGTH: 1781
<212> TYPE: RNA
<213> ORGANISM: Artificial Sequence
<220> FEATURE:
<223> OTHER INFORMATION: Synthetic Polynucleotide

<400> SEQUENCE: 53
gggaauuaag agagaaaaga agaguaagaa gaaauauaag accccggcgc cgccaccaug      60
gagcugcuga uccucaaggc uaacgccauc accaccaucc ugaccgccgu gaccuucugc     120
uucgccagcg ggcagaacau caccgaggag uucuaccaga gcacuugcag cgccgugagc     180
aagggcuacc ugucagcccu gcggaccggu gguacacca gcgugaucac caucgagcug     240
agcaacauca aggagaacaa gugcaacggc accgacgcca aggugaagcu gaucaagcag     300
gagcuggaca aguacaagaa cgccgugacc gagcugcagc ugcugaugca guccacgccc     360
gcuaccgggu caggcagcgc caucugcucc ggcguggccg ugugcaaggu gcugcaccug     420
gagggcgagg ugaacaagau caagagcgcc cugcugagca ccaacaaggc cguggugagc     480
cugagcaacg gcgugagcgu gcugaccuuc aaggugcugg accugaagaa cuacaucgac     540
aagcagcugc ugcccauccu gaacaagcag uccugcucca ucuccaacau cgaaacugug     600
aucgaguucc agcagaagaa caaccgccug cuggagauca cccgcgaguu cagcgugaac     660
gccggcguga ccaccccagu gagcaccuac augcugacca cagcgagcu gcugagccug     720
aucaacgaca ugcccaucac caacgaccag aagaagcuga ugagcaacaa cgugcagauc     780
gugcgccagc aguccuacuc uaucaugugc aucaucaagg aggagugcu ggccuacgug     840
gugcagcugc cccuguacgg cgugaucgac acaccugcu ggaagcugca caccuccccu     900
cugugcacca cuaacaccaa ggaggggagc aacaucugcc ugacccggac cgaccgcggc     960
ugguacugcg acaacgccgg cagcgugagc uucuuccuc aggccgaaac cugcaaggug    1020
cagagcaaca ggguguucug cgacaccaug aacucccgga cccugcccag cgaggugaac    1080
cugugcaacg uggacaucuu caaccccaag uacgauugca agaucaugac cuccaagacc    1140
gacgugagca gcuccgugau caccucccug ggcgccaucg ugaguugcua cggcaagacc    1200
aagugcaccg ccagcaacaa gaaccgcggc aucaucaaga ccuucagcaa cggcugcgac    1260
uacgugucca caagggcgu ggacaccgug agcgugggca cacccugua cugcgugaac    1320
aagcaggagg gcaagagccu guacgugaag ggcgagccca ucaucaacuu cuacgauccg    1380
cugguguucc ccuccgacga guucgacgcc uccaucagcc aggugaacga aagaucaac    1440
cagagccugg ccuucauccg caaguccgac gagcugcugc acaacgucaa cgccgguaag    1500
agcaccacca acaucaugau caccacaauc aucaucguga ucauugugau cuugcucucc    1560
uuaaucgccg ugggccugcu gcuguacugc aaggcccgga gcaccccagu gaccugagc    1620
aaagaucagc ugucggcau caacaacauc gccuucucca cugauaaua ggcuggagcc    1680
ucgguggccu agcuucugc cccugggcc uccccccagc ccucccccc cuuccugcac    1740
ccguaccccc guggucuuug aauaaagucu gaguggggcg g                     1781

<210> SEQ ID NO 54
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 54
auggagcugc ugauccucaa ggcuaacgcc aucaccacca uccugaccgc cgugaccuuc      60
```

```
ugcuucgcca gcgggcagaa caucaccgag gaguucuacc agagcacuug cagcgccgug    120
agcaagggcu accugucagc ccugcggacc ggcugguaca ccagcugau caccaucgag     180 cugagcaaca ucaaggagaa caagugcaac ggcaccgacg ccaaggugaa gcugaucaag    240
caggagcugg acaaguacaa gaacgccgug accgagcugc agcugcugau gcagcuccacg   300 cccgcuaccg ggucaggcag cgccaucugc uccggcgugg ccgugugcaa ggugcugcac    360
cuggagggcg aggugaacaa gaucaagagc gcccugcuga gcaccaacaa ggccguggug    420
agccugagca acggcgugag cgugcugacc uucaaggugc uggaccugaa gaacuacauc    480
gacaagcagc ugcugcccau ccugaacaag caguccugcu ccaucuccaa caucgaaacu    540
gugaucgagu ccagcagaa gaacaaccgc cugcuggaga ucaccgcga guucagcgug      600 aacgccggcg ugaccacccc agugagcacc uacaugcuga ccaacagcga gcugcugagc    660
cugaucaacg acaugcccau caccaacgac cagaagaagc ugaugagcaa caacgugcag    720
aucgugcgcc agcaguccua cucuaucaug ugcaucauca aggaggaggu gcuggccuac    780
guggugcagc ugccccugua cggcgugauc gacacacccu gcuggaagcu gcacaccucc    840
ccucugugca ccacuaacac caaggagggg agcaacaucu gccugacccg gaccgaccgc    900
ggcugguacu gcgacaacgc cggcagcgug agcuucuucc ucaggccga aaccugcaag    960 gugcagagca caggguguu cugcgacacc augaacuccc ggaccugcc cagcgaggug     1020 aaccugugca acgggacau cuucaacccc aaguacgauu gcaagaucau gaccuccaag    1080
accgacguga gcagcuccgu gaucaccucc cugggcgcca ucgugaguug cuacggcaag    1140
accaagugca ccgccagcaa caagaaccgc ggcaucauca agaccuucag caacggcugc    1200 gacuacugu ccaacaaggg cguggacacc gugagcgugg gcaacacccu guacugcgug    1260
aacaagcagg agggcaagag ccuguacgug aagggcgagc ccaucaucaa cuucuacgau    1320
ccgcuggugu uccccuccga cgaguucgac gccuccauca gccaggugaa cgagaagauc    1380
aaccagagcc uggccuucau ccgcaagucc gacgagcugc ugcacaacgu caacgccggu    1440
aagagcacca ccaacaucau gaucaccaca aucaucaucg ugaucauugu gaucuugcuc    1500
uccuuaaucg ccguggggcu gcugcuguac ugcaaggccc ggagcacccc agugacccug    1560
agcaaagauc agcuguccgg caucaacaac aucgccuucu ccaac                   1605
```

<210> SEQ ID NO 55
<211> LENGTH: 1781
<212> TYPE: RNA
<213> ORGANISM: Artificial Sequence
<220> FEATURE:
<223> OTHER INFORMATION: Synthetic Polynucleotide

<400> SEQUENCE: 55

```
gggaaauaag agagaaaaga agaguaagaa gaaauauaag accccggcgc cgccaccaug    60
gagcugcuga uucugaaggc caacgccauu accaccauuc ugaccgccgu gaccuucugc    120
uucgccagcg gccagaauau uaccgaggag uucuaccagu caaccugcag cgccgugagc    180
aagggcuacc ugagcgcccu acggaccggg uguacaccu ccgugaucac cauugagcug     240
agcaauauua aggagaauaa gugcaacggg accgacgcca aggugaagcu caucaagcag    300
gagcuggaua aguacaagaa cgccgugacc gagcugcagc ugcugaugca gcacaccg      360 gccacgggcu ccggcagcgc cauuugcuca ggcguggccg ugugcaaggu gcugcaccuc    420
gagggcgagg ucaauaagau uaagagcgcc cguugagca ccaauaaggc cguggugagc     480
```

| | |
|---|---|
| cugagcaacg gcgugagcgu gcugaccuuc aaggugcugg aucucaagaa uuacauugau | 540 |
| aagcagcugc ugccaauucu caauaagcag agcugcagca uuagcaauau cgaaaccgug | 600 |
| auugaguucc agcagaagaa uaaucgccug cuggagauua cccgcgaguu cagcgucaac | 660 |
| gccgggguga ccaccccagu cagcaccuac augcugacca auagcgagcu gcugagccug | 720 |
| auuaacgaua ugcccauuac caacgaccag aagaagcuga ugagcaauaa cgugcagauu | 780 |
| gugcgccagc agagcuacag cauuaugugc auuauuaagg aggaggugcu ggccuacgug | 840 |
| gugcagcugc cccucuacgg cgugauugau acgcccugcu ggaagcugca caccagccca | 900 |
| cugugcacca ccaauaccaa ggagggcagc aauauuugcc ugacccgcac cgaucgcggg | 960 |
| ugguacugcg auaacgccgg cagcgugagc uucuucccac aggccgaaac augcaaggug | 1020 |
| caguccaauc gcguguucug cgauaccaug aacagccgca cccugcccag cgaggugaau | 1080 |
| cucugcaacg uggauauuuu caauccaaag uacgauugca agauuaugac cagcaagacc | 1140 |
| gacgugagcu ccagcgugau uaccucacuc ggcgccauug ugagcugcua cggcaagacc | 1200 |
| aagugcaccg ccucaaauaa gaaucgcggc auuauuaaga ccuucagcaa cggcugcgau | 1260 |
| uacgugagca auaagggcgu ggauaccgug agcgugggaa auacccugua cgcgugaau | 1320 |
| aagcaggagg gcaagagccu guacgugaag ggcgagccaa uuauuaauuu cuacgauccc | 1380 |
| cuggguguucc cagcgacga guucgacgcc agcauuagcc aggugaacga gaagauuaau | 1440 |
| cagagccugg ccuucauucg caaguccgac gagcuccugc acaacgugaa cgccggcaag | 1500 |
| agcaccacca acaucaugau uaccaccauc aucauguga uuaucgugau ccuccucagc | 1560 |
| cucauugccg ugggccuccu ccuguacugc aaggcccgca gcaccccugu gacccucagc | 1620 |
| aaggaucagc ugagcggcau caauaauauc gccuucagca auugauaaua ggcuggagcc | 1680 |
| ucgguggccu agcuucuugc cccuugggcc ucccccagc cccuccuccc cuuccugcac | 1740 |
| ccguaccccc guggucuuug aauaaagucu gaguggggcgg c | 1781 |

<210> SEQ ID NO 56
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 56

| | |
|---|---|
| auggagcugc ugauucugaa ggccaacgcc auuaccacca uucugaccgc cgugaccuuc | 60 |
| ugcuucgcca gcggccagaa uauuaccgag gaguucuacc agucaaccug cagcgccgug | 120 |
| agcaagggcu accugagcgc ccuacggacc ggguguaca ccuccgugau caccauugag | 180 |
| cugagcaaua uuaaggagaa uaagugcaac gggaccgacg ccaaggugaa gcucaucaag | 240 |
| caggagcugg auaaguacaa gaacgccgug accgagcugc agcugcugau gcagagcaca | 300 |
| ccggccacgg gcuccggcag cgccauuugc ucaggcgugg ccgugugcaa ggucugcac | 360 |
| cucgagggcg aggucaauaa gauuaagagc gcccuguuga gcaccaauaa ggccgugggu | 420 |
| agccugagca acggcgugag cgugcugacc uucaaggugc uggaucucaa gaauuacauu | 480 |
| gauaagcagc ugcugccaau ucucaauaag cagagcugca gcauuagcaa uaucgaaacc | 540 |
| gugauugagu ccagcagaa gaauaaucgc cugcuggaga uuacccgcga guucagcguc | 600 |
| aacgccgggg ugaccacccc agucagcacc uacaugcuga ccaauagcga gcugcugagc | 660 |
| cugauuaacg auaugcccau uaccaacgac cagaagaagc ugaugagcaa uaacgugcag | 720 |
| auugugcgcc agcagagcua cagcauuaug ugcauuauua aggaggaggu gcuggccuac | 780 |

```
guggugcagc ugccccucua cggcgugauu gauacgcccu gcuggaagcu gcacaccagc    840
ccacugugca ccaccaauac caaggagggc agcaauauuu gccugacccg caccgaucgc    900 ggguggacu gcgauaacgc cggcagcgug agcuucuucc cacaggccga aacaugcaag    960
gugcagucca aucgcguguu cugcgauacc augaacagcc gcacccugcc cagcgaggug   1020
aaucucugca acguggauau uuucaaucca aguacgauu gcaagauuau gaccagcaag    1080
accgacguga gcuccagcgu gauuaccuca cucggcgcca uugugagcug cuacggcaag   1140
accaagugca ccgccucaaa uaagaaucgc ggcauuauua agaccuucag caacggcugc   1200
gauuacguga gcaauaaggg cguggauacc gugagcgugg aaauacccu guacugcgug    1260 aauaagcagg agggcaagag ccuguacgug aagggcgagc caauuauuaa uuucuacgau   1320 ccccugugu uccccagcga cgaguucgac gccagcauua gccaggugaa cgagaagauu    1380
aaucagagcc uggccuucau ucgcaaguc gacgagcucc ugcacaacgu gaacgccggc    1440
aagagcacca ccaacaucau gauuaccacc aucaucauu ugauuaucgu gauccuccuc    1500
agccucauug ccgugggccu ccuccuguac ugcaaggccc gcagcacucc ugugacccuc   1560
agcaaggauc agcugagcgg caucaauaau aucgccuuca gcaau                  1605
```

<210> SEQ ID NO 57
<211> LENGTH: 1781
<212> TYPE: RNA
<213> ORGANISM: Artificial Sequence
<220> FEATURE:
<223> OTHER INFORMATION: Synthetic Polynucleotide

<400> SEQUENCE: 57

```
gggaauaag agagaaaaga agaguaagaa gaaauauaag accccggcgc cgccaccaug      60
gagcugcuga uccugaaggc caacgccauc accaccauc ugaccgccgu gaccuucugc     120
uucgccagcg ccagaacau uaccgaggag uucuaccagu ccaccugcag cgccgugagc    180
aagggcuacc ugagcgcccu gcgcaccggg ugguacacca gcgugaucac caucgagcug    240
uccaacauca aggagaacaa gugcaacggc acagacgcca aggugaagcu gaucaagcag    300
gagcuggaca aguacaagaa cgccgugacc gagcuccagc ugcugaugca guccaccccg    360
gccaccggca guggaagugc uaucugcagc ggggguggccg ugcaaggu gcugcaccug    420 gagggcgagg ugaacaagau caagagcgcc cugcugagca ccaacaaggc cguggugagc    480
cugagcaacg ggguguccgu gcugacauuc aaggugcugg accugaagaa cuacaucgac    540
aagcagcugc ugcccauccu caacaagcag agcugucca ucucaauau cgaaaccgug    600 aucgaguuuc agcagaagaa caaccggcug cuggagauca cccgggaguu uccgugaac    660 gccggggug ccaccccagu gagcaccuac augcugacca cuccgagcu gcugagccug    720 aucaacgaua ugccaaucac aaacgaucag aagaagcuga ugagcaacaa cgugcagauc    780
gugcggcagc aguccuacag caucaugugc aucaucaagg aggaggugcu ggccuacgug    840
gugcagcugc cccuguacgg cgugaucgac acuccuugcu ggaagcugca caccucaccg    900
cugugcacca cgaacacuaa ggagggcagc aacaucugcc ugacccggac cgaccgaggc    960
uggaacugcg acaacgccgg cagcgucucu ucuuuccgc aggccgagac ugcaagguc    1020 cagguccaacc ggguguucug cgacaccaug aacucccgga cccugccccu cgaggugaac    1080
cugugcaacg uggacauuuu caaccccaag uacgacugca agaucaugac caguaagacc    1140
gacgugucca gcuccguaau caccagccug ggcgccaucg uguccuguua cggcaagacc    1200
```

| | |
|---|---|
| aaguguaccg ccuccaacaa gaaccgaggu aucaucaaga ccuucuccaa cggguggcgac | 1260 |
| uacgugucca acaagggcgu ggacaccgug agcgugggaa auacccucua cugcugaac | 1320 |
| aagcaggagg ggaagucccu guacgugaag ggugagccca ucaucaacuu uuacgauccc | 1380 |
| cuggguguucc ccagcgacga guucgacgca uccauuagcc aggugaacga gaagaucaac | 1440 |
| cagagucugg ccuucauccg caagcccgac gagcugcugc acaacgugaa cgcuggcaag | 1500 |
| ucaacaacca acaucaugau cacgaccauc auuaucguga ucaucgugau ccugcugucc | 1560 |
| cugaucgcag ugggccugcu ccuguacugc aaggcccgca gcacaccgu gacccucagc | 1620 |
| aaggaucagc ucagcggcau caacaacauc gccuucagca acugauaaua ggcuggagcc | 1680 |
| ucgguggccu agcuucuugc cccuugggcc uccccccagc cccuccuccc cuuccugcac | 1740 |
| ccguaccccc guggucuuug aauaaagucu gagugggcgg c | 1781 |

<210> SEQ ID NO 58
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 58

| | |
|---|---|
| auggagcugc ugauccugaa ggccaacgcc aucaccacca uccugaccgc cgugaccuuc | 60 |
| ugcuucgcca gcggcagaa cauuaccgag gaguucuacc aguccaccug cagcgccgug | 120 |
| agcaagggcu accugagcgc ccugcgcacc ggguggugua ccagcgugau caccaucgag | 180 |
| cuguccaaca ucaaggagaa caagugcaac ggcacagacg ccaaggugaa gcugaucaag | 240 |
| caggagcugg acaaguacaa gaacgccgug accgagcucc agcugcugau gcaguccacc | 300 |
| ccggccaccg gcaguggaag ugcuaucugc agcggggugg ccgugugcaa ggucgcugcac | 360 |
| cuggagggcg aggugaacaa gaucaagagc gcccugcuga gcaccaacaa ggccguggug | 420 |
| agccugagca cgggguguc cgugcugaca uucaaggugc uggaccugaa gaacuacauc | 480 |
| gacaagcagc ugcugcccau ccucaacaag cagagcugcu ccaucuccaa uaucgaaacc | 540 |
| gugaucgagu uucagcagaa gaacaaccgg cugcuggaga ucacccggga guucuccgug | 600 |
| aacgccgggg ugaccacccc agugagcacc uacaugcuga ccaacuccga gcugcugagc | 660 |
| cugaucaacg auaugccaau cacaaacgau cagaagaagc ugaugagcaa caacgugcag | 720 |
| aucgugcggc agcaguccua cagcaucaug ugcaucauca aggaggaggu gcuggccuac | 780 |
| guggugcagc ugccccugua cggcgugauc gacaccccuu gcuggaagcu gcacaccuca | 840 |
| ccgcugugca ccacgaacac uaaggagggc agcaacaucu gccugacccg gaccgaccga | 900 |
| ggcuggacu gcgacaacgc cggcagcguc ucuuucuuuc cgcaggccga gacgugcaag | 960 |
| gugcaguca accggguguu cugcgacacc augaacuccc ggaccugcc cucccgaggug | 1020 |
| aaccugugca cguggacau uucaaccccc aaguacgacu gcaagaucau gaccaguaag | 1080 |
| accgacgugu ccagcuccgu aaucaccagc cugggcgcca ucgugccug uuacggcaag | 1140 |
| accaagugua ccgccuccaa caagaaccga gguaucauca gaccuucuc caacgggugc | 1200 |
| gacuacgugu ccaacaaggg cguggacacc gugagcgugg gaaauacccu cuacugcgug | 1260 |
| aacaagcagg aggggaaguc ccuguacgug aagggugagc ccaucaucaa cuuuuacgau | 1320 |
| ccccuggugu ccccagcga cgaguucgac gcauccauua gccaggugaa cgagaagauc | 1380 |
| aaccagaguc uggccuucau ccgcaagccc gacgagcugc ugcacaacgu gaacgcuggc | 1440 |
| aagucaacaa ccaacaucau gaucacgacc aucauuaucg ugaucaucgu gauccugcug | 1500 |

| | |
|---|---|
| ucccugaucg cagugggccu gcuccuguac ugcaaggccc gcagcacacc cgugacccuc | 1560 |
| agcaaggauc agcucagcgg caucaacaac aucgccuuca gcaac | 1605 |

<210> SEQ ID NO 59
<211> LENGTH: 1597
<212> TYPE: RNA
<213> ORGANISM: Artificial Sequence
<220> FEATURE:
<223> OTHER INFORMATION: Synthetic Polynucleotide

<400> SEQUENCE: 59

| | |
|---|---|
| gggaauaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugagugcgcu ccgcacagga ugguacaccu ccgugaucac caucgagcuc agcaauauua | 240 |
| aagagaacaa gugcaauggu accgacgcua aagucaaacu uaucaagcag gaacucgaca | 300 |
| aauauaagaa cgcugugacc gagcugcagu auugauggg aggcgguagc ggugcggau | 360 |
| ccggcggugg aagcggcucu gccauugcuu ccggcgugcc uguauguaaa guucuccacc | 420 |
| ucgagggaga gguuaauaag auuaagucgg cccugcugag uacuaacaaa gcaguggugu | 480 |
| cgcugaguaa cggaguaagu uguuaacau uuaaggugcu ggaccucaag aauuauauug | 540 |
| acaaacaguu gcuuccuauu cuaaacaaac agagcuguuc aauaaguaau auugaaacug | 600 |
| uuauugaguu ucagcagaag aacaacaggc uucuugagau uacacgcgag uucaguguca | 660 |
| augccggcgu uacaacaccc gugucuaccu acaugcugac gaauucugag cuucucucuc | 720 |
| ucauaaacga caugcccauu acgaaugacc aaaagaaacu uauguccaac aacgugcaga | 780 |
| uugugcgaca gcaauccuau agcauuaugu guaucaucaa ggaagaggua ucgcuuaug | 840 |
| uugugcagcu accacucuau ggugugauug acaccccccug uuggaagcug cauaccaguc | 900 |
| cacucugcac cacuaacaca aaggaaggga gcaauauuug ccucacucga accgacaggg | 960 |
| ggugguauug cgauaaugcg ggcuccgugu ccuucuuucc acaggcugaa acuuguaagg | 1020 |
| uacagucaaa ccgcguguuc ugugauacua ugaauucucu gacucuuccc agcgagguua | 1080 |
| aucucugcaa cgucgacauu uucaauccua aauaugacug caagaucaug accagcaaga | 1140 |
| ccgacgucuc cagcucagua aucacuagcc uaggggccau uguaagcugc uaggcaaaa | 1200 |
| ccaaguguac ugccucuaau aagaacagag gcauaauuaa aaccuuuuca aauggcugug | 1260 |
| acuauguguc gaauaagggc gucgacacgu ucucaguagg gaauacccuc uacuacguua | 1320 |
| acaaacagga aggcaaaucc cuuuauguaa agggcgagcc caucauaaau uucuacgacc | 1380 |
| cacuuuccgc caucggugc uauauccag aagcccaag agacgacaa gcguacgucc | 1440 |
| ggaaagaugg ugaguggguc cuccucucua ccuuucuuug auaauaggcu ggagccucgg | 1500 |
| uggccaugcu ucuugcccu ugggccuccc ccagcccu ccucccuuc cugcacccgu | 1560 |
| accccgugg ucuuugaaua aagucugagu gggcggc | 1597 |

<210> SEQ ID NO 60
<211> LENGTH: 1431
<212> TYPE: RNA
<213> ORGANISM: Artificial Sequence
<220> FEATURE:
<223> OTHER INFORMATION: Synthetic Polynucleotide

<400> SEQUENCE: 60

| | |
|---|---|
| auggaacugc ucauuuugaa ggcaaacgcu aucacgacaa uacucacugc agugaccuuc | 60 |
| uguuuugccu caggccagaa cauaaccgag gaguuuuauc aaucuacaug cagcgcugua | 120 |
| ucuaaaggcu accugagugc gcuccgcaca ggaugguaca ccuccgugau caccaucgag | 180 |
| cucagcaaua uuaaagagaa caagugcaau gguaccgacg cuaaagucaa acuuaucaag | 240 |
| caggaacucg acaaauauaa gaacgcugug accgagcugc aguuauugau gggaggcggu | 300 |
| agcgguggcg gauccggcgg uggaagcggc ucugccauug cuccggcgu ggcuguaugu | 360 |
| aaaguucucc accucgaggg agagguuaau aagauuaagu cggcccugcu gaguacuaac | 420 |
| aaagcagugg ugucgcugag uaacggagua aguguguuaa cauuuaaggu gcuggaccuc | 480 |
| aagaauuaua uugacaaaca guugcuuccu auucuaaaca aacagagcug uucaauaagu | 540 |
| aauauugaaa cuguuauuga guuucagcag aagaacaaca ggcuucuuga gauuacacgc | 600 |
| gaguucagug ucaaugccgg cguuacaaca cccgugucua ccacaugcu gacgaauucu | 660 |
| gagcuucucu cucucauaaa cgacaugccc auuacgaaug accaaaagaa acuuaugucc | 720 |
| aacaacgugc agauugugcg acagcaaucc uauagcauua uguguaucau caaggaagag | 780 |
| guacucgcuu auguugugca gcuaccacuc uaugguguga uugacacccc cguuggaag | 840 |
| cugcauacca guccacucug caccacuaac acaaaggaag ggagcaauau uugcccucacu | 900 |
| cgaaccgaca gggggugguga uugcgauaau gcgggcuccg uguccuucuu uccacaggcu | 960 |
| gaaacuugua agguacaguc aaaccgcugu ucugugauua cuaugaauuc ucugacucuu | 1020 |
| cccagcgagg uuaaucucug caacgucgac auuucaauc cuaaauauga cugcaagauc | 1080 |
| augaccagca gaccgacgu cuccagcuca guaaucacua gccuagggc cauuguaagc | 1140 |
| ugcuauggca aaccaagug uacugccucu aauaagaaca gaggcauaau uaaaaccuuu | 1200 |
| ucaaauggcu gugacuaugu gucgaauaag ggcgucgaca cgguucuag agggaauacc | 1260 |
| cucuacuacg uuaacaaaca ggaaggcaaa ucccuuuaug uaaagggcga gcccaucaua | 1320 |
| aauuucuacg acccacuuuc cgccaucggu ggcuauaucc cagaagcccc aagagacgga | 1380 |
| caagcguacg uccggaaaga guggagugg guccuccucu cuaccuuucu u | 1431 |

<210> SEQ ID NO 61
<211> LENGTH: 477
<212> TYPE: PRT
<213> ORGANISM: Artificial Sequence
<220> FEATURE:
<223> OTHER INFORMATION: Synthetic Polypeptide

<400> SEQUENCE: 61

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Gly Ser Gly Gly Gly Ser Gly Gly Gly Ser Gly Ser Ala
            100                 105                 110

```
Ile Ala Ser Gly Val Ala Val Cys Lys Val Leu His Leu Glu Gly Glu
            115                 120                 125

Val Asn Lys Ile Lys Ser Ala Leu Leu Ser Thr Asn Lys Ala Val Val
        130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Ser Ala
        435                 440                 445

Ile Gly Gly Tyr Ile Pro Glu Ala Pro Arg Asp Gly Gln Ala Tyr Val
450                 455                 460

Arg Lys Asp Gly Glu Trp Val Leu Leu Ser Thr Phe Leu
465                 470                 475
```

<210> SEQ ID NO 62
<211> LENGTH: 1702
<212> TYPE: RNA
<213> ORGANISM: Artificial Sequence
<220> FEATURE:
<223> OTHER INFORMATION: Synthetic Polynucleotide

<400> SEQUENCE: 62

-continued

| | |
|---|---|
| gggaaauaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugagugcgcu ccgcacagga ugguacaccu ccgugaucac caucgagcuc agcaauauua | 240 |
| aagagaacaa gugcaauggu accgacgcua aagucaaacu uaucaagcag gaacucgaca | 300 |
| aauauaagaa cgcugugacc gagcugcagu uauugaugca gaauacaccu gccaccaaua | 360 |
| acagagcuag gagggaguug ccuagguuua ugaacuacac ucuaacaac gcgaagaaaa | 420 |
| ccaaugugac gcuauccaag aaacggaaga ggagguccu gggguuucuu uuaggggugg | 480 |
| gcucugccau ugcuuccggc guggcuguau guaaaguucu ccaccucgag ggagagguua | 540 |
| auaagauuaa gucggcccug cugagaacua acaaagcagu ggugucgcug aguaacggag | 600 |
| uaagugaguu aacauuuaag gugcuggacc ucaagaauua uauugacaaa caguugcuuc | 660 |
| cuauucuaaa caaacagagc uguucaauaa guauauuga aacguuuauu gaguuucagc | 720 |
| agaagaacaa caggcuucuu gagauuacac gcgaguucag ugucaaugcc ggcguuacaa | 780 |
| cacccguguc uaccuacaug cugacgaauu cugagcuucu cucucucaua aacgacaugc | 840 |
| ccauuacgaa ugaccaaaag aaacuuaugu ccaacaacgu gcagauugug cgacagcaau | 900 |
| ccuauagcau uaugugnauc aucaaggaag agguacucgc uuauguugug cagcuaccac | 960 |
| ucuaugugu gauugacacc cccguugga agcugcauac caguccacuc ugcaccacua | 1020 |
| acacaaagga agggagcaau auuugccuca cucgaaccga cagggggugg uauugcgaua | 1080 |
| augcgggcuc cgugccuuc uuccacagg cugaaacuug uaaggacag ucaaaccgcg | 1140 |
| uguucuguga uacuaugaau ucucugacuc uucccagcga gguuaaucuc ugcaacgucg | 1200 |
| acauuuucaa uccuaaauau gacugcaaga ucaugaccag caagaccgac gucuccagcu | 1260 |
| caguaaucac uagccuaggg gccauuguaa gcugcuaugg caaaaccaag uguacugccu | 1320 |
| cuaauaagaa cagaggcaua auuaaaaccu uucaaaugg cugugacuau gugucgaaua | 1380 |
| agggcgucga cacggucuca guagggaaua cccucuacua cguuaacaaa caggaaggca | 1440 |
| aaucccuuua uguaaagggc gagcccauca uaaauuucua cgaccacuu uccgccaucg | 1500 |
| guggcuauau cccagaagcc ccaagagacg gacaagcgua cguccggaaa gauggugagu | 1560 |
| gguccuccu cucuaccuuu cuugauaau aggcuggagc cucggguggcc augcuucuug | 1620 |
| ccccuugggc cuccccccag ccccuccucc ccuuccugca cccguacccc cgugggucuuu | 1680 |
| gaauaaaguc ugaguggggcg gc | 1702 |

<210> SEQ ID NO 63
<211> LENGTH: 1536
<212> TYPE: RNA
<213> ORGANISM: Artificial Sequence
<220> FEATURE:
<223> OTHER INFORMATION: Synthetic Polynucleotide

<400> SEQUENCE: 63

| | |
|---|---|
| auggaacugc ucauuuugaa ggcaaacgcu aucacgacaa uacucacugc agugaccuuc | 60 |
| uguuuugccu caggccagaa cauaaccgag gaguuuuauc aaucuacaug cagcgcugua | 120 |
| ucuaaaggcu accugagugc gcuccgcaca ggaugguaca ccuccgugau caccaucgag | 180 |
| cucagcaaua uuaagagaa caagugcaau gguaccgacg cuaaagucaa acuuaucaag | 240 |
| caggaacucg acaaauauaa gaacgcugug accgagcugc aguuauugau gcagaauaca | 300 |
| ccugccacca auaacagagc uaggagggag uugccuaggu uuaugaacua cacucucaac | 360 |

-continued

```
aacgcgaaga aaaccaaugu gacgcuaucc aagaaacgga agaggagguu ccuggguuu      420 cuuuuaggg uggcucugc cauugcuucc ggcguggcug uauguaaagu ucuccaccuc       480
gagggagagg uuaauaagau uaagucggcc cugcugagua cuaacaaagc agugguguucg    540 cugaguaacg gaguaagugu guuaacauuu aaggugcugg accucaagaa uuauauugac     600
aaacaguugc uuccuauucu aaacaaacag agcuguucaa uaaguaauau ugaaacuguu     660
auugaguuuc agcagaagaa caacaggcuu cuugagauua cacgcgaguu cagugucaau     720
gccggcguua caacacccgu gucuaccuac augcugacga auucugagcu ucucucucuc     780
auaaacgaca ugcccauuac gaaugaccaa agaaacuua uguccaacaa cgugcagauu      840
gugcgacagc aauccuauag cauuaugugu aucaucaagg aagagguacu cgcuuauguu     900
gugcagcuac cacucuaugg ugugauugac accccccuguu ggaagcugca uaccaguca    960 cucugcacca cuaacacaaa ggaagggagc aauauuugcc ucacucgaac cgacagggg     1020 ugguauugcg auaaugcggg ucccguguccc uucuuuccac aggcugaaac uuguaaggua   1080
cagucaaacc gcguguucug ugauacuaug aauucucuga cucuucccag cgagguuaau   1140
cucugcaacg ucgacauuuu caauccuaaa uaugacugca agaucaugac cagcaagacc   1200
gacgucucca gcucaguaau cacuagccua gggccauug uaagcugcua uggcaaaacc    1260 aagguacug ccucuaauaa gaacagaggc auaauuaaaa ccuuucaaa uggcugugac    1320 uauguguga auaagggcgu cgacacgguc ucaguaggga auccccucua cuacguuaac   1380
aaacaggaag gcaaauccu uuauguaaag ggcgagccca ucauaaauuu cuacgaccca   1440 cuuccgcca ucgguggcua uauccccagaa gccccaagag acggacaagc guacguccgg  1500
aaagauggug agugggucccu ccucucuacc uuucuu                           1536
```

<210> SEQ ID NO 64
<211> LENGTH: 512
<212> TYPE: PRT
<213> ORGANISM: Artificial Sequence
<220> FEATURE:
<223> OTHER INFORMATION: Synthetic Polypeptide

<400> SEQUENCE: 64

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
```

```
                    145                 150                 155                 160
            Glu Gly Glu Val Asn Lys Ile Lys Ser Ala Leu Leu Ser Thr Asn Lys
                            165                 170                 175

Ala Val Val Ser Leu Ser Asn Gly Val Ser Val Leu Thr Phe Lys Val
                        180                 185                 190

Leu Asp Leu Lys Asn Tyr Ile Asp Lys Gln Leu Leu Pro Ile Leu Asn
                    195                 200                 205

Lys Gln Ser Cys Ser Ile Ser Asn Ile Glu Thr Val Ile Glu Phe Gln
                210                 215                 220

Gln Lys Asn Asn Arg Leu Leu Glu Ile Thr Arg Glu Phe Ser Val Asn
            225                 230                 235                 240

Ala Gly Val Thr Thr Pro Val Ser Thr Tyr Met Leu Thr Asn Ser Glu
                            245                 250                 255

Leu Leu Ser Leu Ile Asn Asp Met Pro Ile Thr Asn Asp Gln Lys Lys
                        260                 265                 270

Leu Met Ser Asn Asn Val Gln Ile Val Arg Gln Gln Ser Tyr Ser Ile
                    275                 280                 285

Met Cys Ile Ile Lys Glu Glu Val Leu Ala Tyr Val Val Gln Leu Pro
                290                 295                 300

Leu Tyr Gly Val Ile Asp Thr Pro Cys Trp Lys Leu His Thr Ser Pro
            305                 310                 315                 320

Leu Cys Thr Thr Asn Thr Lys Glu Gly Ser Asn Ile Cys Leu Thr Arg
                            325                 330                 335

Thr Asp Arg Gly Trp Tyr Cys Asp Asn Ala Gly Ser Val Ser Phe Phe
                        340                 345                 350

Pro Gln Ala Glu Thr Cys Lys Val Gln Ser Asn Arg Val Phe Cys Asp
                    355                 360                 365

Thr Met Asn Ser Leu Thr Leu Pro Ser Glu Val Asn Leu Cys Asn Val
                370                 375                 380

Asp Ile Phe Asn Pro Lys Tyr Asp Cys Lys Ile Met Thr Ser Lys Thr
            385                 390                 395                 400

Asp Val Ser Ser Ser Val Ile Thr Ser Leu Gly Ala Ile Val Ser Cys
                            405                 410                 415

Tyr Gly Lys Thr Lys Cys Thr Ala Ser Asn Lys Asn Arg Gly Ile Ile
                        420                 425                 430

Lys Thr Phe Ser Asn Gly Cys Asp Tyr Val Ser Asn Lys Gly Val Asp
                    435                 440                 445

Thr Val Ser Val Gly Asn Thr Leu Tyr Val Asn Lys Gln Glu Gly
                450                 455                 460

Lys Ser Leu Tyr Val Lys Gly Glu Pro Ile Ile Asn Phe Tyr Asp Pro
            465                 470                 475                 480

Leu Ser Ala Ile Gly Gly Tyr Ile Pro Glu Ala Pro Arg Asp Gly Gln
                            485                 490                 495

Ala Tyr Val Arg Lys Asp Gly Glu Trp Val Leu Leu Ser Thr Phe Leu
                        500                 505                 510

<210> SEQ ID NO 65
<211> LENGTH: 1798
<212> TYPE: RNA
<213> ORGANISM: Artificial Sequence
<220> FEATURE:
<223> OTHER INFORMATION: Synthetic Polynucleotide

<400> SEQUENCE: 65
gggaauaaag agagaaaaga agaguaagaa gaaauauaag agccaccaug gaacugcuca      60
```

| | | | |
|---|---|---|---|
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugagugcgcu ccgcacagga ugguacaccu ccgugaucac caucgagcuc agcaauauua | 240 |
| aagagaacaa gugcaauggu accgacgcua aagucaaacu uaucaagcag gaacucgaca | 300 |
| aauauaagaa cgcugugacc gagcugcagu auugaugca gaguacaccu gccaccaaua | 360 |
| acagagcuag gagggaguug ccagguuua ugaacuacac ucaacaac gcaagaaaa | 420 |
| ccaaugugac gcuauccaag aaacggaaga ggagguuccu gggguuucuu uugggguggg | 480 |
| gcucugccau ugcuuccggc guggcuguau guaaaguucu ccaccucgag ggagagguua | 540 |
| auaagauuaa gucggcccug cugaguacua acaaagcagu ggugucgcug aguaacggag | 600 |
| uaagugguguu aacauuuaag gugcuggacc ucaagaauua uaugacaaa caguugcuuc | 660 |
| cuauucuaaa caaacagagc uguucaauaa guaauauuga aacuguuauu gaguuucagc | 720 |
| agaagaacaa caggcuucuu gagauucac gcgaguucag ugucaaugcc ggcguuacaa | 780 |
| cacccguguc uaccuacaug cugacgaauu cugagcuucu cucucuauua aacgacaugc | 840 |
| ccauuacgaa ugaccaaaag aaacuuaugu ccaacaacgu gcagauugug cgacagcaau | 900 |
| ccuauagcau uauguguauc aucaaggaag agguacucgc uuauguugug cagcuaccac | 960 |
| ucuauggugu gauugacacc cccguuggaa agcugcauac cagucacacuc ugcaccacua | 1020 |
| acacaaagga aggagcaau auuugccuca cucgaaccga cagggggugg uauugcgaua | 1080 |
| augcgggcuc cgugccuuc uuuccacagg cugaaacuug uaaggucaag ucaaaccgcg | 1140 |
| uguucuguga uacuaugaau ucucugacuc uucccagcga gguuaaucuc ugcaacgucg | 1200 |
| acauuuucaa uccuaaauau gacugcaaga ucaugaccag caagaccgac gucuccagcu | 1260 |
| caguaaucac uagccuaggg gccauuguaa gcugcuaugg caaaaccaag uguacugccu | 1320 |
| cuaauaagaa cagaggcaua auuaaaaccu uucaaaugg cugugacuau gucgaaua | 1380 |
| agggcgucga cacggucuca guagggaaua cccucuacua cguuaacaaa caggaaggca | 1440 |
| aaucccuuua uguaaagggc gagcccauca uaaauuucua cgaccacuu uguuccccca | 1500 |
| guugcgaauu cugcgcauca aucucccagg ugaacgaaaa gaucaaucaa ucccuugcuu | 1560 |
| uuauacgaaa gucagaugaa cuccuguccg ccaucggugg cuauauccca gaagccccaa | 1620 |
| gagacggaca agcgucgucg cggaaagaug gugagugggu ccuccucucu accuuucuuu | 1680 |
| gauaauaggc uggagccucg guggccaugc uucuugcccc uugggccucc ccccagcccc | 1740 |
| uccuccccuu ccugcacccg uacccccgug gucuuugaau aaagucugag ugggcggc | 1798 |

<210> SEQ ID NO 66
<211> LENGTH: 1632
<212> TYPE: RNA
<213> ORGANISM: Artificial Sequence
<220> FEATURE:
<223> OTHER INFORMATION: Synthetic Polynucleotide

<400> SEQUENCE: 66

| | | |
|---|---|
| auggaacugc ucauuuugaa ggcaaacgcu aucacgacaa uacucacugc agugaccuuc | 60 |
| uguuuugccu caggccagaa cauaaccgag gaguuuauc aaucuacaug cagcgcugua | 120 |
| ucuaaaggcu accugagugc gcuccgcaca ggaugguaca ccuccgugau caccaucgag | 180 |
| cucagcaaua uuaagagaa caagugcaau gguaccgacg cuaaagucaa acuuaucaag | 240 |
| caggaacucg acaaauauaa gaacgcugug accgagcugc aguauugau gcagaguaca | 300 |

| | | |
|---|---|---|
| ccugccacca auaacagagc uaggagggag uugccuaggu uuaugaacua cacucucaac | 360 | |
| aacgcgaaga aaaccaaugu gacgcuaucc aagaaacgga agaggagguu ccuggguuu | 420 | |
| cuuuuagggg uggcucugc cauugcuucc ggcguggcug uauguaaagu ucuccaccuc | 480 | |
| gagggagagg uuaauaagau uaagucggcc cugcugagua cuaacaaagc aguggugucg | 540 | |
| cugaguaacg gaguaagugu guuaacauuu aaggugcugg accucaagaa uuauauugac | 600 | |
| aaacaguugc uuccuauucu aaacaaacag agcuguucaa uaaguaauau ugaaacuguu | 660 | |
| auugaguuuc agcagaagaa caacaggcuu cuugagauua cacgcgaguu cagugucaau | 720 | |
| gccggcguua caacacccgu gucuaccuac augcugacga auucugagcu ucucucucuc | 780 | |
| auaaacgaca ugcccauuac gaaugaccaa agaaacuua guccaacaa cgugcagauu | 840 | |
| gugcgacagc aauccuauag cauuaugugu aucaucaagg aagagguacu cgcuuauguu | 900 | |
| gugcagcuac cacucuaugg ugugauugac accccccuguu ggaagcugca uaccaguca | 960 | |
| cucugcacca cuaacacaaa ggaagggagc aauauuugcc ucacucgaac cgacaggggg | 1020 | |
| ugguauugcg auaaugcggg cuccgugucc uucuuuccac aggcugaaac uuguaaggua | 1080 | |
| cagucaaacc gcguguucug ugauacuaug aauucucuga cucuucccag cgagguuaau | 1140 | |
| cucugcaacg ucgacauuuu caauccuaaa uaugacugca agaucaugac cagcaagacc | 1200 | |
| gacgucucca gcucaguaau cacuagccua ggggccauug uaagcugcua uggcaaaaacc | 1260 | |
| aaguguacug ccucuaauaa gaacagaggc auaauuaaaa ccuuuucaaa uggcugugac | 1320 | |
| uauguguucga auaagggcgu cgacacgguc ucaguaggga auacccucua cuacguuaac | 1380 | |
| aaacaggaag gcaaauccu uuauguaaag ggcgagccca ucauaaauuu cuacgaccca | 1440 | |
| cuuguguucc ccaguugcga auucugcgca ucaaucuccc aggugaacga aaagaucaau | 1500 | |
| caaucccuug cuuuuauacg aaagucagau gaacuccugu ccgccaucgg uggcuauauc | 1560 | |
| ccagaagccc caagagacgg acaagcguac guccggaaag auggugagug gguccuccuc | 1620 | |
| ucuaccuuuc uu | 1632 | |

<210> SEQ ID NO 67
<211> LENGTH: 544
<212> TYPE: PRT
<213> ORGANISM: Artificial Sequence
<220> FEATURE:
<223> OTHER INFORMATION: Synthetic Polypeptide

<400> SEQUENCE: 67

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125
```

-continued

```
Leu Ser Lys Lys Arg Lys Arg Arg Phe Leu Gly Phe Leu Leu Gly Val
        130             135                 140
Gly Ser Ala Ile Ala Ser Gly Val Ala Val Cys Lys Val Leu His Leu
145             150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Phe Lys Val
            180                 185                 190
Leu Asp Leu Lys Asn Tyr Ile Asp Lys Gln Leu Leu Pro Ile Leu Asn
        195                 200                 205
Lys Gln Ser Cys Ser Ile Ser Asn Ile Glu Thr Val Ile Glu Phe Gln
210                 215                 220
Gln Lys Asn Asn Arg Leu Leu Glu Ile Thr Arg Glu Phe Ser Val Asn
225             230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Cys Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305             310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385             390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
450                 455                 460
Lys Ser Leu Tyr Val Lys Gly Glu Pro Ile Ile Asn Phe Tyr Asp Pro
465             470                 475                 480
Leu Val Phe Pro Ser Cys Glu Phe Cys Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu Ser Ala Ile Gly Gly Tyr Ile Pro Glu Ala Pro Arg Asp Gly Gln
        515                 520                 525
Ala Tyr Val Arg Lys Asp Gly Glu Trp Val Leu Leu Ser Thr Phe Leu
530                 535                 540
```

<210> SEQ ID NO 68
<211> LENGTH: 1693
<212> TYPE: RNA
<213> ORGANISM: Artificial Sequence
<220> FEATURE:
<223> OTHER INFORMATION: Synthetic Polynucleotide

<400> SEQUENCE: 68

| | | | | | |
|---|---|---|---|---|---|
| gggaaauaag | agagaaaaga | agaguaagaa | gaaauauaag | agccaccaug | gaacugcuca | 60 |
| uuuugaaggc | aaacgcuauc | acgacaauac | ucacugcagu | gaccuucugu | uuugccucag | 120 |
| gccagaacau | aaccgaggag | uuuuaucaau | cuacaugcag | cgcuguaucu | aaaggcuacc | 180 |
| ugagugcgcu | ccgcacagga | ugguacaccu | ccgugaucac | caucgagcuc | agcaauauua | 240 |
| aagagaacaa | gugcaauggu | accgacgcua | aagucaaacu | uaucaagcag | gaacucgaca | 300 |
| aauauaagaa | cgcugugacc | gagcugcagu | uauugauggg | aggcgguagc | ggugcggau | 360 |
| ccggcggugg | aagcggcucu | gccauugcuu | ccggcguggc | uguauguaaa | guucuccacc | 420 |
| ucgagggaga | gguuaauaag | auuaagucgg | cccugcugau | uacuaacaaa | gcaguggugu | 480 |
| cgcugaguaa | cggaguaagu | uguuuaacau | uuaaggugcu | ggaccucaag | aauuauauug | 540 |
| acaaacaguu | gcuuccuauu | cuaaacaaac | agagcuguuc | aauuaaguaau | auugaaacug | 600 |
| uuauugaguu | ucagcagaag | aacaacaggu | ucuugagau | uacacgcgag | uucaguguca | 660 |
| augccggcgu | uacaacaccc | gugucuaccu | acaugcugac | gaauucgag | cuucucucuc | 720 |
| ucauaaacga | caugcccauu | acgaaugacc | aaaagaaacu | uaugccaac | aacgugcaga | 780 |
| uugugcgaca | gcaauccuau | agcauuaugu | guaucaucaa | ggaagaggua | cucgcuuaug | 840 |
| uugugcagcu | accacucuau | ggugugauug | acaccccccug | uuggaagcug | cauaccaguc | 900 |
| cacucugcac | cacuaacaca | aaggaaggga | gcaauauuug | ccucacucga | accgacaggg | 960 |
| ggugguauug | cgauaaugcg | ggcuccgugu | ccuucuuucc | acaggcugaa | acuuguaagg | 1020 |
| uacagucaaa | ccgcguguuc | ugugauacua | ugaauucucu | gacucuuccc | agcgagguua | 1080 |
| aucucugcaa | cgucgacauu | uucaauccua | aauaugacug | caagaucaug | accagcaaga | 1140 |
| ccgacgucuc | cagcucagua | aucacuagcc | uaggggccau | uguaagcugc | uauggcaaaa | 1200 |
| ccaaguguac | ugccucuaau | aagaacagag | gcauaauuaa | aaccuuuuca | aauggcugug | 1260 |
| acuauguguc | gaauaagggc | gucgacacgg | ucucaguagg | gaauacccuc | uacuacguua | 1320 |
| acaaacagga | aggcaaauc | cuuuauguaa | agggcgagcc | caucauaaau | uucuacgacc | 1380 |
| cacuuguguu | ccccaguugc | gaauucgcg | caucaaucuc | ccaggugaac | gaaaagauca | 1440 |
| aucaaucccu | ugcuuuuaua | cgaaagucag | augaacuccu | guccgccauc | gguggcuaua | 1500 |
| ucccagaagc | cccaagagac | ggacaagcgu | acguccggaa | agauggugag | ugggucccc | 1560 |
| ucucuaccuu | ucuuugauaa | uaggcuggag | ccucgggggc | caugcuucuu | gccccuuggg | 1620 |
| ccucccccca | gccccuccuc | cccuuccugc | acccguaccc | ccgugggucuu | ugaauaaagu | 1680 |
| cugaguggc | ggc | | | | | 1693 |

<210> SEQ ID NO 69
<211> LENGTH: 1527
<212> TYPE: RNA
<213> ORGANISM: Artificial Sequence
<220> FEATURE:
<223> OTHER INFORMATION: Synthetic Polynucleotide

<400> SEQUENCE: 69

| | | | | | |
|---|---|---|---|---|---|
| auggaacugc | ucauuuugaa | ggcaaacgcu | aucacgacaa | uacucacugc | agugaccuuc | 60 | uguuuugccu caggccagaa cauaaccgag gaguuuuauc aaucuacaug cagcgcugua    120 ucuaaaggcu accugagugc gcuccgcaca ggauggauaca ccuccgugau caccaucgag    180 cucagcaaua uuaaagagaa caagugcaau gguaccgacg cuaaagucaa acuuaucaag    240 caggaacucg acaaauauaa gaacgcugug accgagcugc aguuauugau gggaggcggu    300 agcgguggcg gauccggcgg uggaagcggc ucugccauug cuuccggcgu ggcuguaugu    360 aaaguucucc accucgaggg agagguuaau aagauuaagu cggcccugcu gaguacuaac    420 aaagcagugg ugucgcugag uaacggagua agugugulaa cauuuaaggu gcuggaccuc    480 aagaauuaua uugacaaaca guugcuuccu auucuaaaca aacagagcug uucaauaagu    540 aauauugaaa cuguuauuga guucagcag aagaacaaca ggcuucuuga gauuacacgc    600 gaguucagug ucaaugccgg cguuacaaca cccgugucua ccuacaugcu gacgaauucu    660 gagcuucucu cucucauaaa cgacaugccc auuacgaaug accaaaagaa acuuaugucc    720 aacaacgugc agauugugcg acagcaaucc uauagcauua uguguaucau caaggaagag    780 guacucgcuu auguugugca gcuaccacuc uaugguguga uugacacccc cguuggaag    840 cugcauacca guccacucug caccacuaac acaaaggaag ggagcaauau uugccucacu    900 cgaaccgaca gggguggua uugcgauaau gcgggcuccg uguccuucuu uccacaggcu    960 gaaacuugua agguacaguc aaaccgcgug uucugugaua cuaugaauuc ucugacucuu   1020 cccagcgagg uuaaucucug caacgucgac auuucaauc cuaaauauga cugcaagauc   1080 augaccagca agaccgacgu uccagcuca guaaucacua gccuagggc cauuguaagc   1140 ugcuauggca aaccaagug uacugccucu aauaagaaca gaggcauaau uaaaaccuuu   1200 ucaaauggcu gugacuaugu gucgaauaag ggcgucgaca cggucucagu agggaauacc   1260 cucuacuacg uuaacaaaca ggaaggcaaa ucccuuuaug uaaagggcga gcccaucaua   1320 aauuucuacg acccacugu guccccagu ugcgaauucu gcgcaucaau ucccagguv   1380 aacgaaaaga ucaaucaauc ccuugcuuuu auacgaaagu cagaugaacu ccugucccgcc   1440 aucgguggcu auaucccaga agccccaaga gacggacaag cguacguccg aaagauggu   1500 gaguggguc uccucucuac cuuucuu                                          1527

<210> SEQ ID NO 70
<211> LENGTH: 509
<212> TYPE: PRT
<213> ORGANISM: Artificial Sequence
<220> FEATURE:
<223> OTHER INFORMATION: Synthetic Polypeptide

<400> SEQUENCE: 70

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

```
Met Gly Gly Gly Ser Gly Gly Ser Gly Gly Ser Gly Ser Ala
            100             105             110
Ile Ala Ser Gly Val Ala Val Cys Lys Val Leu His Leu Glu Gly Glu
            115             120             125
Val Asn Lys Ile Lys Ser Ala Leu Leu Ser Thr Asn Lys Ala Val Val
    130                 135             140
Ser Leu Ser Asn Gly Val Ser Val Leu Thr Phe Lys Val Leu Asp Leu
145             150             155                 160
Lys Asn Tyr Ile Asp Lys Gln Leu Leu Pro Ile Leu Asn Lys Gln Ser
                165                 170             175
Cys Ser Ile Ser Asn Ile Glu Thr Val Ile Glu Phe Gln Gln Lys Asn
            180             185             190
Asn Arg Leu Leu Glu Ile Thr Arg Glu Phe Ser Val Asn Ala Gly Val
        195             200             205
Thr Thr Pro Val Ser Thr Tyr Met Leu Thr Asn Ser Glu Leu Leu Ser
    210             215             220
Leu Ile Asn Asp Met Pro Ile Thr Asn Asp Gln Lys Lys Leu Met Ser
225             230             235                 240
Asn Asn Val Gln Ile Val Arg Gln Gln Ser Tyr Ser Ile Met Cys Ile
            245             250             255
Ile Lys Glu Glu Val Leu Ala Tyr Val Val Gln Leu Pro Leu Tyr Gly
        260             265             270
Val Ile Asp Thr Pro Cys Trp Lys Leu His Thr Ser Pro Leu Cys Thr
        275             280             285
Thr Asn Thr Lys Glu Gly Ser Asn Ile Cys Leu Thr Arg Thr Asp Arg
        290             295             300
Gly Trp Tyr Cys Asp Asn Ala Gly Ser Val Ser Phe Phe Pro Gln Ala
305             310             315                 320
Glu Thr Cys Lys Val Gln Ser Asn Arg Val Phe Cys Asp Thr Met Asn
            325             330             335
Ser Leu Thr Leu Pro Ser Glu Val Asn Leu Cys Asn Val Asp Ile Phe
        340             345             350
Asn Pro Lys Tyr Asp Cys Lys Ile Met Thr Ser Lys Thr Asp Val Ser
        355             360             365
Ser Ser Val Ile Thr Ser Leu Gly Ala Ile Val Ser Cys Tyr Gly Lys
370             375             380
Thr Lys Cys Thr Ala Ser Asn Lys Asn Arg Gly Ile Ile Lys Thr Phe
385             390             395             400
Ser Asn Gly Cys Asp Tyr Val Ser Asn Lys Gly Val Asp Thr Val Ser
            405             410             415
Val Gly Asn Thr Leu Tyr Tyr Val Asn Lys Gln Glu Gly Lys Ser Leu
        420             425             430
Tyr Val Lys Gly Glu Pro Ile Ile Asn Phe Tyr Asp Pro Leu Val Phe
        435             440             445
Pro Ser Cys Glu Phe Cys Ala Ser Ile Ser Gln Val Asn Glu Lys Ile
    450             455             460
Asn Gln Ser Leu Ala Phe Ile Arg Lys Ser Asp Glu Leu Leu Ser Ala
465             470             475                 480
Ile Gly Gly Tyr Ile Pro Glu Ala Pro Arg Asp Gly Gln Ala Tyr Val
                485             490             495
Arg Lys Asp Gly Glu Trp Val Leu Leu Ser Thr Phe Leu
            500             505
```

<210> SEQ ID NO 71
<211> LENGTH: 1888
<212> TYPE: RNA
<213> ORGANISM: Artificial Sequence
<220> FEATURE:
<223> OTHER INFORMATION: Synthetic Polynucleotide

<400> SEQUENCE: 71

| | | | | | |
|---|---|---|---|---|---|
| gggaaauaag | agagaaaaga | agaguaagaa | gaaauauaag | agccaccaug | gaacugcuca | 60 |
| uuuugaaggc | aaacgcuauc | acgacaauac | ucacugcagu | gaccuucugu | uuugccucag | 120 |
| gccagaacau | aaccgaggag | uuuuaucaau | cuacaugcag | cgcuguaucu | aaaggcuacc | 180 |
| ugagugcgcu | ccgcacagga | ugguacaccu | ccgugaucac | caucgagcuc | agcaauauua | 240 |
| aagagaacaa | gugcaauggu | accgacgcua | aagucaaacu | uaucaagcag | gaacucgaca | 300 |
| aauauaagaa | cgcugugacc | gagcugcagu | uauugaugca | gaguacaccu | gccaccaaua | 360 |
| acagagcuag | gagggaguug | ccuagguuua | ugaacuacac | ucucaacaac | gcgaagaaaa | 420 |
| ccaaugugac | gcuauccaag | aaacggaaga | ggagguuccu | ggggguucuu | uuagggguqg | 480 |
| gcucugccau | ugcuuccggc | guggcuguau | guaaaguucu | ccaccucgag | ggagagguua | 540 |
| auaagauuaa | gucggcccug | cugaguacua | acaaagcagu | ggugucgcug | aguaacggag | 600 |
| uaagugucuuu | aacauuuaag | gugcuggacc | ucaagaauua | uauugacaaa | caguugcuuc | 660 |
| cuauucuaaa | caaacagagc | uguucaauaa | guaauauuga | aacguuuauu | gaguuucagc | 720 |
| agaagaacaa | caggcuucuu | gagauuacac | gcgaguucag | ugucaaugcc | ggcguuacaa | 780 |
| caccegugue | uaccuacaug | cugacgaauu | cugagcuucu | cucucucaua | aacgacaugc | 840 |
| ccauuacgaa | ugaccaaaag | aaacuuaugu | ccaacaacgu | gcagauugug | cgacagcaau | 900 |
| ccuaugcau | uauguguauc | aucaaggaag | aguacucgc | uuauguugug | cagcuaccac | 960 |
| ucuauggugu | gauugacacc | cccguuggaa | agcugcauac | caguccacuc | ugcaccacua | 1020 |
| acacaaagga | agggagcaau | auuugccuca | cucgaaccga | caggggguqg | uauugcgaua | 1080 |
| augcgggcuc | cgugccuuc | uuuccacagg | cugaaacuug | uaagguacag | ucaaaccgcg | 1140 |
| uguucuguga | uacuaugaau | ucucugacuc | uucccagcga | gguuaaucuc | ugcaacgucg | 1200 |
| acauuuucaa | uccuaaauau | gacugcaaga | ucaugaccaa | caagaccgac | gucuccagcu | 1260 |
| caguaaucac | uagccuaggg | gccauuguaa | gcugcuaugg | caaaaccaag | uguacugccu | 1320 |
| cuaauaagaa | cagaggcaua | auuaaaaccu | uuucaaaugg | cugugacuau | gucgaauaa | 1380 |
| agggcgucga | cacgucucua | guagggaaua | cccucuacua | cguuaacaaa | caggaaggca | 1440 |
| aaucccuuua | uguaaagggc | gagcccauca | uaaauuucua | cgaccacuu | uguucccca | 1500 |
| guugcgaauu | cugcgcauca | aucucccagg | ugaacgaaaa | gaucaaucaa | ucccuugcuu | 1560 |
| uuauacgaaa | gucagaugaa | cuccugcaua | acgugaaugc | uggaaaaucu | acaaccaaca | 1620 |
| ucaugaucac | uaccaucauu | auugugauua | ucguaauucu | gcuauccuug | auugcugucg | 1680 |
| ggcugcuucu | guacuguaag | gccagaucga | cgccugugac | ccuuucaaaa | gaccaacuua | 1740 |
| gcgguaucaa | uaauauugcc | uuuagcaauu | gauaauaggc | uggagccucg | guggccaugc | 1800 |
| uucuugcccc | uugggccucc | ccccagcccc | uccuccccuu | ccugcacccg | uaccccgug | 1860 |
| gucuuugaau | aaagucugag | ugggcggc | | | | 1888 |

<210> SEQ ID NO 72
<211> LENGTH: 1722
<212> TYPE: RNA
<213> ORGANISM: Artificial Sequence
<220> FEATURE:

<223> OTHER INFORMATION: Synthetic Polynucleotide

<400> SEQUENCE: 72

| | | | | | |
|---|---|---|---|---|---|
| auggaacugc | ucauuuugaa | ggcaaacgcu | aucacgacaa | uacucacugc | agugaccuuc | 60 |
| uguuuugccu | caggccagaa | cauaaccgag | gaguuuuauc | aaucuacaug | cagcgcugua | 120 |
| ucuaaaggcu | accugagugc | gcuccgcaca | ggaugguaca | ccuccgugau | caccaucgag | 180 |
| cucagcaaua | uuaaagagaa | caagugcaau | gguaccgacg | cuaaagucaa | acuuaucaag | 240 |
| caggaacucg | acaaauauaa | gaacgcugug | accgagcugc | aguuauugau | gcagaguaca | 300 |
| ccugccacca | uaacagagc | uaggaggag | uugccuaggu | uaugaacua | cacucucaac | 360 |
| aacgcgaaga | aaaccaaugu | gacgcuaucc | aagaaacgga | gaggaggu | ccggggguuu | 420 |
| cuuuuagggg | ugggcucugc | cauugcuucc | ggcguggcug | uauguaaagu | ucuccaccuc | 480 |
| gagggagagg | uuaauaagau | uaagucggcc | cugcugagua | cuaacaaagc | aguggugucg | 540 |
| cugaguaacg | gaguaagugu | guuaacauuu | aaggugcugg | accucaagaa | uuauauugac | 600 |
| aaacaguugc | uuccuauucu | aaacaaacag | agcuguucaa | uaaguaauau | ugaaacuguu | 660 |
| auugaguuuc | agcagaagaa | caacaggcuu | cuugagauua | cacgcgaguu | cagugucaau | 720 |
| gccggcguua | caacacccgu | gucuaccuac | augcugacga | auucugagcu | ucucucucuc | 780 |
| auaaacgaca | ugcccauuac | gaaugaccaa | agaaacuua | ugccaacaa | cgugcagauu | 840 |
| gugcgacagc | aauccuauag | cauuaugugu | aucaucaagg | aagagguacu | cgcuuaguu | 900 |
| gugcagcuac | cacucuaugg | ugugauugac | accccccuguu | ggaagcugca | uaccaguca | 960 |
| cucugcacca | cuaacacaaa | ggaagggagc | aauauuugcc | ucacucgaac | cgacaggggg | 1020 |
| ugguauugcg | auaaugcggg | cuccgugucc | uucuuccac | aggcugaaac | uuguaaggua | 1080 |
| cagucaaacc | gcguguucug | ugauacuaug | aauucucuga | cucuucccag | cgagguuaau | 1140 |
| cucugcaacg | ucgacauuuu | caauccuaaa | uaugacugca | agaucaugac | cagcaagacc | 1200 |
| gacgucucca | gcucaguaau | cacuagccua | ggggccauug | uaagcugcua | uggcaaaacc | 1260 |
| aagguacug | ccucuaauaa | gaacagaggc | auaauuaaaa | ccuuuucaaa | uggcugugac | 1320 |
| uaugugucga | auaagggcgu | cgacacgguc | ucaguaggga | auaccccucua | cuacguuaac | 1380 |
| aaacaggaag | gcaaaucccu | uuauguaaag | ggcgagccca | ucauaaauuu | cuacgaccca | 1440 |
| cuuguguucc | ccaguugcga | auucugcgca | ucaaucuccc | aggugaacga | aaagaucaau | 1500 |
| caaucccuug | cuuuuauacg | aaagucagau | gaacuccugc | auaacgugaa | ugcugggaaa | 1560 |
| ucuacaacca | acaucaugau | cacuaccauc | auuauuguga | uuaucguaau | ucugcuaucc | 1620 |
| uugauugcug | ucgggcugcu | ucuguacugu | aaggccagau | cgacgccugu | gacccuuuca | 1680 |
| aaagaccaac | uuagcgguau | caauaauauu | gccuuuagca | au | | 1722 |

<210> SEQ ID NO 73
<211> LENGTH: 574
<212> TYPE: PRT
<213> ORGANISM: Artificial Sequence
<220> FEATURE:
<223> OTHER INFORMATION: Synthetic Polypeptide

<400> SEQUENCE: 73

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
```

```
            35                  40                  45
Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
                180                 185                 190

Leu Asp Leu Lys Asn Tyr Ile Asp Lys Gln Leu Leu Pro Ile Leu Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
            275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460
```

| | | | | | | | | | | | | |
|---|---|---|---|---|---|---|---|---|---|---|---|---|
|Lys|Ser|Leu|Tyr|Val|Lys|Gly|Glu|Pro|Ile|Ile|Asn|Phe|Tyr|Asp|Pro|
|465| | | |470| | | |475| | | |480|

Lys Ser Leu Tyr Val Lys Gly Glu Pro Ile Ile Asn Phe Tyr Asp Pro
465                 470                 475                 480

Leu Val Phe Pro Ser Cys Glu Phe Cys Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Val Ile Val Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 74
<211> LENGTH: 1783
<212> TYPE: RNA
<213> ORGANISM: Artificial Sequence
<220> FEATURE:
<223> OTHER INFORMATION: Synthetic Polynucleotide

<400> SEQUENCE: 74
gggaauaaag agagaaaaga agaguaagaa gaaauauaag agccaccaug gaacugcuca       60
uuuugaaggc aaacgcuauc acgacaauac ucacugcagu gaccuucugu uuugccucag      120
gccagaacau aaccgaggag uuuuaucaau cuacaugcag cgcuguaucu aaaggcuacc      180
ugagugcgcu ccgcacagga ugguacaccu ccgugaucac caucgagcuc agcaauauua      240
aagagaacaa gugcaauggu accgacgcua aagucaaacu uaucaagcag gaacucgaca      300
aauauaagaa cgcugugacc gagcugcagu auugaugggg aggcgguagc gguggcggau      360
ccggcgugg aagcggcucu gccauugcuu ccggcguggc uguauguaaa guucuccacc      420
ucgagggaga gguuaauaag auuaagucgg cccugcugag uacuaacaaa gcaguggugu      480
cgcugaguaa cggaguaagu uguuaacau uuaaggugcu ggaccucaag aauuauauug      540
acaaacaguu gcuuccuauu cuaaacaaac agagcuguuc aauaaguaau auugaaacug      600
uuauugaguu ucagcagaag aacaacaggc uucuugagau uacacgcgag uucaguguca      660
augccggcgu uacaacaccc gugucuaccu acaugcugac gaauucugag cuucucucuc      720
ucauaaacga caugcccauu acgaaugacc aaaagaaacu uauguccaac aacgugcaga      780
uugugcgaca gcaauccuau agcauuaugu guaucaucaa ggaagaggua cucgcuuaug      840
uugugcagcu accacucuau ggugugauug acaccccccug uuggaagcug cauaccaguc      900
cacucugcac cacuaacaca aaggaaggga gcaauauuug ccucacucga accgacaggg      960
ggugguauug cgauaaugcg ggcuccgugu ccuucuuucc acaggcugaa acuuguaagg     1020
uacagucaaa ccgcguguuc ugugauacua ugaauucucu gacucuuccc agcgagguua     1080
aucucugcaa cgucgacauu uucaauccua auaugacug caagaucaug accagcaaga     1140
ccgacgucuc cagcucagua aucacuagcc uaggggccau uguaagcugc uauggcaaaa     1200
ccaagugac ugccucuaau aagaacagag gcauaauuaa aaccuuuuca aauggcugug     1260
acuauguguc gaauaagggc gucgacacgu ucucaguagg gaauccccuc uacuacguua     1320
acaaacagga aggcaaaucc cuuuauguaa agggcgagcc caucauaaau uucuacgacc     1380
cacuugug cccccaguugc gaauucugcg caucaaucuc ccaggugaac gaaaagauca     1440

```
aucaaucccu ugcuuuuaua cgaaagucag augaacuccu gcauaacgug aaugcuggga    1500
aaucuacaac caacaucaug aucacuacca ucauuauugu gauuaucgua auucugcuau    1560
ccuugauugc ugucgggcug cuucuguacu guaaggccag aucgacgccu gugacccuuu    1620
caaaagacca acuuagcggu aucaauaaua ugccuuuag caauugauaa uaggcuggag     1680
ccucgguggc caugcuucuu gccccuuggg ccucccccca gccccuccuc cccuccugc     1740 acccguaccc ccguggucuu ugaauaaagu cugaguggc ggc                      1783
```

<210> SEQ ID NO 75
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 75

```
auggaacugc ucauuuugaa ggcaaacgcu aucacgacaa uacucacugc agugaccuuc      60
uguuuugccu caggccagaa cauaaccgag gaguuuuauc aaucuacaug cagcgcugua    120
ucuaaaggcu accugagugc gcuccgcaca ggaugguaca ccccgugau caccaucgag     180 cucagcaaua uuaagagaaa caagugcaau gguaccgacg cuaaagucaa acuuaucaag    240
caggaacucg acaaauauaa gaacgcugug accgagcugc aguuauugau gggaggcggu    300
agcgguggcg gauccggcgg uggaagcggc ucugccauug cuuccggcgu ggcuguaugu    360
aaaguucucc accucgaggg agagguuaau aagauuaagu cggcccugcu gaguacuaac    420
aaagcagugg ugucgcugag uaacggaguga agugguuaa cauuuaaggu gcuggaccuc    480
aagaauuaua uugacaaaca guugcuuccu auucuaaaca aacagagcug uucaauaagu    540
aauauugaaa cuguuauuga guucagcag aagaacaaca ggcuucuuga gauuacacgc     600
gaguucagug ucaaugccgg cguuacaaca cccgugucua ccacaugcu gacgaauucu     660 gagcuucucu cucucauaaa cgacaugccc auuacgaaug accaaaagaa acuuaugucc     720
aacaacgugc agauugugcg acagcaaucc uauagcauua uguguaucau caaggaagag     780
guacucgcuu auguugugca gcuaccacuc uaugguguga uugacacccc cguuggaag      840 cugcauacca guccacucug caccacuaac acaaaggaag ggagcaauau ugccucacu      900 cgaaccgaca gggggguggua uugcgauau gcgggcuccg uguccuucuu uccacaggcu     960
gaaacuugua agguacaguc aaaccgcgug uucugugaua cuaugaauuc ucugacucuu    1020
cccagcgagg uuaaucucug caacgucgac auuuucaauc cuaaauauga cugcaagauc    1080
augaccagca agaccgacgu cuccagcuca guaaucacua gccuagggc cauuguaagc     1140 ugcuauggca aaaccaagug uacugccucu aauaagaaca gaggcauaau uaaaaccuuu    1200
ucaaauggcu gugacuaugu gucgaauaag ggcgucgaca cggucucagu agggaauacc    1260
cucuacuacg uuaacaaaca ggaaggcaaa ucccuuuaug uaaagggcga gcccaucaua    1320
aauuucuacg acccacuugu guccccagu ugcgaauucu gcgcaucaau cucccagug      1380 aacgaaaaga ucaaucaauc ccuugcuuuu auacgaaagu cagaugaacu ccugcauaac    1440
gugaaugcug ggaaaucuac aaccaacauc augaucacua ccaucauuau ugugauuauc    1500 guauucugc uaccuugau ugcugucggg cugcuucugu acguaaggc cagaucgacg        1560 ccugugaccc uucaaaaga ccaacuuagc gguaucaaua auauugcuuu agcaau         1617
```

<210> SEQ ID NO 76

<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 76

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Ser Gly Gly Ser Gly Gly Ser Gly Ser Ala
            100                 105                 110

Ile Ala Ser Gly Val Ala Val Cys Lys Val Leu His Leu Glu Gly Glu
        115                 120                 125

Val Asn Lys Ile Lys Ser Ala Leu Leu Ser Thr Asn Lys Ala Val Val
    130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
    210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
    290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
    370                 375                 380
```

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
            405                 410                 415

Val Gly Asn Thr Leu Tyr Tyr Val Asn Lys Gln Glu Gly Lys Ser Leu
        420                 425                 430

Tyr Val Lys Gly Glu Pro Ile Ile Asn Phe Tyr Asp Pro Leu Val Phe
    435                 440                 445

Pro Ser Cys Glu Phe Cys Ala Ser Ile Ser Gln Val Asn Glu Lys Ile
450                 455                 460

Asn Gln Ser Leu Ala Phe Ile Arg Lys Ser Asp Glu Leu Leu His Asn
465                 470                 475                 480

Val Asn Ala Gly Lys Ser Thr Thr Asn Ile Met Ile Thr Thr Ile Ile
            485                 490                 495

Ile Val Ile Ile Val Ile Leu Leu Ser Leu Ile Ala Val Gly Leu Leu
        500                 505                 510

Leu Tyr Cys Lys Ala Arg Ser Thr Pro Val Thr Leu Ser Lys Asp Gln
    515                 520                 525

Leu Ser Gly Ile Asn Asn Ile Ala Phe Ser Asn
    530                 535

<210> SEQ ID NO 77
<211> LENGTH: 57
<212> TYPE: RNA
<213> ORGANISM: Artificial Sequence
<220> FEATURE:
<223> OTHER INFORMATION: Synthetic Polynucleotide

<400> SEQUENCE: 77
gggaauuaag agagaaaaga agaguaagaa gaaauauaag accccggcgc cgccacc     57

<210> SEQ ID NO 78
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 78
ugauaauagg cuggagccuc gguggccuag cuucuugccc cuugggccuc ccccagccc     60 cuccuccccu uccugcaccc guaccccgu ggucuuugaa uaaagucuga gugggcggc    119

<210> SEQ ID NO 79
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 79

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly
            20                  25                  30

<210> SEQ ID NO 80
<211> LENGTH: 18
<212> TYPE: PRT
<213> ORGANISM: Artificial Sequence
<220> FEATURE:

-continued

```
<223> OTHER INFORMATION: Synthetic Polypeptide

<400> SEQUENCE: 80

Met Asp Trp Thr Trp Ile Leu Phe Leu Val Ala Ala Thr Arg Val
1               5                   10                  15

His Ser

<210> SEQ ID NO 81
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 81

Met Glu Thr Pro Ala Gln Leu Leu Phe Leu Leu Leu Leu Trp Leu Pro
1               5                   10                  15

Asp Thr Thr Gly
            20

<210> SEQ ID NO 82
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 82

Met Leu Gly Ser Asn Ser Gly Gln Arg Val Val Phe Thr Ile Leu Leu
1               5                   10                  15

Leu Leu Val Ala Pro Ala Tyr Ser
            20

<210> SEQ ID NO 83
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 83

Met Lys Cys Leu Leu Tyr Leu Ala Phe Leu Phe Ile Gly Val Asn Cys
1               5                   10                  15

Ala

<210> SEQ ID NO 84
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 84

Met Trp Leu Val Ser Leu Ala Ile Val Thr Ala Cys Ala Gly Ala
1               5                   10                  15

<210> SEQ ID NO 85
<211> LENGTH: 9
<212> TYPE: RNA
<213> ORGANISM: Artificial Sequence
<220> FEATURE:
<223> OTHER INFORMATION: Synthetic Polynucleotide

<400> SEQUENCE: 85
``` ccrccaugg                                                             9

<210> SEQ ID NO 86
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 86
gggauccuac c                                                         11

<210> SEQ ID NO 87
<211> LENGTH: 9
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(9)
<223> OTHER INFORMATION: n may be u or a

<400> SEQUENCE: 87 uuauuuann                                                             9

<210> SEQ ID NO 88
<211> LENGTH: 1722
<212> TYPE: RNA
<213> ORGANISM: Artificial Sequence
<220> FEATURE:
<223> OTHER INFORMATION: Synthetic Polynucleotide

<400> SEQUENCE: 88
auggaacugc ucauuuugaa ggcaaacgcu aucacgacaa uacucacugc agugaccuuc     60
uguuuugccu caggccagaa cauaaccgag gaguuuuauc aaucuacaug cagcgcugua    120
ucuaaaggcu accugagugc gcuccgcaca ggauggauaca ccuccgugau caccaucgag   180
cucagcaaua uuaagagaaa caagugcaau gguaccgacg cuaaagucaa acuuaucaag   240
caggaacucg acaaauauaa aaacgcugug accgagcugc aguuauugau gcagaguaca   300
ccugccacca auaacagagc uaggagggag uugccuaggu uuaugaacua cacucucaac   360
aacgcgaaaa aaaccaaugu gacgcuaucc aagaaacgga agaggagguu ccuggggmuu   420
cuuuuagggg ugggcucugc cauugcuucc ggcguggcug uauguaaagu ucuccaccuc   480
gagggagagg uuaauaagau uaagucggcc cugcugagua cuaacaaagc aguggugucg   540
cugaguaacg gaguaagugu guuaacauuu aaggugcugg accuaagaa uuauauugac    600
aaacaguugc uuccuauucu aaacaaacag agcuguucaa uaaguaauau ugaaacuguu   660
auugaguuuc agcagaagaa caacaggcuu cuugagauua cacgcgaguu caguguaau    720
gccggcguua caacacccgu gucuaccuac augcugacga auucgagcu ucucucucuc    780
auaaacgaca ugcccauuac gaaugaccaa aaaaaacuua guccaacaa cgucagauu     840
gugcgacagc aauccuauag cauuaugugu aucaucaagg aagagguacu cgcuuauguu   900
gugcagcuac cacucuaugg ugugauugac accccccuguu ggaagcugca uaccaguccca  960
cucugcacca cuaacacaaa ggaagggagc aauauuugcc ucacucgaac cgacaggggg   1020
ugguauugcg auaaugcggg cuccgugucc uucuuccac aggcugaaac uuguaaggua   1080
cagucaaacc gcguguucug ugauacaug aauucgcuga cucuucccag cgagguuaau   1140
cucugcaacg ucgacauuuu caauccuaaa uaugacugca gaucaugac cagcaagacc   1200

```
gacgucucca gcucaguaau cacuagccua ggggccauug uaagcugcua uggcaaaacc      1260
aaguguacug ccucuaauaa gaacagaggc auaauuaaaa ccuuuucaaa uggcugugac      1320
uaugugucga auaagggcgu cgacacgguc ucaguaggga auaccucuca cuacguuaac      1380
aaacaggaag gcaaaucccu uuauguaaag ggcgagccca ucauaaauuu cuacgaccca      1440 cuugguguucc ccagugauga auucgaugca ucaaucuccc aggugaacga aaagaucaau     1500
caaucccuug cuuuuauacg aaagucagau gaaccucugc auaacgugaa ugcugggaaa      1560
ucuacaacca acaucaugau cacuaccauc auuauguga uuaucguaau ucugcuaucc       1620
uugauugcug ucgggcugcu ucuguacugu aaggccagau cgacgccugu gacccuuuca     1680
aaagaccaac uuagcgguau caauaauauu gccuuuagca au                        1722
```

<210> SEQ ID NO 89
<211> LENGTH: 574
<212> TYPE: PRT
<213> ORGANISM: Artificial Sequence
<220> FEATURE:
<223> OTHER INFORMATION: Synthetic Polypeptide

<400> SEQUENCE: 89

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

Leu Met Ser Asn Asn Val Gln Ile Val Arg Gln Gln Ser Tyr Ser Ile
         275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 90
<211> LENGTH: 1888
<212> TYPE: RNA
<213> ORGANISM: Artificial Sequence
<220> FEATURE:
<223> OTHER INFORMATION: Synthetic Polynucleotide

<400> SEQUENCE: 90
gggaaauaag agagaaaaga agaguaagaa gaaauauaag agccaccaug gaacugcuca     60
uuuugaaggc aaacgcuauc acgacaauac ucacugcagu gaccuucugu uuugccucag    120
gccagaacau aaccgaggag uuuuaucaau cuacaugcag cgcuguaucu aaaggcuacc    180
ugagugcgcu ccgcacagga ugguacaccu ccgugaucac caucgagcuc agcaauauua    240 aagaaacaa gugcaauggu accgacgcua aagucaaacu uaucaagcag gaacucgaca    300
aauauaaaaa cgcugugacc gagcugcagu uauugaugca gaguacaccu gccaccaaua    360

```
acagagcuag gagggaguug ccuagguuua ugaacuacac ucucaacaac gcgaaaaaaa        420
ccaaugugac gcuauccaag aaacggaaga ggaggguuccu gggguuucuu uuaggggugg        480
gcucugccau ugcuuccggc guggcuguau guaaaguucu ccaccucgag ggagagguua        540
auaagauuaa gucggcccug cugaguacua acaaagcagu ggugucgcug aguaacggag        600 uaagugguguu aacauuuaag gugcuggacc ucaagaauua uauugacaaa caguugcuuc        660
cuauucuaaa caaacagagc uguucaauaa guaauauuga aacguuauu gaguuucagc         720 agaagaacaa caggcuucuu gagauuacac gcgaguucag ugucaaugcc ggcguuacaa        780
cacccguguc uaccuacaug cugacgaauu cugagcuucu cucucucaua aacgacaugc        840
ccauuacgaa ugaccaaaaa aaacuuaugu ccaacaacgu gcagauugug cgacagcaau        900
ccuauagcau uauguguauc aucaaggaag agguacucgc uuauguugug cagcuaccac        960
ucuauggugu gauugacacc cccguuggaa agcugcauac caguccacuc ugcaccacua       1020
acacaaagga agggagcaau auuugccuca cucgaaccga caggggggugg uauugcgaua       1080 augcgggcuc cguguccuuc uuuccacagg cugaaacuug uaaggauacag ucaaaccgcg      1140 uguucuguga uacuaugaau ucucugacuc uucccagcga gguuaaucuc ugcaacgucg       1200
acauuuucaa uccuaaauau gacugcaaga ucaugaccag caagaccgac gucuccagcu       1260
caguaaucac uagccuaggg gccauuguaa gcugcuaugg caaaaccaag guacugccu       1320 cuaauaagaa cagaggcaua auuaaaaccu uucaaauugg cugugacuau gugucgaaua      1380
agggcgucga cacggucuca guagggaaua cccucuacua cguuaacaaa caggaaggca      1440
aaucccuuua uguaaagggc gagcccauca uaaauuucua cgacccacuu uguuccca        1500 gugaugaauu cgaugcauca aucucccagg ugaacgaaaa gaucaaucaa ucccuugcuu      1560
uuauacgaaa gucagaugaa cucccugcaua acgugaaugc ugggaaaucu acaaccaaca      1620
ucaugaucac uaccaucauu auugugauua ucguaauucu gcuauccuug auugcugucg      1680
ggcugcuucu guacuguaag gccagaucga cgccugugac ccuuucaaaa gaccaacuua      1740
gcgguaucaa uaauauugcc uuuagcaauu gauaauaggc uggagcccug guggccaugc      1800
uucuugcccc uugggccucc ccccagcccc uccucccccuu ccugcacccg uaccccgug       1860 gucuuugaau aaagucugag ugggcggc                                           1888
```

<210> SEQ ID NO 91
<211> LENGTH: 1722
<212> TYPE: RNA
<213> ORGANISM: Artificial Sequence
<220> FEATURE:
<223> OTHER INFORMATION: Synthetic Polynucleotide

<400> SEQUENCE: 91

```
auggaacugc ucauuuugaa ggcaaacgcu aucacgacaa uacucacugc agugaccuuc         60
uguuuugccu caggccagaa cauaaccgag gaguuuuauc aaucuacaug cagcgcugua       120
ucuaaaggcu accugagugc gcuccgcaca ggauggguaca ccuccgugau caccaucgag      180
cucagcaaua uuaagagaaa caagugcaau gguaccgacg cuaaagucaa acuuaucaag      240
caggaacucg acaaauauaa gacgcugug accgagcugc aguauugau gcagaguaca       300 ccugccacca auaacagagc uaggagggag uugccuaggu uuaugaacua cacucucaac      360
aacgcgaaga aaaccaaugu gacgcuaucc aagaaacgga agaggagguu ccggggguuu      420
cuuuuagggg ugggcucugc cauugcuucc ggcguggcug uauguaaagu ucuccaccuc      480
```

| | |
|---|---|
| gagggagagg uuaauaagau uaagucggcc cugcugagua cuaacaaagc agugguguucg | 540 |
| cugaguaacg gaguaagugu guuaacauuu aaggugcugg accucaagaa uuauauugac | 600 |
| aaacaguugc uuccuauucu aaacaaacag agcuguucaa uaaguaauau ugaaacuguu | 660 |
| auugaguuuc agcagaagaa caacaggcuu cuugagauua cacgcgaguu cagugucaau | 720 |
| gccggcguua caacacccgu gucuaccuac augcugacga auucugagcu ucucucucuc | 780 |
| auaaacgaca ugcccauuac gaaugaccaa agaaacuua uguccaacaa cgugcagauu | 840 |
| gugcgacagc aauccuauag cauuaugugu aucaucaagg aagagguacu cgcuuauguu | 900 |
| gugcagcuac cacucuaugg ugugauugac accccccuguu ggaagcugca uaccagucca | 960 |
| cucugcacca cuaacacaaa ggaagggagc aauauuugcc ucacucgaac cgacaggggg | 1020 |
| ugguauugcg auaaugcggg ucccgugucc uucuuuccac aggcugaaac uuguaaggua | 1080 |
| cagucaaacc gcguguucug ugauacuaug aauucucuga cucuucccag cgagguuaau | 1140 |
| cucugcaacg ucgacauuuu caauccuaaa uaugacugca agaucaugac cagcaagacc | 1200 |
| gacgucucca gcucaguaau cacuagccua ggggccauug uaagcugcua uggcaaaacc | 1260 |
| aaguguacug ccucuaauaa gaacagaggc auaauuaaaa ccuuucaaa uggcugugac | 1320 |
| uaugugucga uaagggcgu cgacacgguc ucaguaggga auacccucua cuacguuaac | 1380 |
| aaacaggaag gcaaauccccu uuauguaaag ggcgagccca ucauaaauuu cuacgaccca | 1440 |
| cuuguguucc ccagugauga auucgaugca ucaaucucccc aggugaacga aaagaucaau | 1500 |
| caaucccuug cuuuuauacg aaagucagau gaacccugc auaacgugaa agcugggaaa | 1560 |
| ucuacaacca acaucaugau cacuaccauc auuaugugua uuaucguaau ucugcuaucc | 1620 |
| uugauugcug ucggggcugcu ucuguacugu aaggccagau cgacgccugu gaccccuuuca | 1680 |
| aaagaccaac uuagcgguau caauaauauu gccuuuagca au | 1722 |

<210> SEQ ID NO 92
<211> LENGTH: 1888
<212> TYPE: RNA
<213> ORGANISM: Artificial Sequence
<220> FEATURE:
<223> OTHER INFORMATION: Synthetic Polynucleotide

<400> SEQUENCE: 92

| | |
|---|---|
| gggaauaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugagugcgcu ccgcacagga ugguacaccu ccgugaucac caucgagcuc agcaauauua | 240 |
| aagagaacaa gugcaauggu accgacgcua aagucaaacu uaucaagcag gaacucgaca | 300 |
| aauauaagaa cgcugugacc gagcugcagu uauugaugca gaguacaccu gccaccaaua | 360 |
| acagagcuag gagggaguug ccuagguuua ugaacuacac ucaacaac gcgaagaaaa | 420 |
| ccaaugugac gcuauccaag aaacggaaga ggagguuccu ggggguucuu uuaggggugg | 480 |
| gcucugccau ugcuuccggc guggcuguau guaaaguucu ccaccucgag ggagagguua | 540 |
| auaagauuaa gucggcccug cugaguacua acaaagcagu ggucgcugcu aguaacggag | 600 |
| uaagugguguu aacauuuaag gugcuggacc ucaagaauua uauugacaaa caguugcuuc | 660 |
| cuauucuaaa caaacagagc uguucaauaa guaauauuga aacguuauu gaguucagc | 720 |
| agaagaacaa caggcuucuu gagauucacac gcgaguucag ugucaaugcc ggcguuacaa | 780 |
| cacccgguguc uaccuacaug cugacgaauu cugagcuucu cucucucaua aacgacaugc | 840 |

```
ccauuacgaa ugaccaaaag aaacuuaugu ccaacaacgu gcagauugug cgacagcaau    900
ccuauagcau uauguguauc aucaaggaag agguacucgc uuauguugug cagcuaccac    960
ucuauggugu gauugacacc cccuguugga agcugcauac caguccacuc ugcaccacua   1020
acacaaagga agggagcaau auuugccuca cucgaaccga caggggguggg uauugcgaua   1080 augcgggcuc cgugccuuc uuccacagg cugaaacuug uaagguacag ucaaaccgcg    1140
uguucuguga uacuaugaau ucucugacuc uucccagcga gguuaaucuc ugcaacgucg   1200 acauuucaa uccuaaauau gacugcaaga ucaugaccag caagaccgac gucuccagcu    1260
caguaaucac uagccuaggg gccauuguaa gcugcuaugg caaaaccaag uacugccu    1320 cuaauaagaa cagaggcaua auuaaaaccu uucaaaugg cugugacuau gugucgaaua    1380
agggcgucga cacggucuca guagggaaua cccucuacua cguuaacaaa caggaaggca   1440
aaucccuuua uguaaagggc gagcccauca uaaauuucua cgacccacuu guguucccca   1500
gugaugaauu cgaugcauca aucucccagg ugaacgaaaa gaucaaucaa uccuugcuu    1560 uuauacgaaa gucagaugaa cuccugcaua acgugaaugc ugggaaaucu acaaccaaca   1620
ucaugaucac uaccaucauu auugugauua ucguaauucu gcuauccuug auugcugucg   1680
ggcugcuucu guacuguaag gccagaucga cgccugugac ccuucaaaa gaccaacuua    1740 gcgguaucaa uaauauugcc uuuagcaauu gauaauaggc uggagccucg guggccaugc   1800
uucuugcccc uugggccucc cccagccccc uccucccccuu ccugcacccg uaccccgug   1860 gucuuugaau aaagucugag ugggcggc                                      1888

<210> SEQ ID NO 93
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 93
ctcaatttcc tcacttctcc agtgt                                           25

<210> SEQ ID NO 94
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 94
cttgattcct cggtgtacct ctgt                                            24

<210> SEQ ID NO 95
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 95
tcccattatg cctaggccag cagca                                           25

<210> SEQ ID NO 96
<211> LENGTH: 1515
<212> TYPE: RNA
<213> ORGANISM: Artificial Sequence
<220> FEATURE:
```

<223> OTHER INFORMATION: Synthetic Polynucleotide

<400> SEQUENCE: 96

| | | | | | |
|---|---|---|---|---|---|
| auggaacugc | ucauuuugaa | ggcaaacgcu | aucacgacaa | uacucacugc | agugaccuuc | 60 |
| uguuuugccu | caggccagaa | cauaaccgag | gaguuuuauc | aaucuacaug | cagcgcugua | 120 |
| ucuaaaggcu | accugggcgc | gcuccgcaca | ggaugguaca | ccuccgugau | caccaucgag | 180 |
| cucagcaaua | uuaaagagau | caagugcaau | gguaccgacg | cuaaagucaa | acuuaucaag | 240 |
| caggaacucg | acaaauauaa | gaacgcugug | accgaccugc | aguuauugau | gcagaguaca | 300 |
| ccugccaccg | ggucgggcuc | ugccauuugc | uccggcgugg | cuguauguaa | aguucuccac | 360 |
| cucgagggag | agguuaauaa | gauuaagucg | gcccugcuga | guacuaacaa | agcaguggug | 420 |
| ucgcugagua | acggaguaag | uguguuaaca | uuuaaggugc | uggaccucaa | gaauuauauu | 480 |
| gacaaacagu | ugcuuccuau | ucuaaacaaa | cagagcuguu | caauacccaa | uauugaaacu | 540 |
| guuauugagu | ucagcagaa | gaacaacagg | cuucuugaga | uuacgcgcga | guucagugac | 600 |
| aaugccggcg | uuacaacacc | cgugucuacc | uacaugcuga | cgaauucuga | gcuucucucu | 660 |
| cucauaaacg | acaugcccau | uacgaauagc | caaaagaaac | uuaugccaa | caacgugcag | 720 |
| auugugcgac | agcaauccua | uagcauuaug | uguaucauca | aggaagaggu | acucgcuuau | 780 |
| guugugcagc | uaccacucua | uggugugauu | gacacccccu | guuggaagcu | gcauaccagu | 840 |
| ccacucugca | ccacuaacac | aaaggaaggg | agcaauauuu | gccucacucg | aaccgacagg | 900 |
| ggugguauu | gcgauaaugc | gggcuccgug | uccuucuuc | cacaggcuga | aacuuguaag | 960 |
| guacagucaa | accgcguguu | cugugauacu | augaauucuc | guacucuucc | cagcgagguu | 1020 |
| aaucucugca | acgucgacau | uuucaauccu | aaauaugacu | gcaagaucau | gaccagcaag | 1080 |
| accgacgucu | ccagcucagu | aaucacuagc | cuaggggcca | uuguaagcug | cuauggcaaa | 1140 |
| accaagugua | cugccucuaa | uaagaacaga | ggcauaauua | aaaccuuuuc | aaauggcugu | 1200 |
| gacuaugugu | cgaauaaggg | cgucgacacg | gucucaguag | ggaauacccu | cuacugcguu | 1260 |
| aacaaacagg | aaggccaguc | ccuuuaugua | aagggcgagc | ccaucauaaa | uuucuacgac | 1320 |
| ccacuugugu | uccccaguga | ugaauucgau | gcaucaaucu | cccaggugaa | cgaaaagauc | 1380 |
| aaucaaucc | uugcuuuuau | acgaaaguca | gaugaacucc | uguccgccau | cgguggcuau | 1440 |
| aucccagaag | ccccaagaga | cggacaagcg | uacguccgga | agaugguga | gugggucuc | 1500 |
| cucucuaccu | uucuu | | | | | 1515 |

<210> SEQ ID NO 97
<211> LENGTH: 1518
<212> TYPE: RNA
<213> ORGANISM: Artificial Sequence
<220> FEATURE:
<223> OTHER INFORMATION: Synthetic Polynucleotide

<400> SEQUENCE: 97

| | | | | | |
|---|---|---|---|---|---|
| auggaacugc | ucauuuugaa | ggcaaacgcu | aucacgacaa | uacucacugc | agugaccuuc | 60 |
| uguuuugccu | caggccagaa | cauaaccgag | gaguuuuauc | aaucuacaug | cagcgcugua | 120 |
| ucuaaaggcu | accugggcgc | gcuccgcaca | ggaugguaca | ccuccgugau | caccaucgag | 180 |
| cucagcaaua | uuaaagagau | caagugcaau | gguaccgacg | cuaaagucaa | acuuaucaag | 240 |
| caggaacucg | acaaauauaa | gaacgcugug | accgaccugc | aguuauugau | gcagaguaca | 300 |
| ccugccaccg | ggucgggcuc | ugccauugcu | uccggcgugg | cuguauguaa | aguucuccac | 360 |
| cucgagggag | agguuaauaa | gauuaagucg | gcccugcuga | guacuaacaa | agcaguggug | 420 |

| | |
|---|---:|
| ucgcugagug gcugcggagu aagugguuua acauuuaagg ugcuggaccu caagaauuau | 480 |
| auugacaaac aguugcuucc uauucuaaac aaacagagcu guucaauacc caauauugaa | 540 |
| acuguuauug aguuucagca gaagaacaac aggcuucuug agauuacacg cgaguucagu | 600 |
| gucaaugccg gcguuacaac acccgugucu accuacaugc ugacgaauuc ugagcuucuc | 660 |
| ucucucauaa acgacaugcc cauuacgaau gaccaaaaga aacuuaugue caacaacgug | 720 |
| cagauugugc gacagcaauc cuauagcauu auguguauca ucaaggaaga gguacucgcu | 780 |
| uauguugugc agcuaccacu cuauggugug auugacaccc ccguuggaa gcugcauacc | 840 |
| aguccacucu gcaccacuaa cacaaaggaa gggagcaaua uuugccucac ucgaaccgac | 900 |
| agggggugu auugcgauaa ugcgggcucc uguccuucu uccacaggc ugaaacuugu | 960 |
| aagguacagu caaaccgcgu guucugugau acuaugaauu cucguacucu ucccagcgag | 1020 |
| guuaaucucu gcaacgucga cauuuucaau ccuaaauaug acugcaagau caugaccagc | 1080 |
| aagaccgacg ucuccagcuc aguaaucacu agccuagggg ccauuguaag cugcuauggc | 1140 |
| aaaaccaagu guacugccuc uaauaagugc agaggcauaa uuaaaaccuu ucaaauggc | 1200 |
| ugugacuaug ugucgaauaa gggcgucgac acggucucag uagggaauac ccucuacuac | 1260 |
| guuaacaaac aggaaggcca guccuuuau guaaagggcg agcccaucau aaauuucuac | 1320 |
| gacccacuug uguccccag ugaugaauuc gaugcaucaa ucuccaggu gaacgaaaag | 1380 |
| aucaaucaau cccuugcuuu uauacgaaag ucagaugaac uccugccgc caucggugge | 1440 |
| uauaucccag aagccccaag agacggacaa gcguacgucc ggaaagaugg ugagugggue | 1500 |
| cuccucucua ccuuucuu | 1518 |

<210> SEQ ID NO 98
<211> LENGTH: 1681
<212> TYPE: RNA
<213> ORGANISM: Artificial Sequence
<220> FEATURE:
<223> OTHER INFORMATION: Synthetic Polynucleotide

<400> SEQUENCE: 98

| | |
|---|---:|
| gggaauaaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| ugggcgcgcu ccgcacagga ugguacaccu ccgugaucac caucgagcuc agcaauauua | 240 |
| aagagaucaa gugcaauggu accgacgcua aagucaaacu uaucaagcag gaacucgaca | 300 |
| aauauaagaa cgcugugacc gaccugcagu auugaugca gaguacaccu gccaccgggu | 360 |
| cgggcucugc cauugcucc ggcguggcug uauguaaagu ucuccaccuc gagggagagg | 420 |
| uuaauaagau uaagucggcc cugcugagua cuaacaaagc aguggugucg cugaguaacg | 480 |
| gaguaagugu guuaacauuu aaggugcugg accuccaagaa uuauauugac aaacaguugc | 540 |
| uuccuauucu aaacaaacag agcuguucaa uaccaauau ugaaacuguu auugaguuuc | 600 |
| agcagaagaa caacaggcuu cuugagauua cacgcgaguu caguqucaau gccggcguua | 660 |
| caacacccgu gucuaccuac augcugacga auucugagcu cucucucuc auaaacgaca | 720 |
| ugcccauuac gaaugaccaa aagaaacuua ugccaacaa cgugcagauu gugcgacagc | 780 |
| aauccuauag cauuaugugu aucaucaagg aagaggauac cgcuuauguu gugcagcuac | 840 |
| cacucuaugg ugugauugac accccguguu ggaagcugca uaccagucca cucugcacca | 900 |

| | |
|---|---|
| cuaacacaaa ggaagggagc aauauuugcc ucacucgaac cgacagggg ugguauugcg | 960 |
| auaaugcggg cuccgugucc uucuuuccac aggcugaaac uuguaaggua cagucaaacc | 1020 |
| gcguguucug ugauacuaug aauucucgua cucuucccag cgagguuaau cucugcaacg | 1080 |
| ucgacauuuu caauccuaaa uaugacugca agaucaugac cagcaagacc gacgucucca | 1140 |
| gcucaguaau cacuagccua ggggccauug uaagcugcua uggcaaaacc aaguguacug | 1200 |
| ccucuaauaa gaacagaggc auaauuaaaa ccuuuucaaa uggcugugac uaugugucga | 1260 |
| auaagggcgu cgacacgguc ucaguaggga aucccucua cugcguuaac aaacaggaag | 1320 |
| gccagucccu uuauguaaag ggcgagccca ucauaaauuu cuacgaccca cuuguguucc | 1380 |
| ccagugauga auucgaugca ucaaucuccc aggugaacga aaagaucaau caauccccuug | 1440 |
| cuuuuauacg aaagucagau gaacuccugu ccgccaucgg uggcuauauc ccagaagccc | 1500 |
| caagagacgg acaagcguac guccggaaag augguggagug gguccuccuc ucuaccuuuc | 1560 |
| uuugauaaua ggcuggagcc ucgguggcca ugcuucuugc cccuugggcc ucccccagc | 1620 |
| ccuccuccc cuuccugcac ccguacccc guggucuuug aauaaagucu gaguggggcgg | 1680 |
| c | 1681 |

<210> SEQ ID NO 99
<211> LENGTH: 1684
<212> TYPE: RNA
<213> ORGANISM: Artificial Sequence
<220> FEATURE:
<223> OTHER INFORMATION: Synthetic Polynucleotide

<400> SEQUENCE: 99

| | |
|---|---|
| gggaaauaag agagaaaaga agaguaagaa gaaauauaag agccaccaug gaacugcuca | 60 |
| uuuugaaggc aaacgcuauc acgacaauac ucacugcagu gaccuucugu uuugccucag | 120 |
| gccagaacau aaccgaggag uuuuaucaau cuacaugcag cgcuguaucu aaaggcuacc | 180 |
| uggggcgcgcu ccgcacagga ugguacaccu ccgugaucac caucgagcuc agcaauauua | 240 |
| aagagaucaa gugcaauggu accgacgcua agucaaacu uaucaagcag gaacucgaca | 300 |
| aauauaagaa cgcugugacc gaccugcagu uauugaugca gaguacaccu gccaccgggu | 360 |
| cgggcucugc cauugcuucc ggcguggcug uauguaaagu ucuccaccuc gagggagagg | 420 |
| uuaauaagau uaagucggcc cugcugagua cuaacaaagc aguggugucg cugagugcu | 480 |
| gcggaguaag uguguuaaca uuuaaggugc uggaccucaa gaauuauauu gacaaacagu | 540 |
| ugcuuccuau ucuaaacaaa cagagcuguu caauacccaa uauugaaacu guuauugagu | 600 |
| uucagcagaa gaacaacagg cuucuugaga uuacacgcga uucagugac aaugccggcg | 660 |
| uuacaacacc cgugucuacc acaugcugcga cgaauucuga gcuucucucu ucuauaaacg | 720 |
| acaugcccau uacgaaugac caaaagaaac uuaugccaa caacgugcag auugugcgac | 780 |
| agcaauccua uagcauuaug uguaucauca aggaagaggu acucgcuuau guugugcagc | 840 |
| uaccacucua ugguguqauu gacaccccu guuggaagcu gcauaccagu ccacucugca | 900 |
| ccacuaacac aaaggaaggg agcaauauuu gccucacucg aaccgacagg ggugguauu | 960 |
| gcgauaaugc gggcuccgug uccuucuuuc cacaggcuga aacuuguaag guacagucaa | 1020 |
| accgcguguu cugugauacu augaauucuc guacucuucc cagcgagguu aaucucugca | 1080 |
| acgucgacau uuucaauccu aaauaugacu gcaagaucau gaccagcaag accgacgucu | 1140 |
| ccagcucagu aaucacuagc cuaggggcca uguaagcug cuauggcaaa accaaguggua | 1200 |
| cugccucuaa uaagugcaga ggcauaauua aaaccuuuuc aaauggcugu gacuaugugu | 1260 |

```
cgaauaaggg cgucgacacg gucucaguag ggaauacccu cuacuacguu aacaaacagg    1320
aaggccaguc ccuuuaugua aagggcgagc ccaucauaaa uuucuacgac ccacuugugu    1380
uccccaguga ugaauucgau gcaucaaucu cccaggugaa cgaaaagauc aaucaauccc    1440
uugcuuuuau acgaaaguca gaugaaccuc uguccgccau cgguggcuau aucccagaag    1500
ccccaagaga cggacaagcg uacguccgga aagaugguga guggguccuc cucucuaccu    1560
uucuuugaua auaggcugga gccucggugg ccaugcuucu ugccccuugg gccucccccc    1620
agcccCuccu cCCcuuccug cacccguacc cccguggucu uugaauaaag ucugagúggg    1680 cggc                                                                1684

<210> SEQ ID NO 100
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 100

Met Glu Leu Leu Ile Leu Lys Ala Asn Ala Ile Thr Thr Ile Leu Thr
1               5                   10                  15

Ala Val Thr Phe Cys Phe Ala Ser Gly
            20                  25
```